(12) United States Patent
Haydar et al.

(10) Patent No.: US 9,012,642 B2
(45) Date of Patent: Apr. 21, 2015

(54) PYRROLOPYRIDINONE COMPOUNDS AND METHODS FOR TREATING HIV

(71) Applicant: ViiV Healthcare UK Limited, Brentford, Middlesex (GB)

(72) Inventors: Simon N. Haydar, Research Triangle Park, NC (US); Brian Alvin Johns, Research Triangle Park, NC (US); Emile Johann Velthuisen, Research Triangle Park, NC (US)

(73) Assignee: ViiV Healthcare UK Limited, Brentford, Middlesex (GB)

( * ) Notice: Subject to any disclaimer, the term of this patent is extended or adjusted under 35 U.S.C. 154(b) by 0 days.

(21) Appl. No.: 14/344,915

(22) PCT Filed: Sep. 18, 2012

(86) PCT No.: PCT/US2012/055838
§ 371 (c)(1),
(2) Date: Mar. 14, 2014

(87) PCT Pub. No.: WO2013/043553
PCT Pub. Date: Mar. 28, 2013

(65) Prior Publication Data
US 2014/0343092 A1      Nov. 20, 2014

Related U.S. Application Data

(60) Provisional application No. 61/537,649, filed on Sep. 22, 2011.

(51) Int. Cl.
| | |
|---|---|
| *C07D 471/04* | (2006.01) |
| *A61K 31/437* | (2006.01) |
| *C07D 491/147* | (2006.01) |
| *A61K 45/06* | (2006.01) |
| *C07D 495/04* | (2006.01) |

(52) U.S. Cl.
CPC ............ *C07D 491/147* (2013.01); *A61K 45/06* (2013.01); *C07D 471/04* (2013.01); *A61K 31/437* (2013.01); *C07D 495/04* (2013.01)

(58) Field of Classification Search
CPC ........................... C07D 471/04; A61K 31/437
USPC .......................................... 546/113; 514/300
See application file for complete search history.

(56) References Cited

U.S. PATENT DOCUMENTS

| | | |
|---|---|---|
| 6,635,638 B2 | 10/2003 | Sui et al. |
| 7,354,924 B2 | 4/2008 | Wang et al. |
| 2005/0137201 A1* | 6/2005 | Aronov et al. ................ 514/249 |
| 2007/0142414 A1 | 6/2007 | Vanotti et al. |

* cited by examiner

*Primary Examiner* — David K O Dell
(74) *Attorney, Agent, or Firm* — Robert H. Brink

(57) ABSTRACT

Provided are compounds and pharmaceutically acceptable salts thereof, their pharmaceutical compositions, their methods of preparation, and their use for treating viral infections mediated by a member of the retrovirus family of viruses such as the Human Immunodeficiency Virus (HIV).

6 Claims, No Drawings

PYRROLOPYRIDINONE COMPOUNDS AND METHODS FOR TREATING HIV

CROSS-REFERENCE TO RELATED APPLICATIONS

This application is filed pursuant to 35 USC 371 as a United States National Phase Application of International Patent Application Serial No. PCT/US2012/055838 filed on Sep. 18, 2012, which claims priority from 61/537,649 filed on Sep. 22, 2011 filed in the United States.

FIELD OF THE INVENTION

The present invention relates to substituted pyrrolopyridinone compounds, pharmaceutical compositions, and methods of use thereof for (i) inhibiting HIV replication in a subject infected with HIV, or (ii) treating a subject infected with HIV, by administering such compounds.

BACKGROUND OF THE INVENTION

Presently, long-term suppression of viral replication with antiretroviral drugs is the only option for treating HIV-1 infection. To date, a number of approved drugs have been shown to greatly increase patient survival. However, therapeutic regimens known as highly active antiretroviral therapy (HAART) are often complex because a combination of different drugs must be administered to the patient to avoid the rapid emergence of drug-resistant HIV-1 variants. Despite the positive impact of HAART on patient survival, drug resistance can still occur.

The emergence of multidrug-resistant (MDR) HIV-1 isolates has serious clinical consequences and must be suppressed with a new drug regimen, known as salvage therapy. Current guidelines recommend that salvage therapy includes at least two, and preferably three, fully active drugs. Typically, first-line therapies combine three to four drugs targeting the viral enzymes RT and protease (PR). One option for salvage therapy is to administer different combinations of drugs from the same mechanistic class that remain active against the resistant isolates. However, the options for this approach are often limited, as resistant mutations frequently confer broad cross-resistance to different drugs in the same class. Alternative therapeutic strategies have recently become available with the development of fusion, entry, and integrase (IN) inhibitors. However, resistance to all three new drug classes has already been reported both in vitro and in vivo. Sustained successful treatment of HIV-1-infected patients with antiretroviral drugs will therefore require the continued development of new and improved drugs with new targets and mechanisms of action.

SUMMARY OF THE INVENTION

In accordance with one embodiment of the present invention, there is provided a compound of Formula I:

Formula I

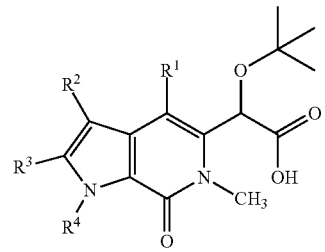

or a pharmaceutically acceptable salt thereof, wherein:

$R^1$ is selected from the group consisting of $(C_7-C_{12})$aryl, $(C_3-C_7)$cycloalkyl, $(C_2-C_9)$heterocycle, and $(C_2-C_9)$heteroaryl;

$R^2$ is selected from the group consisting of H, halo and alkyl;

$R^2$ is selected from the group consisting of —H, $(C_1-C_6)$alkyl, $(C_1-C_6)$alkoxy, halo, nitrile, $(C_3-C_7)$cycloalkyl, —$OR^5(C_5-C_{14})$aryl, —$OR^5R^8$, —$OR^5(C_5-C_{14})$aryl$(R^8)_m$, —$R^5(Y)(R^7)_n$, —$OR^5R^{11}$, —$R^5R^{11}$, —$OR^5(R^8)_q$, —$OR^5(Y)$, —$OR^5R^{13}$, —$OSO_2R^9$, —$R^9$, —$(C_5-C_{14})$aryl, —(Y), —$(Y)(R^7)_n$, —$C(O)(Y)$, —$C(O)R^9$, —$R^5(C_5-C_{14})$aryl, —$R^5R^9$, and —$(C_5-C_{14})$aryl$R^9$, wherein $R^2$ and $R^3$ together with the carbon atoms to which they are bonded may optionally join together to form a $(C_5-C_{14})$aryl, or alternatively, $R^7$ and $R^8$ together with the carbon atoms to which they are bonded may optionally join together to form a (C3-C7)heterocycle or cycloalkyl;

$R^4$ is selected from —H, $(C_1-C_6)$alkyl, $(C_1-C_6)$alkoxy, halo, nitrile, $(C_3-C_7)$cycloalkyl, —$OR^5(C_5-C_{14})$aryl, —$OR^5R^8$, —$OR^5(C_5-C_{14})$aryl$(R^8)_m$, —$R^5(Y)(R^7)_n$, —$OR^5R^{11}$, —$R^5R^{11}$, —$OR^5(R^8)_q$, —$OR^5(Y)$, —$OR^5R^{13}$, —$OSO_2R^9$, —$R^9$, —$(C_5-C_{14})$aryl, —(Y), —$(Y)(R^7)_n$, —$C(O)(Y)$, —$C(O)R^9$, —$R^5(C_5-C_{14})$aryl, —$R^5R^9$, and —$(C_5-C_{14})$aryl$R^9$;

$R^5$ is $(C_1-C_6)$alkyl;

$R^6$ and $R^7$ are selected from the group consisting of $(C_1-C_6)$alkyl, $(C_1-C_6)$alkoxy, oxo, halo, —$R^5(R^9)_q$, —$OR^5(R^9)_q$, —$SO_2R^5$, —$C(O)R^5$, —$C(O)R^{10}$; and —$R^5(R^6)$;

$R^8$ is selected is halo;

$R^9$ is —$N(R^{10})_2$;

$R^{10}$ is independently selected from the group consisting of —H, $(C_1-C_6)$alkyl, hydroxyl, —$SO_2R^5$, —$SO_2N(R^5)$, —$C(O)NHR^{12}$, and —$(C_5-C_{14})$aryl$(R^5)$;

$R^{11}$ is —$OR^{12}$;

$R^{12}$ is independently selected from —H and $(C_1-C_6)$alkyl;

$R^{13}$ is —$CO_2R^{12}$;

Y is independently selected from $(C_2-C_9)$heterocycle or $(C_2-C_9)$heteroaryl, each having one to three heteroatoms selected from S, N and O;

m is zero or an integer selected from 1, 2, 3, or 4;

n is zero or an integer selected from 1, 2, or 3; and q is an integer selected from 1, 2, or 3.

In another embodiment of the present invention, there is provided a compound of Formula I or a pharmaceutically acceptable salt thereof, wherein $R^1$ is selected from the group consisting of,

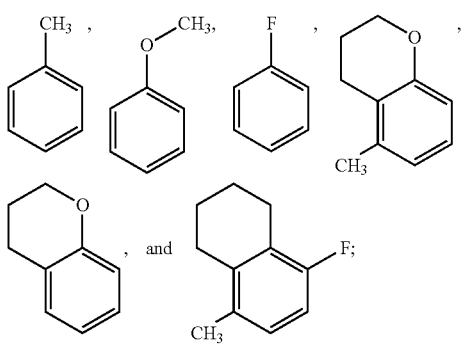

$R^2$ is selected from the group consisting of H, halo and alkyl;

$R^3$ is selected from —H, $(C_1\text{-}C_6)$alkyl, $(C_1\text{-}C_6)$alkoxy, halo, nitrile, $(C_3\text{-}C_7)$cycloalkyl, —OR$^4(C_5\text{-}C_{14})$aryl, —OR$^4$R$^7$, —OR$^4(C_5\text{-}C_{14})$aryl(R$^5)_m$, —R$^4$(Y)(R$^6)_n$, —OR$^4$R$^{10}$, —R$^4$R$^{10}$, —R$^{17}$R$^8$, —OR$^4$(R$^7)_q$, —OR$^4$(Y), —OR$^4$R$^{12}$, —OSO$_2$R$^8$, —R$^8$, —$(C_5\text{-}C_{14})$aryl, —(Y), —(Y)(R$^6)_n$, —C(O)(Y), —C(O)R$^8$, —R$^4(C_5\text{-}C_{14})$aryl, —R$^4$R$^8$, and —$(C_5\text{-}C_{14})$arylR$^8$, wherein $R^5$ and $R^6$ together with the carbon atoms to which they are bonded may optionally join together to form a $(C_5\text{-}C_{14})$ aryl, or alternatively, $R^6$ and $R^7$ together with the carbon atoms to which they are bonded may optionally join together to form a (C3-C7)heterocycle or cycloalkyl;

$R^4$ is $(C_1\text{-}C_6)$alkyl;

$R^5$ and $R^6$ are selected from the group consisting of $(C_1\text{-}C_6)$alkyl, $(C_1\text{-}C_6)$alkoxy, oxo, halo, —R$^4$(R$^8)_q$, —OR$^4$(R$^8)_q$, —SO$_2$R$^4$, —C(O)R$^4$, —C(O)R$^9$; and —R$^4$(R$^5$);

$R^7$ is selected is halo;

$R^8$ is —N(R$^9)_2$;

$R^9$ is independently selected from the group consisting of —H, $(C_1\text{-}C_6)$alkyl, hydroxyl, —SO$_2$R$^4$, —SO$_2$N(R$^4$), —C(O)NHR$^{11}$, and —$(C_5\text{-}C_{14})$aryl(R$^4$);

$R^{10}$ is —OR$^{11}$;

$R^{11}$ is independently selected from —H and $(C_1\text{-}C_6)$alkyl;

$R^{12}$ is —CO$_2$R$^{11}$;

Y is independently selected from $(C_2\text{-}C_9)$heterocycle or $(C_2\text{-}C_9)$heteroaryl, each having one to three heteroatoms selected from S, N and O;

m is zero or an integer selected from 1, 2, 3, or 4;

n is zero or an integer selected from 1, 2, or 3; and q is an integer selected from 1, 2, or 3.

In another embodiment of the present invention, there is provided a compound of Formula I or a pharmaceutically acceptable salt thereof, wherein $R^1$ is selected from the group consisting of,

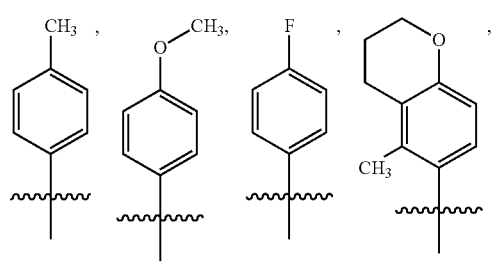

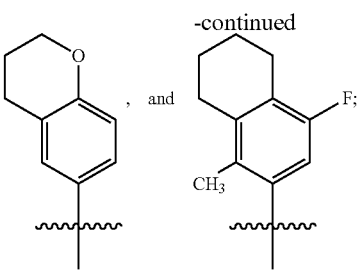

$R^2$ is selected from the group consisting of H, halo and alkyl;

$R^3$ is selected from —H, $(C_1\text{-}C_6)$alkyl, $(C_1\text{-}C_6)$alkoxy, halo, nitrile, $(C_3\text{-}C_7)$cycloalkyl, —OR$^4(C_5\text{-}C_{14})$aryl, —OR$^4$R$^7$, —OR$^4(C_5\text{-}C_{14})$aryl(R$^5)_m$, —R$^4$(Y)(R$^6)_n$, —OR$^4$R$^{10}$, —R$^4$R$^{10}$, —R$^{17}$R$^8$, —OR$^4$(R$^7)_q$, —OR$^4$(Y), —OR$^4$R$^{12}$, —OSO$_2$R$^8$, —R$^8$, —$(C_5\text{-}C_{14})$aryl, —(Y), —(Y)(R$^6)_n$, —C(O)(Y), —C(O)R$^8$, —R$^4(C_5\text{-}C_{14})$aryl, —R$^4$R$^8$, and —$(C_5\text{-}C_{14})$arylR$^8$, wherein $R^5$ and $R^6$ together with the carbon atoms to which they are bonded may optionally join together to form a $(C_5\text{-}C_{14})$ aryl, or alternatively, $R^6$ and $R^7$ together with the carbon atoms to which they are bonded may optionally join together to form a (C3-C7)heterocycle or cycloalkyl;

$R^4$ is $(C_1\text{-}C_6)$alkyl;

$R^5$ and $R^6$ are selected from the group consisting of $(C_1\text{-}C_6)$alkyl, $(C_1\text{-}C_6)$alkoxy, oxo, halo, —R$^4$(R$^8)_q$, —OR$^4$(R$^8)_q$, —SO$_2$R$^4$, —C(O)R$^4$, —C(O)R$^9$; and —R$^4$(R$^5$);

$R^7$ is selected is halo;

$R^8$ is —N(R$^9)_2$;

$R^9$ is independently selected from the group consisting of —H, $(C_1\text{-}C_6)$alkyl, hydroxyl, —SO$_2$R$^4$, —SO$_2$N(R$^4$), —C(O)NHR$^{11}$, and —$(C_5\text{-}C_{14})$aryl(R$^4$);

$R^{10}$ is —OR$^{11}$;

$R^{11}$ is independently selected from —H and $(C_1\text{-}C_6)$alkyl;

$R^{12}$ is —CO$_2$R$^{11}$;

Y is independently selected from $(C_2\text{-}C_9)$heterocycle or $(C_2\text{-}C_9)$heteroaryl, each having one to three heteroatoms selected from S, N and O;

m is zero or an integer selected from 1, 2, 3, or 4;

n is zero or an integer selected from 1, 2, or 3; and q is an integer selected from 1, 2, or 3.

Also provided is a pharmaceutical composition comprising a pharmaceutically acceptable carrier or excipient and a therapeutically effective amount of a compound of Formula I, or a pharmaceutically acceptable salt thereof.

Also provided are synthetic intermediates, methods for preparing the compounds of Formula I, or a pharmaceutically acceptable salt or solvate thereof, and compositions thereof and for their therapeutic uses.

In some embodiments, provided is a method for treating a viral infection in a patient mediated at least in part by a virus in the retrovirus family of viruses, comprising administering to said patient a composition comprising a compound of any of Formulas I or II, or a pharmaceutically acceptable salt thereof. In some embodiments, the viral infection is mediated by the HIV virus. Those and other embodiments are further described in the text that follows.

In another aspect, a particular embodiment of the present invention provides a method of treating a subject infected with HIV comprising administering to the subject a therapeutically effective amount of the compound of Formula I, or a pharmaceutically acceptable salt thereof.

In yet another aspect, a particular embodiment of the present invention provides a method of inhibiting progression of HIV infection in a subject at risk for infection with HIV comprising administering to the subject a therapeutically effective amount of the compound of Formulas I or II, or a pharmaceutically acceptable salt thereof.

DETAILED DESCRIPTION OF REPRESENTATIVE EMBODIMENTS

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings.

As used herein unless otherwise specified, "alkyl" refers to a monovalent saturated aliphatic hydrocarbyl group having from 1 to 14 carbon atoms and, in some embodiments, from 1 to 6 carbon atoms. "$(C_x-C_y)$alkyl" refers to alkyl groups having from x to y carbon atoms. The term "alkyl" includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkylidene" or "alkylene" refers to divalent saturated aliphatic hydrocarbyl groups having from 1 to 10 carbon atoms and, in some embodiments, from 1 to 6 carbon atoms. "$(C_{u-v})$alkylene" refers to alkylene groups having from u to v carbon atoms. The alkylidene and alkylene groups include branched and straight chain hydrocarbyl groups. For example "$(C_{1-6})$alkylene" is meant to include methylene, ethylene, propylene, 2-methypropylene, pentylene, and so forth.

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, $(C_x-C_y)$alkenyl refers to alkenyl groups having from x to y carbon atoms and is meant to include for example, ethenyl, propenyl, isopropylene, 1,3-butadienyl, and the like.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, $(C_2-C_6)$alkynyl is meant to include ethynyl, propynyl, and the like.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Acyl" refers to the groups H—C(O)—, alkyl-C(O)—, alkenyl-C(O)—, alkynyl-C(O)—, cycloalkyl-C(O)—, aryl-C(O)—, heteroaryl-C(O)—, and heterocyclic-C(O)—. Acyl includes the "acetyl" group $CH_3C(O)$—.

"Acylamino" refers to the groups —$NR^{20}C(O)$alkyl, —$NR^{20}C(O)$cycloalkyl, —$NR^{20}C(O)$alkenyl, —$NR^{20}C(O)$alkynyl, —$NR^{20}C(O)$aryl, —$NR^{20}C(O)$heteroaryl, and —$NR^{20}C(O)$heterocyclic, wherein $R^{20}$ is hydrogen or alkyl.

"Acyloxy" refers to the groups alkyl-C(O)O—, alkenyl-C(O)O—, alkynyl-C(O)O—, aryl-C(O)O—, cycloalkyl-C(O)O—, heteroaryl-C(O)O—, and heterocyclic-C(O)O—.

"Amino" refers to the group —$NR^{21}R^{22}$ where $R^{21}$ and $R^{22}$ are independently selected from hydrogen, alkyl, alkenyl, alkynyl, aryl, cycloalkyl, heteroaryl, heterocyclic, —$SO_2$-alkyl, —$SO_2$-alkenyl, —$SO_2$-cycloalkyl, —$SO_2$-aryl, —$SO_2$-heteroaryl, and —$SO_2$-heterocyclic, and wherein $R^{21}$ and $R^{22}$ are optionally joined together with the nitrogen bound thereto to form a heterocyclic group. When $R^{21}$ is hydrogen and $R^{22}$ is alkyl, the amino group is sometimes referred to herein as alkylamino. When $R^{21}$ and $R^{22}$ are alkyl, the amino group is sometimes referred to herein as dialkylamino. When referring to a monosubstituted amino, it is meant that either $R^{21}$ or $R^{22}$ is hydrogen but not both. When referring to a disubstituted amino, it is meant that neither $R^{21}$ nor $R^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —$C(O)NR^{26}R^{27}$ where $R^{26}$ and $R^{27}$ are independently selected from hydrogen, alkyl, alkenyl, alkynyl, aryl, cycloalkyl, heteroaryl, heterocyclic, hydroxy, alkoxy, amino, and acylamino, and where $R^{26}$ and $R^{27}$ are optionally joined together with the nitrogen bound thereto to form a heterocyclic group.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring).

"Cyano" or "nitrile" refers to the group —CN.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8,-tetrahydronaphthalene-5-yl). The term "Cycloalkyl" includes cycloalkenyl groups, such as cyclohexenyl. Examples of cycloalkyl groups include, for instance, adamantyl, cyclopropyl, cyclobutyl, cyclohexyl, cyclopentyl, cyclooctyl, cyclopentenyl, and cyclohexenyl. Examples of cycloalkyl groups that include multiple bicycloalkyl ring systems are bicyclohexyl, bicyclopentyl, bicyclooctyl, and the like. Two such bicycloalkyl multiple ring structures are exemplified and named below:

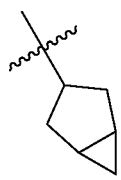 [SMILES: *C1CC2CC2C1]

bicyclohexyl, and

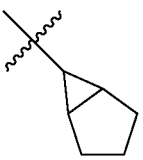 [SMILES: *C1C2CCCC12]

bicyclohexyl.

"$(C_u-C_v)$cycloalkyl" refers to cycloalkyl groups having u to v carbon atoms.

"Spiro cycloalkyl" refers to a 3 to 10 member cyclic substituent formed by replacement of two hydrogen atoms at a common carbon atom in a cyclic ring structure or in an alkylene group having 2 to 9 carbon atoms, as exemplified by the following structure wherein the group shown here attached to bonds marked with wavy lines is substituted with a spiro cycloalkyl group:

"Fused cycloalkyl" refers to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused cycloalkyl group:

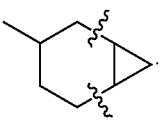

"Halo" or "halogen" refers to fluoro, chloro, bromo, and iodo.

"Haloalkoxy" refers to substitution of alkoxy groups with 1 to 5 (e.g. when the alkoxy group has at least 2 carbon atoms) or in some embodiments 1 to 3 halo groups (e.g. trifluoromethoxy).

"Hydroxy" or "hydroxyl" refers to the group —OH.

"Heteroaryl" refers to an aromatic group of from 1 to 14 carbon atoms and 1 to 6 heteroatoms selected from oxygen, nitrogen, and sulfur and includes single ring (e.g. imidazolyl) and multiple ring systems (e.g. benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from nitrogen, sulfur, phosphorus or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In one embodiment, the nitrogen, phosphorus and/or sulfur atom(s) of the heterocyclic group are optionally oxidized to provide for the N-oxide, phosphinane oxide, sulfinyl, sulfonyl moieties. More specifically the heterocyclyl includes, but is not limited to, tetrahydropyranyl, piperidinyl, piperazinyl, 3-pyrrolidinyl, 2-pyrrolidon-1-yl, morpholinyl, and pyrrolidinyl. A prefix indicating the number of carbon atoms (e.g., $C_3-C_{10}$) refers to the total number of carbon atoms in the portion of the heterocyclyl group exclusive of the number of heteroatoms.

Examples of heterocycle and heteroaryl groups include, but are not limited to, azetidine, pyrrole, imidazole, pyrazole, pyridine, pyrazine, pyrimidine, pyridazine, pyridone, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholine, thiomorpholine (also referred to as thiamorpholine), piperidine, pyrrolidine, and tetrahydrofuranyl.

"Fused heterocyclic" refers to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused heterocyclic group:

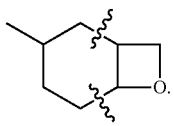

"Compound", "compounds", "chemical entity", and "chemical entities" as used herein refers to a compound encompassed by the generic formulae disclosed herein, any subgenus of those generic formulae, and any forms of the compounds within the generic and subgeneric formulae, including the racemates, stereoisomers, and tautomers of the compound or compounds.

The term "heteroatom" means nitrogen, oxygen, or sulfur and includes any oxidized form of nitrogen, such as N(O)

{N⁺—O⁻} and sulfur such as S(O) and S(O)₂, and the quaternized form of any basic nitrogen.

"Oxazolidinone" refers to a 5-membered heterocyclic ring containing one nitrogen and one oxygen as heteroatoms and also contains two carbons and is substituted at one of the two carbons by a carbonyl group as exemplified by any of the following structures, wherein the oxazolidinone groups shown here are bonded to a parent molecule, which is indicated by a wavy line in the bond to the parent molecule:

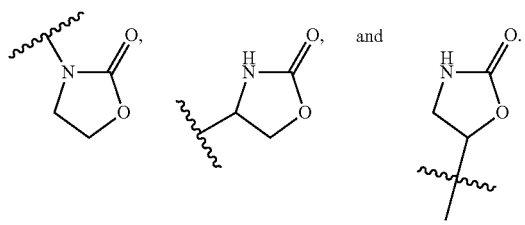 [SMILES: *N1CCOC1=O ; *C1COC(=O)N1 ; "and" ; *C1CNC(=O)O1]

"Racemates" refers to a mixture of enantiomers. In an embodiment of the invention, the compounds of Formulas I or II, or pharmaceutically acceptable salts thereof, are enantiomerically enriched with one enantiomer wherein all of the chiral carbons referred to are in one configuration. In general, reference to an enantiomerically enriched compound or salt, is meant to indicate that the specified enantiomer will comprise more than 50% by weight of the total weight of all enantiomers of the compound or salt.

"Solvate" or "solvates" of a compound refer to those compounds, as defined above, which are bound to a stoichiometric or non-stoichiometric amount of a solvent. Solvates of a compound includes solvates of all forms of the compound. In certain embodiments, solvents are volatile, non-toxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The term 'atropisomer' refers to a stereoisomer resulting from an axis of asymmetry. This can result from restricted rotation about a single bond where the rotational barrier is high enough to allow differentiation of the isomeric species up to and including complete isolation of stable non-interconverting diastereomer or enantiomeric species [Eliel ref]. One skilled in the art will recognize that upon installing a non-symmetrical $R^x$ to core, the formation of atropisomers is possible. In addition, once a second chiral center is installed in a given molecule containing an atropisomer, the two chiral elements taken together can create diastereomeric and enantiomeric stereochemical species. Depending upon the substitution about the Cx axis, interconversion between the atropisomers may or may not be possible and may depend on temperature. In some instances, the atropisomers may interconvert rapidly at room temperature and not resolve under ambient conditions. Other situations may allow for resolution and isolation but interconversion can occur over a period of seconds to hours or even days or months such that optical purity is degraded measurably over time. Yet other species may be completely restricted from interconversion under ambient and/or elevated temperatures such that resolution and isolation is possible and yields stable species. When known, the resolved atropisomers were named using the helical nomenclature. For this designation, only the two ligands of highest priority in front and behind the axis are considered. When the turn priority from the front ligand 1 to the rear ligand 1 is clockwise, the configuration is P, if counterclockwise it is M.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

"Patient" refers to mammals and includes humans and non-human mammals.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—. In a term such as "—C($R^x$)₂", it should be understood that the two Rx groups can be the same, or they can be different if $R^x$ is defined as having more than one possible identity. In addition, certain substituents are drawn as —$R^xR^y$, where the "—" indicates a bond adjacent to the parent molecule and $R^y$ being the terminal portion of the functionality. Similarly, it is understood that the above definitions are not intended to include impermissible substitution patterns (e.g., methyl substituted with 5 fluoro groups). Such impermissible substitution patterns are well known to the skilled artisan.

In accordance with one preferred embodiment of the present invention, there is provided a compound of Formula I:

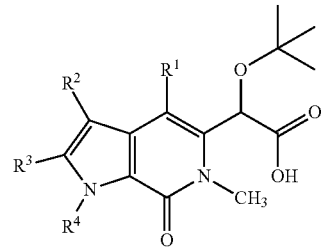

Formula I or a pharmaceutically acceptable salt thereof, wherein:

$R^1$ is selected from the group consisting of ($C_7$-$C_{12}$)aryl, ($C_3$-$C_7$)cycloalkyl, ($C_2$-$C_9$)heterocycle, and ($C_2$-$C_9$) heteroaryl;

$R^2$ is selected from the group consisting of H, halo and alkyl;

$R^2$ is selected from the group consisting of —H, ($C_1$-$C_6$) alkyl, ($C_1$-$C_6$)alkoxy, halo, nitrile, ($C_3$-$C_7$)cycloalkyl, —$OR^5$($C_5$-$C_{14}$)aryl, —$OR^5R^8$, —$OR^5$($C_5$-$C_{14}$)aryl $(R^6)_m$, $-R^5(Y)(R^7)_n$, $-OR^5R^{11}$, $-R^5R^{11}$, $-OR^5(R^8)_q$, $-OR^5(Y)$, $-OR^5R^{13}$, $-OSO_2R^9$, $-R^9$, $-(C_5-C_{14})$aryl, $-(Y)$, $-(Y)(R^7)_n$, $-C(O)(Y)$, $-C(O)R^9$, $-R^5(C_5-C_{14})$aryl, $-R^5R^9$, and $-(C_5-C_{14})$aryl$R^9$, wherein $R^2$ and $R^3$ together with the carbon atoms to which they are bonded may optionally join together to form a $(C_5-C_{14})$aryl, or alternatively, $R^7$ and $R^8$ together with the carbon atoms to which they are bonded may optionally join together to form a $(C_3-C_7)$heterocycle or cycloalkyl or cycloalkyl;

$R^4$ is selected from $-H$, $(C_1-C_6)$alkyl, $(C_1-C_6)$alkoxy, halo, nitrile, $(C_3-C_7)$cycloalkyl, $-OR^5(C_5-C_{14})$aryl, $-OR^5R^8$, $-OR^5(C_5-C_{14})$aryl$(R^6)_m$, $-R^5(Y)(R^7)_n$, $-OR^5R^{11}$, $-R^5R^{11}$, $-OR^5(R^8)_q$, $-OR^5(Y)$, $-OR^5R^{13}$, $-OSO_2R^9$, $-R^9$, $-(C_5-C_{14})$aryl, $-(Y)$, $-(Y)(R^7)_n$, $-C(O)(Y)$, $-C(O)R^9$, $-R^5(C_5-C_{14})$aryl, $-R^5R^9$, and $-(C_5-C_{14})$aryl$R^9$;

$R^5$ is $(C_1-C_6)$alkyl;

$R^6$ and $R^7$ are selected from the group consisting of $(C_1-C_6)$alkyl, $(C_1-C_6)$alkoxy, oxo, halo, $-R^5(R^9)_q$, $-OR^5(R^9)_q$, $-SO_2R^5$, $-C(O)R^5$, $-C(O)R^{10}$; and $-R^5(R^6)$;

$R^8$ is selected is halo;

$R^9$ is $-N(R^{10})_2$;

$R^{10}$ is independently selected from the group consisting of $-H$, $(C_1-C_6)$alkyl, hydroxyl, $-SO_2R^5$, $-SO_2N(R^5)$, $-C(O)NHR^{12}$, and $-(C_5-C_{14})$aryl$(R^5)$;

$R^{11}$ is $-OR^{12}$;

$R^{12}$ is independently selected from $-H$ and $(C_1-C_6)$alkyl;

$R^{13}$ is $-CO_2R^{12}$;

Y is independently selected from $(C_2-C_9)$heterocycle or $(C_2-C_9)$heteroaryl, each having one to three heteroatoms selected from S, N and O;

m is zero or an integer selected from 1, 2, 3, or 4;

n is zero or an integer selected from 1, 2, or 3; and q is an integer selected from 1, 2, or 3.

In another embodiment of the present invention, there is provided a compound of Formula I or a pharmaceutically acceptable salt thereof, wherein $R^1$ is selected from the group consisting of,

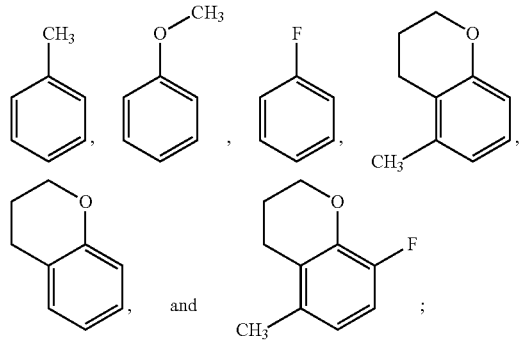

$R^2$ is selected from the group consisting of H, halo and alkyl;

$R^3$ is selected from $-H$, $(C_1-C_6)$alkyl, $(C_1-C_6)$alkoxy, halo, nitrile, $(C_3-C_7)$cycloalkyl, $-OR^4(C_5-C_{14})$aryl, $-OR^4R^7$, $-OR^4(C_5-C_{14})$aryl$(R^5)_m$, $-R^4(Y)(R^6)_n$, $-OR^4R^{10}$, $-R^4R^{10}$, $-R^{17}R^8$, $-OR^4(R^7)_q$, $-OR^4(Y)$, $-OR^4R^{12}$, $-OSO_2R^8$, $-R^8$, $-(C_5-C_{14})$aryl, $-(Y)$, $-(Y)(R^6)_n$, $-C(O)(Y)$, $-C(O)R^8$, $-R^4(C_5-C_{14})$aryl, $-R^4R^8$, and $-(C_5-C_{14})$aryl$R^8$, wherein $R^5$ and $R^6$ together with the carbon atoms to which they are bonded may optionally join together to form a $(C_5-C_{14})$aryl, or alternatively, $R^6$ and $R^7$ together with the carbon atoms to which they are bonded may optionally join together to form a $(C_3-C_7)$heterocycle or cycloalkyl;

$R^4$ is $(C_1-C_6)$alkyl;

$R^5$ and $R^6$ are selected from the group consisting of $(C_1-C_6)$alkyl, $(C_1-C_6)$alkoxy, oxo, halo, $-R^4(R^8)_q$, $-OR^4(R^8)_q$, $-SO_2R^4$, $-C(O)R^4$, $-C(O)R^9$; and $-R^4(R^5)$;

$R^7$ is selected is halo;

$R^8$ is $-N(R^9)_2$;

$R^9$ is independently selected from the group consisting of $-H$, $(C_1-C_6)$alkyl, hydroxyl, $-SO_2R^4$, $-SO_2N(R^4)$, $-C(O)NHR^{11}$, and $-(C_5-C_{14})$aryl$(R^4)$;

$R^{10}$ is $-OR^{11}$;

$R^{11}$ is independently selected from $-H$ and $(C_1-C_6)$alkyl;

$R^{12}$ is $-CO_2R^{11}$;

Y is independently selected from $(C_2-C_9)$heterocycle or $(C_2-C_9)$heteroaryl, each having one to three heteroatoms selected from S, N and O;

m is zero or an integer selected from 1, 2, 3, or 4;

n is zero or an integer selected from 1, 2, or 3; and q is an integer selected from 1, 2, or 3.

In another embodiment of the present invention, there is provided a compound of Formula I or a pharmaceutically acceptable salt thereof, wherein $R^1$ is selected from the group consisting of,

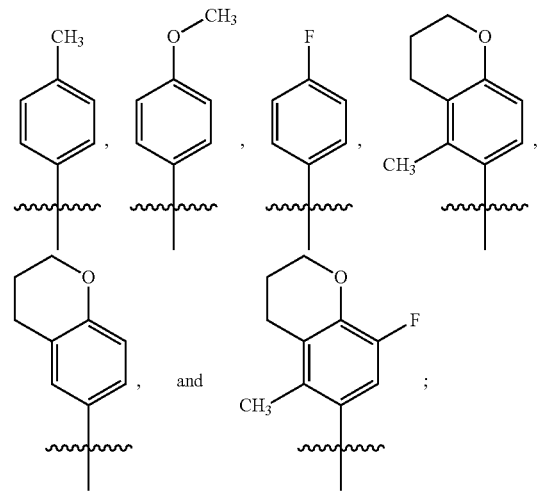

$R^2$ is selected from the group consisting of H, halo and alkyl;

$R^3$ is selected from $-H$, $(C_1-C_6)$alkyl, $(C_1-C_6)$alkoxy, halo, nitrile, $(C_3-C_7)$cycloalkyl, $-OR^4(C_5-C_{14})$aryl, $-OR^4R^7$, $-OR^4(C_5-C_{14})$aryl$(R^5)_m$, $-R^4(Y)(R^6)_n$, $-OR^4R^{10}$, $-R^4R^{10}$, $-R^{17}R^8$, $-OR^4(R^7)_q$, $-OR^4(Y)$, $-OR^4R^{12}$, $-OSO_2R^8$, $-R^8$, $-(C_5-C_{14})$aryl, $-(Y)$, $-(Y)(R^6)_n$, $-C(O)(Y)$, $-C(O)R^8$, $-R^4(C_5-C_{14})$aryl, $-R^4R^8$, and $-(C_5-C_{14})$aryl$R^8$, wherein $R^5$ and $R^6$ together with the carbon atoms to which they are bonded may optionally join together to form a $(C_5-C_{14})$ aryl, or alternatively, $R^6$ and $R^7$ together with the carbon atoms to which they are bonded may optionally join together to form a $(C_3-C_7)$heterocycle or cycloalkyl or cycloalkyl;

$R^4$ is $(C_1-C_6)$alkyl;

$R^5$ and $R^6$ are selected from the group consisting of $(C_1-C_6)$alkyl, $(C_1-C_6)$alkoxy, oxo, halo, $-R^4(R^8)_q$, $-OR^4(R^8)_q$, $-SO_2R^4$, $-C(O)R^4$, $-C(O)R^9$; and $-R^4(R^5)$;

$R^7$ is selected is halo;

R⁸ is —N(R⁹)₂;
R⁹ is independently selected from the group consisting of —H, $(C_1-C_6)$alkyl, hydroxyl, —SO₂R⁴, —SO₂N(R⁴), —C(O)NHR¹¹, and —$(C_5-C_{14})$aryl(R⁴);
R¹⁰ is —OR¹¹;
R¹¹ is independently selected from —H and $(C_1-C_6)$alkyl;
R¹² is —CO₂R¹¹;
Y is independently selected from $(C_2-C_9)$heterocycle or $(C_2-C_9)$heteroaryl, each having one to three heteroatoms selected from S, N and O;
m is zero or an integer selected from 1, 2, 3, or 4;
n is zero or an integer selected from 1, 2, or 3; and
q is an integer selected from 1, 2, or 3.

In another embodiment of the present invention, there is provided a compound of Formula I, wherein a compound suitable for use with the present invention is selected from the group consisting of those compounds described in Table 1.

In another embodiment of the present invention, there is provided a compound of Formula I, wherein a compound suitable for use with the present invention is selected from the group consisting of:

2-(1-benzyl-4-(4-chlorophenyl)-6-methyl-7-oxo-6,7-dihydro-1H-pyrrolo[2,3-c]pyridin-5-yl)-2-(tert-butoxy)acetic acid,
2-(tert-butoxy)-2-(4-(4-chlorophenyl)-1-(4-fluorobenzyl)-6-methyl-7-oxo-6,7-dihydro-1H-pyrrolo[2,3-c]pyridin-5-yl)acetic acid,
2-(tert-butoxy)-2-(4-(4-chlorophenyl)-1-(4-methoxybenzyl)-6-methyl-7-oxo-6,7-dihydro-1H-pyrrolo[2,3-c]pyridin-5-yl)acetic acid,
2-(tert-butoxy)-2-(4-(4-chlorophenyl)-1-(2-methoxyethyl)-6-methyl-7-oxo-6,7-dihydro-1H-pyrrolo[2,3-c]pyridin-5-yl)acetic acid,
2-(tert-butoxy)-2-(4-(4-chlorophenyl)-1-isobutyl-6-methyl-7-oxo-6,7-dihydro-1H-pyrrolo[2,3-c]pyridin-5-yl)acetic acid,
(S)-2-(tert-butoxy)-2-(4-(4-chlorophenyl)-1-(3,4-difluorobenzyl)-6-methyl-7-oxo-6,7-dihydro-1H-pyrrolo[2,3-c]pyridin-5-yl)acetic acid,
2-(tert-butoxy)-2-(4-(4-chlorophenyl)-6-methyl-7-oxo-1-(2-(piperidin-1-yl)ethyl)-6,7-dihydro-1H-pyrrolo[2,3-c]pyridin-5-yl)acetic acid,
2-(tert-butoxy)-2-(4-(4-chlorophenyl)-6-methyl-7-oxo-1-(2-(piperidin-1-yl)ethyl)-6,7-dihydro-1H-pyrrolo[2,3-c]pyridin-5-yl)acetic acid,
2-(tert-butoxy)-2-(4-(4-chlorophenyl)-6-methyl-7-oxo-1-((5-(trifluoromethyl)furan-2-yl)methyl)-6,7-dihydro-1H-pyrrolo[2,3-c]pyridin-5-yl)acetic acid,
2-(tert-butoxy)-2-(4-(4-chlorophenyl)-1-(imidazo[1,2-a]pyridin-2-ylmethyl)-6-methyl-7-oxo-6,7-dihydro-1H-pyrrolo[2,3-c]pyridin-5-yl)acetic acid,
2-(tert-butoxy)-2-(4-(4-chlorophenyl)-6-methyl-1-((2-methylthiazol-4-yl)methyl)-7-oxo-6,7-dihydro-1H-pyrrolo[2,3-c]pyridin-5-yl)acetic acid,
2-(tert-butoxy)-2-(4-(4-chlorophenyl)-1-(2-((2-hydroxy-4-methylphenyl)amino)-2-oxoethyl)-6-methyl-7-oxo-6,7-dihydro-1H-pyrrolo[2,3-c]pyridin-5-yl)acetic acid,
2-(tert-butoxy)-2-(4-(4-chlorophenyl)-6-methyl-7-oxo-1-(1-phenylethyl)-6,7-dihydro-1H-pyrrolo[2,3-c]pyridin-5-yl)acetic acid,
2-(1-benzyl-3-bromo-4-(4-chlorophenyl)-6-methyl-7-oxo-6,7-dihydro-1H-pyrrolo[2,3-c]pyridin-5-yl)-2-(tert-butoxy)acetic acid,
2-(1-benzyl-4-(4-chlorophenyl)-3,6-dimethyl-7-oxo-6,7-dihydro-1H-pyrrolo[2,3-c]pyridin-5-yl)-2-(tert-butoxy)acetic acid,
2-(tert-butoxy)-2-(4-(4-chlorophenyl)-1-((4-fluorophenyl)sulfonyl)-6-methyl-7-oxo-6,7-dihydro-1H-pyrrolo[2,3-c]pyridin-5-yl)acetic acid,
2-(tert-butoxy)-2-(4-(4-chlorophenyl)-6-methyl-7-oxo-1-tosyl-6,7-dihydro-1H-pyrrolo[2,3-c]pyridin-5-yl)acetic acid,
2-(tert-butoxy)-2-(4-(4-chlorophenyl)-1-((1-(2-hydroxyethyl)-1H-1,2,3-triazol-4-yl)methyl)-6-methyl-7-oxo-6,7-dihydro-1H-pyrrolo[2,3-c]pyridin-5-yl)acetic acid,
2-(1-benzyl-6-methyl-7-oxo-4-(p-tolyl)-6,7-dihydro-1H-pyrrolo[2,3-c]pyridin-5-yl)-2-(tert-butoxy)acetic acid,
2-(1-(benzo[c][1,2,5]oxadiazol-5-ylmethyl)-6-methyl-7-oxo-4-(p-tolyl)-6,7-dihydro-1H-pyrrolo[2,3-c]pyridin-5-yl)-2-(tert-butoxy)acetic acid,
2-(1-(4-boronobenzyl)-6-methyl-7-oxo-4-(p-tolyl)-6,7-dihydro-1H-pyrrolo[2,3-c]pyridin-5-yl)-2-(tert-butoxy)acetic acid,
2-(tert-butoxy)-2-(1-(4-carbamoylbenzyl)-6-methyl-7-oxo-4-(p-tolyl)-6,7-dihydro-1H-pyrrolo[2,3-c]pyridin-5-yl)acetic acid,
2-(tert-butoxy)-2-(6-methyl-7-oxo-4-(p-tolyl)-1-(4-((trifluoromethyl)thio)benzyl)-6,7-dihydro-1H-pyrrolo[2,3-c]pyridin-5-yl)acetic acid,
(S)-2-(tert-butoxy)-2-(1-(4-fluorobenzyl)-6-methyl-7-oxo-4-(p-tolyl)-6,7-dihydro-1H-pyrrolo[2,3-c]pyridin-5-yl)acetic acid,
2-(tert-butoxy)-2-(6-methyl-7-oxo-1-(thiophen-2-ylmethyl)-4-(p-tolyl)-6,7-dihydro-1H-pyrrolo[2,3-c]pyridin-5-yl)acetic acid,
2-(tert-butoxy)-2-(1-(4-fluorophenethyl)-6-methyl-7-oxo-4-(p-tolyl)-6,7-dihydro-1H-pyrrolo[2,3-c]pyridin-5-yl)acetic acid,
2-(tert-butoxy)-2-(6-methyl-1-(4-(methylsulfonyl)benzyl)-7-oxo-4-(p-tolyl)-6,7-dihydro-1H-pyrrolo[2,3-c]pyridin-5-yl)acetic acid,
2-(tert-butoxy)-2-(1-(3,4-difluorobenzyl)-6-methyl-7-oxo-4-(p-tolyl)-6,7-dihydro-1H-pyrrolo[2,3-c]pyridin-5-yl)acetic acid,
2-(tert-butoxy)-2-(1-(4-methoxybenzyl)-6-methyl-7-oxo-4-(p-tolyl)-6,7-dihydro-1H-pyrrolo[2,3-c]pyridin-5-yl)acetic acid,
2-(tert-butoxy)-2-(1,6-dimethyl-7-oxo-4-(p-tolyl)-6,7-dihydro-1H-pyrrolo[2,3-c]pyridin-5-yl)acetic acid,
2-(tert-butoxy)-2-(1-(4-chloro-3-fluorobenzyl)-6-methyl-7-oxo-4-(p-tolyl)-6,7-dihydro-1H-pyrrolo[2,3-c]pyridin-5-yl)acetic acid,
2-(tert-butoxy)-2-(6-methyl-7-oxo-4-(p-tolyl)-1-(3,4,5-trifluorobenzyl)-6,7-dihydro-1H-pyrrolo[2,3-c]pyridin-5-yl)acetic acid,
2-(1-(benzo[d][1,3]dioxol-5-ylmethyl)-6-methyl-7-oxo-4-(p-tolyl)-6,7-dihydro-1H-pyrrolo[2,3-c]pyridin-5-yl)-2-(tert-butoxy)acetic acid,
2-(tert-butoxy)-2-(1-(4-fluorophenyl)-6-methyl-7-oxo-4-(p-tolyl)-6,7-dihydro-1H-pyrrolo[2,3-c]pyridin-5-yl)acetic acid,
2-(tert-butoxy)-2-(1-(2-((4-fluorophenyl)amino)-2-oxoethyl)-6-methyl-7-oxo-4-(p-tolyl)-6,7-dihydro-1H-pyrrolo[2,3-c]pyridin-5-yl)acetic acid,
2-(tert-butoxy)-2-(1-(4-fluorobenzyl)-4-(4-methoxyphenyl)-6-methyl-7-oxo-6,7-dihydro-1H-pyrrolo[2,3-c]pyridin-5-yl)acetic acid,
2-(tert-butoxy)-2-(1-(4-fluorobenzyl)-4-(4-fluorophenyl)-6-methyl-7-oxo-6,7-dihydro-1H-pyrrolo[2,3-c]pyridin-5-yl)acetic acid,
2-(1-benzyl-6-methyl-4-(5-methylchroman-6-yl)-7-oxo-6,7-dihydro-1H-pyrrolo[2,3-c]pyridin-5-yl)-2-(tert-butoxy)acetic acid, 2-(1-benzyl-6-methyl-4-(5-methylchroman-6-yl)-7-oxo-6, 7-dihydro-1H-pyrrolo[2,3-c]pyridin-5-yl)-2-(tert-butoxy) acetic acid,
2-(tert-butoxy)-2-(1,6-dimethyl-4-(5-methylchroman-6-yl)-7-oxo-6,7-dihydro-1H-pyrrolo[2,3-c]pyridin-5-yl)acetic acid,
(S)(M)-2-(tert-butoxy)-2-(1-(4-fluorobenzyl)-6-methyl-4-(5-methylchroman-6-yl)-7-oxo-6,7-dihydro-1H-pyrrolo[2,3-c]pyridin-5-yl)acetic acid,
2-(tert-butoxy)-2-(6-methyl-4-(5-methylchroman-6-yl)-7-oxo-1-(pyridin-2-ylmethyl)-6,7-dihydro-1H-pyrrolo[2,3-c]pyridin-5-yl)acetic acid,
2-(tert-butoxy)-2-(1-(2-methoxyethyl)-6-methyl-4-(5-methylchroman-6-yl)-7-oxo-6,7-dihydro-1H-pyrrolo[2,3-c]pyridin-5-yl)acetic acid,
2-(tert-butoxy)-2-(1-(4-chlorobenzyl)-6-methyl-4-(5-methylchroman-6-yl)-7-oxo-6,7-dihydro-1H-pyrrolo[2,3-c]pyridin-5-yl)acetic acid,
2-(tert-butoxy)-2-(1-(3-fluorobenzyl)-6-methyl-4-(5-methylchroman-6-yl)-7-oxo-6,7-dihydro-1H-pyrrolo[2,3-c]pyridin-5-yl)acetic acid,
2-(tert-butoxy)-2-(6-methyl-4-(5-methylchroman-6-yl)-7-oxo-1-(4-(trifluoromethyl)benzyl)-6,7-dihydro-1H-pyrrolo[2,3-c]pyridin-5-yl)acetic acid,
2-(tert-butoxy)-2-(6-methyl-4-(5-methylchroman-6-yl)-1-(4-nitrobenzyl)-7-oxo-6,7-dihydro-1H-pyrrolo[2,3-c]pyridin-5-yl)acetic acid,
2-(tert-butoxy)-2-(1-(2,5-difluorobenzyl)-6-methyl-4-(5-methylchroman-6-yl)-7-oxo-6,7-dihydro-1H-pyrrolo[2,3-c]pyridin-5-yl)acetic acid,
2-(tert-butoxy)-2-(1-(3-fluoro-4-methylbenzyl)-6-methyl-4-(5-methylchroman-6-yl)-7-oxo-6,7-dihydro-1H-pyrrolo[2,3-c]pyridin-5-yl)acetic acid,
2-(tert-butoxy)-2-(6-methyl-4-(5-methylchroman-6-yl)-7-oxo-1-(thiazol-4-ylmethyl)-6,7-dihydro-1H-pyrrolo[2,3-c]pyridin-5-yl)acetic acid,
2-(tert-butoxy)-2-(1-(cyclohexylmethyl)-6-methyl-4-(5-methylchroman-6-yl)-7-oxo-6,7-dihydro-1H-pyrrolo[2,3-c]pyridin-5-yl)acetic acid,
2-(tert-butoxy)-2-(6-methyl-4-(5-methylchroman-6-yl)-7-oxo-1-((tetrahydro-2H-pyran-4-yl)methyl)-6,7-dihydro-1H-pyrrolo[2,3-c]pyridin-5-yl)acetic acid,
2-(tert-butoxy)-2-(6-methyl-4-(5-methylchroman-6-yl)-7-oxo-1-((tetrahydro-2H-pyran-4-yl)methyl)-6,7-dihydro-1H-pyrrolo[2,3-c]pyridin-5-yl)acetic acid,
2-(tert-butoxy)-2-(6-methyl-4-(5-methylchroman-6-yl)-7-oxo-1-((tetrahydro-2H-pyran-4-yl)methyl)-6,7-dihydro-1H-pyrrolo[2,3-c]pyridin-5-yl)acetic acid,
tert-Butoxy-[2-methyl-4-(5-methyl-chroman-6-yl)-1-oxo-1,2,5,6,7,8-hexahydro-benzo[4,5]thieno[2,3-c]pyridin-3-yl]-acetic acid,
2-(tert-butoxy)-2-(9-(4-fluorobenzyl)-2-methyl-1-oxo-4-(p-tolyl)-2,9-dihydro-1H-pyrido[3,4-b]indol-3-yl)acetic acid,
2-(tert-butoxy)-2-(2,9-dimethyl-1-oxo-4-(p-tolyl)-2,9-dihydro-1H-pyrido[3,4-b]indol-3-yl)acetic acid,
2-(tert-butoxy)-2-(5-(4-fluorobenzyl)-7-methyl-6-oxo-9-(p-tolyl)-1,3,4,5,6,7-hexahydropyrano[3',4':4,5]pyrrolo[2,3-c]pyridin-8-yl)acetic acid,
2-(tert-butoxy)-2-(9-(4-fluorobenzyl)-2-methyl-1-oxo-4-(p-tolyl)-2,5,6,7,8,9-hexahydro-1H-pyrido[3,4-b]indol-3-yl)acetic acid,
2-(tert-butoxy)-2-(2,9-dimethyl-1-oxo-4-(p-tolyl)-2,5,6,7,8,9-hexahydro-1H-pyrido[3,4-b]indol-3-yl)acetic acid,
2-(tert-butoxy)-2-(9-(4-methoxybenzyl)-2-methyl-1-oxo-4-(p-tolyl)-2,5,6,7,8,9-hexahydro-1H-pyrido[3,4-b]indol-3-yl)acetic acid, 2-(tert-butoxy)-2-(9-(4-methoxybenzyl)-2-methyl-4-(5-methylchroman-6-yl)-1-oxo-2,5,6,7,8,9-hexahydro-1H-pyrido[3,4-b]indol-3-yl)acetic acid,
2-(tert-Butoxy)-2-(4-(3,4-dimethylphenyl)-1-(4-methoxybenzyl)-6-methyl-7-oxo-6,7-dihydro-1H-pyrazolo[3,4-c]pyridin-5-yl)acetic,
2-(tert-Butoxy)-2-(1-(4-fluorobenzyl)-6-methyl-7-oxo-4-(p-tolyl)-6,7-dihydro-1H-pyrazolo[3,4-c]pyridin-5-yl)acetic acid,
2-(tert-Butoxy)-2-(1-(4-methoxybenzyl)-6-methyl-4-(5-methylchroman-6-yl)-7-oxo-6,7-dihydro-1H-pyrazolo[3,4-c]pyridin-5-yl)acetic acid yl)acetic,
2-(tert-Butoxy)-2-(6-methyl-4-(5-methylchroman-6-yl)-7-oxo-1-(pyridin-2-ylmethyl)-6,7-dihydro-1H-pyrazolo[3,4-c]pyridin-5-yl)acetic acid, and,
2-(tert-butoxy)-2-(1-(4-fluorobenzyl)-6-methyl-4-(5-methylchroman-6-yl)-7-oxo-6,7-dihydro-1H-pyrazolo[3,4-c]pyridin-5-yl)acetic acid,
and pharmaceutically acceptable salts thereof.

Such compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

In another embodiment of the invention, there is provided a compound of Formula I, wherein the compound or salt of the compound is used in the manufacture of a medicament for use in the treatment of a viral infection in a human.

In another embodiment of the invention, there is provided a pharmaceutical composition comprising a pharmaceutically acceptable diluent and a therapeutically effective amount of a compound as defined in Formula I.

In one embodiment, the pharmaceutical formulation containing a compound of Formula I or a salt thereof is a formulation adapted for parenteral administration. In another embodiment, the formulation is a long-acting parenteral formulation. In a further embodiment, the formulation is a nanoparticle formulation.

The compounds of the present invention and their salts, solvates, or other pharmaceutically acceptable derivatives thereof, may be employed alone or in combination with other therapeutic agents. The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The amounts of the compound(s) of Formulas I or salts thereof and the other pharmaceutically active agent(s) and the relative timings of administration will be selected in order to achieve the desired combined therapeutic effect.

As such, the compounds of the present invention may be used in combination with one or more agents useful in the prevention or treatment of HIV.

Examples of such agents include:

Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, GSK2248761, TMC-278, TMC-125, etravirine, and similar agents;

Protease inhibitors such as saquinavir, ritonavir, indinavir, nelfinavir, amprenavir, fosamprenavir, brecanavir, darunavir, atazanavir, tipranavir, palinavir, lasinavir, and similar agents;

Entry, attachment and fusion inhibitors such as enfuvirtide (T-20), T-1249, PRO-542, PRO-140, TNX-355, BMS-806, BMS-663068 and BMS-626529, 5-Helix and similar agents;

Integrase inhibitors such as raltegravir, elvitegravir, GSK1349572, GSK1265744 and similar agents;

Maturation inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

The scope of combinations of compounds of this invention with HIV agents is not limited to those mentioned above, but includes in principle any combination with any pharmaceutical composition useful for the treatment of HIV. As noted, in such combinations the compounds of the present invention and other HIV agents may be administered separately or in conjunction. In addition, one agent may be prior to, concurrent to, or subsequent to the administration of other agent(s).

The present invention may be used in combination with one or more agents useful as pharmacological enhancers as well as with or without additional compounds for the prevention or treatment of HIV. Examples of such pharmacological enhancers (or pharmakinetic boosters) include, but are not limited to, ritonavir, GS-9350, and SPI-452.

Ritonavir is 10-hydroxy-2-methyl-5-(1-methylethyl)-1-1 [2-(1-methylethyl)-4-thiazolyl]-3,6-dioxo-8,11-bis(phenylmethyl)-2,4,7,12-tetraazamidecan-13-oic acid, 5-thiazolylmethyl ester, [5S-(5S*,8R*,10R*,11R*)] and is available from Abbott Laboratories (Abbott Park, Ill.) as Norvir. Ritonavir is an HIV protease inhibitor indicated with other antiretroviral agents for the treatment of HIV infection. Ritonavir also inhibits P450 mediated drug metabolism as well as the P-glycoprotein (Pgp) cell transport system, thereby resulting in increased concentrations of active compound within the organism.

GS-9350 is a compound being developed by Gilead Sciences of Foster City Calif. as a pharmacological enhancer.

SPI-452 is a compound being developed by Sequoia Pharmaceuticals of Gaithersburg, Md., as a pharmacological enhancer.

In one embodiment of the present invention, a compound of Formula I is used in combination with ritonavir. In one embodiment, the combination is an oral fixed dose combination. In another embodiment, the compound of Formula I is formulated as a long acting parenteral injection and ritonavir is formulated as an oral composition. In one embodiment, is a kit containing the compound of Formula I formulated as a long acting parenteral injection and ritonavir formulated as an oral composition. In another embodiment, the compound of Formula I is formulated as a long acting parenteral injection and ritonavir is formulated as an injectable composition. In one embodiment, is a kit containing the compound of Formula I formulated as a long acting parenteral injection and ritonavir formulated as an injectable composition.

In another embodiment of the present invention, a compound of Formula I is used in combination with GS-9350. In one embodiment, the combination is an oral fixed dose combination. In another embodiment, the compound of Formula I is formulated as a long acting parenteral injection and GS-9350 is formulated as an oral composition. In one embodiment, is a kit containing the compound of Formula I formulated as a long acting parenteral injection and GS-9350 formulated as an oral composition. In another embodiment, the compound of Formulas I or II is formulated as a long acting parenteral injection and GS-9350 is formulated as an injectable composition. In one embodiment, is a kit containing the compound of Formulas I or II formulated as a long acting parenteral injection and GS-9350 formulated as an injectable composition.

In one embodiment of the present invention, a compound of Formulas I or II is used in combination with SPI-452. In one embodiment, the combination is an oral fixed dose combination. In another embodiment, the compound of Formula I is formulated as a long acting parenteral injection and SPI-452 is formulated as an oral composition. In one embodiment, is a kit containing the compound of Formula I formulated as a long acting parenteral injection and SPI-452 formulated as an oral composition. In another embodiment, the compound of Formula I is formulated as a long acting parenteral injection and SPI-452 is formulated as an injectable composition. In one embodiment, is a kit containing the compound of Formulas I or II formulated as a long acting parenteral injection and SPI-452 formulated as an injectable composition.

The above other therapeutic agents, when employed in combination with the chemical entities described herein, may be used, for example, in those amounts indicated in the Physicians' Desk Reference (PDR) or as otherwise determined by one of ordinary skill in the art.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I, wherein said virus is an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I, further comprising administration of a therapeutically effective amount of one or more agents active against an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula I, further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

In further embodiments, the compound of the present invention, or a pharmaceutically acceptable salt thereof, is chosen from the compounds set forth in Table 1.

TABLE 1

| Compound and Example No. | Structure | Name | MT4 (IC$_{50}$) M |
|---|---|---|---|
| 1 | 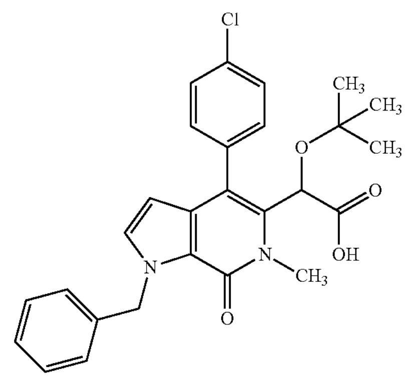 [SMILES: Cn1c(C(OC(C)(C)C)C(=O)O)c(-c2ccc(Cl)cc2)c2ccn(Cc3ccccc3)c2c1=O] | 2-(1-benzyl-4-(4-chlorophenyl)-6-methyl-7-oxo-6,7-dihydro-1H-pyrrolo[2,3-c]pyridin-5-yl)-2-(tert-butoxy)acetic acid | 0.22 |
| 2 | 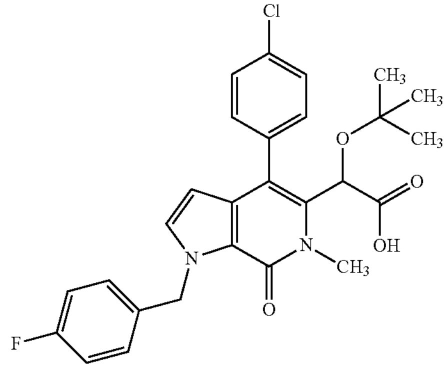 [SMILES: Cn1c(C(OC(C)(C)C)C(=O)O)c(-c2ccc(Cl)cc2)c2ccn(Cc3ccc(F)cc3)c2c1=O] | 2-(tert-butoxy)-2-(4-(4-chlorophenyl)-1-(4-fluorobenzyl)-6-methyl-7-oxo-6,7-dihydro-1H-pyrrolo[2,3-c]pyridin-5-yl)acetic acid | 0.16 |

TABLE 1-continued

| Compound and Example No. | Structure | Name | MT4 (IC$_{50}$) M |
|---|---|---|---|
| 3 | 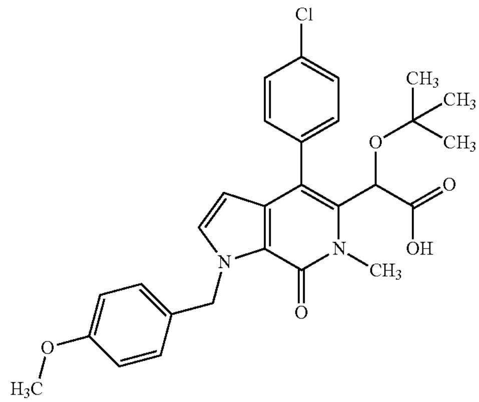 [SMILES: COc1ccc(Cn2ccc3c(-c4ccc(Cl)cc4)c(C(OC(C)(C)C)C(=O)O)n(C)c(=O)c32)cc1] | 2-(tert-butoxy)-2-(4-(4-chlorophenyl)-1-(4-methoxybenzyl)-6-methyl-7-oxo-6,7-dihydro-1H-pyrrolo[2,3-c]pyridin-5-yl)acetic acid | 0.46 |
| 4 | 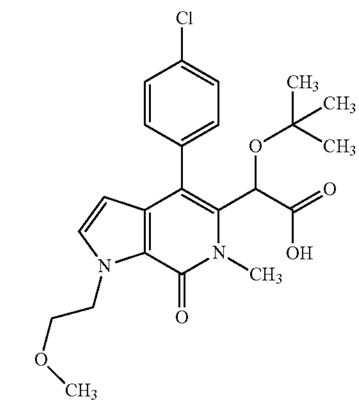 [SMILES: COCCn1ccc2c(-c3ccc(Cl)cc3)c(C(OC(C)(C)C)C(=O)O)n(C)c(=O)c21] | 2-(tert-butoxy)-2-(4-(4-chlorophenyl)-1-(2-methoxyethyl)-6-methyl-7-oxo-6,7-dihydro-1H-pyrrolo[2,3-c]pyridin-5-yl)acetic acid | 1.55 |
| 5 | 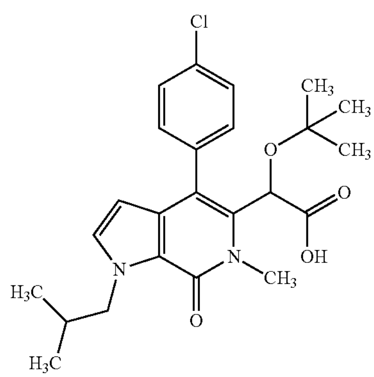 [SMILES: CC(C)Cn1ccc2c(-c3ccc(Cl)cc3)c(C(OC(C)(C)C)C(=O)O)n(C)c(=O)c21] | 2-(tert-butoxy)-2-(4-(4-chlorophenyl)-1-isobutyl-6-methyl-7-oxo-6,7-dihydro-1H-pyrrolo[2,3-c]pyridin-5-yl)acetic acid | 5.00 |
| 6 | 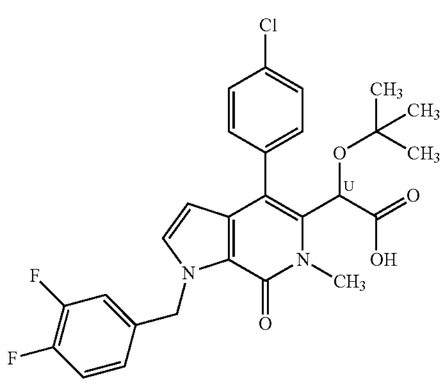 | (S)-2-(tert-butoxy)-2-(4-(4-chlorophenyl)-1-(3,4-difluorobenzyl)-6-methyl-7-oxo-6,7-dihydro-1H-pyrrolo[2,3-c]pyridin-5-yl)acetic acid | 0.14 |

TABLE 1-continued

| Compound and Example No. | Structure | Name | MT4 (IC$_{50}$) M |
|---|---|---|---|
| 7 | 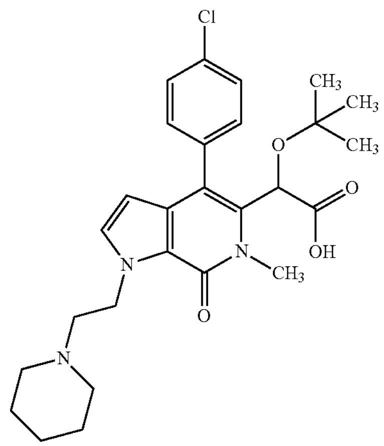 [SMILES: Cn1c(C(OC(C)(C)C)C(=O)O)c(-c2ccc(Cl)cc2)c2ccn(CCN3CCCCC3)c2c1=O] | 2-(tert-butoxy)-2-(4-(4-chlorophenyl)-6-methyl-7-oxo-1-(2-(piperidin-1-yl)ethyl)-6,7-dihydro-1H-pyrrolo[2,3-c]pyridin-5-yl)acetic acid | 1.00 |
| 8 | 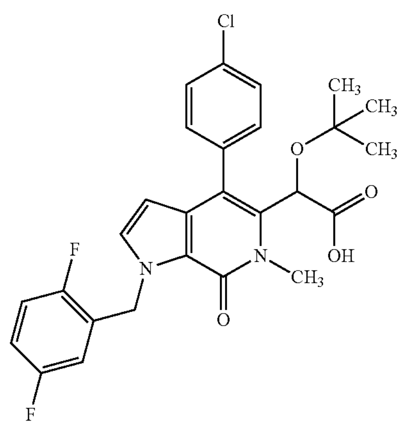 [SMILES: Cn1c(C(OC(C)(C)C)C(=O)O)c(-c2ccc(Cl)cc2)c2ccn(Cc3cc(F)ccc3F)c2c1=O] | 2-(tert-butoxy)-2-(4-(4-chlorophenyl)-6-methyl-7-oxo-1-(2-(piperidin-1-yl)ethyl)-6,7-dihydro-1H-pyrrolo[2,3-c]pyridin-5-yl)acetic acid | 0.13 |
| 9 | 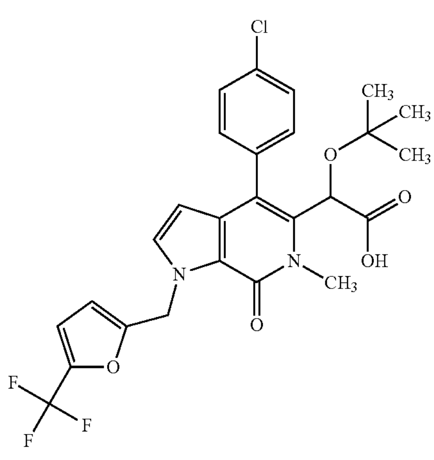 [SMILES: Cn1c(C(OC(C)(C)C)C(=O)O)c(-c2ccc(Cl)cc2)c2ccn(Cc3ccc(C(F)(F)F)o3)c2c1=O] | 2-(tert-butoxy)-2-(4-(4-chlorophenyl)-6-methyl-7-oxo-1-((5-(trifluoromethyl)furan-2-yl)methyl)-6,7-dihydro-1H-pyrrolo[2,3-c]pyridin-5-yl)acetic acid | 1.25 |

TABLE 1-continued

| Compound and Example No. | Structure | Name | MT4 (IC$_{50}$) M |
|---|---|---|---|
| 10 | 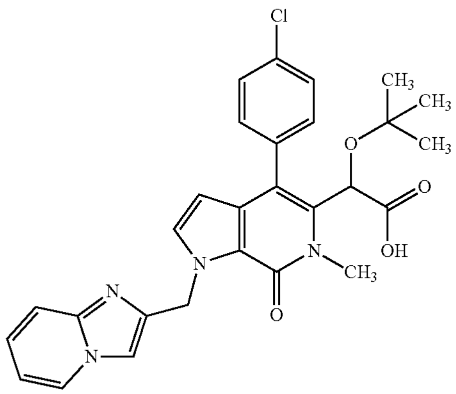 [SMILES: Cn1c(C(OC(C)(C)C)C(=O)O)c(-c2ccc(Cl)cc2)c2ccn(Cc3cn4ccccc4n3)c2c1=O] | 2-(tert-butoxy)-2-(4-(4-chlorophenyl)-1-(imidazo[1,2-a]pyridin-2-ylmethyl)-6-methyl-7-oxo-6,7-dihydro-1H-pyrrolo[2,3-c]pyridin-5-yl)acetic acid | 3.00 |
| 11 | 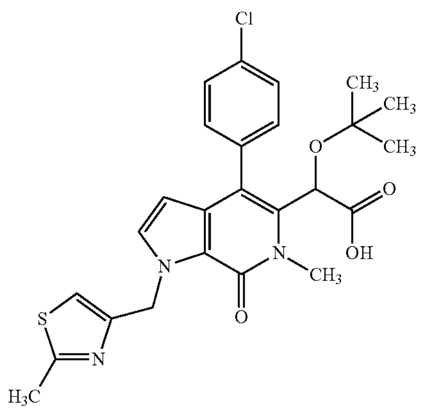 [SMILES: Cc1nc(Cn2ccc3c(-c4ccc(Cl)cc4)c(C(OC(C)(C)C)C(=O)O)n(C)c(=O)c32)cs1] | 2-(tert-butoxy)-2-(4-(4-chlorophenyl)-6-methyl-1-((2-methylthiazol-4-yl)methyl)-7-oxo-6,7-dihydro-1H-pyrrolo[2,3-c]pyridin-5-yl)acetic acid | 0.31 |
| 12 | 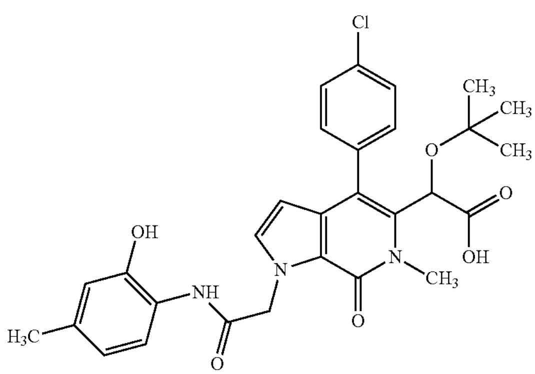 [SMILES: Cc1ccc(NC(=O)Cn2ccc3c(-c4ccc(Cl)cc4)c(C(OC(C)(C)C)C(=O)O)n(C)c(=O)c32)c(O)c1] | 2-(tert-butoxy)-2-(4-(4-chlorophenyl)-1-(2-((2-hydroxy-4-methylphenyl)amino)-2-oxoethyl)-6-methyl-7-oxo-6,7-dihydro-1H-pyrrolo[2,3-c]pyridin-5-yl)acetic acid | 3.25 |
| 13 | 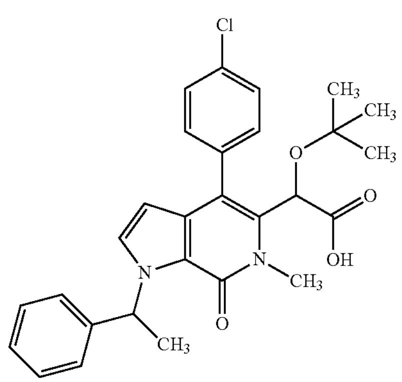 [SMILES: CC(c1ccccc1)n1ccc2c(-c3ccc(Cl)cc3)c(C(OC(C)(C)C)C(=O)O)n(C)c(=O)c21] | 2-(tert-butoxy)-2-(4-(4-chlorophenyl)-6-methyl-7-oxo-1-(1-phenylethyl)-6,7-dihydro-1H-pyrrolo[2,3-c]pyridin-5-yl)acetic acid | 0.40 |

TABLE 1-continued

| Compound and Example No. | Structure | Name | MT4 (IC$_{50}$) μM |
|---|---|---|---|
| 14 | 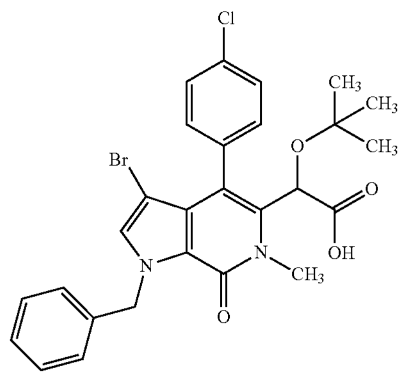 [SMILES: Cn1c(C(OC(C)(C)C)C(=O)O)c(-c2ccc(Cl)cc2)c2c(Br)cn(Cc3ccccc3)c2c1=O] | 2-(1-benzyl-3-bromo-4-(4-chlorophenyl)-6-methyl-7-oxo-6,7-dihydro-1H-pyrrolo[2,3-c]pyridin-5-yl)-2-(tert-butoxy)acetic acid | 0.75 |
| 15 | 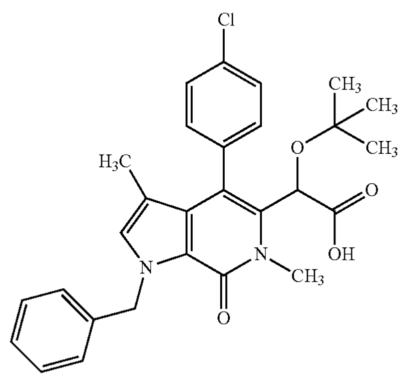 [SMILES: Cc1cn(Cc2ccccc2)c2c(=O)n(C)c(C(OC(C)(C)C)C(=O)O)c(-c3ccc(Cl)cc3)c12] | 2-(1-benzyl-4-(4-chlorophenyl)-3,6-dimethyl-7-oxo-6,7-dihydro-1H-pyrrolo[2,3-c]pyridin-5-yl)-2-(tert-butoxy)acetic acid | 1.62 |
| 16 | 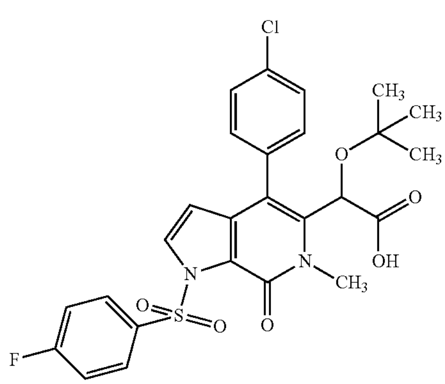 [SMILES: Cn1c(C(OC(C)(C)C)C(=O)O)c(-c2ccc(Cl)cc2)c2ccn(S(=O)(=O)c3ccc(F)cc3)c2c1=O] | 2-(tert-butoxy)-2-(4-(4-chlorophenyl)-1-((4-fluorophenyl)sulfonyl)-6-methyl-7-oxo-6,7-dihydro-1H-pyrrolo[2,3-c]pyridin-5-yl)acetic acid | 1.80 |

TABLE 1-continued

| Compound and Example No. | Structure | Name | MT4 (IC$_{50}$) M |
|---|---|---|---|
| 17 | 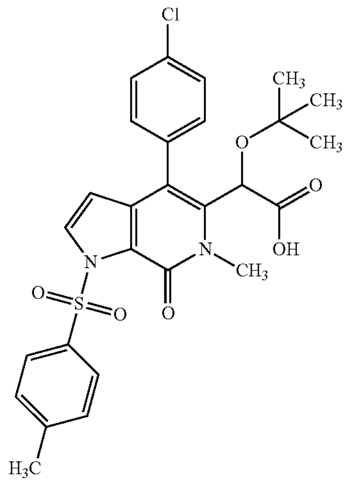 [SMILES: Cc1ccc(S(=O)(=O)n2ccc3c(-c4ccc(Cl)cc4)c(C(OC(C)(C)C)C(=O)O)n(C)c(=O)c32)cc1] | 2-(tert-butoxy)-2-(4-(4-chlorophenyl)-6-methyl-7-oxo-1-tosyl-6,7-dihydro-1H-pyrrolo[2,3-c]pyridin-5-yl)acetic acid | 1.20 |
| 18 | 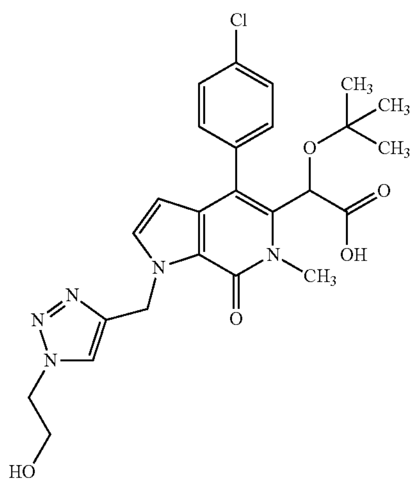 [SMILES: Cn1c(C(OC(C)(C)C)C(=O)O)c(-c2ccc(Cl)cc2)c2ccn(Cc3cn(CCO)nn3)c2c1=O] | 2-(tert-butoxy)-2-(4-(4-chlorophenyl)-1-((1-(2-hydroxyethyl)-1H-1,2,3-triazol-4-yl)methyl)-6-methyl-7-oxo-6,7-dihydro-1H-pyrrolo[2,3-c]pyridin-5-yl)acetic acid | 50.00 |
| 19 | 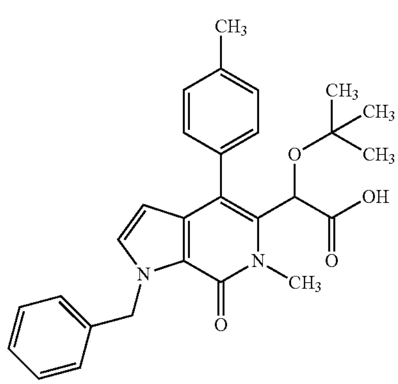 [SMILES: Cc1ccc(-c2c(C(OC(C)(C)C)C(=O)O)n(C)c(=O)c3c2ccn3Cc2ccccc2)cc1] | 2-(1-benzyl-6-methyl-7-oxo-4-(p-tolyl)-6,7-dihydro-1H-pyrrolo[2,3-c]pyridin-5-yl)-2-(tert-butoxy)acetic acid | 0.08 |

TABLE 1-continued

| Compound and Example No. | Structure | Name | MT4 (IC$_{50}$) M |
|---|---|---|---|
| 20 | 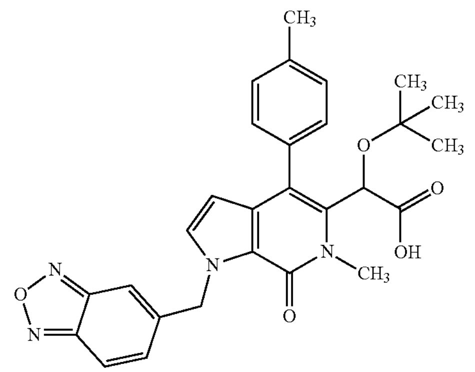 [SMILES: Cc1ccc(-c2c(C(OC(C)(C)C)C(=O)O)n(C)c(=O)c3c2ccn3Cc2ccc3nonc3c2)cc1] | 2-(1-(benzo[c][1,2,5]oxadiazol-5-ylmethyl)-6-methyl-7-oxo-4-(p-tolyl)-6,7-dihydro-1H-pyrrolo[2,3-c]pyridin-5-yl)-2-(tert-butoxy)acetic acid | 0.16 |
| 21 | 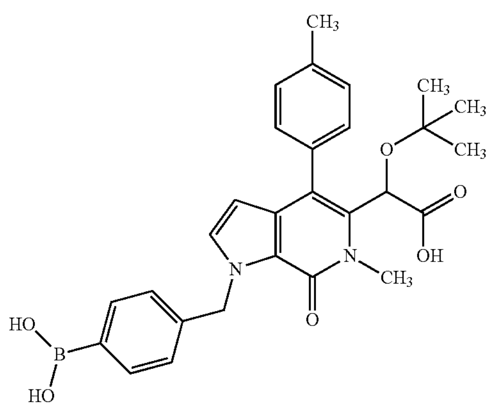 [SMILES: Cc1ccc(-c2c(C(OC(C)(C)C)C(=O)O)n(C)c(=O)c3c2ccn3Cc2ccc(B(O)O)cc2)cc1] | 2-(1-(4-boronobenzyl)-6-methyl-7-oxo-4-(p-tolyl)-6,7-dihydro-1H-pyrrolo[2,3-c]pyridin-5-yl)-2-(tert-butoxy)acetic acid | 2.70 |
| 22 | 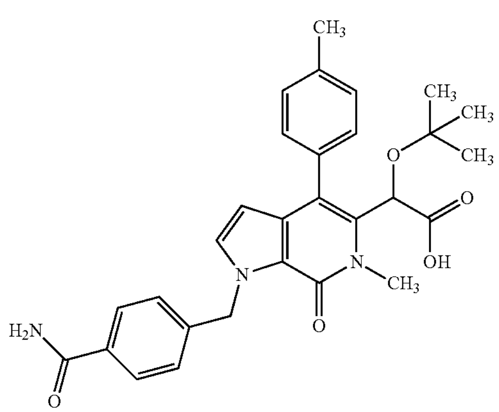 [SMILES: Cc1ccc(-c2c(C(OC(C)(C)C)C(=O)O)n(C)c(=O)c3c2ccn3Cc2ccc(C(N)=O)cc2)cc1] | 2-(tert-butoxy)-2-(1-(4-carbamoylbenzyl)-6-methyl-7-oxo-4-(p-tolyl)-6,7-dihydro-1H-pyrrolo[2,3-c]pyridin-5-yl)acetic acid | 8.70 |

TABLE 1-continued

| Compound and Example No. | Structure | Name | MT4 (IC$_{50}$) M |
|---|---|---|---|
| 23 | 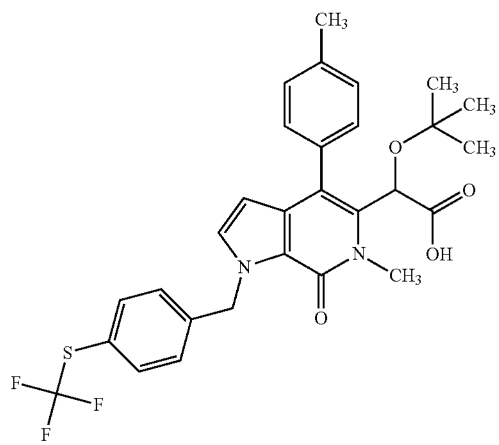 [SMILES: Cc1ccc(-c2c(C(OC(C)(C)C)C(=O)O)n(C)c(=O)c3c2ccn3Cc2ccc(SC(F)(F)F)cc2)cc1] | 2-(tert-butoxy)-2-(6-methyl-7-oxo-4-(p-tolyl)-1-(4-((trifluoromethyl)thio)benzyl)-6,7-dihydro-1H-pyrrolo[2,3-c]pyridin-5-yl)acetic acid | 1.50 |
| 24 | 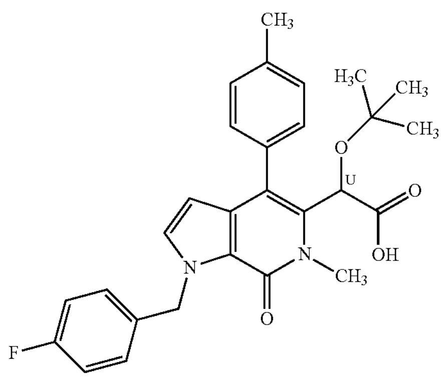 | (S)-2-(tert-butoxy)-2-(1-(4-fluorobenzyl)-6-methyl-7-oxo-4-(p-tolyl)-6,7-dihydro-1H-pyrrolo[2,3-c]pyridin-5-yl)acetic acid | 0.04 |
| 25 | 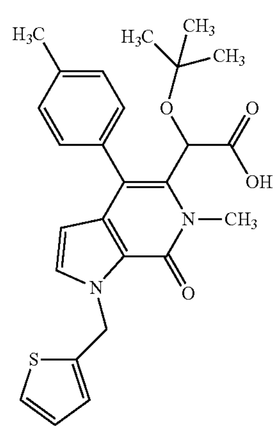 [SMILES: Cc1ccc(-c2c(C(OC(C)(C)C)C(=O)O)n(C)c(=O)c3c2ccn3Cc2cccs2)cc1] | 2-(tert-butoxy)-2-(6-methyl-7-oxo-1-(thiophen-2-ylmethyl)-4-(p-tolyl)-6,7-dihydro-1H-pyrrolo[2,3-c]pyridin-5-yl)acetic acid | 0.22 |

TABLE 1-continued

| Compound and Example No. | Structure | Name | MT4 (IC$_{50}$) M |
|---|---|---|---|
| 26 | 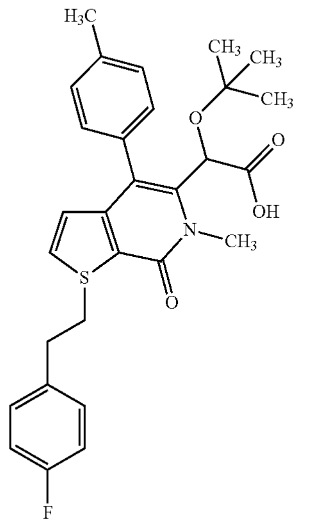 | 2-(tert-butoxy)-2-(1-(4-fluorophenethyl)-6-methyl-7-oxo-4-(p-tolyl)-6,7-dihydro-1H-pyrrolo[2,3-c]pyridin-5-yl)acetic acid | 2.25 |
| 27 | 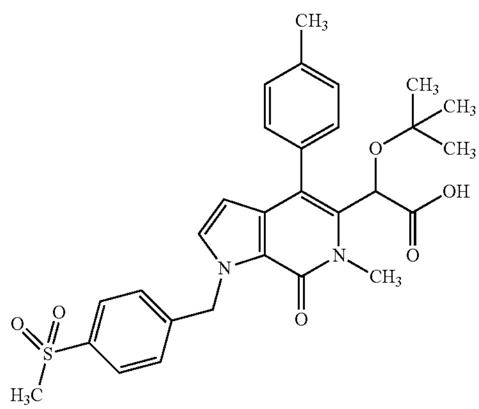 [SMILES: Cc1ccc(-c2c(C(OC(C)(C)C)C(=O)O)n(C)c(=O)c3c2ccn3Cc2ccc(S(C)(=O)=O)cc2)cc1] | 2-(tert-butoxy)-2-(6-methyl-1-(4-(methylsulfonyl)benzyl)-7-oxo-4-(p-tolyl)-6,7-dihydro-1H-pyrrolo[2,3-c]pyridin-5-yl)acetic acid | 3.85 |
| 28 | 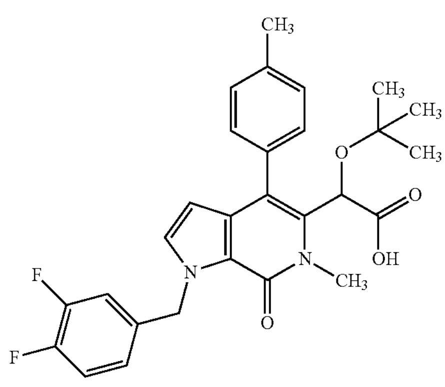 [SMILES: Cc1ccc(-c2c(C(OC(C)(C)C)C(=O)O)n(C)c(=O)c3c2ccn3Cc2ccc(F)c(F)c2)cc1] | 2-(tert-butoxy)-2-(1-(3,4-difluorobenzyl)-6-methyl-7-oxo-4-(p-tolyl)-6,7-dihydro-1H-pyrrolo[2,3-c]pyridin-5-yl)acetic acid | 0.08 |

TABLE 1-continued

| Compound and Example No. | Structure | Name | MT4 (IC$_{50}$) M |
|---|---|---|---|
| 29 | 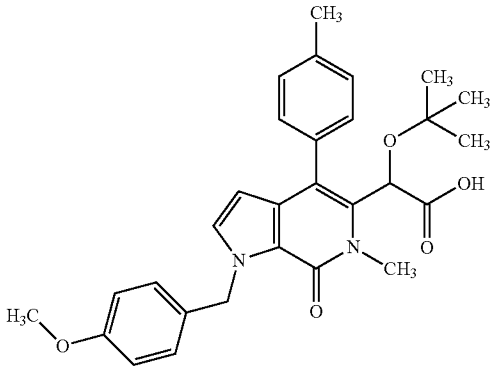 [SMILES: COc1ccc(Cn2ccc3c(-c4ccc(C)cc4)c(C(OC(C)(C)C)C(=O)O)n(C)c(=O)c32)cc1] | 2-(tert-butoxy)-2-(1-(4-methoxybenzyl)-6-methyl-7-oxo-4-(p-tolyl)-6,7-dihydro-1H-pyrrolo[2,3-c]pyridin-5-yl)acetic acid | 0.17 |
| 30 | 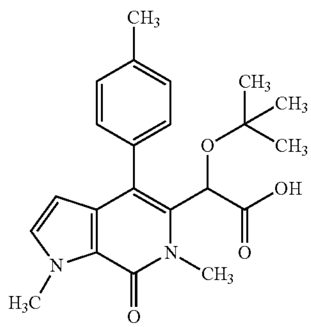 [SMILES: Cc1ccc(-c2c(C(OC(C)(C)C)C(=O)O)n(C)c(=O)c3c2ccn3C)cc1] | 2-(tert-butoxy)-2-(1,6-dimethyl-7-oxo-4-(p-tolyl)-6,7-dihydro-1H-pyrrolo[2,3-c]pyridin-5-yl)acetic acid | 1.10 |
| 31 | 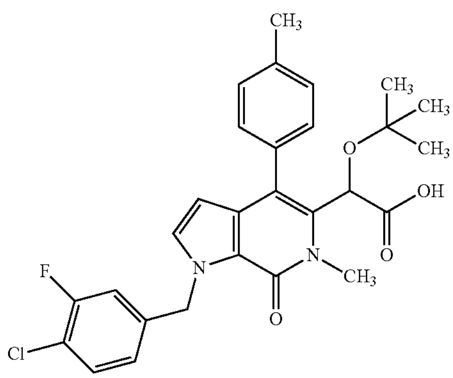 [SMILES: Cc1ccc(-c2c(C(OC(C)(C)C)C(=O)O)n(C)c(=O)c3c2ccn3Cc2ccc(Cl)c(F)c2)cc1] | 2-(tert-butoxy)-2-(1-(4-chloro-3-fluorobenzyl)-6-methyl-7-oxo-4-(p-tolyl)-6,7-dihydro-1H-pyrrolo[2,3-c]pyridin-5-yl)acetic acid | 0.11 |
| 32 | 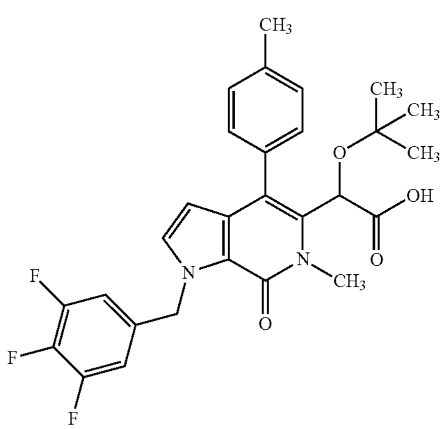 [SMILES: Cc1ccc(-c2c(C(OC(C)(C)C)C(=O)O)n(C)c(=O)c3c2ccn3Cc2cc(F)c(F)c(F)c2)cc1] | 2-(tert-butoxy)-2-(6-methyl-7-oxo-4-(p-tolyl)-1-(3,4,5-trifluorobenzyl)-6,7-dihydro-1H-pyrrolo[2,3-c]pyridin-5-yl)acetic acid | 0.08 |

TABLE 1-continued

| Compound and Example No. | Structure | Name | MT4 (IC$_{50}$) M |
|---|---|---|---|
| 33 | 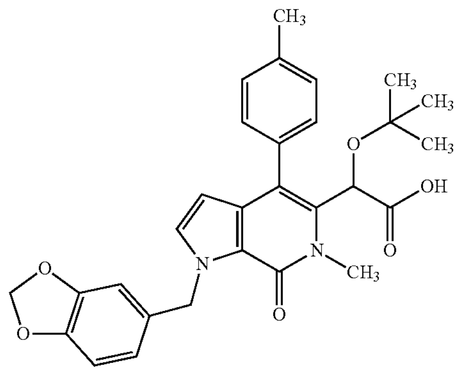 [SMILES: Cc1ccc(-c2c(C(OC(C)(C)C)C(=O)O)n(C)c(=O)c3c2ccn3Cc2ccc3c(c2)OCO3)cc1] | 2-(1-(benzo[d][1,3]dioxol-5-ylmethyl)-6-methyl-7-oxo-4-(p-tolyl)-6,7-dihydro-1H-pyrrolo[2,3-c]pyridin-5-yl)-2-(tert-butoxy)acetic acid | 0.21 |
| 34 | 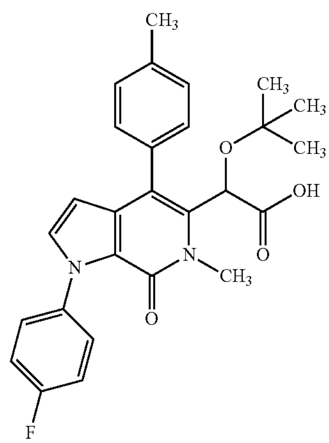 [SMILES: Cc1ccc(-c2c(C(OC(C)(C)C)C(=O)O)n(C)c(=O)c3c2ccn3-c2ccc(F)cc2)cc1] | 2-(tert-butoxy)-2-(1-(4-fluorophenyl)-6-methyl-7-oxo-4-(p-tolyl)-6,7-dihydro-1H-pyrrolo[2,3-c]pyridin-5-yl)acetic acid | 0.77 |
| 35 | 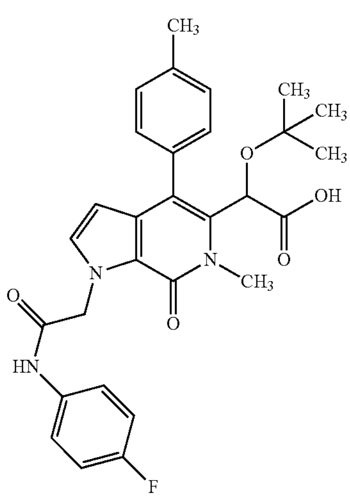 [SMILES: Cc1ccc(-c2c(C(OC(C)(C)C)C(=O)O)n(C)c(=O)c3c2ccn3CC(=O)Nc2ccc(F)cc2)cc1] | 2-(tert-butoxy)-2-(1-(2-((4-fluorophenyl)amino)-2-oxoethyl)-6-methyl-7-oxo-4-(p-tolyl)-6,7-dihydro-1H-pyrrolo[2,3-c]pyridin-5-yl)acetic acid | 1.00 |

TABLE 1-continued

| Compound and Example No. | Structure | Name | MT4 (IC$_{50}$) μM |
|---|---|---|---|
| 36 | 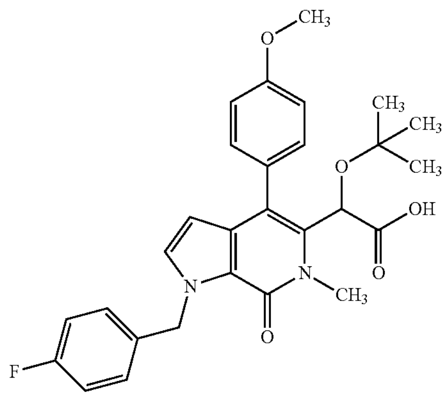 [SMILES: COc1ccc(-c2c(C(OC(C)(C)C)C(=O)O)n(C)c(=O)c3c2ccn3Cc2ccc(F)cc2)cc1] | 2-(tert-butoxy)-2-(1-(4-fluorobenzyl)-4-(4-methoxyphenyl)-6-methyl-7-oxo-6,7-dihydro-1H-pyrrolo[2,3-c]pyridin-5-yl)acetic acid | 0.06 |
| 37 | 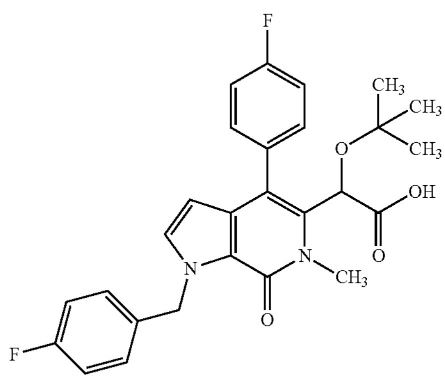 [SMILES: Cn1c(C(OC(C)(C)C)C(=O)O)c(-c2ccc(F)cc2)c2ccn(Cc3ccc(F)cc3)c2c1=O] | 2-(tert-butoxy)-2-(1-(4-fluorobenzyl)-4-(4-fluorophenyl)-6-methyl-7-oxo-6,7-dihydro-1H-pyrrolo[2,3-c]pyridin-5-yl)acetic acid | 0.67 |
| 38 | 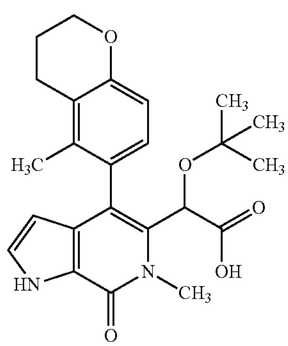 [SMILES: Cc1c(-c2c(C(OC(C)(C)C)C(=O)O)n(C)c(=O)c3[nH]ccc23)ccc2c1CCCO2] | 2-(1-benzyl-6-methyl-4-(5-methylchroman-6-yl)-7-oxo-6,7-dihydro-1H-pyrrolo[2,3-c]pyridin-5-yl)-2-(tert-butoxy)acetic acid | 0.07 |
| 39 | 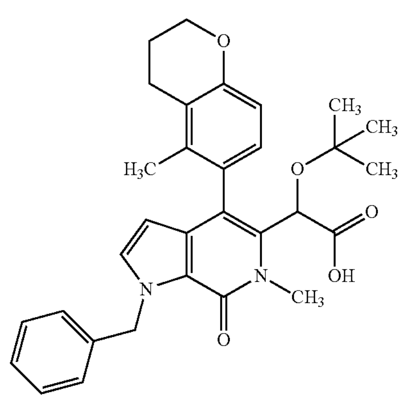 [SMILES: Cc1c(-c2c(C(OC(C)(C)C)C(=O)O)n(C)c(=O)c3c2ccn3Cc2ccccc2)ccc2c1CCCO2] | 2-(1-benzyl-6-methyl-4-(5-methylchroman-6-yl)-7-oxo-6,7-dihydro-1H-pyrrolo[2,3-c]pyridin-5-yl)-2-(tert-butoxy)acetic acid | 1.36 |

TABLE 1-continued

| Compound and Example No. | Structure | Name | MT4 (IC$_{50}$) M |
|---|---|---|---|
| 40 | 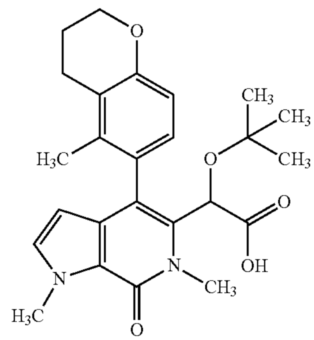 [SMILES: Cc1c(-c2c(C(OC(C)(C)C)C(=O)O)n(C)c(=O)c3c2ccn3C)ccc2c1CCCO2] | 2-(tert-butoxy)-2-(1,6-dimethyl-4-(5-methylchroman-6-yl)-7-oxo-6,7-dihydro-1H-pyrrolo[2,3-c]pyridin-5-yl)acetic acid | 0.50 |
| 41 | 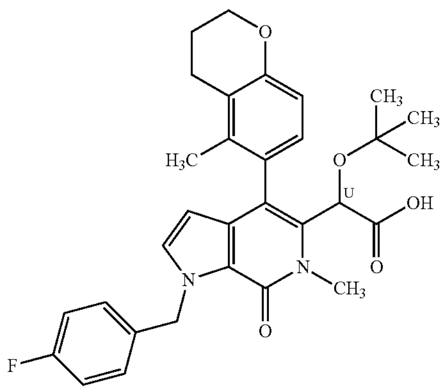 | (S)(M)-2-(tert-butoxy)-2-(1-(4-fluorobenzyl)-6-methyl-4-(5-methylchroman-6-yl)-7-oxo-6,7-dihydro-1H-pyrrolo[2,3-c]pyridin-5-yl)acetic acid | 0.01 |
| 42 | 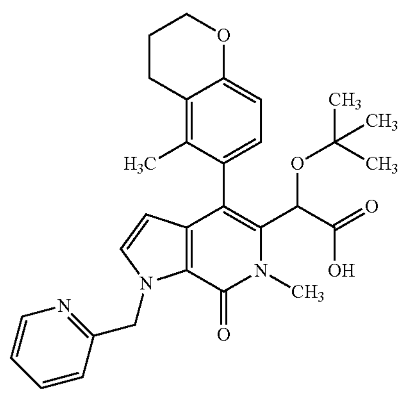 [SMILES: Cc1c(-c2c(C(OC(C)(C)C)C(=O)O)n(C)c(=O)c3c2ccn3Cc2ccccn2)ccc2c1CCCO2] | 2-(tert-butoxy)-2-(6-methyl-4-(5-methylchroman-6-yl)-7-oxo-1-(pyridin-2-ylmethyl)-6,7-dihydro-1H-pyrrolo[2,3-c]pyridin-5-yl)acetic acid | 0.54 |
| 43 | 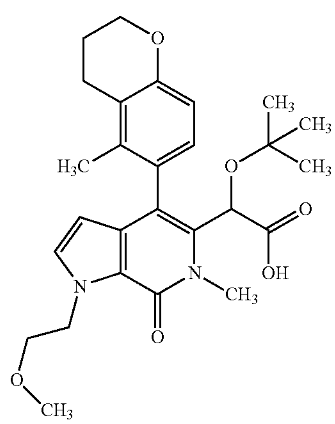 [SMILES: COCCn1ccc2c(-c3ccc4c(c3C)CCCO4)c(C(OC(C)(C)C)C(=O)O)n(C)c(=O)c21] | 2-(tert-butoxy)-2-(1-(2-methoxyethyl)-6-methyl-4-(5-methylchroman-6-yl)-7-oxo-6,7-dihydro-1H-pyrrolo[2,3-c]pyridin-5-yl)acetic acid | 1.10 |

TABLE 1-continued

| Compound and Example No. | Structure | Name | MT4 (IC$_{50}$) M |
|---|---|---|---|
| 44 | 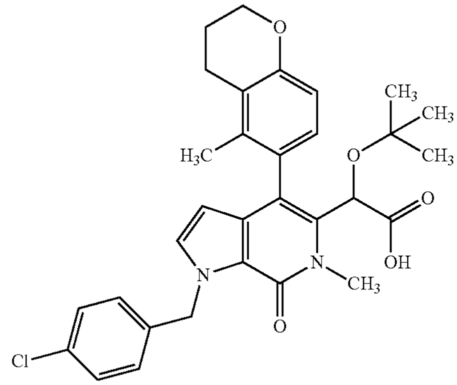 [SMILES: Cc1c(-c2c(C(OC(C)(C)C)C(=O)O)n(C)c(=O)c3c2ccn3Cc2ccc(Cl)cc2)ccc2c1CCCO2] | 2-(tert-butoxy)-2-(1-(4-chlorobenzyl)-6-methyl-4-(5-methylchroman-6-yl)-7-oxo-6,7-dihydro-1H-pyrrolo[2,3-c]pyridin-5-yl)acetic acid | 0.05 |
| 45 | 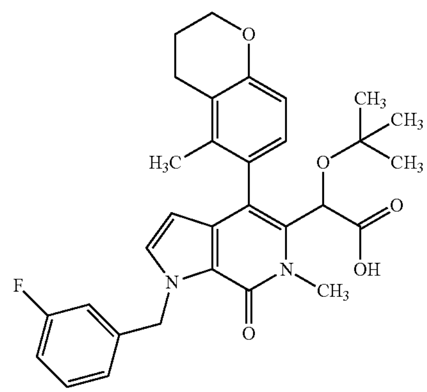 [SMILES: Cc1c(-c2c(C(OC(C)(C)C)C(=O)O)n(C)c(=O)c3c2ccn3Cc2cccc(F)c2)ccc2c1CCCO2] | 2-(tert-butoxy)-2-(1-(3-fluorobenzyl)-6-methyl-4-(5-methylchroman-6-yl)-7-oxo-6,7-dihydro-1H-pyrrolo[2,3-c]pyridin-5-yl)acetic acid | 0.08 |
| 46 | 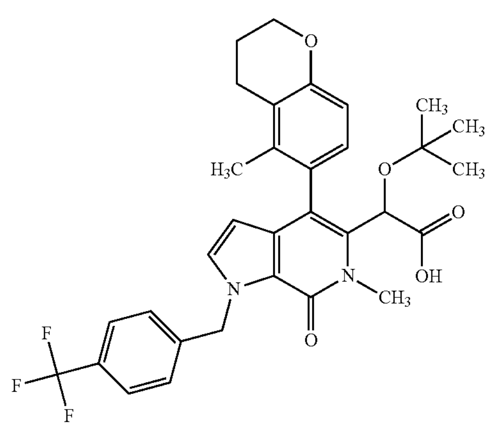 [SMILES: Cc1c(-c2c(C(OC(C)(C)C)C(=O)O)n(C)c(=O)c3c2ccn3Cc2ccc(C(F)(F)F)cc2)ccc2c1CCCO2] | 2-(tert-butoxy)-2-(6-methyl-4-(5-methylchroman-6-yl)-7-oxo-1-(4-(trifluoromethyl)benzyl)-6,7-dihydro-1H-pyrrolo[2,3-c]pyridin-5-yl)acetic acid | 0.09 |

TABLE 1-continued

| Compound and Example No. | Structure | Name | MT4 (IC$_{50}$) M |
|---|---|---|---|
| 47 | 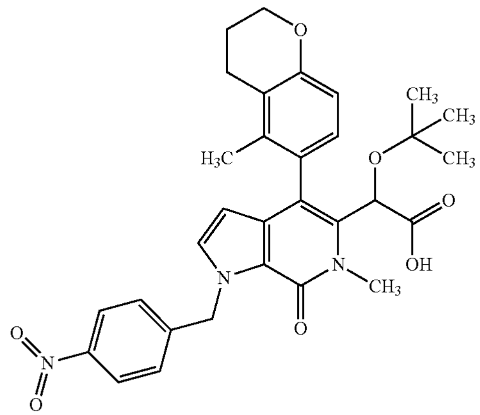 [SMILES: Cc1c(-c2c(C(OC(C)(C)C)C(=O)O)n(C)c(=O)c3c2ccn3Cc2ccc([N+](=O)[O-])cc2)ccc2c1CCCO2] | 2-(tert-butoxy)-2-(6-methyl-4-(5-methylchroman-6-yl)-1-(4-nitrobenzyl)-7-oxo-6,7-dihydro-1H-pyrrolo[2,3-c]pyridin-5-yl)acetic acid | 0.04 |
| 48 | 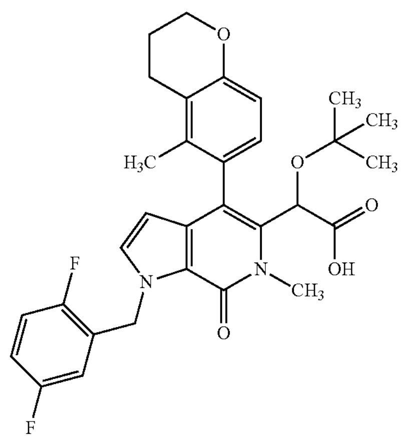 [SMILES: Cc1c(-c2c(C(OC(C)(C)C)C(=O)O)n(C)c(=O)c3c2ccn3Cc2cc(F)ccc2F)ccc2c1CCCO2] | 2-(tert-butoxy)-2-(1-(2,5-difluorobenzyl)-6-methyl-4-(5-methylchroman-6-yl)-7-oxo-6,7-dihydro-1H-pyrrolo[2,3-c]pyridin-5-yl)acetic acid | 0.03 |
| 49 | 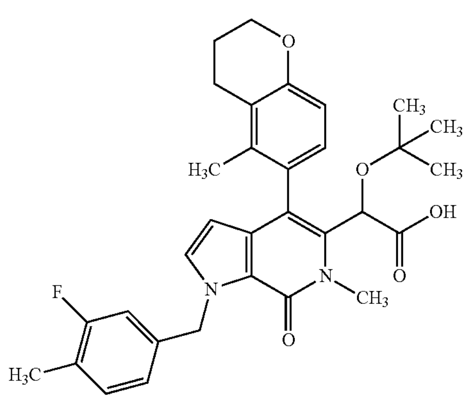 [SMILES: Cc1ccc(Cn2ccc3c(-c4ccc5c(c4C)CCCO5)c(C(OC(C)(C)C)C(=O)O)n(C)c(=O)c32)cc1F] | 2-(tert-butoxy)-2-(1-(3-fluoro-4-methylbenzyl)-6-methyl-4-(5-methylchroman-6-yl)-7-oxo-6,7-dihydro-1H-pyrrolo[2,3-c]pyridin-5-yl)acetic acid | 0.04 |

TABLE 1-continued

| Compound and Example No. | Structure | Name | MT4 (IC$_{50}$) M |
|---|---|---|---|
| 50 | 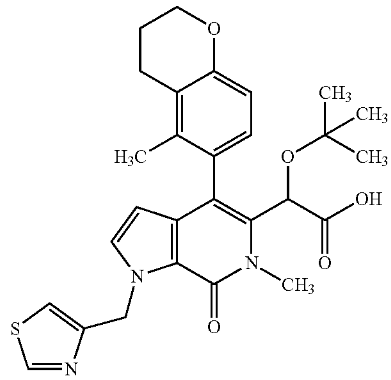 [SMILES: Cc1c(-c2c(C(OC(C)(C)C)C(=O)O)n(C)c(=O)c3c2ccn3Cc2cscn2)ccc2c1CCCO2] | 2-(tert-butoxy)-2-(6-methyl-4-(5-methylchroman-6-yl)-7-oxo-1-(thiazol-4-ylmethyl)-6,7-dihydro-1H-pyrrolo[2,3-c]pyridin-5-yl)acetic acid | 0.23 |
| 51 | 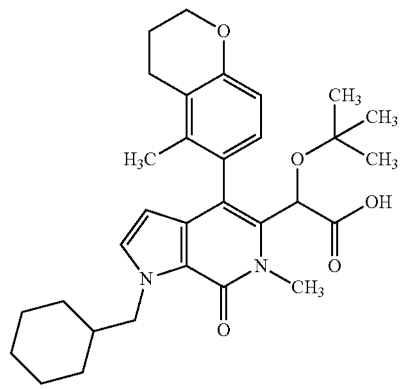 [SMILES: Cc1c(-c2c(C(OC(C)(C)C)C(=O)O)n(C)c(=O)c3c2ccn3CC2CCCCC2)ccc2c1CCCO2] | 2-(tert-butoxy)-2-(1-(cyclohexylmethyl)-6-methyl-4-(5-methylchroman-6-yl)-7-oxo-6,7-dihydro-1H-pyrrolo[2,3-c]pyridin-5-yl)acetic acid | 0.10 |
| 52 | 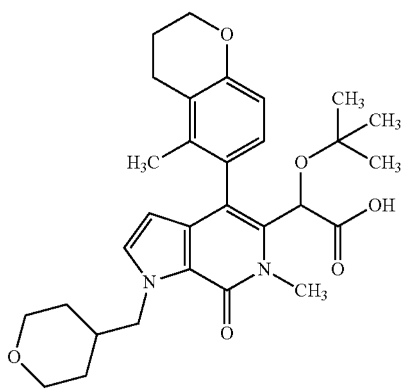 [SMILES: Cc1c(-c2c(C(OC(C)(C)C)C(=O)O)n(C)c(=O)c3c2ccn3CC2CCOCC2)ccc2c1CCCO2] | 2-(tert-butoxy)-2-(6-methyl-4-(5-methylchroman-6-yl)-7-oxo-1-((tetrahydro-2H-pyran-4-yl)methyl)-6,7-dihydro-1H-pyrrolo[2,3-c]pyridin-5-yl)acetic acid | 0.35 |
| 53 | 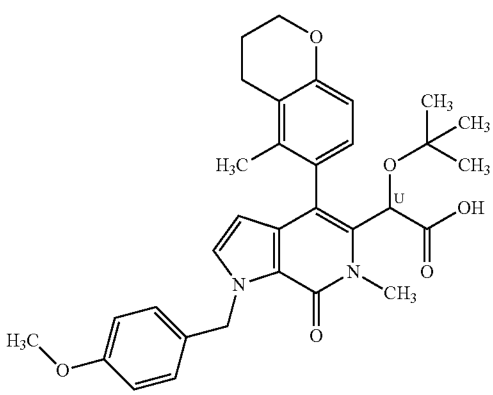 | (S)(M)-2-(tert-butoxy)-2-(1-(4-methoxybenzyl)-6-methyl-4-(5-methylchroman-6-yl)-7-oxo-6,7-dihydro-1H-pyrrolo[2,3-c]pyridin-5-yl)acetic acid | 0.01 |

TABLE 1-continued

| Compound and Example No. | Structure | Name | MT4 (IC$_{50}$) M |
|---|---|---|---|
| 54 | 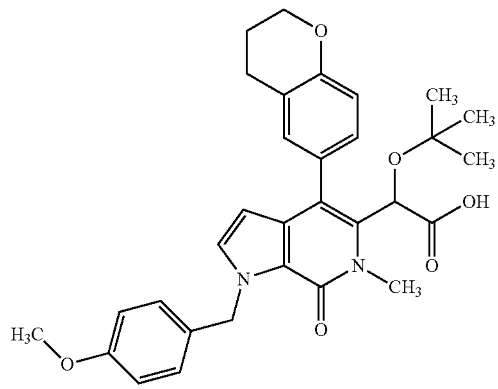 [SMILES: COc1ccc(Cn2ccc3c(-c4ccc5c(c4)CCCO5)c(C(OC(C)(C)C)C(=O)O)n(C)c(=O)c32)cc1] | 2-(tert-butoxy)-2-(6-methyl-4-(5-methylchroman-6-yl)-7-oxo-1-((tetrahydro-2H-pyran-4-yl)methyl)-6,7-dihydro-1H-pyrrolo[2,3-c]pyridin-5-yl)acetic acid | 0.10 |
| 55 | 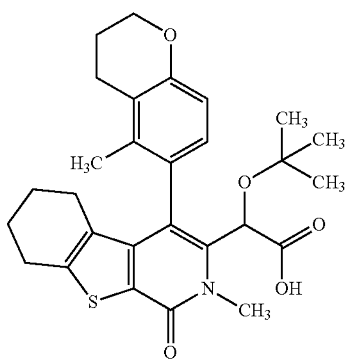 [SMILES: Cc1c(-c2c(C(OC(C)(C)C)C(=O)O)n(C)c(=O)c3sc4c(c23)CCCC4)ccc2c1CCCO2] | tert-Butoxy-[2-methyl-4-(5-methyl-chroman-6-yl)-1-oxo-1,2,5,6,7,8-hexahydro-benzo[4,5]thieno[2,3-c]pyridin-3-yl]-acetic acid | 0.13 |
| 56 | 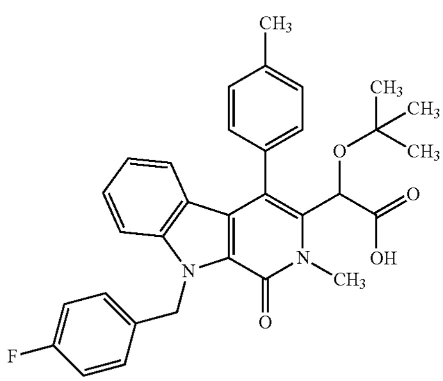 [SMILES: Cc1ccc(-c2c(C(OC(C)(C)C)C(=O)O)n(C)c(=O)c3c2c2ccccc2n3Cc2ccc(F)cc2)cc1] | 2-(tert-butoxy)-2-(9-(4-fluorobenzyl)-2-methyl-1-oxo-4-(p-tolyl)-2,9-dihydro-1H-pyrido[3,4-b]indol-3-yl)acetic acid | 0.74 |
| 57 | 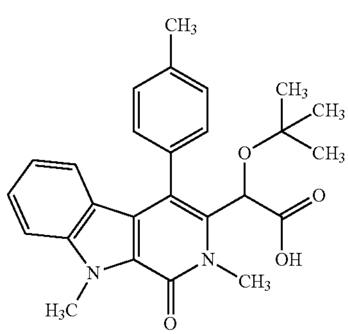 [SMILES: Cc1ccc(-c2c(C(OC(C)(C)C)C(=O)O)n(C)c(=O)c3c2c2ccccc2n3C)cc1] | 2-(tert-butoxy)-2-(2,9-dimethyl-1-oxo-4-(p-tolyl)-2,9-dihydro-1H-pyrido[3,4-b]indol-3-yl)acetic acid | 0.08 |

TABLE 1-continued

| Compound and Example No. | Structure | Name | MT4 (IC$_{50}$) M |
|---|---|---|---|
| 58 | 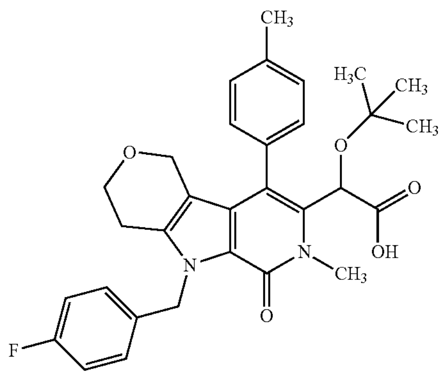 [SMILES: Cc1ccc(-c2c(C(OC(C)(C)C)C(=O)O)n(C)c(=O)c3c2c2c(n3Cc3ccc(F)cc3)CCOC2)cc1] | 2-(tert-butoxy)-2-(5-(4-fluorobenzyl)-7-methyl-6-oxo-9-(p-tolyl)-1,3,4,5,6,7-hexahydropyrano[3',4':4,5]pyrrolo[2,3-c]pyridin-8-yl)acetic acid | 0.75 |
| 59 | 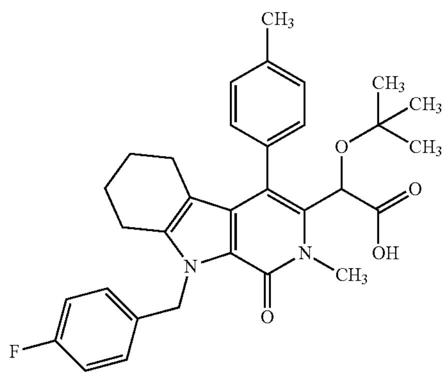 [SMILES: Cc1ccc(-c2c(C(OC(C)(C)C)C(=O)O)n(C)c(=O)c3c2c2c(n3Cc3ccc(F)cc3)CCCC2)cc1] | 2-(tert-butoxy)-2-(9-(4-fluorobenzyl)-2-methyl-1-oxo-4-(p-tolyl)-2,5,6,7,8,9-hexahydro-1H-pyrido[3,4-b]indol-3-yl)acetic acid | 0.28 |
| 60 | 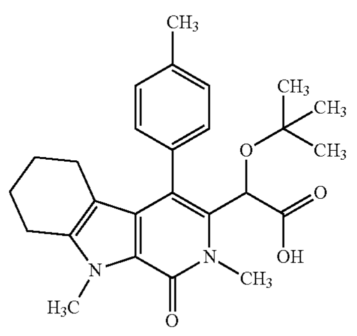 [SMILES: Cc1ccc(-c2c(C(OC(C)(C)C)C(=O)O)n(C)c(=O)c3c2c2c(n3C)CCCC2)cc1] | 2-(tert-butoxy)-2-(2,9-dimethyl-1-oxo-4-(p-tolyl)-2,5,6,7,8,9-hexahydro-1H-pyrido[3,4-b]indol-3-yl)acetic acid | 0.05 |
| 61 | 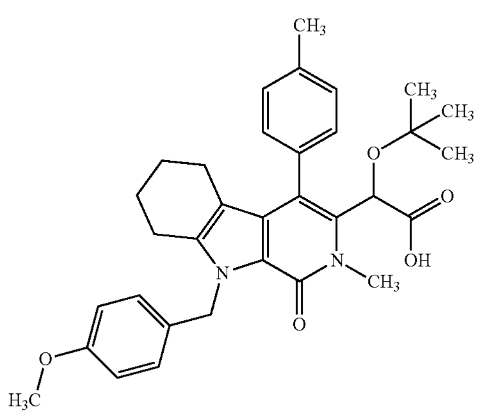 [SMILES: COc1ccc(Cn2c3c(c4c(-c5ccc(C)cc5)c(C(OC(C)(C)C)C(=O)O)n(C)c(=O)c42)CCCC3)cc1] | 2-(tert-butoxy)-2-(9-(4-methoxybenzyl)-2-methyl-1-oxo-4-(p-tolyl)-2,5,6,7,8,9-hexahydro-1H-pyrido[3,4-b]indol-3-yl)acetic acid | 0.10 |

TABLE 1-continued

| Compound and Example No. | Structure | Name | MT4 (IC$_{50}$) M |
|---|---|---|---|
| 62 | 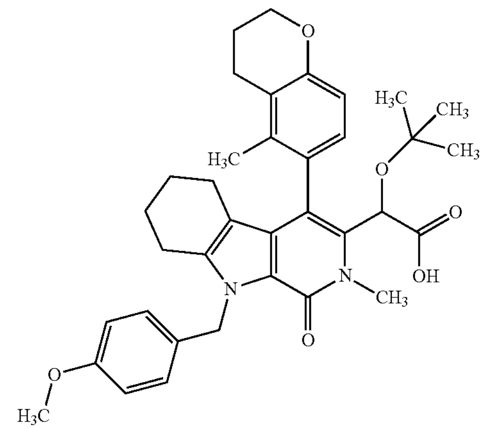 [SMILES: COc1ccc(Cn2c3c(c4c(-c5ccc6c(c5C)CCCO6)c(C(OC(C)(C)C)C(=O)O)n(C)c(=O)c42)CCCC3)cc1] | 2-(tert-butoxy)-2-(9-(4-methoxybenzyl)-2-methyl-4-(5-methylchroman-6-yl)-1-oxo-2,5,6,7,8,9-hexahydro-1H-pyrido[3,4-b]indol-3-yl)acetic acid | 0.05 |
| 63 | 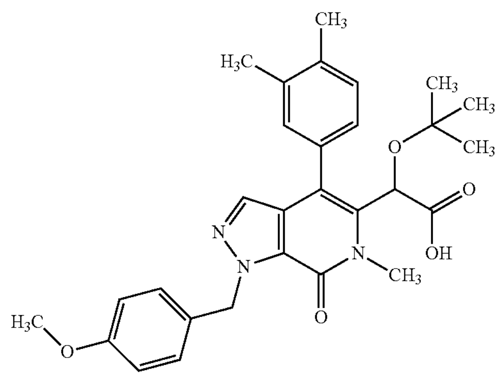 [SMILES: COc1ccc(Cn2ncc3c(-c4ccc(C)c(C)c4)c(C(OC(C)(C)C)C(=O)O)n(C)c(=O)c32)cc1] | 2-(tert-Butoxy)-2-(4-(3,4-dimethylphenyl)-1-(4-methoxybenzyl)-6-methyl-7-oxo-6,7-dihydro-1H-pyrazolo[3,4-c]pyridin-5-yl)acetic | 1.20 |
| 64 | 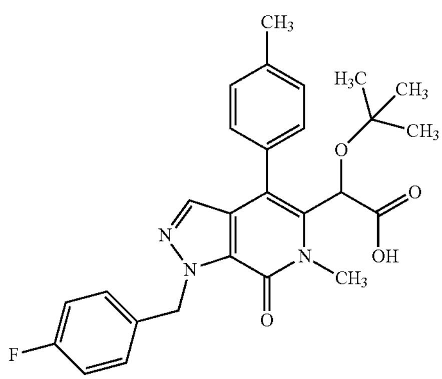 [SMILES: Cc1ccc(-c2c(C(OC(C)(C)C)C(=O)O)n(C)c(=O)c3c2cnn3Cc2ccc(F)cc2)cc1] | 2-(tert-Butoxy)-2-(1-(4-fluorobenzyl)-6-methyl-7-oxo-4-(p-tolyl)-6,7-dihydro-1H-pyrazolo[3,4-c]pyridin-5-yl)acetic acid | 0.18 |
| 65 | 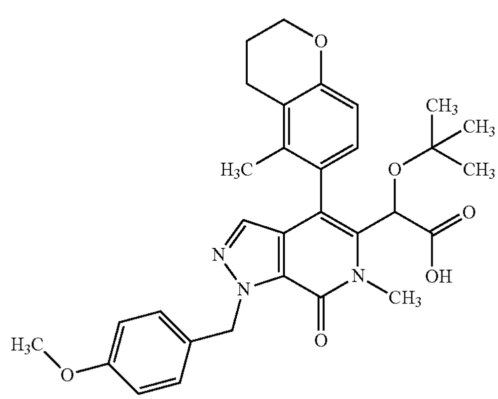 [SMILES: COc1ccc(Cn2ncc3c(-c4ccc5c(c4C)CCCO5)c(C(OC(C)(C)C)C(=O)O)n(C)c(=O)c32)cc1] | 2-(tert-Butoxy)-2-(1-(4-methoxybenzyl)-6-methyl-4-(5-methylchroman-6-yl)-7-oxo-6,7-dihydro-1H-pyrazolo[3,4-c]pyridin-5-yl)acetic acid yl)acetic | 0.41 |

TABLE 1-continued

| Compound and Example No. | Structure | Name | MT4 (IC$_{50}$) M |
|---|---|---|---|
| 66 | 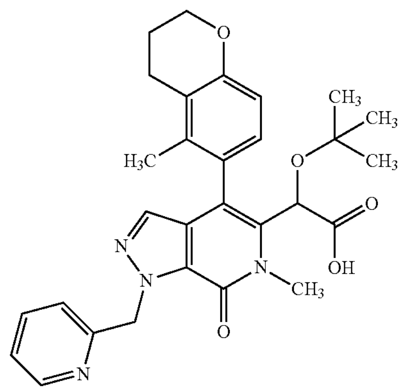 [SMILES: Cc1c(-c2c(C(OC(C)(C)C)C(=O)O)n(C)c(=O)c3c2cnn3Cc2ccccn2)ccc2c1CCCO2] | 2-(tert-Butoxy)-2-(6-methyl-4-(5-methylchroman-6-yl)-7-oxo-1-(pyridin-2-ylmethyl)-6,7-dihydro-1H-pyrazolo[3,4-c]pyridin-5-yl)acetic acid | 1.36 |
| 67 | 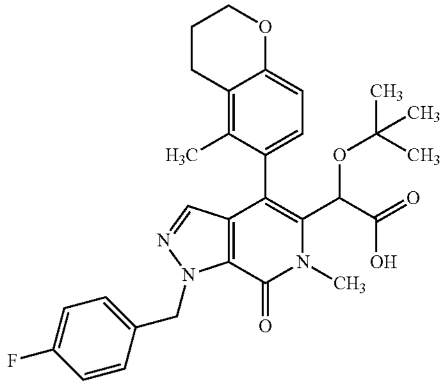 [SMILES: Cc1c(-c2c(C(OC(C)(C)C)C(=O)O)n(C)c(=O)c3c2cnn3Cc2ccc(F)cc2)ccc2c1CCCO2] | 2-(tert-butoxy)-2-(1-(4-fluorobenzyl)-6-methyl-4-(5-methylchroman-6-yl)-7-oxo-6,7-dihydro-1 H-pyrazolo[3,4-c]pyridin-5-yl)acetic acid | 0.08 |

The compounds of Table 1 were synthesized according to the Synthetic Methods, General Schemes, and the Examples described below.

Synthetic Methods

The methods of synthesis for the provided chemical entities employ readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, the methods of this invention may employ protecting groups which prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition (Wiley, New York, 1999) and references cited therein.

Furthermore, the provided chemical entities may contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this specification, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Ernka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989).

Unless specified to the contrary, the reactions described herein take place at atmospheric pressure, generally within a temperature range from −78° C. to 200° C. Further, except as employed in the Examples or as otherwise specified, reaction times and conditions are intended to be approximate, e.g., taking place at about atmospheric pressure within a temperature range of about −78° C. to about 110° C. over a period of about 1 to about 24 hours; reactions left to run overnight average a period of about 16 hours.

The terms "solvent," "organic solvent," and "inert solvent" each mean a solvent inert under the conditions of the reaction being described in conjunction therewith, including, for example, benzene, toluene, acetonitrile, tetrahydrofuranyl ("THF"), dimethylformamide ("DMF"), chloroform, methylene chloride (or dichloromethane), diethyl ether, methanol, N-methylpyrrolidone ("NMP"), pyridine and the like.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

EXAMPLES

The following examples serve to more fully describe the manner of making and using the above-described invention. It is understood that these examples in no way serve to limit the true scope of the invention, but rather are presented for illustrative purposes. In the examples below and the synthetic schemes above, the following abbreviations have the following meanings. If an abbreviation is not defined, it has its generally accepted meaning.

aq.=aqueous
μL=microliters
μM=micromolar
NMR=nuclear magnetic resonance
boc=tert-butoxycarbonyl
br=broad
Cbz=benzyloxycarbonyl
d=doublet
δ=chemical shift
° C.=degrees celcius
DCM=dichloromethane
dd=doublet of doublets
DMEM=Dulbeco's Modified Eagle's Medium
DMF=N,N-dimethylformamide
DMSO=dimethylsulfoxide
EtOAc=ethyl acetate
g=gram
h or hr=hours
HCV=hepatitis C virus
HPLC=high performance liquid chromatography
Hz=hertz
IU=International Units
$IC_{50}$=inhibitory concentration at 50% inhibition
J=coupling constant (given in Hz unless otherwise indicated)
m=multiplet
M=molar
$M+H^+$=parent mass spectrum peak plus $H^+$
mg=milligram
min=minutes
mL=milliliter
mM=millimolar
mmol=millimole
MS=mass spectrum
nm=nanomolar
ppm=parts per million
q.s.=sufficient amount
s=singlet
RT=room temperature
sat.=saturated
t=triplet
TFA=trifluoroacetic acid Examples

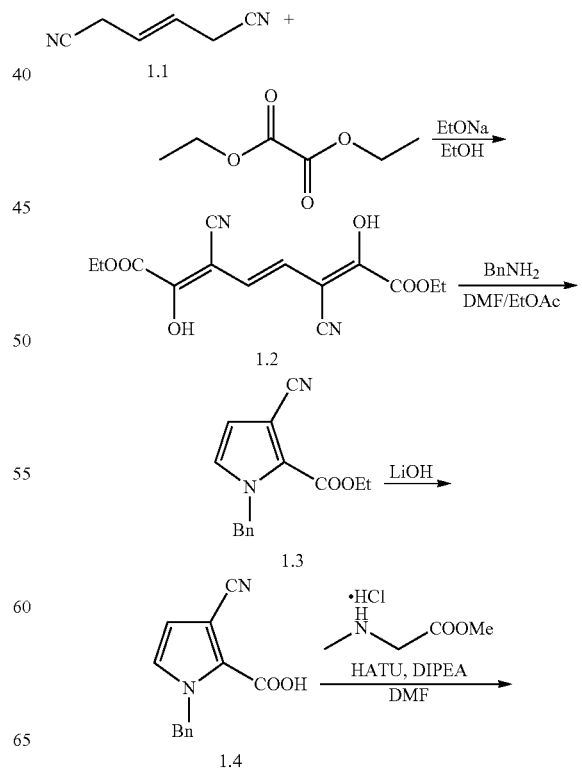

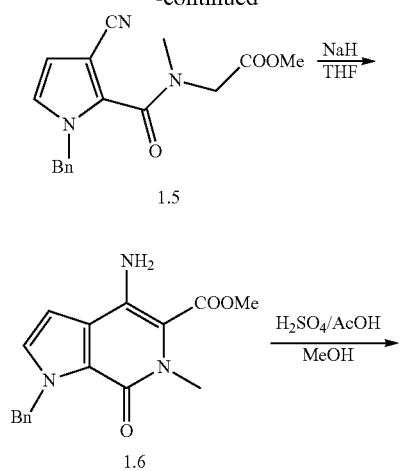
1.5
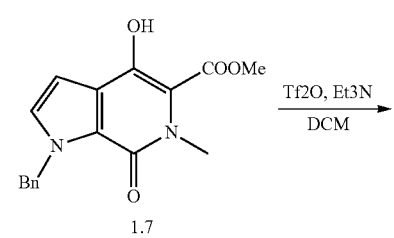
1.6
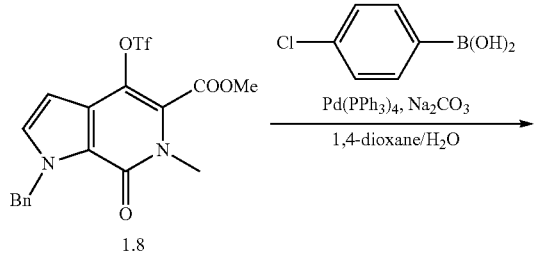
1.7
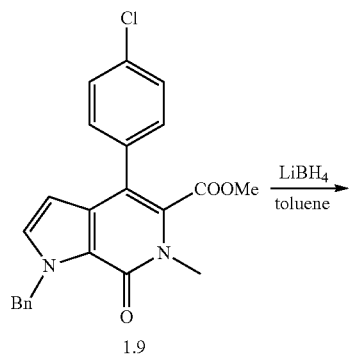
1.8
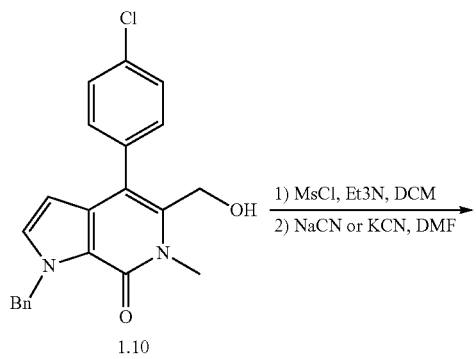
1.9
1.10
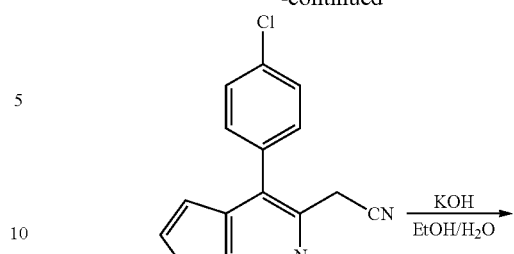
1.11
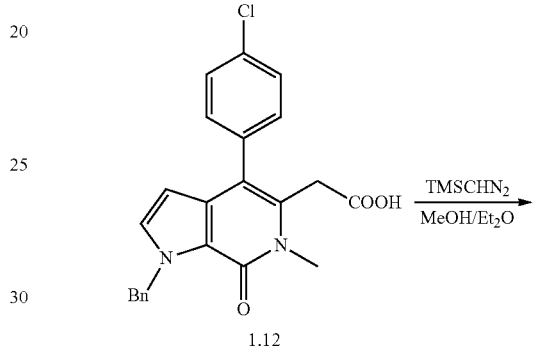
1.12
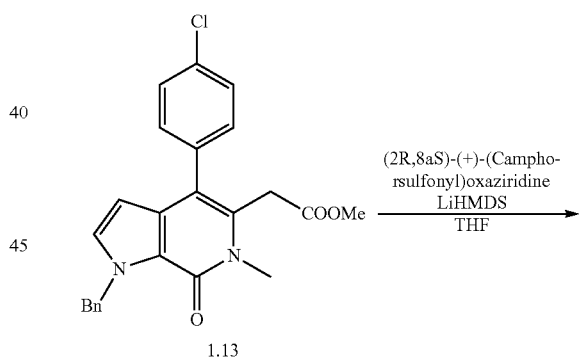
1.13
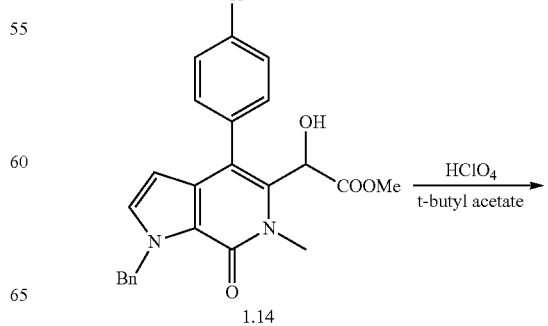
1.14

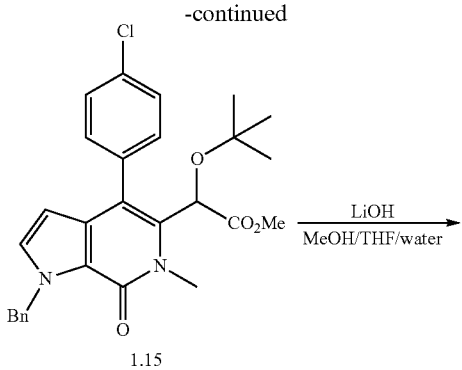

1.15

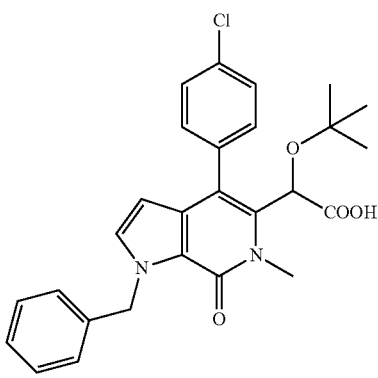 [SMILES: Cn1c(C(OC(C)(C)C)C(=O)O)c(-c2ccc(Cl)cc2)c2ccn(Cc3ccccc3)c2c1=O]

1.16

Example 1

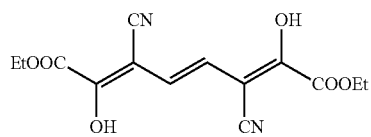 [SMILES: CCOC(=O)/C(O)=C(C#N)/C=C/C(C#N)=C(\O)C(=O)OCC]

2-(1-benzyl-4-(4-chlorophenyl)-6-methyl-7-oxo-6,7-dihydro-1H-pyrrolo[2,3-c]pyridin-5-yl)-2-(tert-butoxy)acetic acid

Step A (2E,4E,6E)-diethyl 3,6-dicyano-2,7-dihydroxyocta-2,4,6-trienedioate

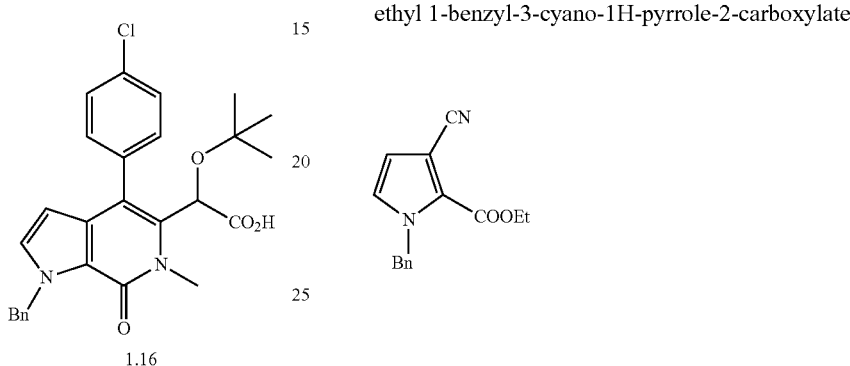

A solution of diethyl oxalate (57.9 mL, 424 mmol) in Methanol (60 mL) was treated with sodium ethoxide (158 mL, 424 mmol) at 0° C., followed by (E)-hex-3-enedinitrile (15 g, 141 mmol) and the resultant was stirred at room temperature overnight. The red mixture was concentrated under vacuum. The residue was diluted with $H_2O$ (150 mL), acidified to pH<2 with concentrated HCl at 0° C. and then filtered. The filter cake was washed with water and then dried under vacuum to afford (2E,4E,6E)-diethyl 3,6-dicyano-2,7-dihydroxyocta-2,4,6-trienedioate (18 g, 58.8 mmol, 42% yield) as a white solid. $^1$H NMR (400 MHz, DMSO-$d_6$) ppm 6.89 (s, 2H) 4.32 (q, J=7.23 Hz, 4H) 1.30 (t, J=7.13 Hz, 6H); LCMS (m/z) ES$^-$=305 (M−1).

Step B ethyl 1-benzyl-3-cyano-1H-pyrrole-2-carboxylate

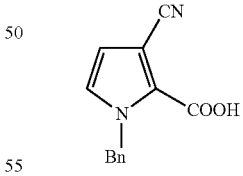

A solution of (2E,4E,6E)-diethyl 3,6-dicyano-2,7-dihydroxyocta-2,4,6-trienedioate (18 g, 58.8 mmol) in N,N-Dimethylformamide (DMF) (100 mL) and Ethyl acetate (100 mL), was treated with benzylamine (15.44 mL, 141 mmol) and the resultant was heated at 95° C. for 3 hours. The dark mixture was concentrated and purified on silica gel (0-70% ethyl acetate/hexanes) to afford ethyl 1-benzyl-3-cyano-1H-pyrrole-2-carboxylate (8.7 g, 34.1 mmol, 60% yield) as a white solid. $^1$H NMR (400 MHz, CHLOROFORM-d) δ ppm 7.25-7.45 (m, 3H) 7.11-7.16 (m, 2H) 6.84-6.87 (m, 1H) 6.53-6.58 (m, 1H) 5.59 (s, 2H) 4.37 (q, J=7.04 Hz, 2H) 1.40 (t, J=7.13 Hz, 3H); LCMS (m/z) ES$^+$=255 (M+1).

Step C 1-benzyl-3-cyano-1H-pyrrole-2-carboxylic acid

A solution of ethyl 1-benzyl-3-cyano-1H-pyrrole-2-carboxylate (8.7 g, 34.1 mmol) in Methanol (40 mL) and Tetrahydrofuran (THF) (40 mL) was treated with 2M LiOH (40 mL, 80 mmol) and then stirred at 50° C. for 1 hour. The mixture was adjusted to pH<2 by adding HCl (1M) and then concentrated to afford 1-benzyl-3-cyano-1H-pyrrole-2-carboxylic acid as a white solid (7.3 g, 32.4 mmol, 95% yield) which was used in the next step without any further purification. $^1$H NMR (400 MHz, DMSO-d6) ppm 7.54 (d, J=6.4 Hz, 1H), 7.45-7.27 (m, 4H), 7.12 (d, J=7.2 Hz, 1H), 6.76-6.69 (d, J=7.2 Hz, 1H), 5.64 (s, 2H); LCMS (m/z) ES$^+$=227 (M+1).

Step D methyl 2-(1-benzyl-3-cyano-N-methyl-1H-pyrrole-2-carboxamido)acetate

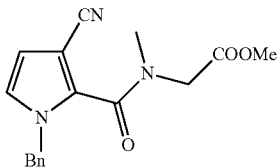 [SMILES: COC(=O)CN(C)C(=O)c1c(C#N)ccn1Cc1ccccc1]

A solution of 1-benzyl-3-cyano-1H-pyrrole-2-carboxylic acid (7.3 g, 32.4 mmol) in N,N-Dimethylformamide (DMF) (100 mL) was treated with sarcosine methyl ester hydrochloride (12 g, 86 mmol) and DIPEA (30 mL, 172 mmol), followed by HATU (26 g, 68.4 mmol). The mixture was stirred at 40° C. for 1 hour. The mixture was cooled to room temperature, brine was added and the resultant was extracted with ethyl acetate. The combined extracts were washed with HCl (1M), followed by brine, dried over $Na_2SO_4$, filtered and concentrated. The residue was purified on silica gel (0-70% ethyl acetate/hexanes) to afford methyl 2-(1-benzyl-3-cyano-N-methyl-1H-pyrrole-2-carboxamido)acetate (9.2 g, 29.6 mmol, 91% yield) as a white solid. $^1$H NMR (400 MHz, CHLOROFORM-d) ppm 7.31-7.38 (m, 3H). 7.20-7.26 (m, 2H) 6.73-6.78 (m, 1H) 6.40-6.46 (m, 1H) 5.17-5.26 (s, 2H) 4.16-4.26 (s, 2H) 3.71-3.80 (s, 3H) 3.06-3.15 (s, 3H); LCMS (m/z) $ES^+$=312 (M+1).

Step E methyl 4-amino-1-benzyl-6-methyl-7-oxo-6,7-dihydro-1H-pyrrolo[2,3-c]pyridine-5-carboxylate

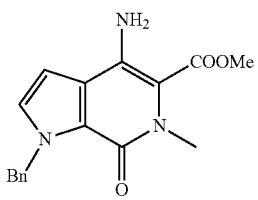 [SMILES: COC(=O)c1c(N)c2ccn(Cc3ccccc3)c2c(=O)n1C]

An ice cold solution of methyl 2-(1-benzyl-3-cyano-N-methyl-1H-pyrrole-2-carboxamido)acetate (9.2 g, 29.6 mmol) in Tetrahydrofuran (THF) (100 mL) was treated with NaH, 60% dispersion in mineral oil, (1.536 g, 38.4 mmol) and the mixture was stirred at 0° C. for 30 minutes, then allowed to warm to room temperature and stirred an additional 2 hours at ambient temperature. The mixture was quenched with saturated $NH_4Cl$ solution at 0° C. and extracted with ethyl acetate. The combined extracts were washed with brine, dried over $Na_2SO_4$, filtered and concentrated to afford methyl 1-benzyl-4-imino-6-methyl-7-oxo-4,5,6,7-tetrahydro-1H-pyrrolo[2,3-c]pyridine-5-carboxylate (9.0 g, 28.9 mmol, 98% yield) as a pale yellow solid which was used in the next step without any further purification. $^1$H NMR (400 MHz, DMSO-$d_6$) ppm 7.42-7.51 (m, 1H) 7.18-7.36 (m, 5H) 6.78-6.89 (m, 1H) 6.39-6.54 (m, 2H) 5.77 (s, 2H) 3.78 (s, 3H) 3.38 (s, 3H); LCMS (m/z) $ES^+$=312 (M+1).

Step F methyl 1-benzyl-4-hydroxy-6-methyl-7-oxo-6,7-dihydro-1H-pyrrolo[2,3-c]pyridine-5-carboxylate

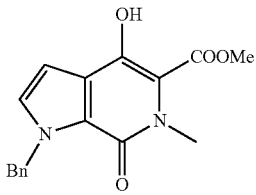 [SMILES: COC(=O)c1c(O)c2ccn(Cc3ccccc3)c2c(=O)n1C]

A solution of methyl 1-benzyl-4-imino-6-methyl-7-oxo-4,5,6,7-tetrahydro-1H-pyrrolo[2,3-c]pyridine-5-carboxylate (9.0 g, 28.9 mmol) in Methanol (100 mL) was treated with Water (40 mL) and Acetic Acid (50 mL), followed by $H_2SO_4$ (1.575 mL, 29.6 mmol), and the resultant was stirred at 90° C. overnight. The mixture was concentrated, diluted with water and then adjusted to pH>6 with saturated sodium bicarbonate. The mixture was extracted with Ethyl acetate, washed with brine, dried over $Na_2SO_4$, filtered and concentrated to afford methyl 1-benzyl-4-hydroxy-6-methyl-7-oxo-6,7-dihydro-1H-pyrrolo[2,3-c]pyridine-5-carboxylate (7.0 g, 22.4 mmol, 76% yield) as a pale yellow solid which was used in the next step without any further purification. $^1$H NMR (400 MHz, CHLOROFORM-d) ppm 11.23 (s, 1H) 7.20-7.36 (m, 5H) 7.04-7.11 (m, 1H) 6.62-6.70 (m, 1H) 5.86 (s, 2H) 3.98 (s, 3H) 3.67 (s, 3H); LCMS (m/z) $ES^+$=313 (M+1).

Step G methyl 1-benzyl-6-methyl-7-oxo-4-(((trifluoromethyl)sulfonyl)oxy)-6,7-dihydro-1H-pyrrolo[2,3-c]pyridine-5-carboxylate

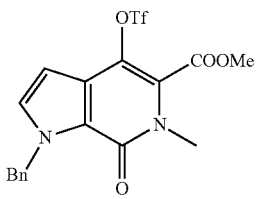 [SMILES: COC(=O)c1c(OS(=O)(=O)C(F)(F)F)c2ccn(Cc3ccccc3)c2c(=O)n1C]

An ice cold solution of methyl 1-benzyl-4-hydroxy-6-methyl-7-oxo-6,7-dihydro-1H-pyrrolo[2,3-c]pyridine-5-carboxylate (7 g, 22.4 mmol) in Dichloromethane (DCM) (50 mL) was treated with triethylamine (12.36 mL, 89 mmol) and triflic anhydride (9.98 mL, 59.1 mmol) and the resultant was stirred at 0° C. for 10 min. The mixture was quenched with saturated $NaHCO_3$ solution and extracted with dichloromethane. The extracts were washed with brine, dried over $Na_2SO_4$, filtered and concentrated. The residue was purified on silica gel (0-50% ethyl acetate/hexane) to afford methyl 1-benzyl-6-methyl-7-oxo-4-(((trifluoromethyl)sulfonyl)oxy)-6,7-dihydro-1H-pyrrolo[2,3-c]pyridine-5-carboxylate (7.5 g, 16.9 mmol, 80% yield) as a pale yellow solid. $^1$H NMR (400 MHz, CHLOROFORM-d) ppm 7.29-7.38 (m, 3H) 7.21-7.26 (m, 2H) 7.14-7.20 (m, 1H) 6.47-6.55 (m, 1H) 5.82 (s, 2H) 4.00 (s, 3H) 3.60 (s, 3H); LCMS (m/z) $ES^+$=445 (M+1).

Step H methyl 1-benzyl-4-(4-chlorophenyl)-6-methyl-7-oxo-6,7-dihydro-1H-pyrrolo[2,3-c]pyridine-5-carboxylate

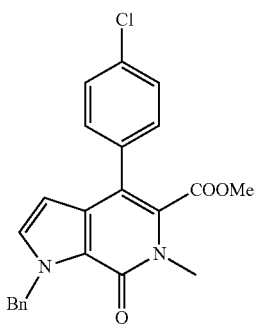 [SMILES: COC(=O)c1c(-c2ccc(Cl)cc2)c2ccn(Cc3ccccc3)c2c(=O)n1C]

A mixture of methyl 1-benzyl-6-methyl-7-oxo-4-(((trifluoromethyl)sulfonyl)oxy)-6,7-dihydro-1H-pyrrolo[2,3-c]pyridine-5-carboxylate (7.5 g, 16.9 mmol), 4-chlorophenylboronic acid (3.89 g, 23.64 mmol) and $Na_2CO_3$ (7.52 g, 70.9 mmol) in 1,4-Dioxane (100 mL) and Water (20 mL) degassed with $N_2$ for 15 minutes. The mixture was treated with palladium tetrakis (1.024 g, 0.887 mmol) and then stirred at 90° C. under $N_2$ atmosphere overnight. The mixture was diluted with water and then extracted with Ethyl acetate. The combined extracts were washed with brine, dried over $Na_2SO_4$, filtered and concentrated. The residue was purified on silica gel (0-40% ethyl acetate/hexanes) to afford methyl 1-benzyl-4-(4-chlorophenyl)-6-methyl-7-oxo-6,7-dihydro-1H-pyrrolo[2,3-c]pyridine-5-carboxylate (6.4 g, 15.7 mmol, 93% yield) as a pale yellow solid. $^1$H NMR (400 MHz, CHLOROFORM-d) ppm 7.40 (s, 2H) 7.31-7.37 (m, 4H) 7.23-7.27 (m, 2H) 7.05 (d, J=2.93 Hz, 1H) 6.12 (d, J=2.93 Hz, 1H) 5.87 (s, 2H) 3.62 (s, 3H) 3.61 (s, 3H); LCMS (m/z) ES$^+$=407 (M+1).

Step I

1-benzyl-4-(4-chlorophenyl)-5-(hydroxymethyl)-6-methyl-1H-pyrrolo[2,3-c]pyridin-7(6H)-one

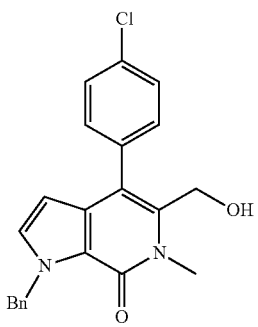 [SMILES: Cn1c(CO)c(-c2ccc(Cl)cc2)c2ccn(Cc3ccccc3)c2c1=O]

A solution of methyl 1-benzyl-4-(4-chlorophenyl)-6-methyl-7-oxo-6,7-dihydro-1H-pyrrolo[2,3-c]pyridine-5-carboxylate (6.4 g, 15.7 mmol) in Toluene (80 mL) was treated with LiBH$_4$ (3.43 g, 157 mmol) and then heated at 90° C. overnight. Additional LiBH$_4$ (3.43 g, 157 mmol) was added and the mixture was allowed to stir for an additional 5 hours at 90° C. The mixture was cooled to 0° C., treated with HCl (1M) until pH<2 and then extracted with ethyl acetate. The combined extracts were washed with brine, dried over $Na_2SO_4$, filtered and concentrated. The residue was purified on silica gel (0-100% ethyl acetate/hexanes) to afford 1-benzyl-4-(4-chlorophenyl)-5-(hydroxymethyl)-6-methyl-1H-pyrrolo[2,3-c]pyridin-7(6H)-one (4.0 g, 10.6 mmol, 67% yield) as a white solid. $^1$H NMR (400 MHz, DMSO-d$_6$) ppm 7.53-7.57 (m, 2H) 7.43-7.47 (m, 4H) 7.28-7.35 (m, 4H) 5.92-5.96 (m, 1H) 5.80 (s, 2H) 5.31 (s, 1H) 4.29-4.37 (m, 2H) 3.70 (s, 3H); LCMS (m/z) ES$^+$=379 (M+1).

Step J

2-(1-benzyl-4-(4-chlorophenyl)-6-methyl-7-oxo-6,7-dihydro-1H-pyrrolo[2,3-c]pyridin-5-yl)acetonitrile

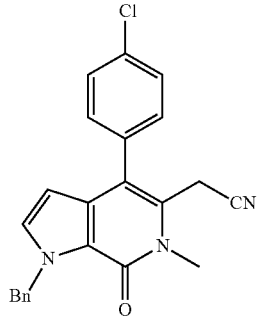 [SMILES: Cn1c(CC#N)c(-c2ccc(Cl)cc2)c2ccn(Cc3ccccc3)c2c1=O]

A suspension of 1-benzyl-4-(4-chlorophenyl)-5-(hydroxymethyl)-6-methyl-1H-pyrrolo[2,3-c]pyridin-7(6H)-one (4 g, 10.6 mmol) in Dichloromethane (DCM) (50 mL) was treated with Et$_3$N (4.38 mL, 31.5 mmol) and MsCl (1.839 mL, 23.60 mmol) at 0° C. and then stirred for 30 min. The mixture was diluted with Dichloromethane, washed with 0.1N HCl and NaHCO$_3$, dried over Na$_2$SO$_4$, filtered and concentrated to afford (1-benzyl-4-(4-chlorophenyl)-6-methyl-7-oxo-6,7-dihydro-1H-pyrrolo[2,3-c]pyridin-5-yl)methyl methanesulfonate as a pale yellow solid (4.8 g, 10.5 mmol, 95% yield) which was used for in next step without any further purification. A solution of (1-benzyl-4-(4-chlorophenyl)-6-methyl-7-oxo-6,7-dihydro-1H-pyrrolo[2,3-c]pyridin-5-yl)methyl methanesulfonate (4.8 g, 10.5 mmol) in N,N-Dimethylformamide (DMF) (30 mL) was treated with KCN (6.15 g, 94 mmol) and the resultant was stirred at ambient temperature overnight. The mixture was quenched with water and then extracted with ethyl acetate. The combined extracts were washed with brine, dried over Na$_2$SO$_4$, filtered and concentrated. The residue was purified on silica gel (0-70% ethyl acetate/hexanes) to afford 2-(1-benzyl-4-(4-chlorophenyl)-6-methyl-7-oxo-6,7-dihydro-1H-pyrrolo[2,3-c]pyridin-5-yl)acetonitrile (2.7 g, 7.0 mmol, 67% yield) as a pale yellow solid. $^1$H NMR (400 MHz, CHLOROFORM-d) ppm 7.47-7.52 (m, 2H) 7.31-7.35 (m, 3H) 7.27-7.30 (m, 4H) 7.04-7.09 (m, 1H) 5.94-5.98 (m, 1H) 5.83-5.88 (s, 2H) 3.81 (s, 3H) 3.64 (s, 2H); LCMS (m/z) ES$^+$=388 (M+1).

Step K methyl 2-(1-benzyl-4-(4-chlorophenyl)-6-methyl-7-oxo-6,7-dihydro-1H-pyrrolo[2,3-c]pyridin-5-yl)acetate

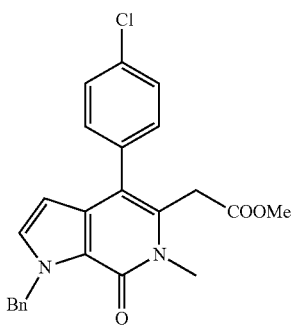 [SMILES: COC(=O)Cc1c(-c2ccc(Cl)cc2)c2ccn(Cc3ccccc3)c2c(=O)n1C]

A suspension of 2-(1-benzyl-4-(4-chlorophenyl)-6-methyl-7-oxo-6,7-dihydro-1H-pyrrolo[2,3-c]pyridin-5-yl)acetonitrile (3 g, 7.04 mmol) in Ethanol (60 mL) and Water (20 mL) was treated with KOH (3.95 g, 70.4 mmol) and then heated to 140° C. in a sealed tube for 24 hours. The mixture was cooled to 0° C. and then treated with 4N HCl until pH<2. The mixture was partly concentrated and then extracted with Ethyl acetate. The combined extracts were washed with brine, dried over sodium sulfate, filtered and then concentrated. The residue was dissolved in Methanol (60.0 mL), cooled to 0° C. and then treated with TMS-diazomethane (35.2 mL, 70.4 mmol). The mixture was warmed to ambient temperature and then stirred for 20 minutes. Upon reaction completion, the mixture was cooled to 0° C., quenched with acetic acid and then concentrated. The residue was purified on silica gel (0-70% ethyl acetate/hexanes) to afford methyl 2-(1-benzyl-4-(4-chlorophenyl)-6-methyl-7-oxo-6,7-dihydro-1H-pyrrolo[2,3-c]pyridin-5-yl)acetate (2.3 g, 5.46 mmol, 78% yield) as a white solid. $^1$H NMR (400 MHz, CHLOROFORM-d) ppm 7.40-7.44 (m, 2H) 7.25-7.35 (m, 7H) 7.00-7.04 (m, 1H) 5.88-5.94 (m, 1H) 5.80-5.88 (m, 2H) 3.74 (s, 3H) 3.63 (s, 2H) 3.59 (s, 3H); LCMS (m/z) ES$^+$=421 (M+1).

Step L methyl 2-(1-benzyl-4-(4-chlorophenyl)-6-methyl-7-oxo-6,7-dihydro-1H-pyrrolo[2,3-c]pyridin-5-yl)-2-hydroxyacetate

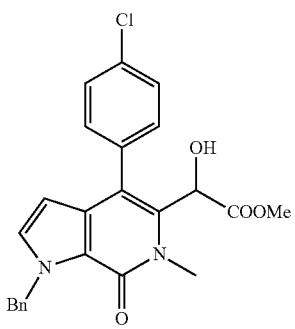 [SMILES: COC(=O)C(O)c1c(-c2ccc(Cl)cc2)c2ccn(Cc3ccccc3)c2c(=O)n1C]

A solution of methyl 2-(1-benzyl-4-(4-chlorophenyl)-6-methyl-7-oxo-6,7-dihydro-1H-pyrrolo[2,3-c]pyridin-5-yl)acetate (2.3 g, 5.46 mmol) in Tetrahydrofuran (THF) (30 mL) was treated with LiHMDS (8.45 mL, 8.45 mmol) at −78° C. and then stirred for 1 hour. A solution of (2R,8aS)-(+)-(Camphorsulfonyl)oxaziridine (2.421 g, 10.56 mmol) in Tetrahydrofuran (THF) (20 mL) was added, the mixture was warmed to 0° C. and then stirred for 20 minutes. The mixture was quenched with HCl (1M) and then extracted with Ethyl acetate. The combined extracts were washed with brine, dried over Na$_2$SO$_4$ and concentrated. The residue was purified on silica gel (0-100% ethyl acetate/hexanes) to afford methyl 2-(1-benzyl-4-(4-chlorophenyl)-6-methyl-7-oxo-6,7-dihydro-1H-pyrrolo[2,3-c]pyridin-5-yl)-2-hydroxyacetate (3.3 g, 4.53 mmol, 82% yield) as a white solid. $^1$H NMR (400 MHz, CHLOROFORM-d) ppm 7.28 (s, 9H) 7.01-7.07 (m, 1H) 5.93-5.99 (m, 1H) 5.85-5.92 (m, 1H) 5.77-5.84 (m, 1H) 5.20-5.27 (m, 1H) 3.79 (s, 3H) 3.58 (s, 3H); LCMS (m/z) ES$^+$=437 (M+1).

Step M methyl 2-(1-benzyl-4-(4-chlorophenyl)-6-methyl-7-oxo-6,7-dihydro-1H-pyrrolo[2,3-c]pyridin-5-yl)-2-(tert-butoxy)acetate

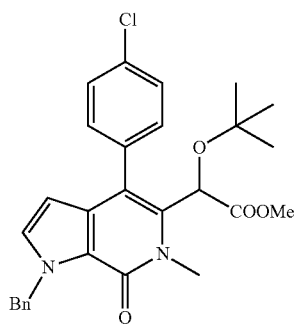 [SMILES: COC(=O)C(OC(C)(C)C)c1c(-c2ccc(Cl)cc2)c2ccn(Cc3ccccc3)c2c(=O)n1C]

A solution of methyl 2-(1-benzyl-4-(4-chlorophenyl)-6-methyl-7-oxo-6,7-dihydro-1H-pyrrolo[2,3-c]pyridin-5-yl)-2-hydroxyacetate (3.3 g, 4.53 mmol) in t-Butyl acetate (30 mL) was treated with perchloric acid (0.423 mL, 7.04 mmol) and the resultant was stirred at room temperature for 3 hours. The mixture was diluted with Ethyl acetate, washed with saturated NaHCO$_3$ and brine, dried over Na$_2$SO$_4$, filtered and concentrated. The residue was purified on silica gel (0-70% ethyl acetate/hexanes) to afford methyl 2-(1-benzyl-4-(4-chlorophenyl)-6-methyl-7-oxo-6,7-dihydro-1H-pyrrolo[2,3-c]pyridin-5-yl)-2-(tert-butoxy)acetate (2.3 g, 4.67 mmol, 73% yield) as a white solid. $^1$H NMR (400 MHz, CHLOROFORM-d) ppm 7.43-7.47 (m, 3H) 7.37-7.41 (m, 1H) 7.32-7.35 (m, 4H) 7.01-7.05 (m, 1H) 5.92-5.96 (m, 1H) 5.83-5.88 (m, 2H) 5.21-5.24 (m, 1H) 3.82 (s, 3H) 3.67 (s, 3H) 0.96 (s, 9H); LCMS (m/z) ES$^+$=493 (M+1).

Step N

2-(1-benzyl-4-(4-chlorophenyl)-6-methyl-7-oxo-6,7-dihydro-1H-pyrrolo[2,3-c]pyridin-5-yl)-2-(tert-butoxy)acetic acid

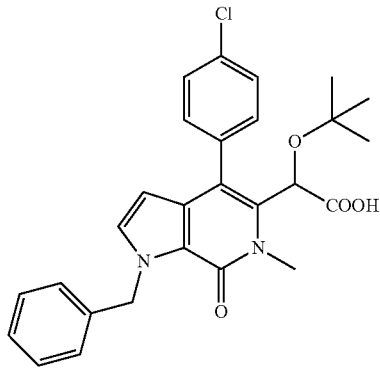 [SMILES: Cn1c(C(OC(C)(C)C)C(=O)O)c(-c2ccc(Cl)cc2)c2ccn(Cc3ccccc3)c2c1=O]

A solution of methyl 2-(1-benzyl-4-(4-chlorophenyl)-6-methyl-7-oxo-6,7-dihydro-1H-pyrrolo[2,3-c]pyridin-5-yl)-2-(tert-butoxy)acetate (30 mg, 0.061 mmol) in Methanol (0.500 mL), Tetrahydrofuran (THF) (0.500 mL) and Water (0.500 mL) was treated with NaOH (54.7 mg, 1.368 mmol) and heated to 70° C. for 3 hours. The mixture was cooled to 0° C., treated with HCl (1M) until pH<2 and extracted with Ethyl acetate. The combined extracts were washed with brine, dried over $Na_2SO_4$, filtered and concentrated. The residue was purified by reverse phase chromatography (10-90% $MeCN_{H_2O}$-0.1% TFA, 12 min) to afford 2-(1-benzyl-4-(4-chlorophenyl)-6-methyl-7-oxo-6,7-dihydro-1H-pyrrolo[2,3-c]pyridin-5-yl)-2-(tert-butoxy)acetic acid (21.5 mg, 0.044 mmol, 73% yield) as white solid. $^1$H NMR (400 MHz, DMSO-$d_6$) ppm 13.33 (s, 1H) 7.58-7.69 (m, 2H) 7.42-7.54 (m, 3H) 7.23-7.38 (m, 4H) 5.89-5.95 (m, 1H) 5.74-5.81 (m, 1H) 5.07-5.15 (m, 1H) 3.50-3.59 (m, 3H) 0.88 (s, 9H); LCMS (m/z) ES$^+$=479 (M+1).

General Scheme II

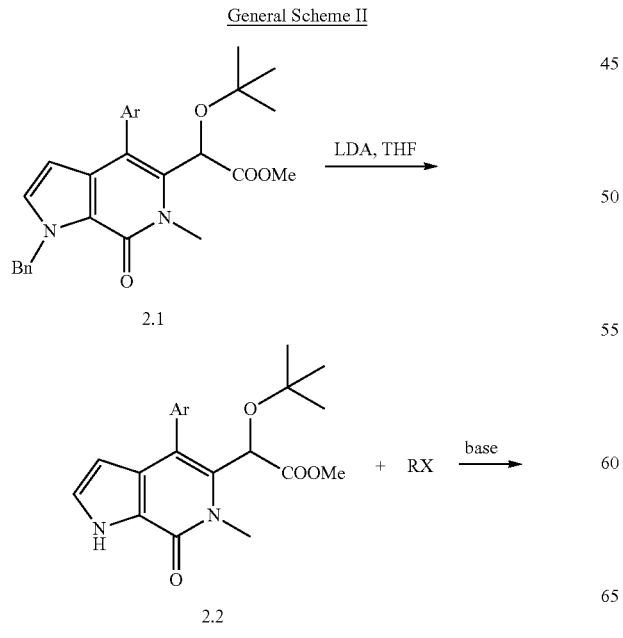

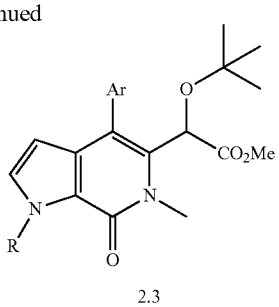

Example 2

2-(tert-butoxy)-2-(4-(4-chlorophenyl)-1-(4-fluorobenzyl)-6-methyl-7-oxo-6,7-dihydro-1H-pyrrolo[2,3-c]pyridin-5-yl)acetic acid

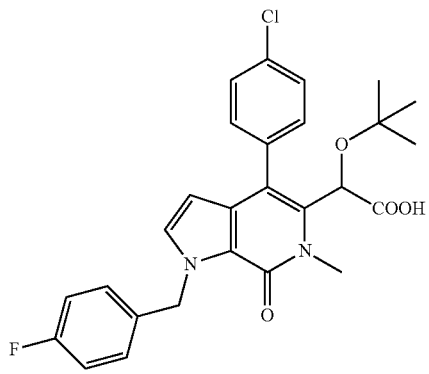 [SMILES: Cn1c(C(OC(C)(C)C)C(=O)O)c(-c2ccc(Cl)cc2)c2ccn(Cc3ccc(F)cc3)c2c1=O]

Step A methyl 2-(tert-butoxy)-2-(4-(4-chlorophenyl)-6-methyl-7-oxo-6,7-dihydro-1H-pyrrolo[2,3-c]pyridin-5-yl)acetate A 0° C. solution of methyl 2-(1-benzyl-4-(4-chlorophenyl)-6-methyl-7-oxo-6,7-dihydro-1H-pyrrolo[2,3-c]pyridin-5-yl)-2-(tert-butoxy)acetate (400 mg, 0.811 mmol) in Tetrahydrofuran (THF) (6 mL) was slowly treated with LDA (2.0 M solution in tetrahydrofuran/heptanes/ethylbenzene) (0.811 mL, 1.623 mmol) and the mixture was allowed to stir at 0° C.

for 20 min. The mixture was quenched with HCl (1M) and extracted with Ethyl acetate. The combined extracts were washed with brine, dried over Na$_2$SO$_4$, filtered and concentrated. The residue was purified on silica gel (0-10% Methanol/DCM) to afford methyl 2-(tert-butoxy)-2-(4-(4-chlorophenyl)-6-methyl-7-oxo-6,7-dihydro-1H-pyrrolo[2,3-c]pyridin-5-yl)acetate (205 mg, 0.511 mmol, 63% yield) as a pale yellow solid. $^1$H NMR (400 MHz, CHLOROFORM-d) ppm 9.46 (s, 1H), 7.50-7.46 (m, 2H), 7.45-7.38 (m, 2H), 7.21-7.19 (m, 1H), 6.10-6.05 (m, 1H), 3.84-3.82 (s, 3H), 3.73-3.71 (s, 3H), 0.96 (s, 9H); LCMS (m/z) ES$^+$=403 (M+1).

Step B methyl 2-(tert-butoxy)-2-(4-(4-chlorophenyl)-1-(4-fluorobenzyl)-6-methyl-7-oxo-6,7-dihydro-1H-pyrrolo[2,3-c]pyridin-5-yl)acetate

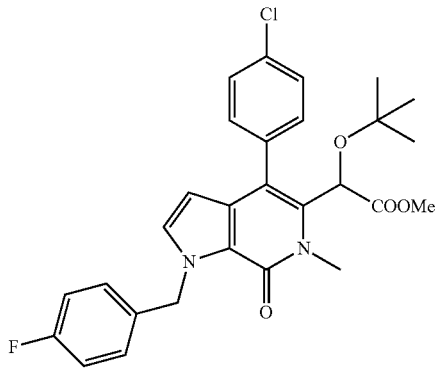 [SMILES: COC(=O)C(OC(C)(C)C)c1c(-c2ccc(Cl)cc2)c2ccn(Cc3ccc(F)cc3)c2c(=O)n1C]

A solution of methyl 2-(tert-butoxy)-2-(4-(4-chlorophenyl)-6-methyl-7-oxo-6,7-dihydro-1H-pyrrolo[2,3-c]pyridin-5-yl)acetate (20 mg, 0.043 mmol) in Acetonitrile (0.5 mL) was treated with 4-fluorobenzyl chloride (0.025 mL, 0.213 mmol) and Cs$_2$CO$_3$ (69 mg, 0.213 mmol) and then stirred at 70° C. for 2 hours. The mixture was diluted with water and then extracted with Ethyl acetate. The combined extracts were washed with brine, dried over Na$_2$SO$_4$, filtered and concentrated to afford methyl 2-(tert-butoxy)-2-(4-(4-chlorophenyl)-1-(4-fluorobenzyl)-6-methyl-7-oxo-6,7-dihydro-1H-pyrrolo[2,3-c]pyridin-5-yl)acetate as pale a yellow solid which was used with no further purification. LCMS (m/z) ES$^+$=511 (M+1).

Step C 2-(tert-butoxy)-2-(4-(4-chlorophenyl)-1-(4-fluorobenzyl)-6-methyl-7-oxo-6,7-dihydro-1H-pyrrolo[2,3-c]pyridin-5-yl)acetic acid The title compound was prepared in a manner similar to that described in Example 1 and was isolated as a white solid (6.1 mg, 0.012 mmol, 29% yield) after purification by reverse phase chromatography (10-90% MeCN/H$_2$O-0.1% TFA, 12 min). $^1$H NMR (400 MHz, CHLOROFORM-d) ppm 7.58-7.67 (m, 1H) 7.43-7.51 (m, 2H) 7.37-7.44 (m, 1H) 7.24-7.33 (m, 2H) 6.97-7.05 (m, 3H) 5.96-6.02 (m, 1H) 5.75-5.86 (m, 2H) 5.30-5.36 (m, 1H) 3.67 (s, 3H) 1.00 (s, 9H); LCMS (m/z) ES$^+$=497 (M+1).

Example 3

2-(tert-butoxy)-2-(4-(4-chlorophenyl)-1-(4-methoxybenzyl)-6-methyl-7-oxo-6,7-dihydro-1H-pyrrolo[2,3-c]pyridin-5-yl)acetic acid

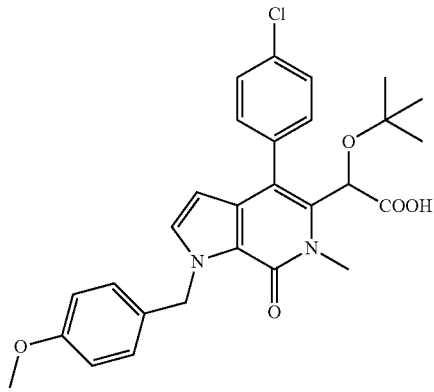 [SMILES: COc1ccc(Cn2ccc3c(-c4ccc(Cl)cc4)c(C(OC(C)(C)C)C(=O)O)n(C)c(=O)c32)cc1]

The title compound was prepared in a manner similar to that described in Example 2 from methyl 2-(tert-butoxy)-2-(4-(4-chlorophenyl)-6-methyl-7-oxo-6,7-dihydro-1H-pyrrolo[2,3-c]pyridin-5-yl)acetate and 4-methoxybenzyl chloride. $^1$H NMR (400 MHz, CHLOROFORM-d) ppm 7.57-7.64 (m, 1H) 7.43-7.49 (m, 2H) 7.37-7.43 (m, 1H) 7.24-7.29 (m, 2H) 6.99-7.06 (m, 1H) 6.83-6.90 (m, 2H) 5.93-6.00 (m, 1H) 5.70-5.83 (m, 2H) 5.30-5.36 (m, 1H) 3.79 (s, 3H) 3.68 (s, 3H) 1.01 (s, 9H); LCMS (m/z) ES$^+$=509 (M+1).

Example 4

2-(tert-butoxy)-2-(4-(4-chlorophenyl)-1-(2-methoxyethyl)-6-methyl-7-oxo-6,7-dihydro-1H-pyrrolo[2,3-c]pyridin-5-yl)acetic acid

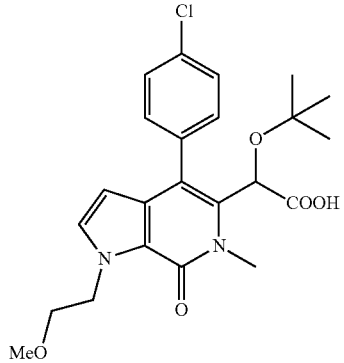 [SMILES: COCCn1ccc2c(-c3ccc(Cl)cc3)c(C(OC(C)(C)C)C(=O)O)n(C)c(=O)c21]

The title compound was prepared in a manner similar to that described in Example 2 from methyl 2-(tert-butoxy)-2-(4-(4-chlorophenyl)-6-methyl-7-oxo-6,7-dihydro-1H-pyrrolo[2,3-c]pyridin-5-yl)acetate and 2-bromoethyl methyl ether. $^1$H NMR (400 MHz, CHLOROFORM-d) ppm 7.59-7.65 (m, 1H) 7.45-7.51 (m, 2H) 7.39-7.45 (m, 1H) 7.10-7.16 (m, 1H) 5.91-5.99 (m, 1H) 5.30-5.38 (m, 1H) 4.67-4.87 (m, 2H) 3.72-3.86 (m, 2H) 3.67 (s, 3H)) 3.34 (s, 3H) 1.01 (s, 9H); LCMS (m/z) ES$^+$=447 (M+1).

Example 5

2-(tert-butoxy)-2-(4-(4-chlorophenyl)-1-isobutyl-6-methyl-7-oxo-6,7-dihydro-1H-pyrrolo[2,3-c]pyridin-5-yl)acetic acid

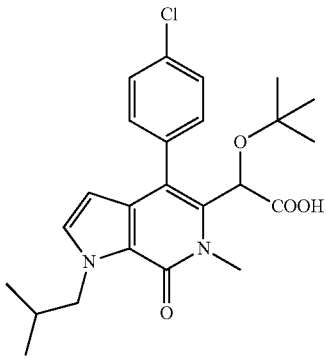 [SMILES: CC(C)Cn1ccc2c(-c3ccc(Cl)cc3)c(C(OC(C)(C)C)C(=O)O)n(C)c(=O)c21]

The title compound was prepared in a manner similar to that described in Example 2 from methyl 2-(tert-butoxy)-2-(4-(4-chlorophenyl)-6-methyl-7-oxo-6,7-dihydro-1H-pyrrolo[2,3-c]pyridin-5-yl)acetate and 1-bromo-2-methylpropane. $^1$H NMR (400 MHz, CHLOROFORM-d) ppm 7.59-7.67 (m, 1H) 7.45-7.51 (m, 2H) 7.39-7.45 (m, 1H) 6.97-7.04 (m, 1H) 5.91-5.98 (m, 1H) 5.30-5.39 (m, 1H) 4.23-4.44 (m, 2H) 3.67 (s, 3H) 2.16-2.31 (m, 1H) 1.01 (s, 9H) 0.88-0.98 (m, 6H); LCMS (m/z) ES$^+$=445 (M+1).

Example 6

(S)-2-(tert-butoxy)-2-(4-(4-chlorophenyl)-1-(3,4-difluorobenzyl)-6-methyl-7-oxo-6,7-dihydro-1H-pyrrolo[2,3-c]pyridin-5-yl)acetic acid

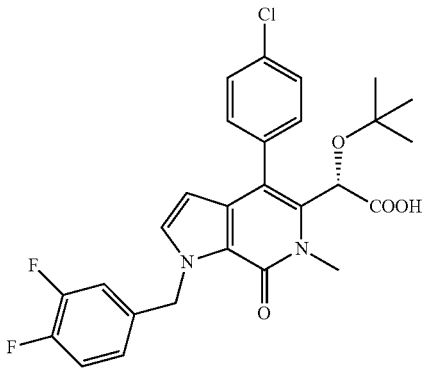 [SMILES: Cn1c([C@H](OC(C)(C)C)C(=O)O)c(-c2ccc(Cl)cc2)c2ccn(Cc3ccc(F)c(F)c3)c2c1=O]

The title compound was prepared in a manner similar to that described in Example 2 from methyl 2-(tert-butoxy)-2-(4-(4-chlorophenyl)-6-methyl-7-oxo-6,7-dihydro-1H-pyrrolo[2,3-c]pyridin-5-yl)acetate and 3,4-difluorobenzyl bromide. The crude racemic mixture was purified by chiral chromatography to give (S)-2-(tert-butoxy)-2-(4-(4-chlorophenyl)-1-(3,4-difluorobenzyl)-6-methyl-7-oxo-6,7-dihydro-1H-pyrrolo[2,3-c]pyridin-5-yl)acetic acid. $^1$H NMR (400 MHz, CHLOROFORM-d) ppm 7.68-7.59 (m, 1H), 7.52-7.45 (m, 1H), 7.46-7.39 (m, 1H), 7.17-6.98 (m, 4H), 6.06-5.99 (m, 1H), 5.86-5.71 (m, 1H), 5.38-5.32 (s, 1H), 3.64 (s, 3H), 1.02 (s, 9H); LCMS (m/z) ES$^+$=515 (M+1).

Example 7

2-(tert-butoxy)-2-(4-(4-chlorophenyl)-6-methyl-7-oxo-1-(2-(piperidin-1-yl)ethyl)-6,7-dihydro-1H-pyrrolo[2,3-c]pyridin-5-yl)acetic acid

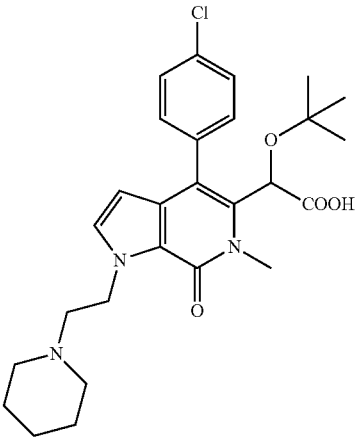 [SMILES: Cn1c(C(OC(C)(C)C)C(=O)O)c(-c2ccc(Cl)cc2)c2ccn(CCN3CCCCC3)c2c1=O]

The title compound was prepared in a manner similar to that described in Example 2 from methyl 2-(tert-butoxy)-2-(4-(4-chlorophenyl)-6-methyl-7-oxo-6,7-dihydro-1H-pyrrolo[2,3-c]pyridin-5-yl)acetate and 1-(2-bromoethyl)piperidine. $^1$H NMR (400 MHz, METHANOL-d$_4$) ppm 7.62-7.52 (m, 3H), 7.48-7.41 (m, 1H), 7.39-7.31 (m, 1H), 6.09-6.03 (m, 1H), 5.27 (s, 1H), 5.00-4.91 (m, 2H), 3.75 (s, 3H), 3.68-3.53 (m, 4H), 3.12-2.95 (m, 2H), 2.04-1.92 (m, 2H), 1.92-1.75 (m, 2H), 1.62-1.46 (m, 2H), 0.96 (s, 9H); LCMS (m/z) ES$^+$=500 (M+1).

Example 8

2-(tert-butoxy)-2-(4-(4-chlorophenyl)-1-(2,5-difluorobenzyl)-6-methyl-7-oxo-6,7-dihydro-1H-pyrrolo[2,3-c]pyridin-5-yl)acetic acid

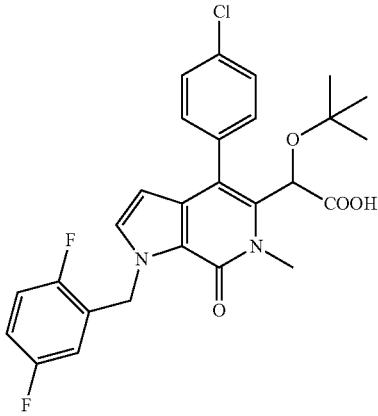 [SMILES: Cn1c(C(OC(C)(C)C)C(=O)O)c(-c2ccc(Cl)cc2)c2ccn(Cc3cc(F)ccc3F)c2c1=O]

The title compound was prepared in a manner similar to that described in Example 2 from methyl 2-(tert-butoxy)-2-(4-(4-chlorophenyl)-6-methyl-7-oxo-6,7-dihydro-1H-pyrrolo[2,3-c]pyridin-5-yl)acetate and 2,5-difluorobenzyl bromide. $^1$H NMR (400 MHz, CHLOROFORM-d) ppm 7.65-7.60 (m, 1H), 7.50-7.45 (m, 2H), 7.44-7.38 (m, 1H), 7.13-7.10 (m, 1H), 7.07-6.99 (m, 2H), 6.97-6.89 (m, 1H), 6.03-5.99 (m, 1H), 5.93-5.82 (m, 2H), 5.35-5.32 (m, 1H), 3.66 (s, 3H), 1.02 (s, 9H); LCMS (m/z) ES$^+$=515 (M+1).

Example 9

2-(tert-butoxy)-2-(4-(4-chlorophenyl)-6-methyl-7-oxo-1-((5-(trifluoromethyl)furan-2-yl)methyl)-6,7-dihydro-1H-pyrrolo[2,3-c]pyridin-5-yl)acetic acid

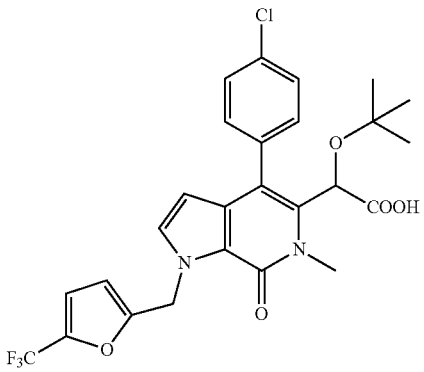 [SMILES: Cn1c(C(OC(C)(C)C)C(=O)O)c(-c2ccc(Cl)cc2)c2ccn(Cc3ccc(C(F)(F)F)o3)c2c1=O]

The title compound was prepared in a manner similar to that described in Example 2 from methyl 2-(tert-butoxy)-2-(4-(4-chlorophenyl)-6-methyl-7-oxo-6,7-dihydro-1H-pyrrolo[2,3-c]pyridin-5-yl)acetate and 2-(bromomethyl)-5-(trifluoromethyl)furan. $^1$H NMR (400 MHz, CHLOROFORM-d) ppm 7.51-7.61 (m, 1H) 7.39-7.47 (m, 2H) 7.32-7.39 (m, 1H) 7.08-7.15 (m, 1H) 6.65-6.73 (m, 1H) 6.43-6.51 (m, 1H) 5.94-6.00 (m, 1H) 5.75-5.91 (m, 2H) 5.26 (s, 1H) 3.63 (s, 3H) 0.96 (s, 9H); LC/MS (m/z) ES$^+$=537 (M+1).

Example 10

2-(tert-butoxy)-2-(4-(4-chlorophenyl)-1-(imidazo[1,2-a]pyridin-2-ylmethyl)-6-methyl-7-oxo-6,7-dihydro-1H-pyrrolo[2,3-c]pyridin-5-yl)acetic acid

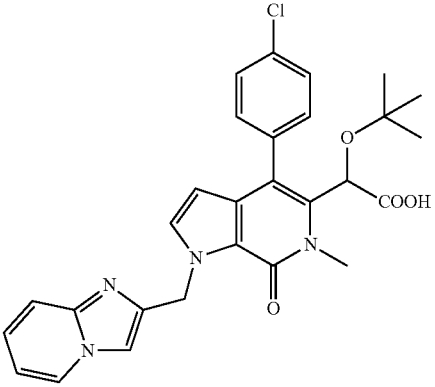 [SMILES: Cn1c(C(OC(C)(C)C)C(=O)O)c(-c2ccc(Cl)cc2)c2ccn(Cc3cn4ccccc4n3)c2c1=O]

The title compound was prepared in a manner similar to that described in Example 2 using methyl 2-(tert-butoxy)-2-(4-(4-chlorophenyl)-6-methyl-7-oxo-6,7-dihydro-1H-pyrrolo[2,3-c]pyridin-5-yl)acetate and 2-(chloromethyl)imidazo[1,2-a]pyridine. $^1$H NMR (400 MHz, CHLOROFORM-d) ppm 8.33-8.40 (m, 1H) 8.18-8.25 (m, 1H) 8.10-8.17 (m, 1H) 7.70-7.79 (m, 1H) 7.59-7.65 (m, 1H) 7.51-7.56 (m, 1H) 7.44-7.50 (m, 2H) 7.34-7.41 (m, 1H) 7.29-7.34 (m, 1H) 6.18-6.25 (m, 1H) 6.00-6.05 (m, 1H) 5.88-5.98 (m, 1H) 5.35 (s, 1H) 3.67 (s, 3H) 1.02 (s, 9H); LCMS (m/z) ES$^+$=519 (M+1).

Example 11

2-(tert-butoxy)-2-(4-(4-chlorophenyl)-6-methyl-1-((2-methylthiazol-4-yl)methyl)-7-oxo-6,7-dihydro-1H-pyrrolo[2,3-c]pyridin-5-yl)acetic acid

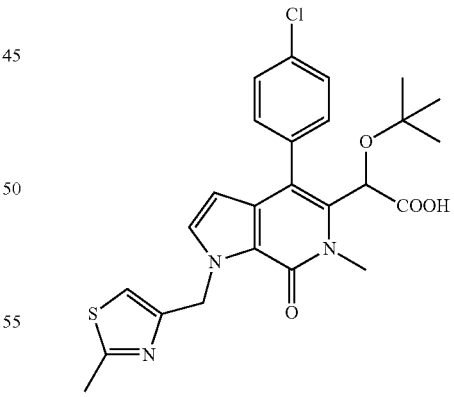

The title compound was prepared in a manner similar to that described in Example 2 from methyl 2-(tert-butoxy)-2-(4-(4-chlorophenyl)-6-methyl-7-oxo-6,7-dihydro-1H-pyrrolo[2,3-c]pyridin-5-yl)acetate and 4-(chloromethyl)-2-methylthiazole. $^1$H NMR (400 MHz, CHLOROFORM-d) ppm 7.61-7.74 (m, 1H) 7.33-7.45 (m, 3H) 7.11-7.21 (m, 1H) 7.00-7.08 (m, 1H) 5.93-6.00 (m, 1H) 5.73-5.89 (m, 2H) 3.65 (s, 3H) 2.63 (s, 3H) 0.86 (s, 9H); LCMS (m/z) ES$^+$=500 (M+1).

Example 12

2-(tert-butoxy)-2-(4-(4-chlorophenyl)-1-(2-((2-hydroxy-4-methylphenyl)amino)-2-oxoethyl)-6-methyl-7-oxo-6,7-dihydro-1H-pyrrolo[2,3-c]pyridin-5-yl)acetic acid

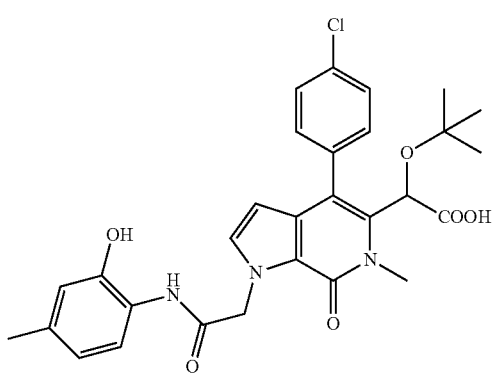 [SMILES: Cc1ccc(NC(=O)Cn2ccc3c(-c4ccc(Cl)cc4)c(C(OC(C)(C)C)C(=O)O)n(C)c(=O)c32)c(O)c1]

The title compound was prepared in a manner similar to that described in Example 2 from methyl 2-(tert-butoxy)-2-(4-(4-chlorophenyl)-6-methyl-7-oxo-6,7-dihydro-1H-pyrrolo[2,3-c]pyridin-5-yl)acetate and 2-(chloromethyl)-6-methyl-1,3-benzoxazole. $^1$H NMR (400 MHz, CHLOROFORM-d) ppm 7.78-7.85 (m, 1H) 7.54-7.61 (m, 1H) 7.45-7.53 (m, 3H) 7.25-7.32 (m, 1H) 6.63-6.67 (m, 1H) 6.55-6.62 (m, 1H) 6.02-6.08 (m, 1H) 5.32-5.44 (m, 2H) 5.15-5.20 (m, 1H) 3.68 (s, 3H) 2.18-2.25 (s, 3H) 0.92 (s, 9H); LC/MS (m/z) ES$^+$=552 (M+1).

Example 13

2-(tert-butoxy)-2-(4-(4-chlorophenyl)-6-methyl-7-oxo-1-(1-phenylethyl)-6,7-dihydro-1H-pyrrolo[2,3-c]pyridin-5-yl)acetic acid

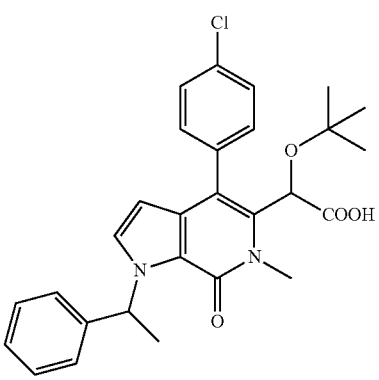 [SMILES: CC(c1ccccc1)n1ccc2c(-c3ccc(Cl)cc3)c(C(OC(C)(C)C)C(=O)O)n(C)c(=O)c21]

The title compound was prepared in a manner similar to that described in Example 2 from methyl 2-(tert-butoxy)-2-(4-(4-chlorophenyl)-6-methyl-7-oxo-6,7-dihydro-1H-pyrrolo[2,3-c]pyridin-5-yl)acetate and (1-bromoethyl)benzene and was isolated as a white solid (4.5 mg, 37% yield). $^1$H NMR (400 MHz, CHLOROFORM-d) ppm 7.65-7.58 (m, 1H), 7.50-7.44 (m, 2H), 7.44-7.38 (m, 1H), 7.38-7.28 (m, 4H), 7.18-7.12 (m, 1H), 7.12-7.04 (m, 1H), 6.02-5.96 (m, 1H), 5.34 (s, 1H), 4.58-4.22 (m, 1H), 3.69 (s, 3H), 1.93-1.82 (m, 3H), 1.02-1.04 (m, 9H); LCMS (m/z) ES$^+$=493 (M+1).

General Scheme III

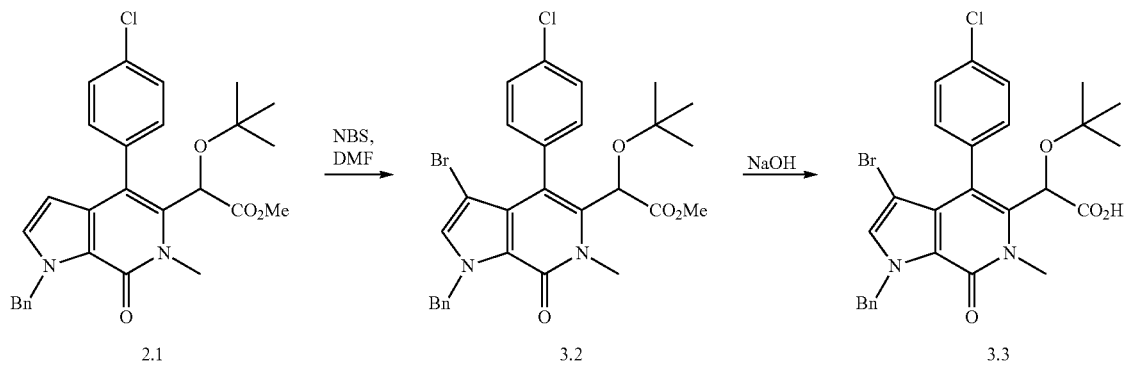

-continued

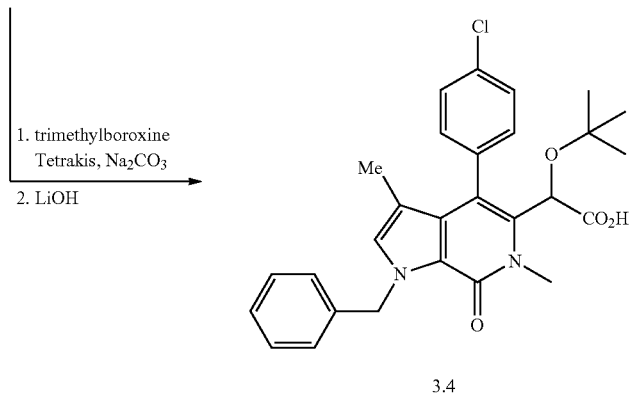

3.4

Example 14

2-(1-benzyl-3-bromo-4-(4-chlorophenyl)-6-methyl-7-oxo-6,7-dihydro-1H-pyrrolo[2,3-c]pyridin-5-yl)-2-(tert-butoxy)acetic acid

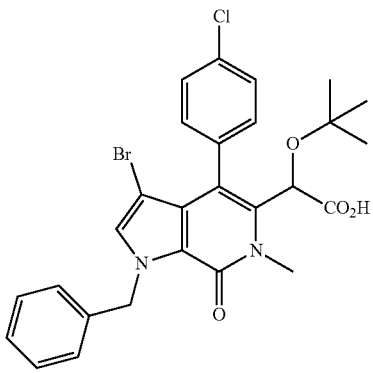 [SMILES: Cn1c(C(OC(C)(C)C)C(=O)O)c(-c2ccc(Cl)cc2)c2c(Br)cn(Cc3ccccc3)c2c1=O]

Step A methyl 2-(1-benzyl-3-bromo-4-(4-chlorophenyl)-6-methyl-7-oxo-6,7-dihydro-1H-pyrrolo[2,3-c]pyridin-5-yl)-2-(tert-butoxy)acetate

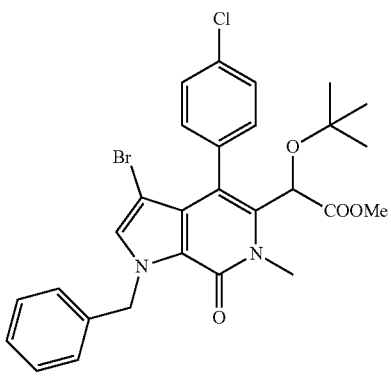 [SMILES: COC(=O)C(OC(C)(C)C)c1c(-c2ccc(Cl)cc2)c2c(Br)cn(Cc3ccccc3)c2c(=O)n1C]

A solution of methyl 2-(1-benzyl-4-(4-chlorophenyl)-6-methyl-7-oxo-6,7-dihydro-1H-pyrrolo[2,3-c]pyridin-5-yl)-2-(tert-butoxy)acetate (480 mg, 0.974 mmol) in N,N-Dimethylformamide (DMF) (1 mL) was treated with NBS (173 mg, 0.974 mmol) and then stirred at room temperature for 20 minutes. Water was added and then mixture was extracted with ethyl acetate. The combined extracts were washed with brine, dried over $Na_2SO_4$, filtered and concentrated. The residue was purified on silica gel (0-50% ethyl acetate/hexanes) to afford methyl 2-(1-benzyl-3-bromo-4-(4-chlorophenyl)-6-methyl-7-oxo-6,7-dihydro-1H-pyrrolo[2,3-c]pyridin-5-yl)-2-(tert-butoxy)acetate (450 mg, 0.787 mmol, 81% yield) as a pale yellow solid. $^1$H NMR (400 MHz, CHLOROFORM-d) ppm 7.45-7.28 (m, 9H), 7.03-7.01 (m, 1H), 5.91-5.76 (m, 2H), 5.09 (s, 1H), 3.77 (s, 3H), 3.65 (s, 3H), 1.00 (s, 9H); LCMS (m/z) ES+=571 (M+1).

Step B 2-(1-benzyl-3-bromo-4-(4-chlorophenyl)-6-methyl-7-oxo-6,7-dihydro-1H-pyrrolo[2,3-c]pyridin-5-yl)-2-(tert-butoxy)acetic acid The title compound was prepared in a manner similar to that described in Example 1 Step N. $^1$H NMR (400 MHz, DMSO-$d_6$) ppm 7.89-7.82 (m, 1H), 7.66-7.62 (m, 1H), 7.50-7.41 (m, 2H), 7.33-7.35 (m, 4H), 7.30-7.24 (m, 2H), 5.76 (s, 2H), 4.62 (s, 1H), 3.56 (s, 3H), 0.84 (s, 9H); LCMS (m/z) ES+=557 (M+1).

Example 15

2-(1-benzyl-4-(4-chlorophenyl)-3,6-dimethyl-7-oxo-6,7-dihydro-1H-pyrrolo[2,3-c]pyridin-5-yl)-2-(tert-butoxy)acetic acid

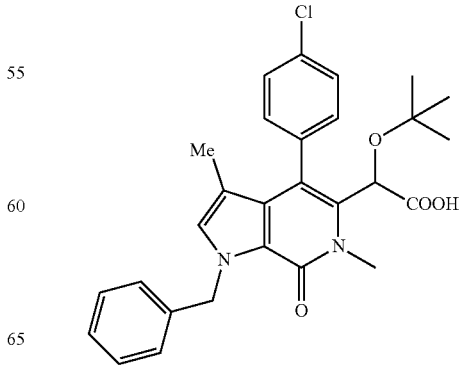

A mixture of the methyl 2-(1-benzyl-3-bromo-4-(4-chlorophenyl)-6-methyl-7-oxo-6,7-dihydro-1H-pyrrolo[2,3-c]pyridin-5-yl)-2-(tert-butoxy)acetate (15 mg, 0.026 mmol), trimethylboroxine (3.65 μL, 0.026 mmol) and $Na_2CO_3$ (5.56 mg, 0.052 mmol) in N,N-Dimethylformamide (DMF) (1 mL), was degassed with $N_2$ for 5 minutes. Palladium tetrakis (3.03 mg, 2.62 μmol) was added and the mixture was degassed again with $N_2$ for 5 minutes. The mixture was irradiated in the microwave at 140° C. for 30 minutes. The mixture was diluted with Methanol (1.000 mL), and Tetrahydrofuran (THF) (1.000 mL), treated with 2M LiOH (1 mL, 2.000 mmol) and then stirred at room temperature overnight. The mixture was treated with HCl (1M) until pH<2 and extracted with ethyl acetate. The combined extracts were concentrated and purified by reverse phase chromatography (10-90% $MeCN/H_2O$-0.1% TFA, 12 min) to afford 2-(1-benzyl-4-(4-chlorophenyl)-3,6-dimethyl-7-oxo-6,7-dihydro-1H-pyrrolo[2,3-c]pyridin-5-yl)-2-(tert-butoxy)acetic acid (4.0 mg, 0.007 mmol, 30% yield) as a white solid. $^1$H NMR (400 MHz, CHLOROFORM-d) ppm 7.63-7.57 (m, 1H), 7.49-7.41 (m, 2H), 7.38-7.29 (m, 6H), 6.81 (s, 1H), 5.81 (s, 2H), 5.18 (s, 1H), 3.67 (s, 3H), 1.44 (s, 3H), 1.07 (s, 9H); LCMS (m/z) $ES^+$=493 (M+1).

Scheme 4

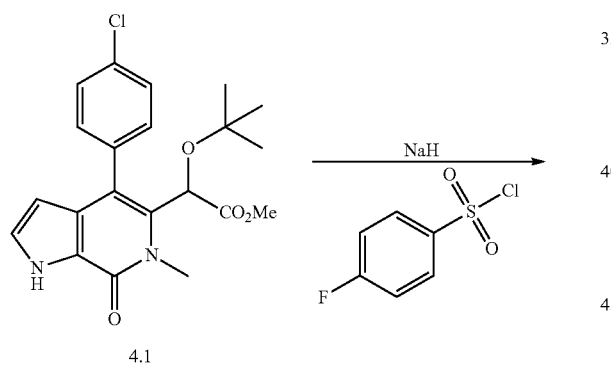

4.1

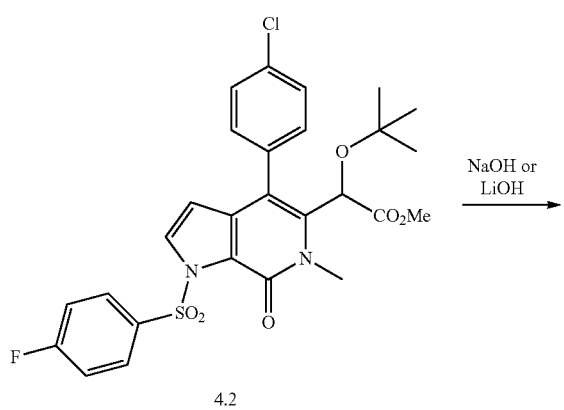

4.2

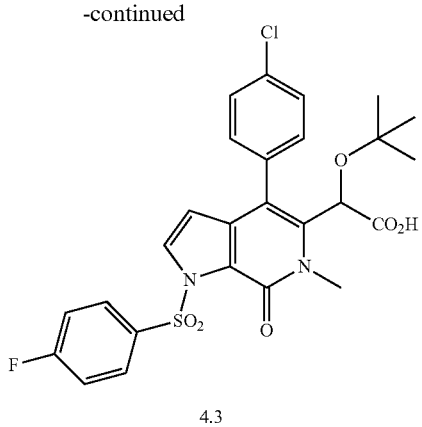

4.3

Example 16

2-(tert-butoxy)-2-(4-(4-chlorophenyl)-1-((4-fluorophenyl)sulfonyl)-6-methyl-7-oxo-6,7-dihydro-1H-pyrrolo[2,3-c]pyridin-5-yl)acetic acid

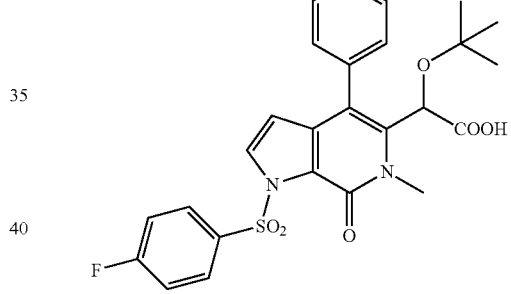

An ice cold solution of methyl 2-(tert-butoxy)-2-(4-(4-chlorophenyl)-6-methyl-7-oxo-6,7-dihydro-1H-pyrrolo[2,3-c]pyridin-5-yl)acetate (20 mg, 0.043 mmol) in Tetrahydrofuran (THF) (0.5 mL) was treated with NaH (9.93 mg, 0.248 mmol) and allowed to stir at 0° C. for 10 minutes. The mixture was then treated with 4-fluorobenzenesulfonyl chloride (39.4 mg, 0.199 mmol) in one portion. The mixture was stirred for 10 minutes, quenched with water and then extracted with ethyl acetate. The combined extracts were washed with brine, dried over $Na_2SO_4$, filtered and concentrated. The resultant was dissolved in Tetrahydrofuran (THF) (0.500 mL), treated with 2M LiOH (0.4 mL, 0.800 mmol) (2 M) and then stirred at ambient temperature overnight. The mixture was cooled to 0° C., treated with HCl (1M) until pH<2 and then extracted with ethyl acetate. The combined extracts were washed with brine, dried over $Na_2SO_4$, filtered and concentrated. The residue was purified by reverse phase chromatography (10-90% $MeCN/H_2O$-0.1% TFA, 12 min) to afford the title compound. $^1$H NMR (400 MHz, CHLOROFORM-d) ppm 8.16-8.29 (m, 2H) 7.81-7.92 (m, 1H) 7.51-7.58 (m, 1H) 7.45-7.51 (m, 2H) 7.28-7.35 (m, 1H) 7.17-7.25 (m, 2H) 6.09-6.18 (m, 1H) 5.21-5.32 (m, 1H) 3.54-3.65 (s, 3H) 0.99 (s, 9H); LCMS (m/z) $ES^+$=547 (M+1).

Example 17

2-(tert-butoxy)-2-(4-(4-chlorophenyl)-6-methyl-7-oxo-1-tosyl-6,7-dihydro-1H-pyrrolo[2,3-c]pyridin-5-yl)acetic acid

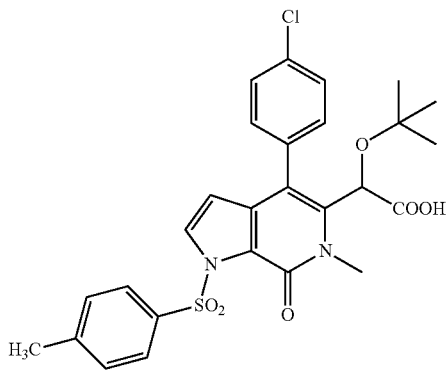 [SMILES: Cc1ccc(S(=O)(=O)n2ccc3c(-c4ccc(Cl)cc4)c(C(OC(C)(C)C)C(=O)O)n(C)c(=O)c32)cc1]

The title compound was prepared in a manner similar to that described in Example 16 from methyl 2-(tert-butoxy)-2-(4-(4-chlorophenyl)-6-methyl-7-oxo-6,7-dihydro-1H-pyrrolo[2,3-c]pyridin-5-yl)acetate and 4-methylbenzenesulfonyl chloride. $^1$H NMR (400 MHz, CHLOROFORM-d) ppm 7.98-8.08 (m, 2H) 7.84-7.92 (m, 1H) 7.52-7.59 (m, 1H) 7.43-7.52 (m, 2H) 7.30-7.37 (m, 3H) 6.07-6.17 (m, 1H) 5.21-5.28 (m, 1H) 3.53-3.65 (m, 3H) 3.47-3.63 (m, 3H) 2.42 (s, 3H) 0.98 (s, 9H); LCMS (m/z) ES$^+$=543 (M+1).

Scheme 5

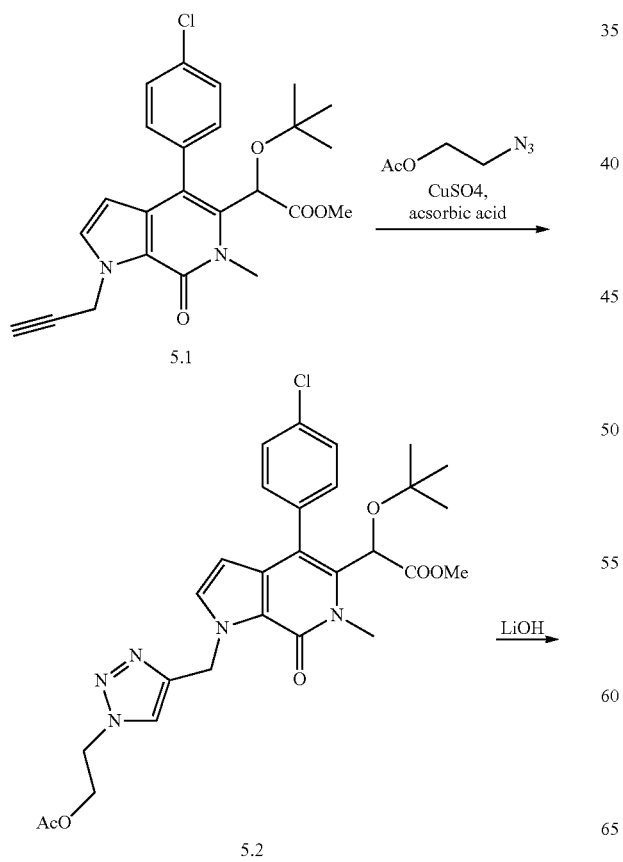

Example 18

2-(tert-butoxy)-2-(4-(4-chlorophenyl)-1-((1-(2-hydroxyethyl)-1H-1,2,3-triazol-4-yl)methyl)-6-methyl-7-oxo-6,7-dihydro-1H-pyrrolo[2,3-c]pyridin-5-yl)acetic acid

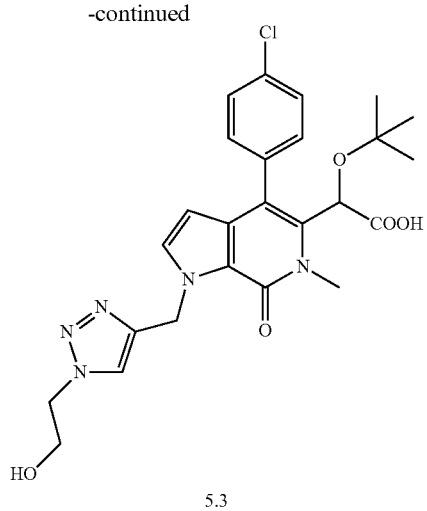

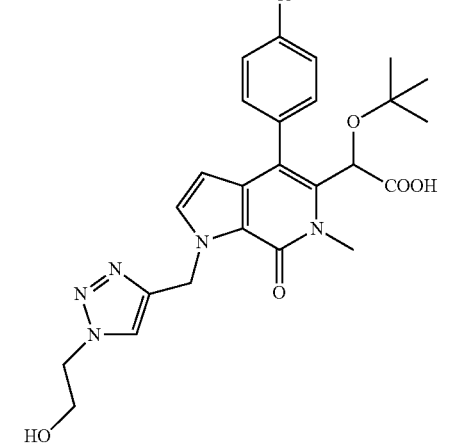

Step A methyl 2-(tert-butoxy)-2-(4-(4-chlorophenyl)-6-methyl-7-oxo-1-(prop-2-yn-1-yl)-6,7-dihydro-1H-pyrrolo[2,3-c]pyridin-5-yl)acetate

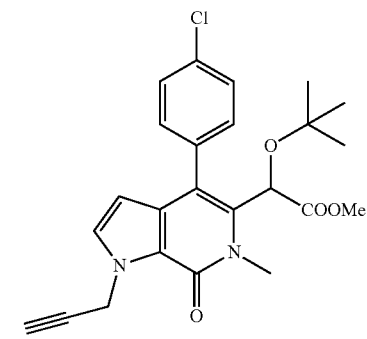 [SMILES: C#CCn1ccc2c(-c3ccc(Cl)cc3)c(C(OC(C)(C)C)C(=O)OC)n(C)c(=O)c21]

The title compound was prepared in a manner similar to that described in Example 2 step B from propargyl bromide. ¹H NMR (400 MHz, CHLOROFORM-d) ppm 7.51-7.35 (m, 4H), 7.30-7.26 (m, 2H), 6.01-5.96 (s, 1H), 5.54 (s, 2H), 5.19 (s, 1H), 3.81 (s, 3H), 3.66 (s, 3H), 0.96 (s, 9H); LCMS (m/z) ES⁺=441 (M+1).

Step B 2-(tert-butoxy)-2-(4-(4-chlorophenyl)-1-((1-(2-hydroxyethyl)-1H-1,2,3-triazol-4-yl)methyl)-6-methyl-7-oxo-6,7-dihydro-1H-pyrrolo[2,3-c]pyridin-5-yl)acetic acid A suspension of methyl 2-(tert-butoxy)-2-(4-(4-chlorophenyl)-6-methyl-7-oxo-1-(prop-2-yn-1-yl)-6,7-dihydro-1H-pyrrolo[2,3-c]pyridin-5-yl)acetate (20 mg, 0.045 mmol), 2-azidoethyl acetate (8.53 µL, 0.074 mmol), copper(II) sulfate pentahydrate (1.240 mg, 4.96 µmol) and L-(+)-ascorbic acid (0.874 mg, 4.96 µmol) in Ethanol (1.000 mL) and Water (0.2 mL) was irradiated in the microwave at 120° C. for 20 minutes. The mixture was diluted with Methanol (1.000 mL), and Tetrahydrofuran (THF) (1.000 mL), treated with 2M LiOH (1 mL, 2.000 mmol) and then stirred at ambient temperature overnight. The mixture was treated with 1M HCl until pH<2, extracted with ethyl acetate, concentrated and purified by reverse phase chromatography (10-90% MeCN/H₂O-0.1% TFA, 12 min) to afford 2-(tert-butoxy)-2-(4-(4-chlorophenyl)-1-((1-(2-hydroxyethyl)-1H-1,2,3-triazol-4-yl)methyl)-6-methyl-7-oxo-6,7-dihydro-1H-pyrrolo[2,3-c]pyridin-5-yl)acetic acid (4.3 mg, 0.08 mmol, 7% yield) as a white solid. ¹H NMR (400 MHz, CHLOROFORM-d) ppm 7.88-7.83 (m, 1H), 7.62-7.56 (m, 1H), 7.50-7.44 (m, 2H), 7.41-7.36 (m, 1H), 7.34-7.31 (m, 1H), 7.23-7.20 (m, 1H), 6.07-5.99 (m, 1H), 5.99-5.94 (m, 1H), 5.78-5.69 (m, 1H), 5.37-5.32 (s, 1H), 4.49-4.43 (m, 2H), 4.09-4.04 (m, 2H), 3.67 (s, 3H), 1.02 (s, 9H); LCMS (m/z) ES⁺=514 (M+1).

Example 19

2-(1-benzyl-6-methyl-7-oxo-4-(p-tolyl)-6,7-dihydro-1H-pyrrolo[2,3-c]pyridin-5-yl)-2-(tert-butoxy)acetic acid

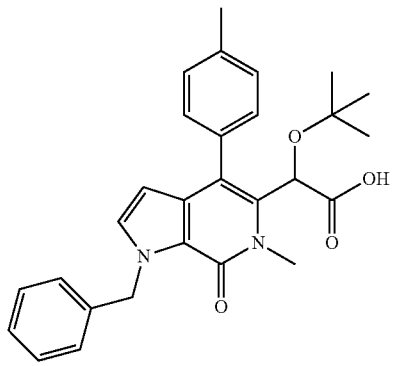 [SMILES: Cc1ccc(-c2c(C(OC(C)(C)C)C(=O)O)n(C)c(=O)c3c2ccn3Cc2ccccc2)cc1]

The title compound was prepared in a manner similar to that described in Example 1 except that 4-methylphenylboronic acid was used in step H. The desired product was isolated as an off-white solid (18.3 mg, 64% yield) after purification by reverse phase chromatography (10-90% MeCN/H₂O-0.1% TFA, 12 min). ¹H NMR (400 MHz, CHLOROFORM-d) ppm 7.59-7.49 (m, 1H), 7.37-7.24 (m, 8H), 7.02 (d, J=2.9 Hz, 1H), 6.03 (d, J=2.9 Hz, 1H), 5.93-5.86 (m, 1H), 5.85-5.78 (m, 1H), 3.67 (s, 3H), 2.43 (s, 3H), 0.99 (s, 9H); LC/MS (m/z) ES⁺=459 (M+1).

Scheme 6

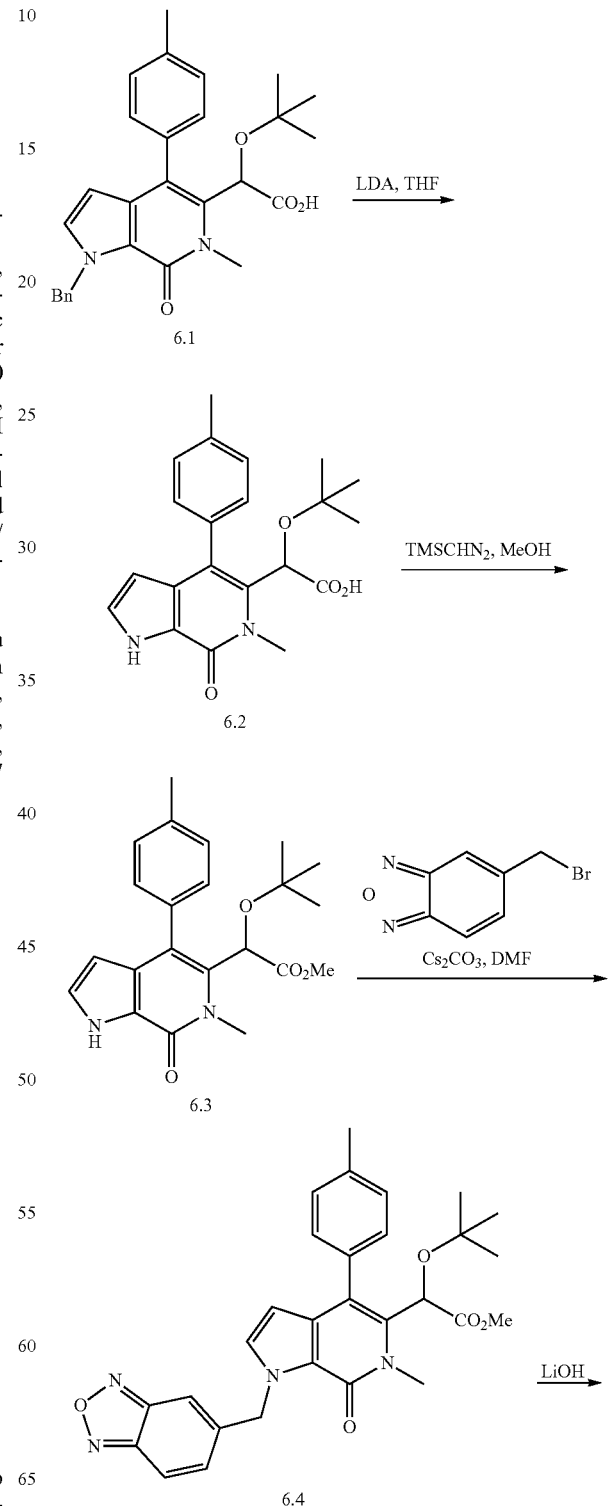

-continued

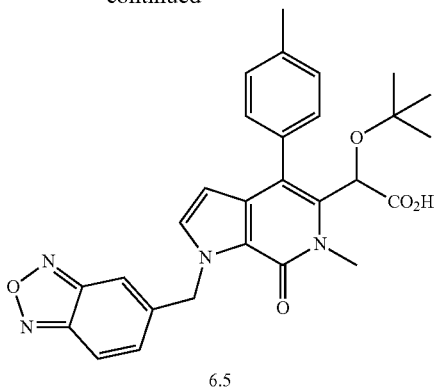

6.5

Example 20

2-(1-(benzo[c][1,2,5]oxadiazol-5-ylmethyl)-6-methyl-7-oxo-4-(p-tolyl)-6,7-dihydro-1H-pyrrolo[2,3-c]pyridin-5-yl)-2-(tert-butoxy)acetic acid

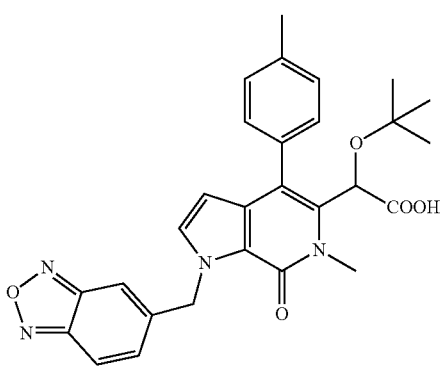 [SMILES: Cc1ccc(-c2c(C(OC(C)(C)C)C(=O)O)n(C)c(=O)c3c2ccn3Cc2ccc3nonc3c2)cc1]

Step A 2-(tert-butoxy)-2-(6-methyl-7-oxo-4-(p-tolyl)-6,7-dihydro-1H-pyrrolo[2,3-c]pyridin-5-yl)acetic acid

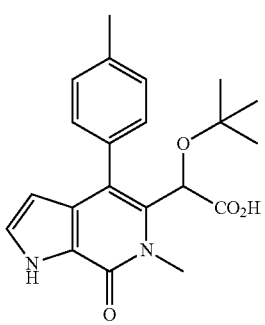 [SMILES: Cc1ccc(-c2c(C(OC(C)(C)C)C(=O)O)n(C)c(=O)c3[nH]ccc23)cc1]

An ice cold mixture of 2-(1-benzyl-6-methyl-7-oxo-4-(p-tolyl)-6,7-dihydro-1H-pyrrolo[2,3-c]pyridin-5-yl)-2-(tert-butoxy)acetic acid (200 mg, 0.423 mmol) in Tetrahydrofuran (THF) (2.0 mL) was treated with dropwise addition of LDA, 2M solution in heptane/THF/ethylbenzene (0.423 mL, 0.846 mmol) and then allowed to stir at 0° C. for 20 minutes. Additional LDA (0.212 mL, 0.423 mmol) was added and then stirred an additional 20 minutes. The mixture was quenched by adding 1N HCl, acidified to pH 2 and then extracted with ethyl acetate. The combined extracts were washed with brine, dried over sodium sulfate, filtered and concentrated to give the crude debenzylation product which was used crude in the next step. LC/MS (m/z) ES$^+$=369 (M+1).

Step B methyl 2-(tert-butoxy)-2-(6-methyl-7-oxo-4-(p-tolyl)-6,7-dihydro-1H-pyrrolo[2,3-c]pyridin-5-yl) acetate

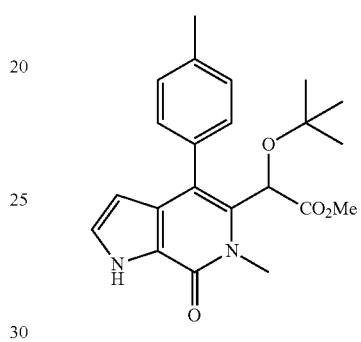

A solution of the crude 2-(tert-butoxy)-2-(6-methyl-7-oxo-4-(p-tolyl)-6,7-dihydro-1H-pyrrolo[2,3-c]pyridin-5-yl)acetic acid in Methanol (4 mL) was treated with TMS-diazomethane (1.481 mL, 2.96 mmol) and then resultant was allowed to stir at ambient temperature for 10 minutes. The mixture was concentrated and then purified on silica gel (0-10% MeOH/DCM) to give the desired product (67 mg, 41% yield over 2 two steps). $^1$H NMR (400 MHz, CHLOROFORM-d) d=9.71 (br. s., 1H), 7.47-7.32 (m, 3H), 7.31-7.23 (m, 1H), 7.19 (t, J=2.4 Hz, 1H), 6.10 (t, J=2.1 Hz, 1H), 5.39 (s, 1H), 3.82 (s, 3H), 3.72 (s, 3H), 2.44 (s, 3H), 0.94 (s, 9H); LC/MS (m/z) ES$^+$=383 (M+1).

Step C methyl 2-(1-(benzo[c][1,2,5]oxadiazol-5-ylmethyl)-6-methyl-7-oxo-4-(p-tolyl)-6,7-dihydro-1H-pyrrolo[2,3-c]pyridin-5-yl)-2-(tert-butoxy)acetate

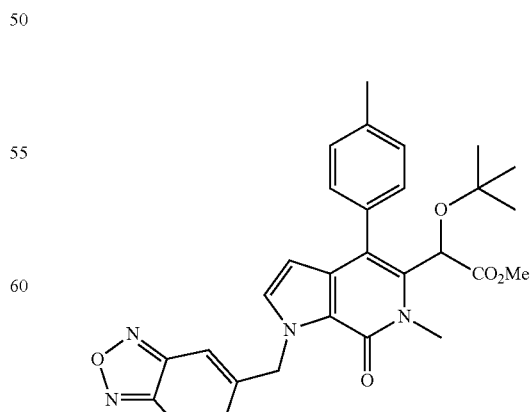

A solution of methyl 2-(tert-butoxy)-2-(6-methyl-7-oxo-4-(p-tolyl)-6,7-dihydro-1H-pyrrolo[2,3-c]pyridin-5-yl)acetate (10 mg, 0.026 mmol) and 5-(bromomethyl)benzo[c][1,2,5]oxadiazole (22.28 mg, 0.105 mmol) in Acetonitrile (1 mL) was treated with cesium carbonate (34.1 mg, 0.105 mmol) and the resultant was stirred at 70° C. for 2 hours. The mixture was cooled to ambient temperature, water was added and the mixture was extracted with ethyl acetate. The combined extracts were washed with brine, dried over sodium sulfate, filtered and concentrated. The residue was used crude in the next step without further purification. LC/MS (m/z) ES$^+$=515 (M+1).

Step D 2-(1-(benzo[c][1,2,5]oxadiazol-5-ylmethyl)-6-methyl-7-oxo-4-(p-tolyl)-6,7-dihydro-1H-pyrrolo[2,3-c]pyridin-5-yl)-2-(tert-butoxy)acetic acid

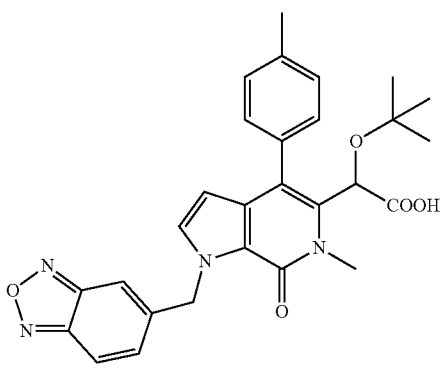 [SMILES: Cc1ccc(-c2c(C(OC(C)(C)C)C(=O)O)n(C)c(=O)c3c2ccn3Cc2ccc3nonc3c2)cc1]

A mixture of the crude methyl 2-(1-(benzo[c][1,2,5]oxadiazol-5-ylmethyl)-6-methyl-7-oxo-4-(p-tolyl)-6,7-dihydro-1H-pyrrolo[2,3-c]pyridin-5-yl)-2-(tert-butoxy)acetate in Tetrahydrofuran (THF) (1 mL) and Methanol (1 mL) was treated with 2M LiOH (1 mL, 2.000 mmol) and then heated to 70° C. for one hour. The mixture was cooled to 0° C., adjusted to pH <2 with 1N HCl and then extracted with ethyl acetate. The combined extracts were washed with brine, dried over sodium sulfate, filtered and concentrated. The residue was purified by reverse phase chromatography (10-90% MeCN/H$_2$O-0.1% TFA, 12 min.) to give the title compound. $^1$H NMR (400 MHz, CHLOROFORM-d) ppm 7.77-7.85 (m, 1H) 7.52-7.59 (m, 1H) 7.41-7.49 (m, 2H) 7.36-7.41 (m, 1H) 7.29-7.34 (m, 2H) 7.05-7.13 (m, 1H) 6.09-6.19 (m, 1H) 5.87-6.02 (m, 2H) 5.46-5.52 (m, 1H) 3.66 (s, 3H) 2.45 (s, 3H) 1.00 (s, 9H); LCMS (m/z) ES$^+$=501 (M+1).

Example 21

2-(1-(4-boronobenzyl)-6-methyl-7-oxo-4-(p-tolyl)-6,7-dihydro-1H-pyrrolo[2,3-c]pyridin-5-yl)-2-(tert-butoxy)acetic acid

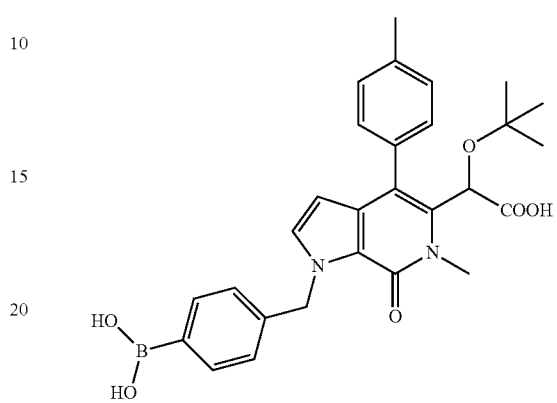

The title compound was prepared in a manner similar to that described in Example 20 except that (4-(bromomethyl)phenyl)boronic acid was used in step C. $^1$H NMR (400 MHz, CHLOROFORM-d) ppm 8.07-8.18 (m, 1H) 7.63-7.76 (m, 1H) 7.48-7.59 (m, 1H) 7.29-7.40 (m, 2H) 7.21-7.26 (m, 1H) 7.02-7.11 (m, 1H) 6.03-6.11 (m, 1H) 5.87-5.96 (m, 1H) 5.73-5.85 (m, 1H) 5.46-5.51 (m, 1H) 3.68 (s, 3H) 2.44 (s, 3H) 1.00 (s, 9H); LC/MS (m/z) ES$^+$=503 (M+1).

Example 22

2-(tert-butoxy)-2-(1-(4-carbamoylbenzyl)-6-methyl-7-oxo-4-(p-tolyl)-6,7-dihydro-1H-pyrrolo[2,3-c]pyridin-5-yl)acetic acid

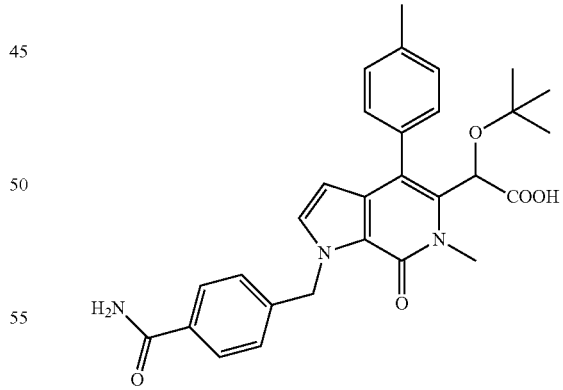

The title compound was prepared in a manner similar to that described in Example 20 except that 4-(chloromethyl)benzamide was used in step C. $^1$H NMR (400 MHz, CHLOROFORM-d) ppm 7.65-7.76 (m, 2H) 7.50-7.61 (m, 1H) 7.32-7.37 (m, 1H) 7.27-7.31 (m, 2H) 7.20-7.25 (m, 2H) 7.02-7.10 (m, 1H) 6.36-6.68 (m, 2H) 6.04-6.12 (m, 1H) 5.95-6.04 (m, 1H) 5.61-5.76 (m, 1H) 5.42-5.50 (m, 1H) 3.58-3.72 (m, 3H) 2.44 (s, 3H) 0.98 (s, 9H); LCMS (m/z) ES$^+$=502 (M+1).

Example 23

2-(tert-butoxy)-2-(6-methyl-7-oxo-4-(p-tolyl)-1-(4-((trifluoromethyl)thio)benzyl)-6,7-dihydro-1H-pyrrolo[2,3-c]pyridin-5-yl)acetic acid

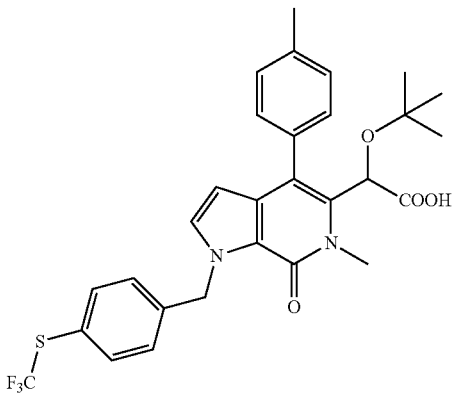 [SMILES: Cc1ccc(-c2c(C(OC(C)(C)C)C(=O)O)n(C)c(=O)c3c2ccn3Cc2ccc(SC(F)(F)F)cc2)cc1]

The title compound was prepared in a manner similar to that described in Example 20 except that (4-(bromomethyl)phenyl)(trifluoromethyl)sulfane was used in step C. $^1$H NMR (400 MHz, CHLOROFORM-d) ppm 7.57-7.66 (m, 2H) 7.51-7.58 (m, 1H) 7.34-7.39 (m, 1H) 7.26-7.33 (m, 4H) 7.01-7.06 (m, 1H) 6.05-6.11 (m, 1H) 5.90-5.97 (m, 1H) 5.81-5.89 (m, 1H) 5.45-5.50 (m, 1H) 3.66 (s, 3H) 2.48 (s, 3H) 1.00 (s, 9H); LCMS (m/z) ES$^+$=559 (M+1).

Example 24

(S)-2-(tert-butoxy)-2-(1-(4-fluorobenzyl)-6-methyl-7-oxo-4-(p-tolyl)-6,7-dihydro-1H-pyrrolo[2,3-c]pyridin-5-yl)acetic acid

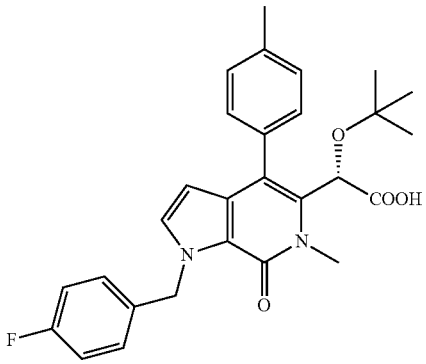 [SMILES: Cc1ccc(-c2c([C@H](OC(C)(C)C)C(=O)O)n(C)c(=O)c3c2ccn3Cc2ccc(F)cc2)cc1]

The title compound was prepared in a manner similar to that described in Example 20 except that 4-fluorophenyl benzyl bromide was used in step C and the racemic material was purified by chiral HPLC (IC Column, 30% IPA/hexanes w/0.1% formic acid; Rt=6.9 min): $^1$H NMR (400 MHz, CHLOROFORM-d)=7.53 (d, J=6.6 Hz, 1H), 7.33 (d, J=2.0 Hz, 1H), 7.31-7.24 (m, 4H), 7.05-6.97 (m, 3H), 6.04 (d, J=2.7 Hz, 1H), 5.92-5.83 (m, 1H), 5.79-5.71 (m, 1H), 5.47 (s, 1H), 3.67 (s, 3H), 2.43 (s, 3H), 1.00 (s, 9H). LCMS (m/z) ES$^+$=477 (M+1).

Example 25

2-(tert-butoxy)-2-(6-methyl-7-oxo-1-(thiophen-2-ylmethyl)-4-(p-tolyl)-6,7-dihydro-1H-pyrrolo[2,3-c]pyridin-5-yl)acetic acid

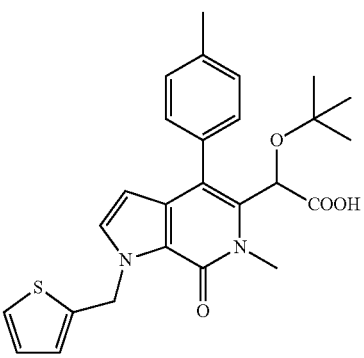 [SMILES: Cc1ccc(-c2c(C(OC(C)(C)C)C(=O)O)n(C)c(=O)c3c2ccn3Cc2cccs2)cc1]

The title compound was prepared in a manner similar to that described in Example 20 except that (4-(bromomethyl)thiophene was used in step C. $^1$H NMR (400 MHz, CHLOROFORM-d) ppm $^1$H NMR (400 MHz, CHLOROFORM-d)=7.54-7.50 (m, 1H), 7.35-7.31 (m, 1H), 7.29-7.23 (m, 5H), 7.13-7.10 (m, 1H), 7.08 (d, J=2.9 Hz, 1H), 6.96 (dd, J=3.5, 5.1 Hz, 1H), 6.03-5.99 (m, 3H), 5.46 (s, 1H), 3.69 (s, 3H), 2.43 (s, 3H), 0.99 (s, 9H). LCMS (m/z) ES$^+$=466 (M+1).

Example 26

2-(tert-butoxy)-2-(1-(4-fluorophenethyl)-6-methyl-7-oxo-4-(p-tolyl)-6,7-dihydro-1H-pyrrolo[2,3-c]pyridin-5-yl)acetic acid

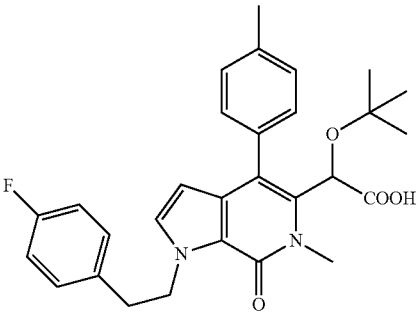 [SMILES: Cc1ccc(-c2c(C(OC(C)(C)C)C(=O)O)n(C)c(=O)c3c2ccn3CCc2ccc(F)cc2)cc1]

The title compound was prepared in a manner similar to that described in Example 20 except that 4-fluorophenethyl-bromide was used in step C. $^1$H NMR (400 MHz, CHLOROFORM-d) ppm $^1$H NMR (400 MHz, CHLOROFORM-d)=7.57-7.51 (m, 1H), 7.37-7.28 (m, 3H), 7.17-7.10 (m, 2H), 6.95 (t, J=8.7 Hz, 2H), 6.75 (d, J=2.8 Hz, 1H), 5.92 (d, J=2.8 Hz, 1H), 5.47 (s, 1H), 4.84-4.58 (m, 2H), 3.69 (s, 3H), 3.23-3.07 (m, 2H), 2.43 (s, 3H), 1.00 (s, 9H). LCMS (m/z) ES$^+$=492 (M+1).

Scheme 7

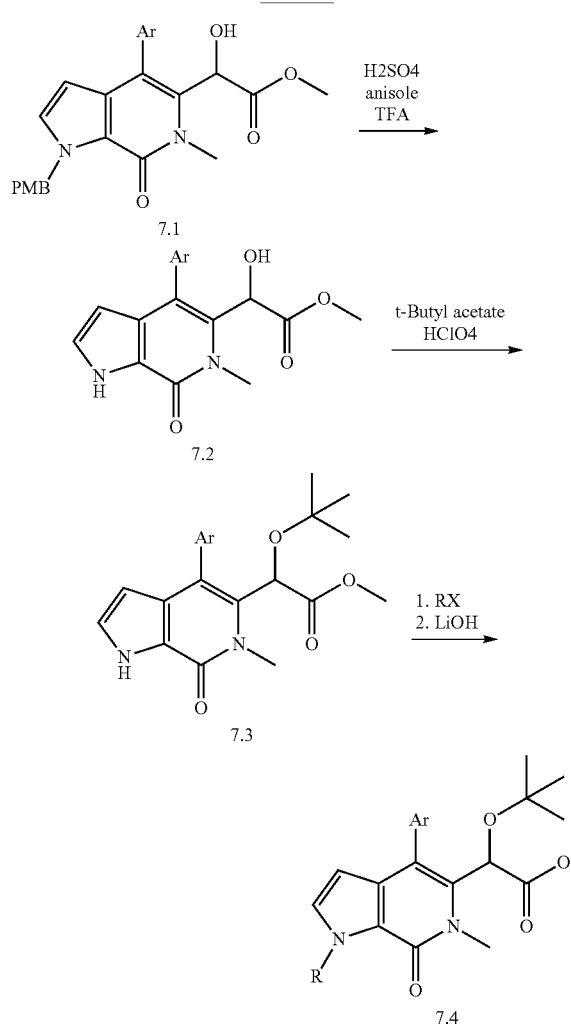

Example 27

2-(tert-butoxy)-2-(6-methyl-1-(4-(methylsulfonyl)benzyl)-7-oxo-4-(p-tolyl)-6,7-dihydro-1H-pyrrolo[2,3-c]pyridin-5-yl)acetic acid

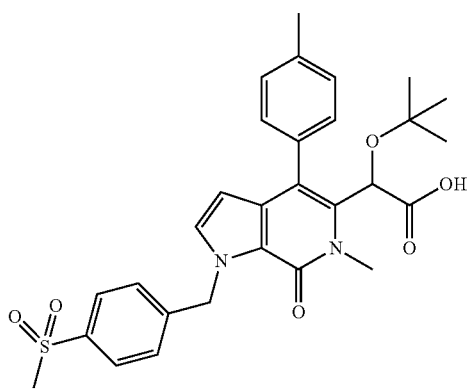 [SMILES: Cc1ccc(-c2c(C(OC(C)(C)C)C(=O)O)n(C)c(=O)c3c2ccn3Cc2ccc(S(C)(=O)=O)cc2)cc1]

Step A methyl 2-hydroxy-2-(1-(4-methoxybenzyl)-6-methyl-7-oxo-4-(p-tolyl)-6,7-dihydro-1H-pyrrolo[2,3-c]pyridin-5-yl)acetate

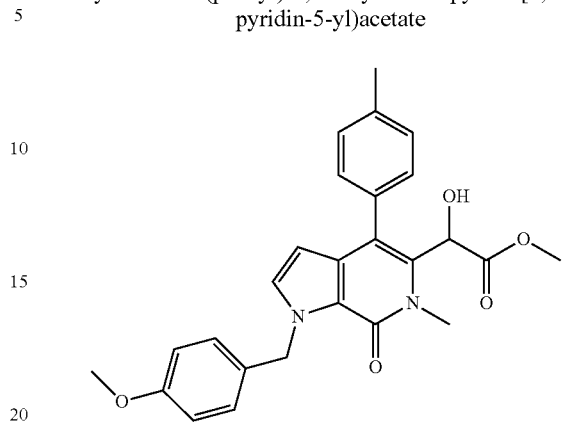

Methyl 2-hydroxy-2-(1-(4-methoxybenzyl)-6-methyl-7-oxo-4-(p-tolyl)-6,7-dihydro-1H-pyrrolo[2,3-c]pyridin-5-yl)acetate was prepared in a manner similar to that described in Example 1 steps A through L, except that para-methoxybenzyl amine was used in step B and p-tolylboronic acid was used in step H, and was isolated as white solid: $^1$H NMR (400 MHz, CHLOROFORM-d) ppm 7.35-7.19 (m, 6H), 7.00 (d, J=2.8 Hz, 1H), 6.90-6.80 (m, 2H), 5.96 (d, J=2.9 Hz, 1H), 5.85-5.68 (m, 2H), 5.32 (d, J=1.4 Hz, 1H), 3.78 (s, 6H), 3.59 (s, 3H), 3.19 (d, J=1.6 Hz, 1H), 2.41 (s, 3H); LCMS (m/z) ES$^+$=447(M+1).

Step B methyl 2-hydroxy-2-(6-methyl-7-oxo-4-(p-tolyl)-6,7-dihydro-1H-pyrrolo[2,3-c]pyridin-5-yl)acetate

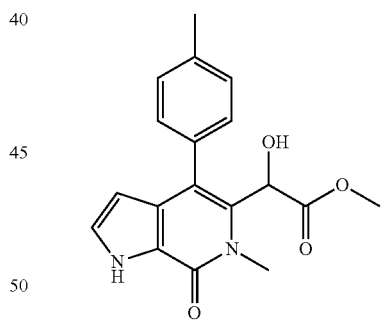

An ice cold solution of methyl 2-hydroxy-2-(1-(4-methoxybenzyl)-6-methyl-7-oxo-4-(p-tolyl)-6,7-dihydro-1H-pyrrolo[2,3-c]pyridin-5-yl)acetate (266 mg, 0.596 mmol) in Trifluoroacetic acid (TFA) (2.5 mL) was treated with conc. H$_2$SO$_4$ (185 µl, 3.47 mmol), and anisole (370 µl, 3.39 mmol). After stirring for 1 hour, the reaction was warmed to rt for 2 hours, and then quenched with sat. NaHCO$_3$ until neutral. The mixture was extracted with EtOAc, washed with Brine, dried with Na$_2$SO$_4$, filtered, and concentrated. Purification with column chromatography (0-100% EtOAc/Hexane) afforded methyl 2-hydroxy-2-(6-methyl-7-oxo-4-(p-tolyl)-6,7-dihydro-1H-pyrrolo[2,3-c]pyridin-5-yl)acetate (130.1 mg, 0.399 mmol, 66.9% yield) as off-white solid. $^1$H NMR (400 MHz, CHLOROFORM-d) ppm 10.94 (br. s., 1H), 7.36 (dd, J=7.3, 12.5 Hz, 2H), 7.30-7.20 (m, 3H), 6.12-6.03 (m, 1H), 5.42 (s, 1H), 3.82-3.73 (m, 4H), 3.67 (s, 3H), 2.42 (s, 3H); LCMS (m/z) ES$^+$=327 (M+1).

Step C methyl 2-(tert-butoxy)-2-(6-methyl-7-oxo-4-(p-tolyl)-6,7-dihydro-1H-pyrrolo[2,3-c]pyridin-5-yl)acetate

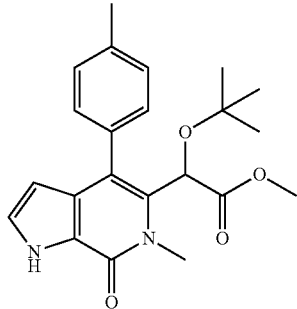 [SMILES: COC(=O)C(OC(C)(C)C)c1c(-c2ccc(C)cc2)c2cc[nH]c2c(=O)n1C]

An ice cold solution of methyl 2-hydroxy-2-(6-methyl-7-oxo-4-(p-tolyl)-6,7-dihydro-1H-pyrrolo[2,3-c]pyridin-5-yl)acetate (142 mg, 0.435 mmol) in tert-butyl acetate (2.94 mL, 21.76 mmol) was treated with perchloric acid (0.075 mL, 0.870 mmol), and then kept in the refrigerator without stirring for 2 days. The reaction was quenched with sat. NaHCO$_3$ at 0° C., extracted with EtOAc, washed with Brine, dried with Na$_2$SO$_4$, filtered, and concentrated. Purification with column chromatography (0-100% EtOAc/Hexane) gave methyl 2-(tert-butoxy)-2-(6-methyl-7-oxo-4-(p-tolyl)-6,7-dihydro-1H-pyrrolo[2,3-c]pyridin-5-yl)acetate (108 mg, 0.282 mmol, 64.9% yield) as off white solid. $^1$H NMR (400 MHz, CHLOROFORM-d) ppm 9.71 (br. s., 1H), 7.39-7.31 (m, 2H), 7.30-7.24 (m, 2H), 7.18 (t, 1H), 6.09 (t, J=2.5 Hz, 1H), 5.38 (s, 1H), 3.81 (s, 3H), 3.71 (s, 3H), 2.44 (s, 3H), 0.94 (s, 9H); LCMS (m/z) ES$^+$=383 (M+1).

Step D 2-(tert-butoxy)-2-(6-methyl-1-(4-(methylsulfonyl)benzyl)-7-oxo-4-(p-tolyl)-6,7-dihydro-1H-pyrrolo[2,3-c]pyridin-5-yl)acetic acid

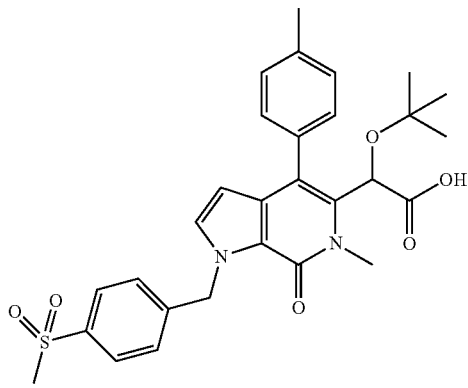 [SMILES: Cc1ccc(-c2c(C(OC(C)(C)C)C(=O)O)n(C)c(=O)c3c2ccn3Cc2ccc(S(C)(=O)=O)cc2)cc1]

A suspension of methyl 2-(tert-butoxy)-2-(6-methyl-7-oxo-4-(p-tolyl)-6,7-dihydro-1H-pyrrolo[2,3-c]pyridin-5-yl)acetate (17 mg, 0.044 mmol) in Acetonitrile (0.4 mL) was treated with Cs$_2$CO$_3$ (57.9 mg, 0.178 mmol), 4-methylsulfonylbenzyl bromide (44.3 mg, 0.089 mmol), and stirred at 70° C. for 1.5 hours. The reaction was cooled to rt, diluted with water and 1N HCl, extracted with EtOAc, washed with Brine, dried with Na$_2$SO$_4$, filtered, and concentrated. Purification with column chromatography (0-100% EtOAc/Hexane) gave methyl 2-(tert-butoxy)-2-(6-methyl-1-(4-(methylsulfonyl)benzyl)-7-oxo-4-(p-tolyl)-6,7-dihydro-1H-pyrrolo[2,3-c]pyridin-5-yl)acetate (22 mg, 0.040 mmol, 90% yield) as yellow oil. The ester intermediate was dissolved in Methanol (0.5 mL) and Tetrahydrofuran (THF) (0.5 mL), treated with 2M LiOH (0.120 mL, 0.24 mmol), and stirred at 60° C. for 2 hours. The reaction was concentrated and purified with reverse phase HPLC (20-100% MeCN/H$_2$O-0.1% TFA) to give title compound (9.3 mg, 0.017 mmol, 37.6 yield) as of white solid. $^1$H NMR (400 MHz, CHLOROFORM-d) ppm 1.00 (s, 9H), 2.44 (s, 3H), 3.02 (s, 3H), 3.64 (s, 3H), 5.47 (s, 1H), 5.81 (d, J=15.7 Hz, 1H), 6.02 (d, J=15.6 Hz, 1H), 6.10 (d, J=2.8 Hz, 1H), 7.05 (d, J=2.9 Hz, 1H), 7.29 (d, J=8.1 Hz, 2H), 7.32-7.43 (m, 3H), 7.47-7.58 (m, 1H), 7.89 (d, J=8.4 Hz, 2H). LCMS (m/z) ES$^+$=537 (M+1).

Example 28

2-(tert-butoxy)-2-(1-(3,4-difluorobenzyl)-6-methyl-7-oxo-4-(p-tolyl)-6,7-dihydro-1H-pyrrolo[2,3-c]pyridin-5-yl)acetic acid

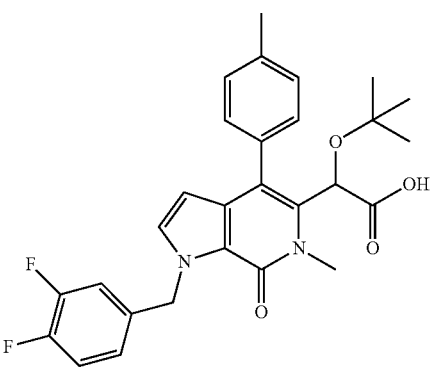 [SMILES: Cc1ccc(-c2c(C(OC(C)(C)C)C(=O)O)n(C)c(=O)c3c2ccn3Cc2ccc(F)c(F)c2)cc1]

The title compound was prepared in two steps in a manner similar to that described in Example 27 step D from methyl 2-(tert-butoxy)-2-(6-methyl-7-oxo-4-(p-tolyl)-6,7-dihydro-1H-pyrrolo[2,3-c]pyridin-5-yl)acetate and 3,4-difluorobenzyl bromide, and was isolated as white solid after reverse phase chromatography (46%): $^1$H NMR (400 MHz, CHLOROFORM-d) ppm 0.98 (s, 9H), 2.43 (s, 3H), 3.66 (s, 3H), 5.45 (s, 1H), 5.68-5.86 (m, 2H), 6.06 (d, J=2.8 Hz, 1H), 6.97-7.05 (m, 2H), 7.05-7.15 (m, 2H), 7.25-7.31 (m, 2H), 7.31-7.38 (m, 1H), 7.49-7.59 (m, 1H); LCMS (m/z) ES$^+$=495 (M+1).

Example 29

2-(tert-butoxy)-2-(1-(4-methoxybenzyl)-6-methyl-7-oxo-4-(p-tolyl)-6,7-dihydro-1H-pyrrolo[2,3-c]pyridin-5-yl)acetic acid

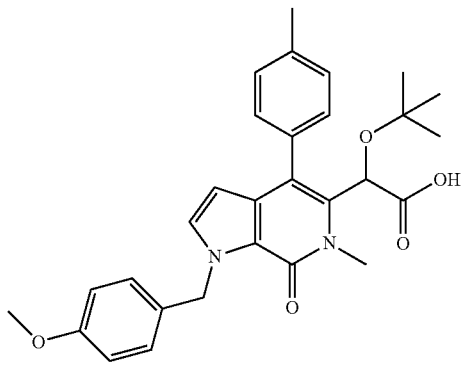 [SMILES: COc1ccc(Cn2ccc3c(-c4ccc(C)cc4)c(C(OC(C)(C)C)C(=O)O)n(C)c(=O)c32)cc1]

The title compound was prepared in a manner similar to that described in Example 1, except that para-methoxybenzyl amine was used in step B, and p-tolylboronic acid was used in step H, and was isolated as white solid: $^1$H NMR (400 MHz, CHLOROFORM-d) ppm 0.99 (s, 9H), 2.43 (s, 3H), 3.68 (s, 3H), 3.79 (s, 3H), 5.46 (s, 1H), 5.68-5.89 (m, 2H), 6.00 (d, J=2.7 Hz, 1H), 6.86 (d, J=8.5 Hz, 2H), 7.00 (d, J=2.7 Hz, 1H), 7.22-7.31 (m, 4H), 7.31-7.39 (m, 1H), 7.48-7.58 (m, 1H); LCMS (m/z) ES$^+$=489 (M+1).

Scheme 8

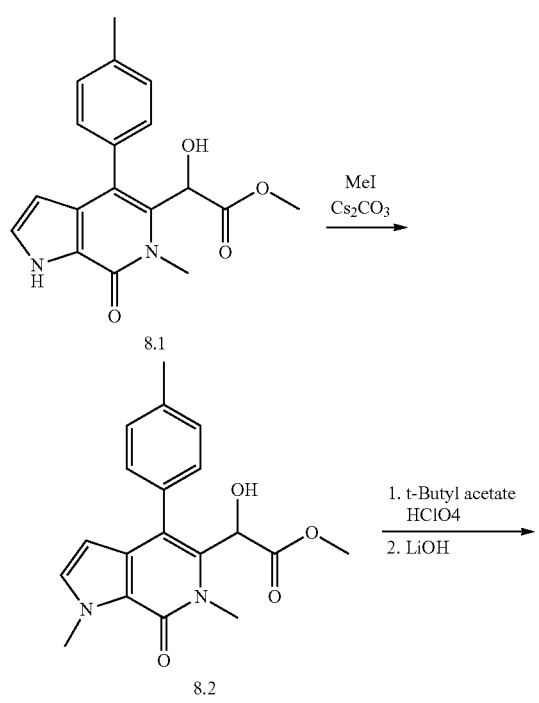

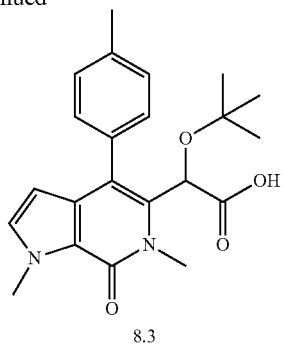

8.3

Example 30

2-(tert-butoxy)-2-(1,6-dimethyl-7-oxo-4-(p-tolyl)-6,7-dihydro-1H-pyrrolo[2,3-c]pyridin-5-yl)acetic acid

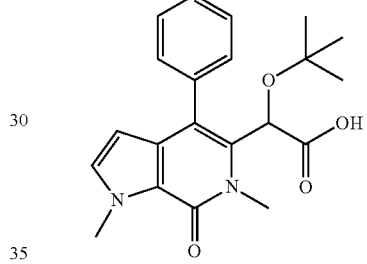

Step A methyl 2-(1,6-dimethyl-7-oxo-4-(p-tolyl)-6,7-dihydro-1H-pyrrolo[2,3-c]pyridin-5-yl)-2-hydroxyacetate

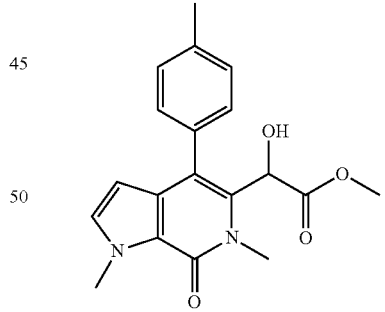

A suspension of methyl 2-hydroxy-2-(6-methyl-7-oxo-4-(p-tolyl)-6,7-dihydro-1H-pyrrolo[2,3-c]pyridin-5-yl)acetate (30 mg, 0.092 mmol) and Cs$_2$CO$_3$ (35.9 mg, 0.110 mmol) in Acetonitrile (1 mL) was treated with MeI (6.90 μL, 0.110 mmol) and heated to 50° C. for 3 hours. Additional MeI (10 uL) was added, the reaction was stirred at 50° C. for 3 hours. The mixture was cooled to rt, diluted with water, acidified with 1N HCl, extracted with EtOAc 3×, washed with brine, dried with Na$_2$SO$_4$, filtered, and concentrated. Combined with crude product from the same reaction (0.040 mol scale) and purified with column chromatography (0-100% EtOAc/Hexane) to give methyl 2-(1,6-dimethyl-7-oxo-4-(p-tolyl)-6, 7-dihydro-1H-pyrrolo[2,3-c]pyridin-5-yl)-2-hydroxyacetate (31.7 mg, 0.093 mmol, 70.6% yield) as clear oil. LCMS (m/z) ES$^+$=341 (M+1).

Step B 2-(tert-butoxy)-2-(1,6-dimethyl-7-oxo-4-(p-tolyl)-6,7-dihydro-1H-pyrrolo[2,3-c]pyridin-5-yl)acetic acid

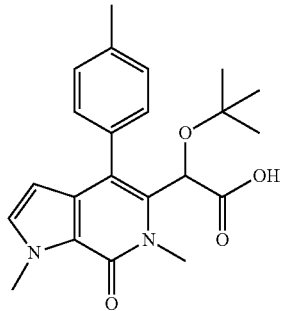 [SMILES: Cc1ccc(-c2c(C(OC(C)(C)C)C(=O)O)n(C)c(=O)c3c2ccn3C)cc1]

An ice cold solution of methyl 2-(1,6-dimethyl-7-oxo-4-(p-tolyl)-6,7-dihydro-1H-pyrrolo[2,3-c]pyridin-5-yl)-2-hydroxyacetate (28 mg, 0.082 mmol) in tert-butyl acetate (1111 µl, 8.23 mmol) was treated with perchloric acid (7.07 µl, 0.082 mmol), and stirred for 20 min. The reaction was then kept in the refrigerator without stirring for 2 days. The reaction was quenched with sat. NaHCO$_3$ at 0° C., extracted with EtOAc 2×, washed with Brine, dried with Na$_2$SO$_4$, filtered, and concentrated. Purification with column chromatography (0-100% EtOAc/Hexane) gave methyl 2-(tert-butoxy)-2-(1,6-dimethyl-7-oxo-4-(p-tolyl)-6,7-dihydro-1H-pyrrolo[2,3-c]pyridin-5-yl)acetate (23.6 mg, 0.060 mmol, 72.4% yield). The intermediate was dissolved in Methanol (500 µl) and Tetrahydrofuran (THF) (500 µl), treated with 2M LiOH (174 µl, 0.348 mmol), and stirred at 60° C. for 4 hours. The mixture was concentrated and purified with reverse phase chromatography (20-100% MeCN/H$_2$O-0.1% TFA, 12 min) to give title compound (19.6 mg, 0.051 mmol, 87% yield) as white solid: $^1$H NMR (400 MHz, CHLOROFORM-d) ppm 0.99 (s, 9H), 2.43 (s, 3H), 3.66 (s, 3H), 4.20 (s, 3H), 5.45 (s, 1H), 5.98 (d, J=2.7 Hz, 1H), 6.96 (d, J=2.7 Hz, 1H), 7.24-7.31 (m, 2H), 7.31-7.38 (m, 1H), 7.49-7.57 (m, 1H); LCMS (m/z) ES$^+$=383 (M+1).

Example 31

2-(tert-butoxy)-2-(1-(4-chloro-3-fluorobenzyl)-6-methyl-7-oxo-4-(p-tolyl)-6,7-dihydro-1H-pyrrolo[2,3-c]pyridin-5-yl)acetic acid

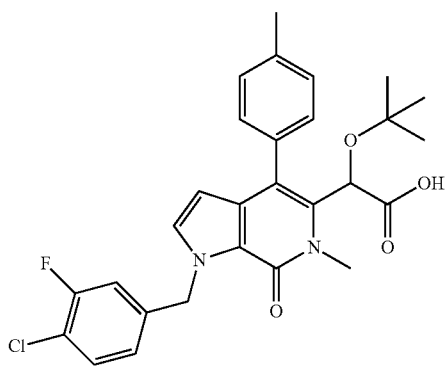 [SMILES: Cc1ccc(-c2c(C(OC(C)(C)C)C(=O)O)n(C)c(=O)c3c2ccn3Cc2ccc(Cl)c(F)c2)cc1]

An ice cold solution of methyl 2-(tert-butoxy)-2-(6-methyl-7-oxo-4-(p-tolyl)-6,7-dihydro-1H-pyrrolo[2,3-c]pyridin-5-yl)acetate (21 mg, 0.055 mmol) in N,N-Dimethylformamide (DMF) (500 µl) was treated with K$_2$CO$_3$ (37.9 mg, 0.275 mmol), DIEA (47.9 µl, 0.275 mmol), and 4-chloro-3-fluorobenzyl bromide (61.4 mg, 0.275 mmol), stirred at rt for 1 hr, and then heated to 70° C. for 18 hours. The reaction was diluted with water, extracted with EtOAc, washed with Brine, dried with Na$_2$SO$_4$, filtered, and concentrated. Purification with column chromatography (0-100% EtOAc/hexane) gave methyl 2-(tert-butoxy)-2-(1-(4-chloro-3-fluorobenzyl)-6-methyl-7-oxo-4-(p-tolyl)-6,7-dihydro-1H-pyrrolo[2,3-c]pyridin-5-yl)acetate (26.2 mg, 0.050 mmol, 91% yield) as clear oil. The ester intermediate was dissolved in Methanol (500 µl) and Tetrahydrofuran (THF) (500 µl), treated with 2M LiOH (150 µl, 0.3 mmol), and stirred at 60° C. for 2.5 hours. The reaction was concentrated and purified with reverse phase HPLC (20-100% MeCN/H$_2$O-0.1% TFA, 12 min) to give title compound (11.6 mg, 0.022 mmol, 40.9% yield) as white solid: $^1$H NMR (400 MHz, CHLOROFORM-d) ppm 0.99 (s, 9H), 2.43 (s, 3H), 3.65 (s, 3H), 5.46 (s, 1H), 5.79 (d, J=2.3 Hz, 2H), 6.06 (d, J=2.8 Hz, 1H), 6.94-7.07 (m, 3H), 7.24-7.31 (m, 2H), 7.30-7.38 (m, 2H), 7.49-7.56 (m, 1H); LCMS (m/z) ES$^+$=511 (M+1).

Example 32

2-(tert-butoxy)-2-(6-methyl-7-oxo-4-(p-tolyl)-1-(3,4,5-trifluorobenzyl)-6,7-dihydro-1H-pyrrolo[2,3-c]pyridin-5-yl)acetic acid

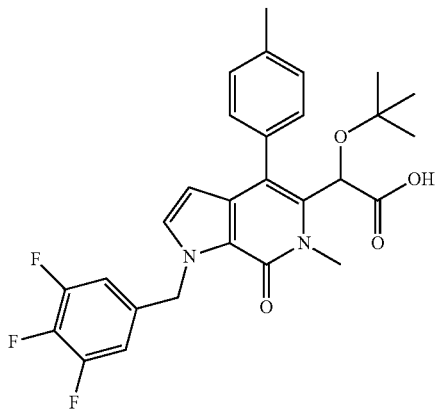 [SMILES: Cc1ccc(-c2c(C(OC(C)(C)C)C(=O)O)n(C)c(=O)c3c2ccn3Cc2cc(F)c(F)c(F)c2)cc1]

The title compound was prepared in a manner similar to that described in Example 27 step D from methyl 2-(tert-butoxy)-2-(6-methyl-7-oxo-4-(p-tolyl)-6,7-dihydro-1H-pyrrolo[2,3-c]pyridin-5-yl)acetate and 3,4,5-trifluorobenzyl bromide, and was isolated as beige solid after reverse phase chromatography (81%): $^1$H NMR (400 MHz, CHLOROFORM-d) ppm 0.99 (s, 9H), 2.43 (s, 3H), 3.65 (s, 3H), 5.46 (s, 1H), 5.75 (s, 2H), 6.08 (d, J=2.7 Hz, 1H), 6.87 (t, J=7.1 Hz, 2H), 7.01 (d, J=2.7 Hz, 1H), 7.28 (d, 2H), 7.31-7.39 (m, 1H), 7.48-7.57 (m, 1H). LCMS (m/z) ES$^+$=513 (M+1).

Example 33

2-(1-(benzo[d][1,3]dioxol-5-ylmethyl)-6-methyl-7-oxo-4-(p-tolyl)-6,7-dihydro-1H-pyrrolo[2,3-c]pyridin-5-yl)-2-(tert-butoxy)acetic acid

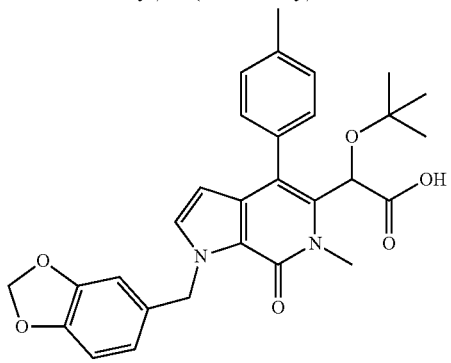

The title compound was prepared in a manner similar to that described in Example 27 step D from methyl 2-(tert-butoxy)-2-(6-methyl-7-oxo-4-(p-tolyl)-6,7-dihydro-1H-pyrrolo[2,3-c]pyridin-5-yl)acetate and 3,4-methylenedioxybenzyl chloride (50% in dcm), and was isolated as beige solid after reverse phase chromatography (41%): $^1$H NMR (400 MHz, CHLOROFORM-d) ppm 0.99 (s, 9H), 2.42 (s, 3H), 3.67 (s, 3H), 5.46 (s, 1H), 5.63-5.81 (m, 2H), 5.92 (s, 2H), 6.01 (d, J=2.9 Hz, 1H), 6.70-6.84 (m, 3H), 7.00 (d, J=2.8 Hz, 1H), 7.27-7.30 (m, 2H), 7.30-7.38 (m, 1H), 7.46-7.58 (m, 1H). LCMS (m/z) ES$^+$=503 (M+1).

Scheme 9

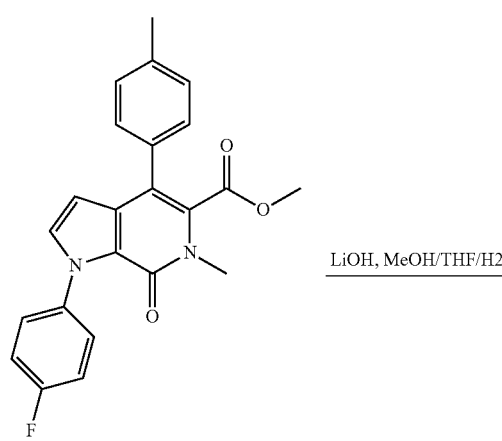

9.1

LiOH, MeOH/THF/H2O →

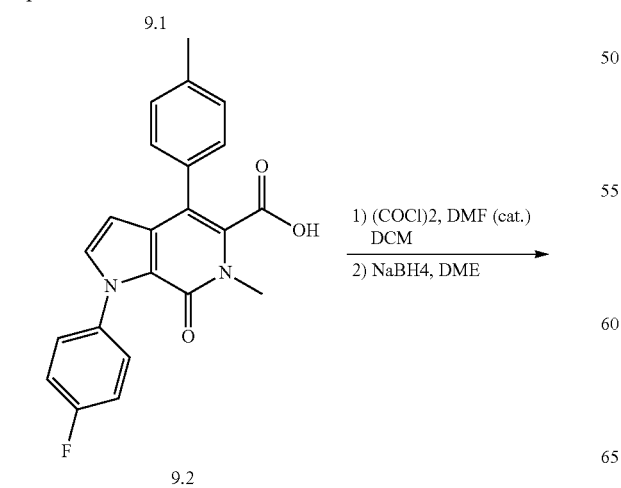

9.2

1) (COCl)2, DMF (cat.) DCM
2) NaBH4, DME
→

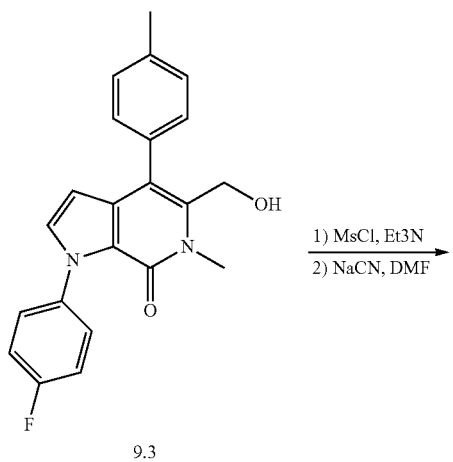

9.3

1) MsCl, Et3N
2) NaCN, DMF
→

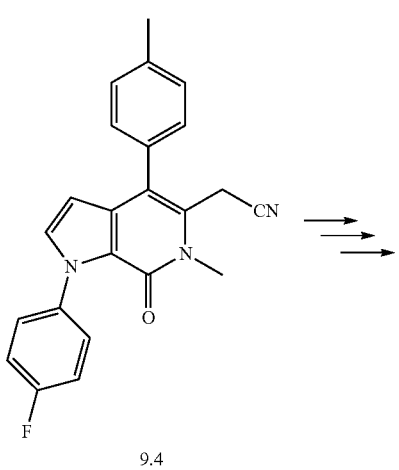

9.4

→ →

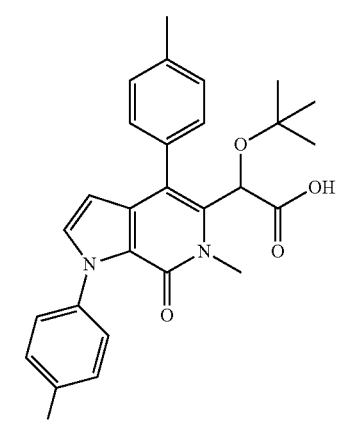

9.5

Example 34

2-(tert-butoxy)-2-(1-(4-fluorophenyl)-6-methyl-7-oxo-4-(p-tolyl)-6,7-dihydro-1H-pyrrolo[2,3-c]pyridin-5-yl)acetic acid

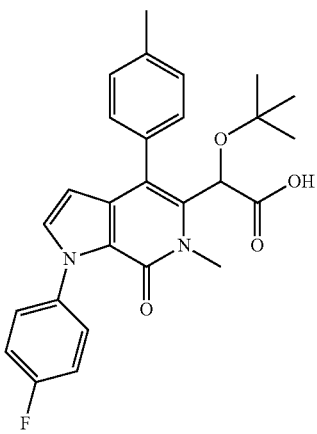 [SMILES: Cc1ccc(-c2c(C(OC(C)(C)C)C(=O)O)n(C)c(=O)c3c2ccn3-c2ccc(F)cc2)cc1]

Step A 2-(1-(4-fluorophenyl)-6-methyl-7-oxo-4-(p-tolyl)-6,7-dihydro-1H-pyrrolo[2,3-c]pyridin-5-yl)acetonitrile

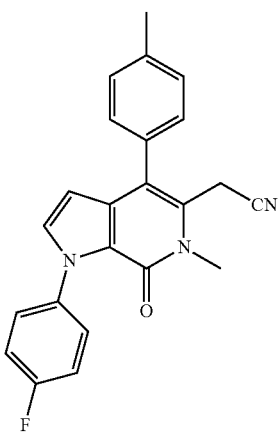 [SMILES: Cc1ccc(-c2c(CC#N)n(C)c(=O)c3c2ccn3-c2ccc(F)cc2)cc1]

The title intermediate was prepared in a manner similar to that described in Example 1 steps A through J from 4-fluoroaniline using the following modified procedure. A mixture of methyl 1-(4-fluorophenyl)-6-methyl-7-oxo-4-(p-tolyl)-6,7-dihydro-1H-pyrrolo[2,3-c]pyridine-5-carboxylate (302 mg, 0.774 mmol) and lithium hydroxide (93 mg, 3.87 mmol) in Methanol (3.0 mL), Tetrahydrofuran (THF) (3.00 mL) and Water (1.0 mL) was heated to 70° C. for three days. The mixture was concentrated, water was added and then adjusted to pH 2 with 1N HCl. The mixture was extracted with ethyl acetate, the extracts washed with brine, dried over sodium sulfate, filtered and concentrated to give the impure carboxylic acid intermediate. An ice cold mixture of the carboxylic acid intermediate in Dichloromethane (DCM) (5.0 mL) was treated with oxalyl chloride (0.090 mL, 1.052 mmol) followed by DMF (one drop) and the mixture was warmed to ambient. After one hour the mixture was concentrated to give the crude acid chloride intermediate. A mixture of the crude acid chloride in 1,2-Dimethoxyethane (DME) (5.0 mL) was treated with NaBH4 (133 mg, 3.51 mmol) and then stirred at ambient temperature for 15 minutes. Water was added and the mixture was concentrated. The mixture was partitioned between saturated sodium bicarbonate and ethyl acetate. The aqueous phase was extracted with ethyl acetate. The combined extracts were washed with brine, dried over sodium sulfate, filtered and concentrated to give the crude hydroxymethyl intermediate. An ice cold mixture of the crude alcohol and triethylamine (0.156 mL, 1.122 mmol) in Dichloromethane (DCM) (5.0 mL) was treated with MsCl (0.065 mL, 0.842 mmol) and then stirred for 10 minutes. Additional triethylamine (0.156 mL, 1.122 mmol) and MsCl (0.065 mL, 0.842 mmol) were added and the mixture was stirred an additional 10 minutes. The mixture was diluted with DCM and washed with 0.1 N HCl, followed by saturated sodium bicarbonate. The organic phase was dried over sodium sulfate, filtered and concentrated to give the crude mesylate intermediate. The crude mesylate in N,N-Dimethylformamide (DMF) (5.00 mL) was treated with sodium cyanide (137 mg, 2.81 mmol) and then stirred at ambient temperature overnight. Water was added and the mixture was extracted with ethyl acetate. The combined extracts were washed with water, then brine, dried over sodium sulfate, filtered and concentrated to give the title intermediate as a tan solid. $^1$H NMR (400 MHz, CHLOROFORM-d) ppm 7.39-7.49 (m, 2H), 7.32 (q, J=8.19 Hz, 4H), 7.11-7.22 (m, 3H), 6.14 (d, J=2.93 Hz, 1H), 3.78 (s, 3H), 3.69 (s, 2H), 2.47 (s, 3H); LC/MS (m/z) ES$^+$=372 (M+1).

The title compound was prepared in a manner similar to that described in Example 1 steps J through N and was isolated as a pale yellow residue (4.8 mg, 85%) after aqueous work-up. $^1$H NMR (400 MHz, CHLOROFORM-d) ppm 7.61-7.52 (m, 1H), 7.47-7.34 (m, 3H), 7.31 (d, J=8.2 Hz, 2H), 7.19-7.08 (m, 3H), 6.18 (d, J=2.9 Hz, 1H), 5.49 (s, 1H), 3.67-3.58 (m, 3H), 2.45 (s, 3H), 1.01 (s, 9H); LC/MS (m/z) ES$^+$=463 (M+1).

Scheme 10

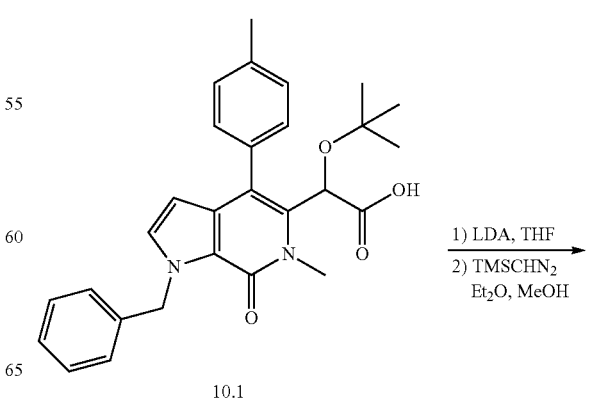

10.1

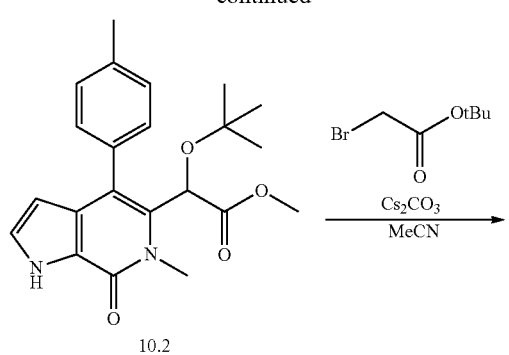
10.2
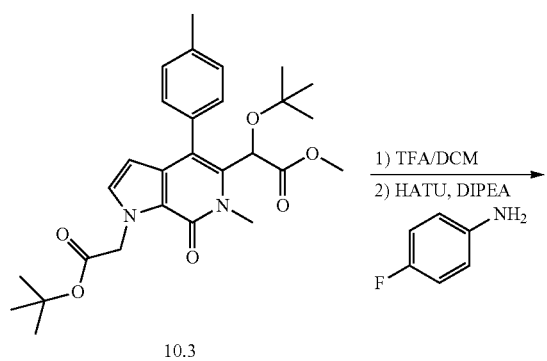
10.3
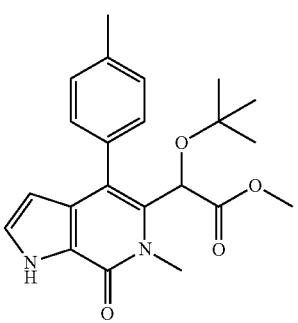
10.4
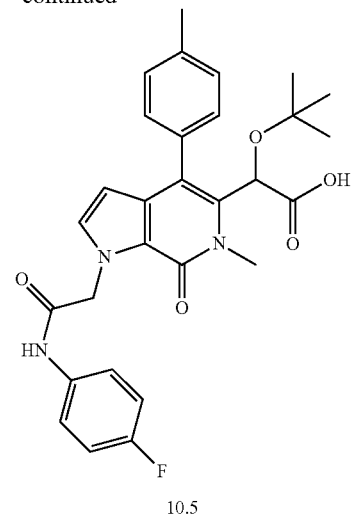
10.5
Example 35
2-(tert-butoxy)-2-(1-(2-((4-fluorophenyl)amino)-2-oxoethyl)-6-methyl-7-oxo-4-(p-tolyl)-6,7-dihydro-1H-pyrrolo[2,3-c]pyridin-5-yl)acetic acid
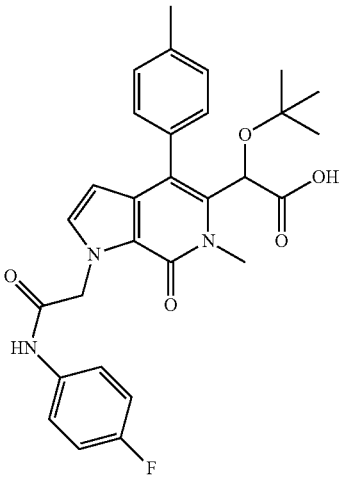 [SMILES: Cc1ccc(-c2c(C(OC(C)(C)C)C(=O)O)n(C)c(=O)c3c2ccn3CC(=O)Nc2ccc(F)cc2)cc1]
Step A
methyl 2-(tert-butoxy)-2-(6-methyl-7-oxo-4-(p-tolyl)-6,7-dihydro-1H-pyrrolo[2,3-c]pyridin-5-yl)acetate An ice cold mixture of 2-(1-benzyl-6-methyl-7-oxo-4-(p-tolyl)-6,7-dihydro-1H-pyrrolo[2,3-c]pyridin-5-yl)-2-(tert-butoxy)acetic acid (64.0 mg, 0.140 mmol) in Tetrahydrofuran (THF) (2.0 mL) was treated with dropwise addition of LDA, 2M solution in heptane/THF/ethylbenzene (0.140 mL, 0.279 mmol) and then allowed to stir at 0° C. for 45 minutes. Additional LDA (70 uL) was added and then stirred an additional 10 minutes. The mixture was quenched by adding 1N HCl and acidified to pH 2. The mixture was extracted with ethyl acetate. The combined extracts were washed with brine, dried over sodium sulfate, filtered and concentrated to give the crude debenzylation product as an orange residue. An ice cold mixture of the crude debenzylation product in methanol (1.0 mL) and diethyl ether (1.0 mL) was treated with trimethylsilyl diazomethane, 2M solution in hexanes (0.140 mL, 0.279 mmol) and then stirred at ambient temperature for 10 minutes. Additional trimethylsilyl diazomethane, 2M solution in hexanes (0.140 mL, 0.279 mmol) was added, the mixture was stirred for 5 minutes, cooled to 0° C. and then quenched with AcOH. The mixture was concentrated and then purified on silica gel (0-10% DCM/MeOH) to give the slightly impure desired product as a yellow residue (39 mg, 73% yield) which was used in the subsequent step without further purification. LC/MS (m/z) ES$^+$=383 (M+1).

Step B methyl 2-(tert-butoxy)-2-(1-(2-(tert-butoxy)-2-oxoethyl)-6-methyl-7-oxo-4-(p-tolyl-6,7-dihydro-1H-pyrrolo[2,3-c]pyridin-5-yl)acetate

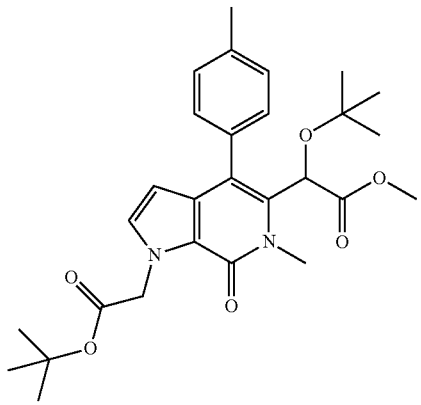 [SMILES: COC(=O)C(OC(C)(C)C)c1c(-c2ccc(C)cc2)c2ccn(CC(=O)OC(C)(C)C)c2c(=O)n1C]

A mixture of methyl 2-(tert-butoxy)-2-(6-methyl-7-oxo-4-(p-tolyl)-6,7-dihydro-1H-pyrrolo[2,3-c]pyridin-5-yl)acetate (39.0 mg, 0.102 mmol), tert-butyl bromoacetate (0.151 mL, 1.020 mmol) and cesium carbonate (100 mg, 0.306 mmol) in acetonitrile (1.0 mL) was heated to 80° C. in a sealed tube for one hour. Water was added and the mixture was extracted with ethyl acetate. The combined extracts were washed with water, then brine, dried over Na$_2$SO$_4$, filtered and concentrated to a yellow residue (49 mg, 97% yield) which was used in the next step without further purification. LC/MS (m/z) ES$^+$=497 (M+1).

Step C methyl 2-(1-(2-((4-fluorophenyl)amino)-2-oxoethyl)-6-methyl-7-oxo-4-(p-tolyl)-6,7-dihydro-1H-pyrrolo[2,3-c]pyridin-5-yl)-2-hydroxyacetate

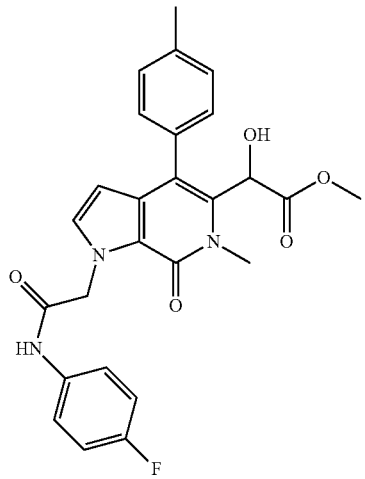 [SMILES: COC(=O)C(O)c1c(-c2ccc(C)cc2)c2ccn(CC(=O)Nc3ccc(F)cc3)c2c(=O)n1C]

A mixture of methyl 2-(tert-butoxy)-2-(1-(2-(tert-butoxy)-2-oxoethyl)-6-methyl-7-oxo-4-(p-tolyl)-6,7-dihydro-1H-pyrrolo[2,3-c]pyridin-5-yl)acetate (49 mg, 0.099 mmol) in Dichloromethane (DCM) (2.0 mL) and TFA (0.4 mL, 0.102 mmol) was stirred at ambient temperature for 60 hours (a dark mixture resulted). LCMS indicated cleavage of both t-butyl ester as well as t-butyl ether. The mixture was concentrated and then used crude in the next step. A mixture of the crude residue, 4-fluoroaniline (0.014 mL, 0.150 mmol) and Hünig's base (0.054 mL, 0.306 mmol) in N,N-Dimethylformamide (DMF) (0.5 mL) was treated with HATU (62.0 mg, 0.163 mmol) and then stirred at ambient temperature for 10 minutes. The mixture was diluted with ethyl acetate, washed with water, then brine, dried over Na$_2$SO$_4$, filtered and concentrated. The residue was purified on silica gel (0-70% Ethyl acetate/hexanes) to give the impure amide product as a pale yellow residue (20.5 mg, 42% yield). LC/MS (m/z) ES$^+$=497 (M+1).

Step D 2-(tert-butoxy)-2-(1-(2-((4-fluorophenyl)amino)-2-oxoethyl)-6-methyl-7-oxo-4-(p-tolyl)-6,7-dihydro-1H-pyrrolo[2,3-c]pyridin-5-yl)acetic acid

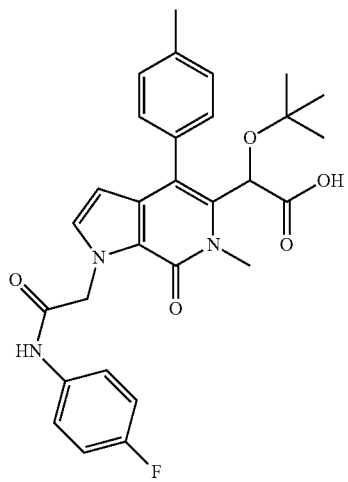 [SMILES: Cc1ccc(-c2c(C(OC(C)(C)C)C(=O)O)n(C)c(=O)c3c2ccn3CC(=O)Nc2ccc(F)cc2)cc1]

An ice cold mixture of methyl 2-(1-(2-((4-fluorophenyl)amino)-2-oxoethyl)-6-methyl-7-oxo-4-(p-tolyl)-6,7-dihydro-1H-pyrrolo[2,3-c]pyridin-5-yl)-2-hydroxyacetate (20.5 mg, 0.043 mmol) in t-Butyl acetate (5.0 mL) was treated with perchloric acid (0.2 mL, 0.102 mmol) and then stirred at ambient temperature for 2 hours. The mixture was quenched with 3M NaOH and extracted with ethyl acetate. The combined extracts were washed with brine, dried over sodium sulfate filtered and concentrated. The residue was dissolved in Methanol (1.000 mL) and Tetrahydrofuran (THF) (1.000 mL), treated with 1N LiOH (0.4 mL, 0.400 mmol) and then heated to 70° C. for 80 minutes. The mixture was concentrated and then purified by reverse phase chromatography (10-90% MeCN/H$_2$O-0.1% TFA, 12 min) to give the desired product as a light brown residue. $^1H$ NMR (400 MHz, CHLOROFORM-d) ppm 10.54 (s, 1H), 7.62-7.44 (m, 3H), 7.36-7.14 (m, 4H), 7.07-6.91 (m, 2H), 6.09 (d, J=2.9 Hz, 1H), 5.50 (s, 1H), 5.22-5.16 (m, 1H), 5.15-5.08 (m, 1H), 3.76 (s, 3H), 2.44 (s, 3H), 1.00 (s, 9H); LC/MS (m/z) ES+=520 (M+1).

Example 36

2-(tert-butoxy)-2-(1-(4-fluorobenzyl)-4-(4-methoxyphenyl)-6-methyl-7-oxo-6,7-dihydro-1H-pyrrolo[2,3-c]pyridin-5-yl)acetic acid

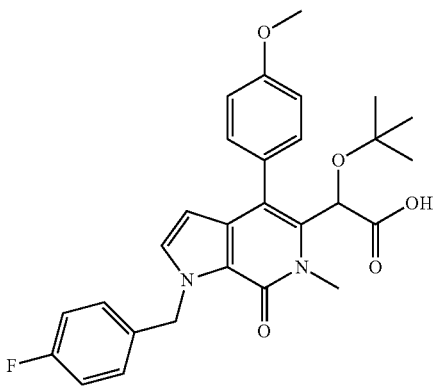 [SMILES: COc1ccc(-c2c(C(OC(C)(C)C)C(=O)O)n(C)c(=O)c3c2ccn3Cc2ccc(F)cc2)cc1]

The title compound was prepared in a manner similar to that described in Example 34 from 4-fluorobenzylamine and 4-methoxyphenylboronic acid and was isolated as a white solid (204 mg, 83%) after reverse phase chromatography (10-90% MeCN/H$_2$O-0.1% TFA, 12 min). $^1$H NMR (400 MHz, CHLOROFORM-d) ppm 7.65-7.52 (m, 1H), 7.43-7.34 (m, 1H), 7.33-7.18 (m, 2H), 7.08-6.92 (m, 5H), 6.04 (d, J=2.7 Hz, 1H), 5.93-5.83 (m, 1H), 5.83-5.67 (m, 1H), 5.48 (s, 1H), 3.88 (s, 3H), 3.67 (s, 3H), 1.01 (s, 9H); LC/MS (m/z) ES$^+$=493 (M+1).

Example 37

2-(tert-butoxy)-2-(1-(4-fluorobenzyl)-4-(4-fluorophenyl)-6-methyl-7-oxo-6,7-dihydro-1H-pyrrolo[2,3-c]pyridin-5-yl)acetic acid

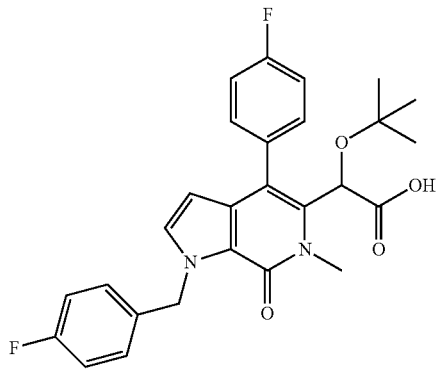 [SMILES: Cn1c(C(OC(C)(C)C)C(=O)O)c(-c2ccc(F)cc2)c2ccn(Cc3ccc(F)cc3)c2c1=O]

The title compound was prepared in a manner similar to that described in Example 34 from 4-fluorobenzylamine and 4-fluorophenylboronic acid and was isolated as a white solid (84 mg, 39%) after reverse phase chromatography (10-90% MeCN/H$_2$O-0.1% TFA, 12 min). $^1$H NMR (400 MHz, CHLOROFORM-d) ppm 7.72-7.60 (m, 1H), 7.50-7.40 (m, 1H), 7.34-7.25 (m, 2H), 7.24-7.11 (m, 2H), 7.08-6.95 (m, 3H), 6.00 (d, J=2.9 Hz, 1H), 5.90-5.82 (m, 1H), 5.81-5.69 (m, 1H), 5.37 (s, 1H), 3.67 (s, 3H), 1.02 (s, 9H); LC/MS (m/z) ES$^+$=481 (M+1).

Scheme 11

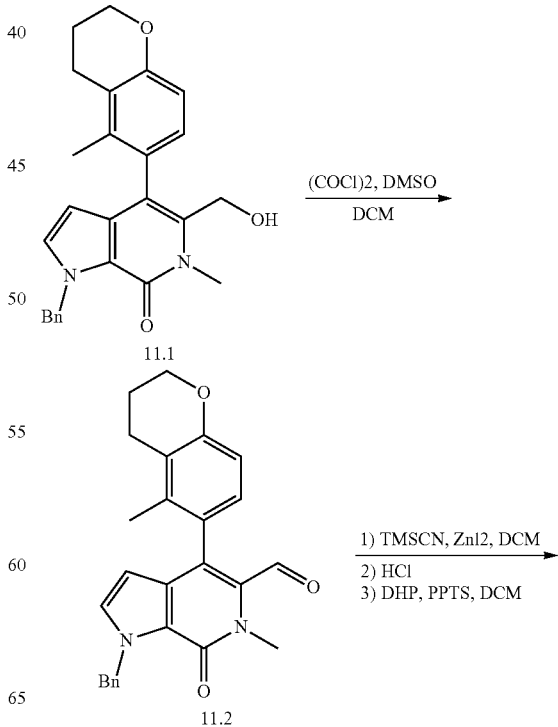

113
-continued

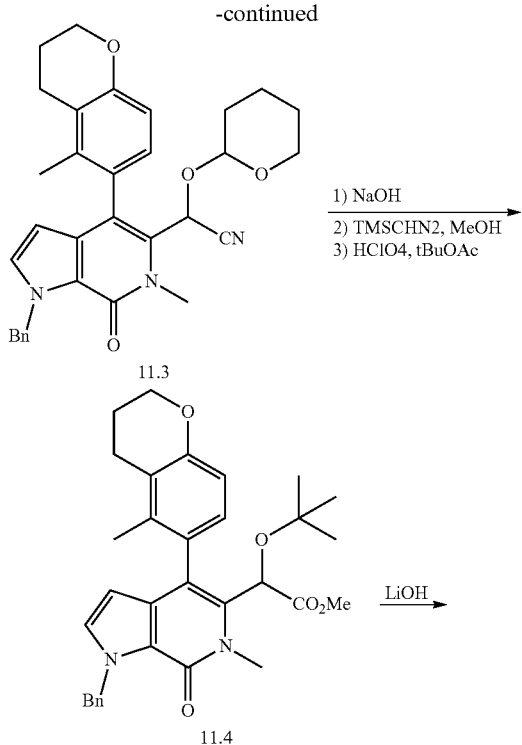

11.3

11.4

11.5

Example 38

2-(1-benzyl-6-methyl-4-(5-methylchroman-6-yl)-7-oxo-6,7-dihydro-1H-pyrrolo[2,3-c]pyridin-5-yl)-2-(tert-butoxy)acetic acid

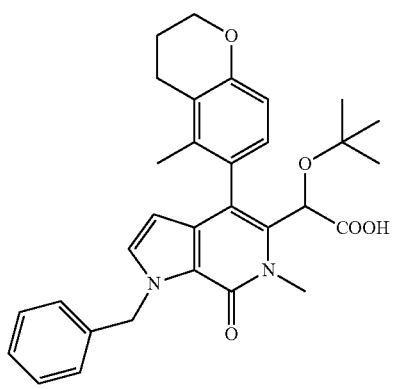 [SMILES: Cc1c(-c2c(C(OC(C)(C)C)C(=O)O)n(C)c(=O)c3c2ccn3Cc2ccccc2)ccc2c1CCCO2]

114

Step A 1-benzyl-5-(hydroxymethyl)-6-methyl-4-(5-methyl-chroman-6-yl)-1H-pyrrolo[2,3-c]pyridin-7(6H)-one

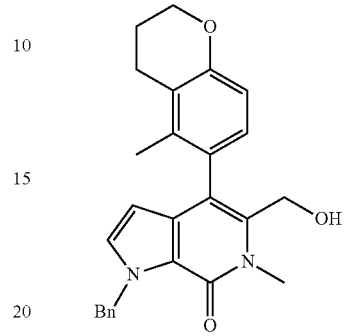

The title compound was prepared in a manner similar to that described in Example 1 steps A through I except that 4,4,5,5-tetramethyl-2-(5-methylchroman-6-yl)-1,3,2-dioxaborolane (WO2009/62308A1) was used in Step H and the product, which was 80% pure, was used crude in the next step without further purification. LC/MS (m/z) ES$^+$=415 (M+1)

Step B 1-benzyl-6-methyl-4-(5-methylchroman-6-yl)-7-oxo-6,7-dihydro-1H-pyrrolo[2,3-c]pyridine-5-carbaldehyde

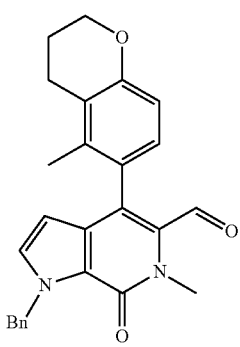

A −78° C. solution of oxalyl chloride (1.816 mL, 20.75 mmol) in Dichloromethane (DCM) (40.0 mL) was treated slowly with DMSO (2.94 mL, 41.5 mmol) and the resultant was stirred at −78° C. for 15 minutes. A solution of 1-benzyl-5-(hydroxymethyl)-6-methyl-4-(5-methylchroman-6-yl)-1H-pyrrolo[2,3-c]pyridin-7(6H)-one (5.1 g, 9.84 mmol) in Dichloromethane (DCM) (40.0 mL) was slowly added and the mixture was stirred at −78° C. for 40 minutes. Triethylamine (11.57 mL, 83 mmol) was then added and the mixture was stirred at −78° C. for 6 hours. The mixture was quenched with saturated sodium bicarbonate and then extracted with

115 dichloromethane. The combined extracts were dried over sodium sulfate, filtered and concentrated. The residue was purified on silica gel (0-100% ethyl acetate/hexanes) to give 1-benzyl-6-methyl-4-(5-methylchroman-6-yl)-7-oxo-6,7-dihydro-1H-pyrrolo[2,3-c]pyridine-5-carbaldehyde (1.53 g, 3.71 mmol, 35.8% yield). $^1$H NMR (400 MHz, CHLOROFORM-d) ppm 9.45 (s, 1H), 7.41-7.24 (m, 5H), 7.06 (m, 1H), 6.99 (d, J=8.2 Hz, 1H), 6.75 (d, J=8.2 Hz, 1H), 6.02 (d, J=2.9 Hz, 1H), 6.00-5.93 (m, 1H), 5.88-5.78 (m, 1H), 4.21 (t, J=5.0 Hz, 2H), 3.95 (s, 3H), 2.70 (t, J=6.4 Hz, 2H), 2.18-2.07 (m, 2H), 1.98 (s, 3H); LC/MS (m/z) ES$^+$=413 (M+1).

Step C 2-(1-benzyl-6-methyl-4-(5-methylchroman-6-yl)-7-oxo-6,7-dihydro-1H-pyrrolo[2,3-c]pyridin-5-yl)-2-((tetrahydro-2H-pyran-2-yl)oxy)acetonitrile

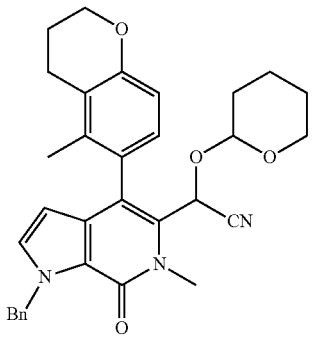 [SMILES: Cc1c(-c2c(C(C#N)OC3CCCCO3)n(C)c(=O)c3c2ccn3Cc2ccccc2)ccc2c1CCCO2]

An ice cold solution of 1-benzyl-6-methyl-4-(5-methylchroman-6-yl)-7-oxo-6,7-dihydro-1H-pyrrolo[2,3-c]pyridine-5-carbaldehyde (1.53 g, 3.34 mmol) in Dichloromethane (DCM) (30 mL) was treated with zinc iodide (2.131 g, 6.68 mmol) and TMSCN (4.48 mL, 33.4 mmol) and the mixture was stirred at ambient temperature for 10 minutes. The mixture was diluted with DCM, washed with brine, dried over Na$_2$SO$_4$, filtered and concentrated. The residue was used crude in the next step with no further purification. A solution of 2-(1-benzyl-6-methyl-4-(5-methylchroman-6-yl)-7-oxo-6,7-dihydro-1H-pyrrolo[2,3-c]pyridin-5-yl)-2-((trimethylsilyl)oxy)acetonitrile (1.73 g, 3.18 mmol, 95% yield) in Dichloromethane (DCM) (30 mL) was treated with 1N HCl (13.35 mL, 13.35 mmol) and allowed to stir at ambient temperature for 2 hours. The mixture was concentrated and used in the next step. A solution of 2-(1-benzyl-6-methyl-4-(5-methylchroman-6-yl)-7-oxo-6,7-dihydro-1H-pyrrolo[2,3-c]pyridin-5-yl)-2-hydroxyacetonitrile (1.55 g, 3.17 mmol, 95% yield) in Dichloromethane (DCM) (30 mL) was treated with pyridinium p-toluenesulfonate (0.042 g, 0.167 mmol) and 3,4-dihydro-2H-pyran (1.221 mL, 13.35 mmol) and then stirred at ambient temperature overnight. The mixture was concentrated and then purified on silica gel (0-50% ethyl acetate/hexanes) to afford the title compound (1.8 g, 93% yield). LC/MS (m/z) ES$^+$=524 (M+1).

116

Step D methyl 2-(1-benzyl-6-methyl-4-(5-methylchroman-6-yl)-7-oxo-6,7-dihydro-1H-pyrrolo[2,3-c]pyridin-5-yl)-2-(tert-butoxy)acetate

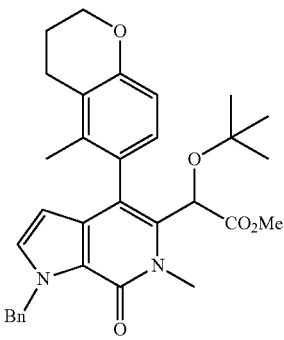 [SMILES: COC(=O)C(OC(C)(C)C)c1c(-c2ccc3c(c2C)CCCO3)c2ccn(Cc3ccccc3)c2c(=O)n1C]

A solution of 2-(1-benzyl-6-methyl-4-(5-methylchroman-6-yl)-7-oxo-6,7-dihydro-1H-pyrrolo[2,3-c]pyridin-5-yl)-2-((tetrahydro-2H-pyran-2-yl)oxy)acetonitrile (1.8 g, 3.09 mmol) in Ethanol (50 mL) was treated with NaOH (25 mL, 144 mmol) and the mixture was heated at 140° C. in a sealed tube overnight. HCl (conc.) was added until pH<2 and then the mixture was extracted with ethyl acetate. The combined organics were washed with brine, dried over Na$_2$SO$_4$, filtered and concentrated. The resulting residue was dissolved in Methanol (30 mL), cooled to 0° C. and then treated with TMS-diazomethane (6.19 mL, 12.38 mmol). The mixture was stirred for 2 hours and then concentrated. The resulting residue was dissolved in t-Butyl acetate (10 mL), treated with perchloric acid (0.186 mL, 3.09 mmol) and then stirred at ambient temperature overnight. The mixture was diluted with ethyl acetate, washed with 1M NaOH, then brine. The organic phase was then dried over Na$_2$SO$_4$, filtered and concentrated. The residue was purified on silica gel (0-70% ethyl acetate/hexanes) to afford the title compound (280 mg) as well as methyl 2-(1-benzyl-6-methyl-4-(5-methylchroman-6-yl)-7-oxo-6,7-dihydro-1H-pyrrolo[2,3-c]pyridin-5-yl)-2-hydroxyacetate (500 mg). An ice cold solution of methyl 2-(1-benzyl-6-methyl-4-(5-methylchroman-6-yl)-7-oxo-6,7-dihydro-1H-pyrrolo[2,3-c]pyridin-5-yl)-2-hydroxyacetate (500 mg) in t-Butyl acetate (5 mL) was treated with perchloric acid (1 eq.) then kept at 0° C. for 2 days without stirring. The mixture was diluted with ethyl acetate, washed with 1M NaOH, then brine. The organic phase was then dried over Na$_2$SO$_4$, filtered and concentrated. The residue was purified on silica gel (0-70% ethyl acetate/hexanes) to afford the title compound (290 mg). The material from each purification was combined to give the title compound (570 mg, 34% yield). $^1$H NMR (400 MHz, CHLOROFORM-d) ppm 7.37-7.29 (m, 5H), 7.15 (m, 1H), 7.02-6.91 (m, 1H), 6.74 (m, 1H), 5.99-5.67 (m, 3H), 5.28 (s, 0.7H), 5.10 (s, 0.3H), 4.27-4.15 (m, 2H), 3.77 (s, 2H), 3.73 (s, 1H), 3.67 (s, 3H), 2.77-2.58 (m, 2H), 2.17-2.03 (m, 2H), 1.92 (s, 3H), 1.12 (s, 3H), 0.97 (s, 6H); LC/MS (m/z) ES$^+$=529 (M+1).

Step E 2-(1-benzyl-6-methyl-4-(5-methylchroman-6-yl)-7-oxo-6,7-dihydro-1H-pyrrolo[2,3-c]pyridin-5-yl)-2-(tert-butoxy)acetic acid

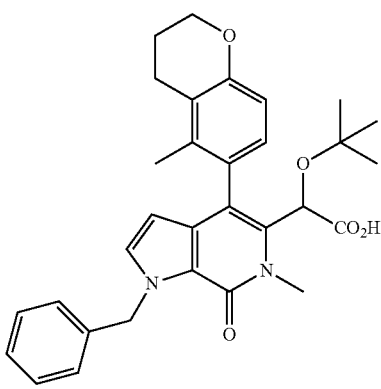 [SMILES: Cc1c(-c2c(C(OC(C)(C)C)C(=O)O)n(C)c(=O)c3c2ccn3Cc2ccccc2)ccc2c1CCCO2]

The title compound was prepared in a manner similar to that described in Example 1 step N to afford an off-white solid after reverse phase chromatography (10-90% MeCN/H$_2$O-0.1% TFA, 12 min). $^1$H NMR (400 MHz, CHLOROFORM-d) ppm 7.39-7.25 (m, 6H), 7.03-6.92 (m, 1H), 6.74 (m, 1H), 5.99-5.87 (m, 1H), 5.85-5.69 (m, 2H), 5.45 (s, 0.5H), 5.18 (s, 0.5H), 4.33-4.08 (m, 2H), 3.68 (d, J=2.9 Hz, 3H), 2.78-2.52 (m, 2H), 2.17-2.07 (m, 2H), 2.03 (s, 1.5H), 1.95 (s, 1.5H), 1.17 (s, 4H), 1.04 (s, 5H); LCMS (m/z) ES$^+$=515 (M+1).

Example 39

2-(tert-butoxy)-2-(6-methyl-4-(5-methylchroman-6-yl)-7-oxo-6,7-dihydro-1H-pyrrolo[2,3-c]pyridin-5-yl)acetic acid

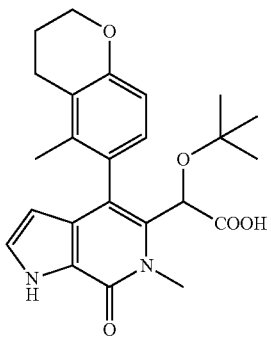 [SMILES: Cc1c(-c2c(C(OC(C)(C)C)C(=O)O)n(C)c(=O)c3[nH]ccc23)ccc2c1CCCO2]

An ice cold solution of 2-(1-benzyl-6-methyl-4-(5-methylchroman-6-yl)-7-oxo-6,7-dihydro-1H-pyrrolo[2,3-c]pyridin-5-yl)-2-(tert-butoxy)acetic acid (210 mg, 0.408 mmol) in Tetrahydrofuran (THF) (3 mL) was treated with KHMDS (8.16 mL, 4.08 mmol) and then heated to 50° C. for 2 hours. Additional KHMDS (8.16 mL, 4.08 mmol) was added and the mixture was stirred at 70° C. overnight. The mixture was quenched with HCl (1M) at 0° C. and extracted with ethyl acetate. The combined extracts were washed with brine, dried over Na$_2$SO$_4$, filtered and concentrated. The residue was purified by reverse phase chromatography (10-90% MeCN/H$_2$O-0.1% TFA, 12 min) to afford 2-(tert-butoxy)-2-(6-methyl-4-(5-methylchroman-6-yl)-7-oxo-6,7-dihydro-1H-pyrrolo[2,3-c]pyridin-5-yl)acetic acid (163 mg, 0.384 mmol, 94% yield) as white solid. $^1$H NMR (400 MHz, CHLOROFORM-d) ppm 11.20-11.38 (m, 1H) 7.28-7.40 (m, 1H) 6.93-7.05 (m, 1H) 6.70-6.82 (m, 1H) 5.84-6.01 (m, 1H) 5.25-5.57 (m, 1H) 4.15-4.28 (m, 2H) 3.74-3.90 (m, 3H) 2.61-2.78 (m, 2H) 2.04-2.19 (m, 2H) 1.87-2.06 (m, 2H) 0.94-1.26 (m, 9H); LCMS (m/z) ES$^+$=425 (M+1).

Example 40

2-(tert-butoxy)-2-(1,6-dimethyl-4-(5-methylchroman-6-yl)-7-oxo-6,7-dihydro-1H-pyrrolo[2,3-c]pyridin-5-yl)acetic acid

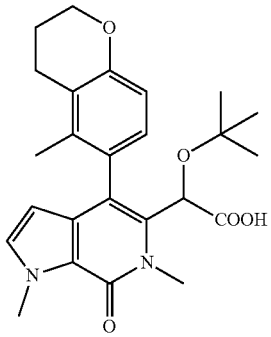 [SMILES: Cc1c(-c2c(C(OC(C)(C)C)C(=O)O)n(C)c(=O)c3c2ccn3C)ccc2c1CCCO2]

A solution of methyl 2-(1-benzyl-6-methyl-4-(5-methylchroman-6-yl)-7-oxo-6,7-dihydro-1H-pyrrolo[2,3-c]pyridin-5-yl)-2-(tert-butoxy)acetate (40 mg, 0.076 mmol) in Tetrahydrofuran (THF) (0.2 mL), Methanol (0.200 mL), Water (0.200 mL) was treated with NaOH (24.21 mg, 0.605 mmol) and heated at 70° C. for 3 hours. The mixture was cooled to 0° C., treated with HCl (1M) until pH <2 and then extracted with ethyl acetate. The combined extracts were washed with brine, dried over Na$_2$SO$_4$, filtered and concentrated. The resultant was dissolved in Tetrahydrofuran (THF) (0.2 mL), treated with KHMDS (0.757 mL, 0.378 mmol) and stirred at ambient temperature for one hour. Additional KHMDS (0.757 mL, 0.378 mmol) was added and the mixture was heated to 70° C. for 2 hours. The mixture was cooled to 0° C., treated with HCl (1M) until pH <2 and then extracted with ethyl acetate. The combined extracts were washed with brine, dried over Na$_2$SO$_4$, filtered and concentrated. The resultant was dissolved in N,N-Dimethylformamide (DMF) (0.5 mL), treated with MeI (0.024 mL, 0.378 mmol) and potassium carbonate (52.3 mg, 0.378 mmol) and then stirred at ambient temperature overnight. Water was added and the mixture was extracted with ethyl acetate. The combined extracts were washed with brine, dried over Na$_2$SO$_4$, filtered and concentrated. The resultant was dissolved in Tetrahydrofuran (THF) (0.2 mL), Methanol (0.200 mL) and Water (0.200 mL), treated with NaOH (24.21 mg, 0.605 mmol) and then heated to 70° C. for 3 hours. The mixture was cooled to 0° C., treated with HCl (1 M) until pH <2 and then extracted with ethyl acetate. The combined extracts were washed with brine, dried over Na₂SO₄, filtered and concentrated. The residue was purified by reverse phase chromatography (10-90% MeCN/H₂O-0.1% TFA, 12 min) to afford 2-(tert-butoxy)-2-(1,6-dimethyl-4-(5-methylchroman-6-yl)-7-oxo-6,7-dihydro-1H-pyrrolo[2,3-c]pyridin-5-yl)acetic acid (6 mg, 0.013 mmol, 17.72% yield) as a white solid. ¹H NMR (400 MHz, CHLOROFORM-d) ppm 7.28-7.33 (m, 1H) 6.96-7.02 (m, 1H) 6.92-6.96 (m, 1H) 6.70-6.81 (m, 1H) 5.70-5.81 (m, 1H) 5.15-5.46 (m, 1H) 4.17-4.25 (m, 5H) 3.66-3.68 (m, 3H) 2.60-2.77 (m, 2H) 2.06-2.16 (m, 2H) 1.92-2.05 (m, 3H) 0.98-1.05 (m, 9H); LCMS (m/z) ES⁺=439 (M+1).

Scheme 12

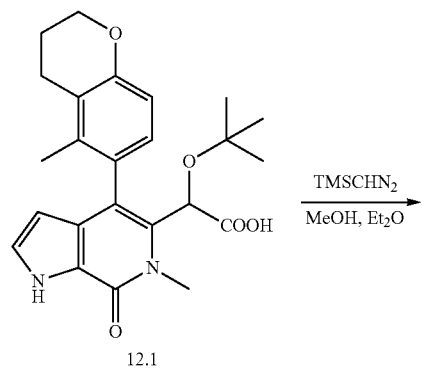

12.1

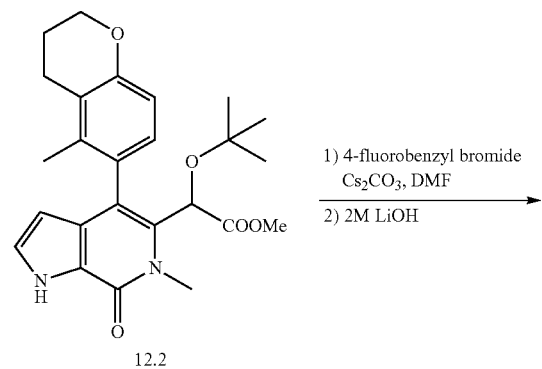

12.2

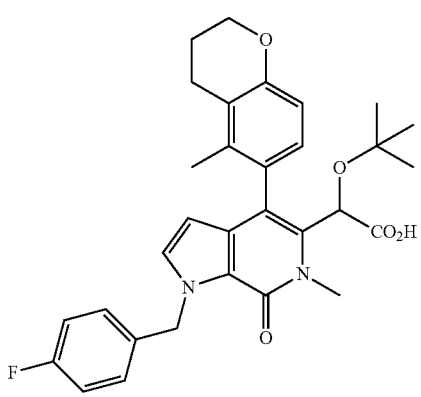

12.3

Example 41

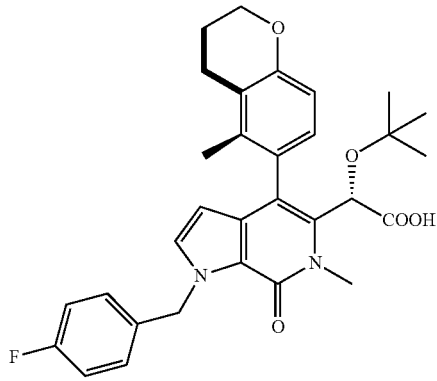

(S)(M)-2-(tert-butoxy)-2-(1-(4-fluorobenzyl)-6-methyl-4-(5-methylchroman-6-yl)-7-oxo-6,7-dihydro-1H-pyrrolo[2,3-c]pyridin-5-yl)acetic acid Step A (methyl 2-(tert-butoxy)-2-(6-methyl-4-(5-methylchroman-6-yl)-7-oxo-6,7-dihydro-1H-pyrrolo[2,3-c]pyridin-5-yl)acetate

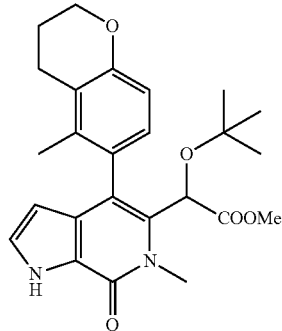 [SMILES: COC(=O)C(OC(C)(C)C)c1c(-c2ccc3c(c2C)CCCO3)c2cc[nH]c2c(=O)n1C]

An ice cold solution of 2-(tert-butoxy)-2-(6-methyl-4-(5-methylchroman-6-yl)-7-oxo-6,7-dihydro-1H-pyrrolo[2,3-c]pyridin-5-yl)acetic acid (170 mg, 0.384 mmol) in Methanol (3.00 mL) was treated with TMS-diazomethane (0.816 mL, 1.632 mmol) and then stirred at ambient temperature for 10 minutes. The mixture was concentrated and then purified on silica gel to give the methyl ester intermediate (0-10% DCM/Methanol). ¹H NMR (400 MHz, CHLOROFORM-d) ppm 7.23 (t, J=2.7 Hz, 0.5H), 7.21 (t, J=2.6 Hz, 0.5H), 7.17 (d, J=8.4 Hz, 0.5H), 7.00 (d, J=8.4 Hz, 0.5H), 6.79-6.67 (m, 1H), 5.89 (t, J=2.4 Hz, 0.5H), 5.81 (t, J=2.4 Hz, 0.5H), 5.34 (s, 0.5H), 5.17 (s, 0.5H), 4.22 (m, 2H), 3.81 (s, 1H), 3.77 (s, 1.5H), 3.75 (s, 1.5H), 3.66 (s, 1H), 2.70 (m, 2H), 2.16-2.04 (m, 2H), 1.93 (m, 3H), 1.13 (s, 4H), 0.98 (s, 5H); LC/MS (m/z) ES⁺=439 (M+1).

Step B

A solution of methyl 2-(tert-butoxy)-2-(6-methyl-4-(5-methylchroman-6-yl)-7-oxo-6,7-dihydro-1H-pyrrolo[2,3-c]

pyridin-5-yl)acetate (30 mg, 0.068 mmol) and 1-(bromomethyl)-4-fluorobenzene (0.043 mL, 0.342 mmol) in N,N-Dimethylformamide (DMF) (0.5 mL) was treated with Hunig's base (0.072 mL, 0.410 mmol) and the mixture was allowed to stir overnight at ambient temperature. Water was added and the mixture was extracted with ethyl acetate. The combined extracts were washed with brine, dried over sodium sulfate, filtered and concentrated. The residue in Tetrahydrofuran (THF) (0.2 mL), Methanol (0.200 mL) and Water (0.200 mL) was treated with NaOH (27.4 mg, 0.684 mmol) and then heated to 70° C. for 3 hours. The mixture was cooled to 0° C., adjusted to pH <2 with 1N HCl and then extracted with ethyl acetate. The combined extracts were washed with brine, dried over sodium sulfate, filtered and concentrated. The residue was purified by reverse phase chromatography. The residue was purified by chiral HPLC (IC Column, 10-20% IPA/hexanes w/0.1% formic acid; Rt=28.1 min) to afford the title compound as a white solid. $^1$H NMR (400 MHz, CHLOROFORM-d) d=7.35-7.20 (m, 1H), 7.06-6.92 (m, 4H), 6.71 (d, J=8.4 Hz, 1H), 5.77 (dd, J=3.2, 17.7 Hz, 3H), 5.19 (s, 1H), 4.19 (t, J=5.2 Hz, 2H), 3.68 (s, 3H), 2.69 (q, J=6.2 Hz, 2H), 2.09 (dd, J=4.3, 6.1 Hz, 2H), 2.03 (s, 3H), 1.17 (s, 9H); LC/MS (m/z) ES$^+$=533 (M+1).

Example 42

2-(tert-butoxy)-2-(6-methyl-4-(5-methylchroman-6-yl)-7-oxo-1-(pyridin-2-ylmethyl)-6,7-dihydro-1H-pyrrolo[2,3-c]pyridin-5-yl)acetic acid

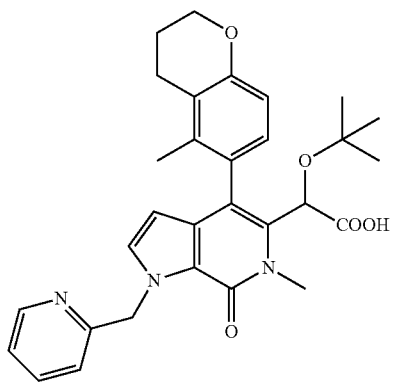 [SMILES: Cc1c(-c2c(C(OC(C)(C)C)C(=O)O)n(C)c(=O)c3c2ccn3Cc2ccccn2)ccc2c1CCCO2]

The title compound was prepared in a manner similar to that described in Example 41 from 2-(tert-butoxy)-2-(6-methyl-4-(5-methylchroman-6-yl)-7-oxo-6,7-dihydro-1H-pyrrolo[2,3-c]pyridin-5-yl)acetic acid and 2-(bromomethyl)pyridine, except that Hunig's base (10 eq.) was used instead of cesium carbonate and was isolated by reverse phase chromatography (10-90% MeCN/H$_2$O-0.1% TFA, 12 min) on an achiral column. $^1$H NMR (400 MHz, CHLOROFORM-d) ppm 8.75-8.91 (m, 1H) 8.14-8.27 (m, 1H) 7.85-8.01 (m, 1H) 7.62-7.75 (m, 1H) 7.30-7.42 (m, 1H) 6.68-6.80 (m, 1H) 6.38-6.47 (m, 2H) 5.80-6.03 (m, 2H) 5.25-5.54 (m, 1H) 4.15-4.28 (m, 2H) 3.68 (s, 3H) 2.61-2.74 (m, 2H) 2.06-2.16 (m, 2H) 1.89-2.02 (m, 3H) 1.04 (s, 9H); LCMS (m/z) ES$^+$=516 (M+1).

Example 43

2-(tert-butoxy)-2-(1-(2-methoxyethyl)-6-methyl-4-(5-methylchroman-6-yl)-7-oxo-6,7-dihydro-1H-pyrrolo[2,3-c]pyridin-5-yl)acetic acid

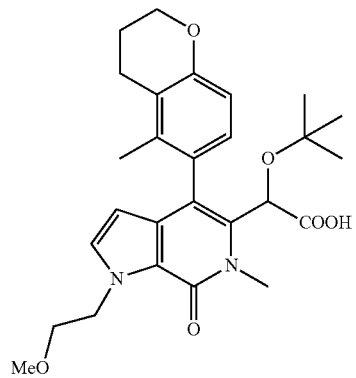 [SMILES: COCCn1ccc2c(-c3ccc4c(c3C)CCCO4)c(C(OC(C)(C)C)C(=O)O)n(C)c(=O)c21]

The title compound was prepared in a manner similar to that described in example 41 from 2-(tert-butoxy)-2-(6-methyl-4-(5-methylchroman-6-yl)-7-oxo-6,7-dihydro-1H-pyrrolo[2,3-c]pyridin-5-yl)acetic acid and 2-bromoethyl methyl ether and was isolated by reverse phase chromatography (10-90% MeCN/H$_2$O-0.1% TFA, 12 min) on an achiral column. $^1$H NMR (400 MHz, CHLOROFORM-d) ppm 7.29-7.36 (m, 1H) 6.97-7.12 (m, 1H) 6.69-6.82 (m, 1H) 5.71-5.81 (m, 1H) 5.18-5.49 (m, 1H) 4.82-4.90 (m, 1H) 4.72-4.79 (m, 1H) 4.57-4.67 (m, 1H) 4.16-4.28 (m, 2H) 3.75-3.85 (m, 2H) 3.69-3.72 (m, 3H) 3.51 (s, 2H) 3.34 (s, 3H) 2.63-2.76 (m, 2H) 2.06-2.16 (m, 2H) 1.93-2.06 (m, 3H) 1.01-1.21 (m, 9H); LCMS (m/z) ES$^+$=483 (M+1).

Example 44

2-(tert-butoxy)-2-(1-(4-chlorobenzyl)-6-methyl-4-(5-methylchroman-6-yl)-7-oxo-6,7-dihydro-1H-pyrrolo[2,3-c]pyridin-5-yl)acetic acid

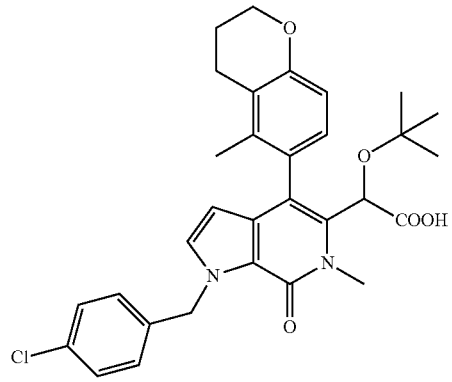 [SMILES: Cc1c(-c2c(C(OC(C)(C)C)C(=O)O)n(C)c(=O)c3c2ccn3Cc2ccc(Cl)cc2)ccc2c1CCCO2]

The title compound was prepared in a manner similar to that described in Example 41 from 2-(tert-butoxy)-2-(6-methyl-4-(5-methylchroman-6-yl)-7-oxo-6,7-dihydro-1H-pyrrolo[2,3-c]pyridin-5-yl)acetic acid and 4-chlorobenzylbromide and was isolated by reverse phase chromatography (10-90% MeCN/H$_2$O-0.1% TFA, 12 min) on an achiral column.

¹H NMR (400 MHz, CHLOROFORM-d) ppm 7.27-7.34 (m, 2H) 7.19-7.26 (m, 2H) 6.95-7.03 (m, 1H) 6.68-6.80 (m, 1H) 5.69-5.89 (m, 2H) 5.16-5.48 (m, 1H) 4.15-4.27 (m, 2H) 3.64-3.71 (m, 3H) 2.63-2.77 (m, 2H) 2.05-2.16 (m, 2H) 1.93-2.04 (m, 3H) 1.01-1.19 (m, 9H); LCMS (m/z) ES⁺=549 (M+1).

Example 45

2-(tert-butoxy)-2-(1-(3-fluorobenzyl)-6-methyl-4-(5-methylchroman-6-yl)-7-oxo-6,7-dihydro-1H-pyrrolo[2,3-c]pyridin-5-yl)acetic acid

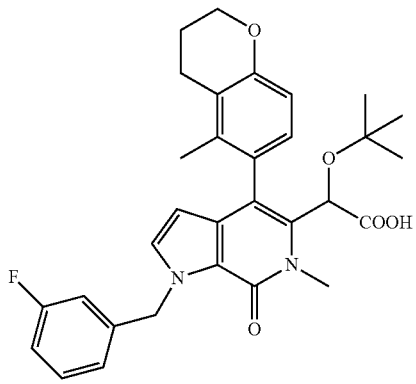 [SMILES: Cc1c(-c2c(C(OC(C)(C)C)C(=O)O)n(C)c(=O)c3c2ccn3Cc2cccc(F)c2)ccc2c1CCCO2]

The title compound was prepared in a manner similar to that described in Example 41 from 2-(tert-butoxy)-2-(6-methyl-4-(5-methylchroman-6-yl)-7-oxo-6,7-dihydro-1H-pyrrolo[2,3-c]pyridin-5-yl)acetic acid and 3-fluorobenzyl bromide and was isolated by reverse phase chromatography (10-90% MeCN/H₂O-0.1% TFA, 12 min) on an achiral column. ¹H NMR (400 MHz, CHLOROFORM-d) ppm 7.29-7.38 (m, 2H) 6.91-7.10 (m, 4H) 6.67-6.81 (m, 1H) 5.74-5.95 (m, 2H) 5.18-5.50 (m, 1H) 4.12-4.30 (m, 2H) 3.62-3.74 (m, 3H) 2.61-2.77 (m, 2H) 2.07-2.17 (m, 2H) 1.93-2.08 (m, 3H) 1.05 (s, 9H); LCMS (m/z) ES⁺=533 (M+1).

Example 46

2-(tert-butoxy)-2-(6-methyl-4-(5-methylchroman-6-yl)-7-oxo-1-(4-(trifluoromethyl)benzyl)-6,7-dihydro-1H-pyrrolo[2,3-c]pyridin-5-yl)acetic acid

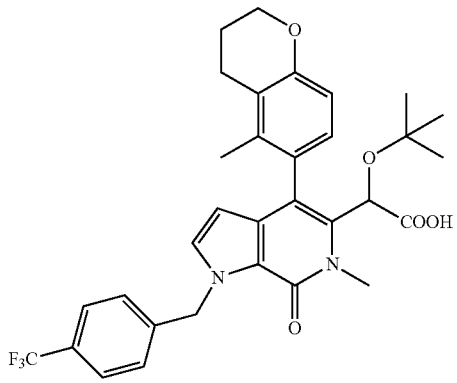 [SMILES: Cc1c(-c2c(C(OC(C)(C)C)C(=O)O)n(C)c(=O)c3c2ccn3Cc2ccc(C(F)(F)F)cc2)ccc2c1CCCO2]

The title compound was prepared in a manner similar to that described in Example 41 from 2-(tert-butoxy)-2-(6-methyl-4-(5-methylchroman-6-yl)-7-oxo-6,7-dihydro-1H-pyrrolo[2,3-c]pyridin-5-yl)acetic acid and 4-trifluorobenzyl bromide and was isolated by reverse phase chromatography (10-90% MeCN/H₂O-0.1% TFA, 12 min) on an achiral column. ¹H NMR (400 MHz, CHLOROFORM-d) ppm 7.51-7.65 (m, 2H) 7.29-7.41 (m, 2H) 6.96-7.04 (m, 1H) 6.69-6.81 (m, 1H) 5.76-6.03 (m, 2H) 5.15-5.48 (m, 1H) 4.13-4.29 (m, 2H) 3.66-3.68 (m, 3H) 2.62-2.78 (m, 2H) 2.05-2.17 (m, 2H) 1.91-2.05 (m, 3H) 0.97-1.22 (m, 9H); LCMS (m/z) ES⁺=583 (M+1).

Example 47

2-(tert-butoxy)-2-(6-methyl-4-(5-methylchroman-6-yl)-1-(4-nitrobenzyl)-7-oxo-6,7-dihydro-1H-pyrrolo[2,3-c]pyridin-5-yl)acetic acid

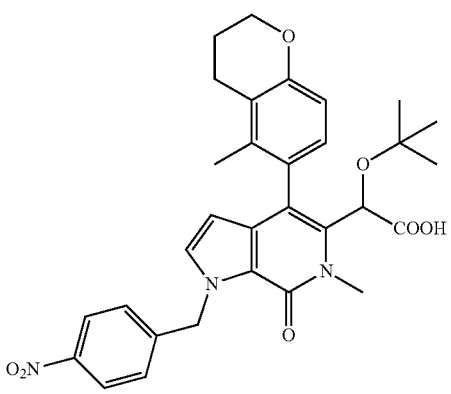 [SMILES: Cc1c(-c2c(C(OC(C)(C)C)C(=O)O)n(C)c(=O)c3c2ccn3Cc2ccc([N+](=O)[O-])cc2)ccc2c1CCCO2]

The title compound was prepared in a manner similar to that described in Example 41 from 2-(tert-butoxy)-2-(6-methyl-4-(5-methylchroman-6-yl)-7-oxo-6,7-dihydro-1H-pyrrolo[2,3-c]pyridin-5-yl)acetic acid and 4-nitrobenzyl bromide and was isolated by reverse phase chromatography (10-90% MeCN/H₂O-0.1% TFA, 12 min) on an achiral column. ¹H NMR (400 MHz, CHLOROFORM-d) ppm 8.15-8.23 (m, 2H) 7.31-7.42 (m, 3H) 6.97-7.05 (m, 1H) 6.71-6.80 (m, 1H) 5.80-6.03 (m, 3H) 5.15-5.44 (m, 1H) 4.16-4.26 (m, 2H) 3.61-3.71 (m, 3H) 2.64-2.76 (m, 2H) 2.07-2.16 (m, 2H) 1.93-2.06 (m, 3H) 0.98-1.19 (m, 9H); LCMS (m/z) ES⁺=560 (M+1).

Example 48

2-(tert-butoxy)-2-(1-(2,5-difluorobenzyl)-6-methyl-4-(5-methylchroman-6-yl)-7-oxo-6,7-dihydro-1H-pyrrolo[2,3-c]pyridin-5-yl)acetic acid

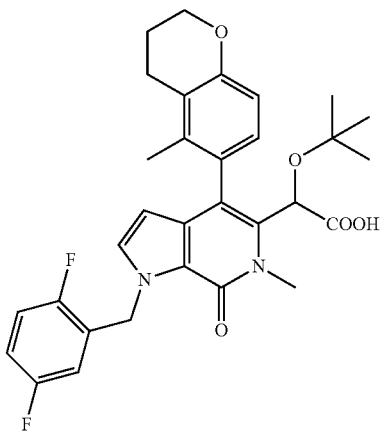 [SMILES: Cc1c(-c2c(C(OC(C)(C)C)C(=O)O)n(C)c(=O)c3c2ccn3Cc2cc(F)ccc2F)ccc2c1CCCO2]

The title compound was prepared in a manner similar to that described in Example 41 from 2-(tert-butoxy)-2-(6-methyl-4-(5-methylchroman-6-yl)-7-oxo-6,7-dihydro-1H-pyr-rolo[2,3-c]pyridin-5-yl)acetic acid and 2,5-difluorobenzyl bromide and was isolated by reverse phase chromatography (10-90% MeCN/H$_2$O-0.1% TFA, 12 min) on an achiral column. $^1$H NMR (400 MHz, CHLOROFORM-d) ppm 7.29-7.37 (m, 1H) 6.97-7.09 (m, 3H) 6.87-6.96 (m, 1H) 6.68-6.80 (m, 1H) 5.92-6.02 (m, 1H) 5.73-5.90 (m, 2H) 5.13-5.45 (m, 1H) 4.13-4.27 (m, 2H) 3.62-3.74 (m, 3H) 2.59-2.78 (m, 2H) 2.05-2.17 (m, 2H) 1.91-2.05 (m, 3H) 0.97-1.22 (m, 9H); LCMS (m/z) ES$^+$=551 (M+1).

Scheme 13

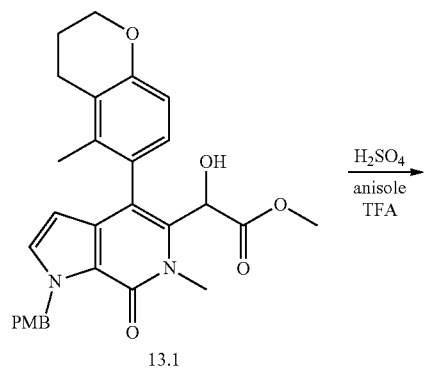

13.1

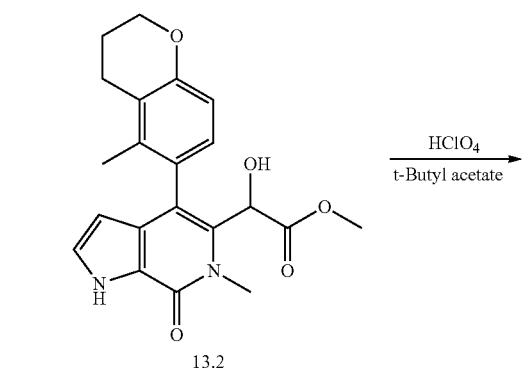

13.2

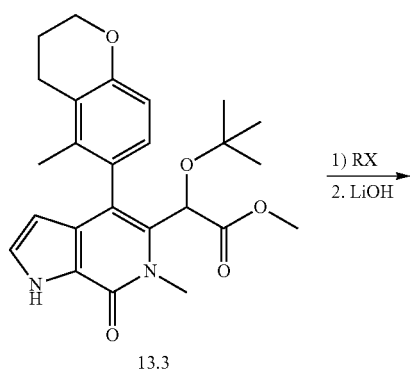

13.3

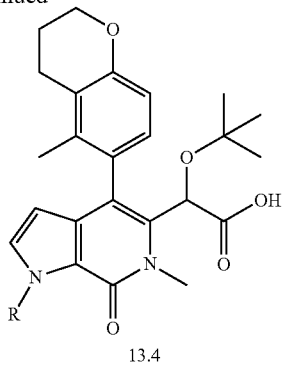

13.4

Example 49

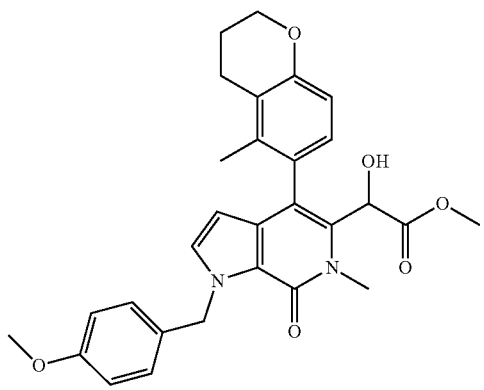

2-(tert-butoxy)-2-(1-(3-fluoro-4-methylbenzyl)-6-methyl-4-(5-methylchroman-6-yl)-7-oxo-6,7-dihydro-1H-pyrrolo[2,3-c]pyridin-5-yl)acetic acid Step A methyl 2-hydroxy-2-(1-(4-methoxybenzyl)-6-methyl-4-(5-methylchroman-6-yl)-7-oxo-6,7-dihydro-1H-pyrrolo[2,3-c]pyridin-5-yl)acetate Methyl 2-hydroxy-2-(1-(4-methoxybenzyl)-6-methyl-4-(5-methylchroman-6-yl)-7-oxo-6,7-dihydro-1H-pyrrolo[2, 3-c]pyridin-5-yl)acetate was prepared in a manner similar to that described in Example 1 steps A through L, except that para-methoxybenzyl amine was used in step B, and 4,4,5,5-tetramethyl-2-(5-methylchroman-6-yl)-1,3,2-dioxaborolane was used in step H, and was isolated as clear oil that slowly solidified to white solid: LCMS (m/z) ES$^+$=503 (M+1).

Step B methyl 2-hydroxy-2-(6-methyl-4-(5-methylchroman-6-yl)-7-oxo-6,7-dihydro-1H-pyrrolo[2,3-c]pyridin-5-yl)acetate

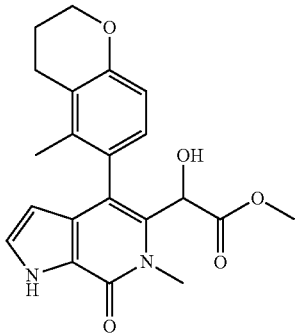 [SMILES: COC(=O)C(O)c1c(-c2ccc3c(c2C)CCCO3)c2cc[nH]c2c(=O)n1C]

An ice cold solution of methyl 2-hydroxy-2-(1-(4-methoxybenzyl)-6-methyl-4-(5-methylchroman-6-yl)-7-oxo-6,7-dihydro-1H-pyrrolo[2,3-c]pyridin-5-yl)acetate (880 mg, 1.751 mmol) in Trifluoroacetic acid (TFA) (3.5 mL) was treated with conc. H$_2$SO$_4$ (0.262 mL, 4.92 mmol) and anisole (0.525 mL, 4.81 mmol). After stirring for 1 hour, the reaction was warmed to rt for 2 hours, and then quenched with sat. NaHCO$_3$ until neutral. The mixture was extracted with EtOAc, washed with Brine, dried with Na$_2$SO$_4$, filtered, and concentrated. Purification with column chromatography (0-100% EtOAc/Hexane, then 0-20% MeOH/DCM) afforded methyl 2-hydroxy-2-(6-methyl-4-(5-methylchroman-6-yl)-7-oxo-6,7-dihydro-1H-pyrrolo[2,3-c]pyridin-5-yl)acetate (421.4 mg, 1.102 mmol, 62.9% yield) as yellow oil: LCMS (m/z) ES$^+$=383 (M+1).

Step C methyl 2-(tert-butoxy)-2-(6-methyl-4-(5-methylchroman-6-yl)-7-oxo-6,7-dihydro-1H-pyrrolo[2,3-c]pyridin-5-yl)acetate

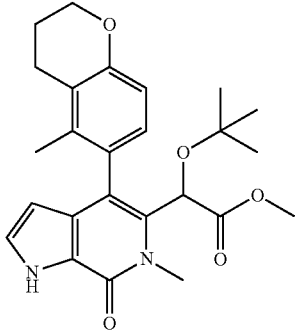 [SMILES: COC(=O)C(OC(C)(C)C)c1c(-c2ccc3c(c2C)CCCO3)c2cc[nH]c2c(=O)n1C]

An ice cold solution of methyl 2-hydroxy-2-(6-methyl-4-(5-methylchroman-6-yl)-7-oxo-6,7-dihydro-1H-pyrrolo[2,3-c]pyridin-5-yl)acetate (425 mg, 1.111 mmol) in tert-butyl acetate (15.000 mL, 111 mmol) was treated with perchloric acid (0.191 mL, 2.223 mmol), and stirred for 5 min. The reaction was then kept in the refrigerator without stirring overnight. The reaction was quenched with sat. NaHCO$_3$ at 0° C., extracted with EtOAc 2×, washed with Brine, dried with Na$_2$SO$_4$, filtered, and concentrated. Purification with column chromatography (0-100% EtOAc/Hexane, then 0-20% MeOH/DCM) gave methyl 2-(tert-butoxy)-2-(6-methyl-4-(5-methylchroman-6-yl)-7-oxo-6,7-dihydro-1H-pyrrolo[2,3-c]pyridin-5-yl)acetate (224.7 mg, 0.512 mmol, 46.1% yield) as off white solid. NMR showed 2:1 diastereomer. $^1$H NMR (400 MHz, CHLOROFORM-d) ppm 9.93 (br. s., 1H), 7.19-7.12 (m, 1.4H), 6.99 (d, J=8.4 Hz, 0.6H), 6.77-6.68 (m, 1H), 5.91-5.77 (m, 1H), 5.36-5.10 (m, 1H), 4.27-4.16 (m, 2H), 3.81-3.74 (m, 3H), 3.74-3.62 (m, 3H), 2.77-2.60 (m, 2H), 2.17-2.06 (m, 2H), 1.95-1.88 (m, 3H), 1.16-1.07 (m, 6H), 1.00-0.94 (m, 3H); LCMS (m/z) ES$^+$=439 (M+1).

Step D 2-(tert-butoxy)-2-(1-(3-fluoro-4-methylbenzyl)-6-methyl-4-(5-methylchroman-6-yl)-7-oxo-6,7-dihydro-1H-pyrrolo[2,3-c]pyridin-5-yl)acetic acid

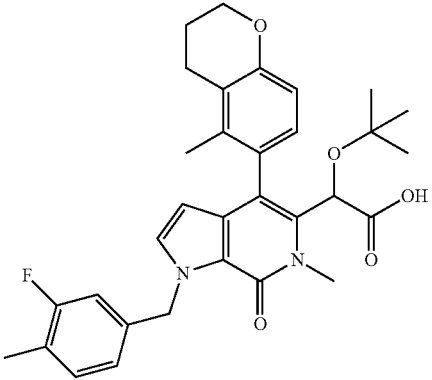 [SMILES: Cc1ccc(Cn2ccc3c(-c4ccc5c(c4C)CCCO5)c(C(OC(C)(C)C)C(=O)O)n(C)c(=O)c32)cc1F]

A solution of methyl 2-(tert-butoxy)-2-(6-methyl-4-(5-methylchroman-6-yl)-7-oxo-6,7-dihydro-1H-pyrrolo[2,3-c]pyridin-5-yl)acetate (20 mg, 0.046 mmol) in Acetonitrile (0.45 mL) was treated with Cs$_2$CO$_3$ (59.4 mg, 0.182 mmol), 3-fluoro-4-methylbenzyl bromide (13.89 mg, 0.068 mmol), and then stirred at 70° C. for 90 min. The reaction was cooled to rt, diluted with water and 1N HCl, extracted with EtOAc, washed Brine, dried with Na$_2$SO$_4$, filtered, and concentrated. Purification with column chromatography (0-60% EtOAc/Hexane) gave methyl 2-(tert-butoxy)-2-(1-(3-fluoro-4-methylbenzyl)-6-methyl-4-(5-methylchroman-6-yl)-7-oxo-6,7-dihydro-1H-pyrrolo[2,3-c]pyridin-5-yl)acetate (21.5 mg, 0.038 mmol, 84% yield) as clear oil: LCMS (m/z) ES$^+$=561 (M+1). The intermediate was dissolved in Methanol (0.5 mL) and Tetrahydrofuran (THF) (0.5 mL), treated with LiOH (0.100 mL, 0.200 mmol), and stirred overnight at 60° C. The reaction was concentrated and purified with reverse phase HPLC (20-100% MeCN/H$_2$O-0.1% TFA) to give title compound (13.5 mg, 0.024 mmol, 64.7% yield) as white solid: $^1$H NMR (400 MHz, CHLOROFORM-d) ppm 7.36-7.29 (m, 0.4H), 7.12 (t, J=7.8 Hz, 1H), 7.04-6.87 (m, 3.6H), 6.80-6.66 (m, 1H), 5.97-5.59 (m, 3H), 5.46-5.40 (m, 0.4H), 5.21-5.11 (m, 0.6H), 4.27-4.10 (m, 2H), 3.71-3.61 (m, 3H), 2.77-2.58 (m, 2H), 2.27-2.19 (m, 3H), 2.16-2.05 (m, 2H), 2.02 (s, 2H), 1.94 (s, 1H), 1.19-1.11 (m, 6H), 1.05-0.99 (m, 3; LCMS (m/z) ES$^+$=547 (M+1).

Example 50

2-(tert-butoxy)-2-(6-methyl-4-(5-methylchroman-6-yl)-7-oxo-1-(thiazol-4-ylmethyl)-6,7-dihydro-1H-pyrrolo[2,3-c]pyridin-5-yl)acetic acid, Trifluoroacetic acid salt

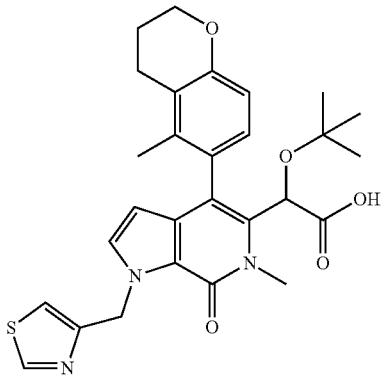 [SMILES: Cc1c(-c2c(C(OC(C)(C)C)C(=O)O)n(C)c(=O)c3c2ccn3Cc2cscn2)ccc2c1CCCO2]

The title compound was prepared in a manner similar to that described in Example 49 step D from methyl 2-(tert-butoxy)-2-(6-methyl-4-(5-methylchroman-6-yl)-7-oxo-6,7-dihydro-1H-pyrrolo[2,3-c]pyridin-5-yl)acetate and 4-(chloromethyl)thiazole, and was isolated as white solid after reverse phase chromatography (39%): $^1$H NMR (400 MHz, CHLOROFORM-d) ppm 8.83 (d, 1H), 7.55-7.46 (m, 1H), 7.32-7.27 (m, 0.4H), 7.23 (dd, J=3.0, 4.5 Hz, 1H), 6.96 (d, J=8.4 Hz, 0.6H), 6.80-6.65 (m, 1H), 6.12-5.73 (m, 3H), 5.43 (s, 0.4H), 5.20-5.14 (m, 0.6H), 4.29-4.11 (m, 2H), 3.72-3.65 (m, 3H), 2.77-2.54 (m, 2H), 2.16-2.05 (m, 2H), 2.00 (s, 2H), 1.93 (s, 1H), 1.18-1.10 (m, 6H), 1.02 (s, 3H); LCMS (m/z) ES$^+$=522 (M+1).

Example 51

2-(tert-butoxy)-2-(1-(cyclohexylmethyl)-6-methyl-4-(5-methylchroman-6-yl)-7-oxo-6,7-dihydro-1H-pyrrolo[2,3-c]pyridin-5-yl)acetic acid

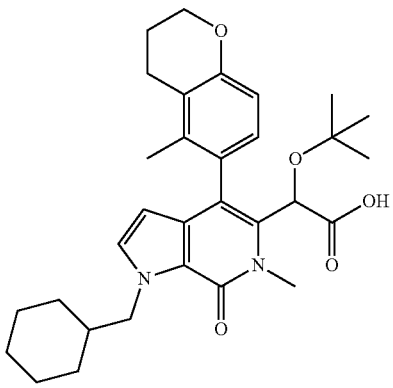 [SMILES: Cc1c(-c2c(C(OC(C)(C)C)C(=O)O)n(C)c(=O)c3c2ccn3CC2CCCCC2)ccc2c1CCCO2]

The title compound was prepared in a manner similar to that described in Example 49 step D from methyl 2-(tert-butoxy)-2-(6-methyl-4-(5-methylchroman-6-yl)-7-oxo-6,7-dihydro-1H-pyrrolo[2,3-c]pyridin-5-yl)acetate and (bromomethyl)cyclohexane, and was isolated as white solid after reverse phase chromatography (45%): $^1$H NMR (400 MHz, CHLOROFORM-d) ppm 7.35-7.28 (m, 0.4H), 6.99 (d, J=8.4 Hz, 0.6H), 6.90 (t, J=2.5 Hz, 1H), 6.78-6.67 (m, 1H), 5.73 (d, J=2.7 Hz, 0.4H), 5.67 (d, J=2.7 Hz, 0.6H), 5.40 (s, 0.4H), 5.15 (d, J=2.1 Hz, 0.6H), 4.48-4.34 (m, 1H), 4.34-4.23 (m, 1H), 4.23-4.12 (m, 2H), 3.73-3.61 (m, 3H), 2.79-2.57 (m, 2H), 2.16-2.05 (m, 2H), 2.05-1.98 (m, 2H), 1.98-1.83 (m, 2H), 1.75-1.55 (m, 5H), 1.40-0.91 (m, 14H); LCMS (m/z) ES$^+$=521 (M+1).

Example 52

2-(tert-butoxy)-2-(6-methyl-4-(5-methylchroman-6-yl)-7-oxo-1-((tetrahydro-2H-pyran-4-yl)methyl)-6,7-dihydro-1H-pyrrolo[2,3-c]pyridin-5-yl)acetic acid

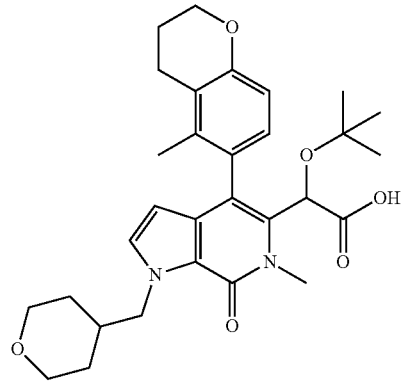 [SMILES: Cc1c(-c2c(C(OC(C)(C)C)C(=O)O)n(C)c(=O)c3c2ccn3CC2CCOCC2)ccc2c1CCCO2]

The title compound was prepared in a manner similar to that described in Example 49 step D from methyl 2-(tert-butoxy)-2-(6-methyl-4-(5-methylchroman-6-yl)-7-oxo-6,7-dihydro-1H-pyrrolo[2,3-c]pyridin-5-yl)acetate and 4-(bromomethyl)tetrahydro-2H-pyran, and was isolated as beige solid after reverse phase chromatography (45%): $^1$H NMR (400 MHz, CHLOROFORM-d) ppm 7.29 (d, J=8.6 Hz, 0.5H), 7.02-6.96 (m, 0.5H), 6.96-6.90 (m, 1H), 6.80-6.66 (m, 1H), 5.81-5.67 (m, 1H), 5.46-5.10 (m, 1H), 4.54-4.28 (m, 2H), 4.28-4.12 (m, 2H), 4.03-3.91 (m, 2H), 3.75-3.64 (m, 3H), 3.46-3.30 (m, 2H), 2.81-2.55 (m, 2H), 2.22 (d, J=3.7 Hz, 1H), 2.17-2.05 (m, 2H), 2.05-1.88 (m, 3H), 1.65-1.46 (m, 2H), 1.46-1.28 (m, 2H), 1.15 (s, 6H), 1.02 (s, 3H); LCMS (m/z) ES$^+$=523 (M+1).

Scheme 14

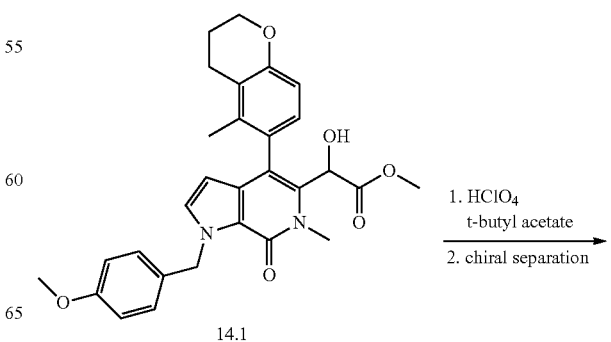

14.1

131

-continued

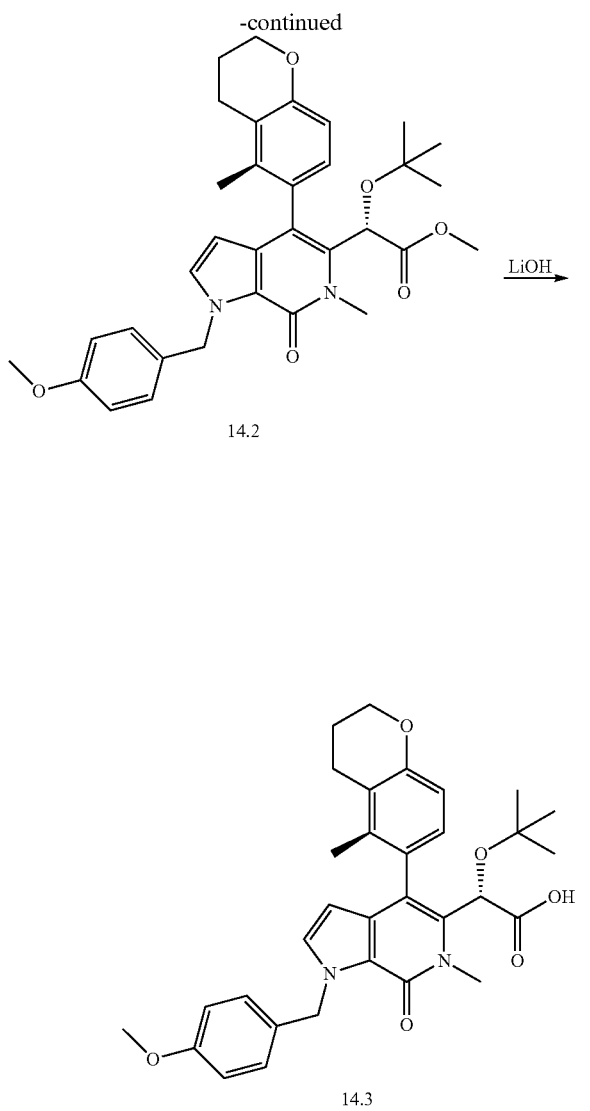

14.2

Example 53

132

(S)(M)-2-(tert-butoxy)-2-(1-(4-methoxybenzyl)-6-methyl-4-(5-methylchroman-6-yl)-7-oxo-6,7-dihydro-1H-pyrrolo[2,3-c]pyridin-5-yl)acetic acid Step A (S)(M)-methyl 2-(tert-butoxy)-2-(1-(4-methoxybenzyl)-6-methyl-4-(5-methylchroman-6-yl)-7-oxo-6,7-dihydro-1H-pyrrolo[2,3-c]pyridin-5-yl)acetate

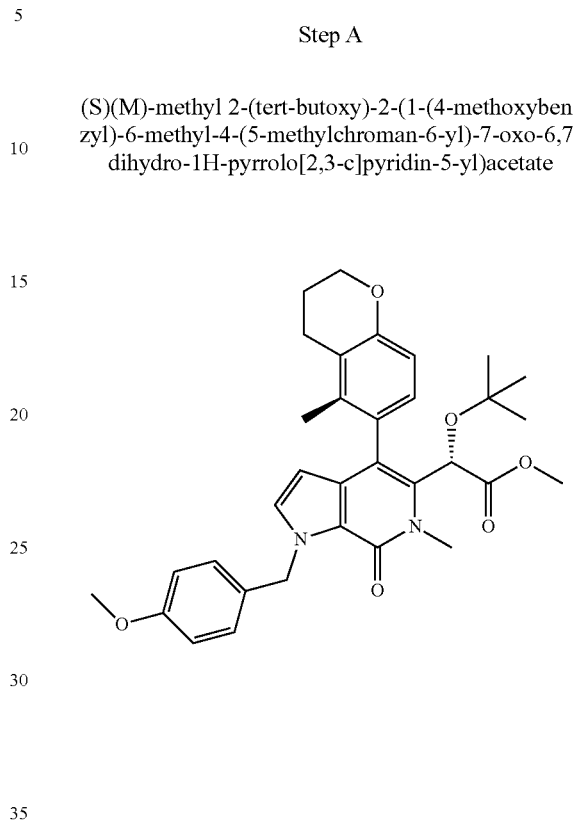

An ice cold solution of methyl 2-hydroxy-2-(1-(4-methoxybenzyl)-6-methyl-4-(5-methylchroman-6-yl)-7-oxo-6,7-dihydro-1H-pyrrolo[2,3-c]pyridin-5-yl)acetate (325 mg, 0.647 mmol) in tert-butyl acetate (8735 µl, 64.7 mmol) was treated with perchloric acid (55.6 µl, 0.647 mmol), and stirred for 20 min. The reaction was then kept in the refrigerator without stirring for 2 days. The reaction was quenched with sat. NaHCO$_3$ at 0° C., extracted with EtOAc 2×, washed with Brine, dried with Na$_2$SO$_4$, filtered, and concentrated. Purification with column chromatography (0-100% EtOAc/Hexane) gave methyl 2-(tert-butoxy)-2-(1-(4-methoxybenzyl)-6-methyl-4-(5-methylchroman-6-yl)-7-oxo-6,7-dihydro-1H-pyrrolo[2,3-c]pyridin-5-yl)acetate (219.3 mg, 0.393 mmol, 60.7% yield, racemate) as white solid. The racemate was resolved using a Chiralpak IC column (30×250 mm) with isocratic conditions of 10% EtOH in hexane. The flow rate was 40 mL/min and the baseline was monitored at 280 nm using an Agilent 1100 series prep LC. The third isomer eluting from the column was isolated to afford (S)(M)-methyl 2-(tert-butoxy)-2-(1-(4-methoxybenzyl)-6-methyl-4-(5-methylchroman-6-yl)-7-oxo-6,7-dihydro-1H-pyrrolo[2,3-c]pyridin-5-yl)acetate (52.9 mg, 0.095 mmol, 14.6% yield) as clear oil: $^1$H NMR (400 MHz, CHLOROFORM-d) ppm 7.29 (d, J=8.5 Hz, 2H), 6.99-6.91 (m, 2H), 6.85 (d, J=8.5 Hz, 2H), 6.69 (d, J=8.4 Hz, 1H), 5.86 (d, J=14.6 Hz, 1H), 5.71-5.61 (m, 2H), 5.09 (s, 1H), 4.20 (t, J=5.2 Hz, 2H), 3.78 (s, 3H), 3.72 (s, 3H), 3.65 (s, 3H), 2.76-2.62 (m, 2H), 2.13-2.04 (m, 2H), 1.91 (s, 3H), 1.11 (s, 9H); LCMS (m/z) ES$^+$=559 (M+1).

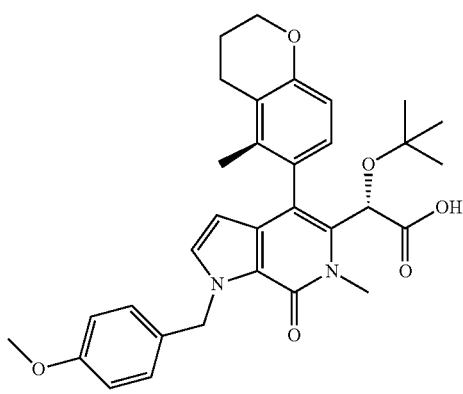

Step B (S)(M)-2-(tert-butoxy)-2-(1-(4-methoxybenzyl)-6-methyl-4-(5-methylchroman-6-yl)-7-oxo-6,7-dihydro-1H-pyrrolo[2,3-c]pyridin-5-yl)acetic acid

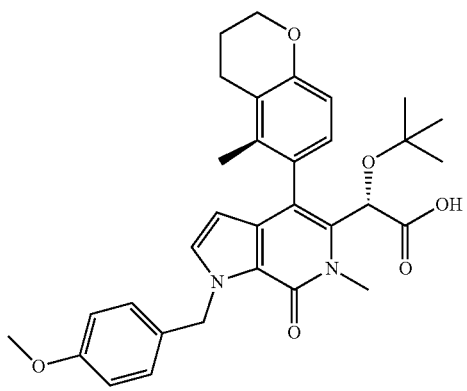

A solution of (S)(M)-methyl 2-(tert-butoxy)-2-(1-(4-methoxybenzyl)-6-methyl-4-(5-methylchroman-6-yl)-7-oxo-6,7-dihydro-1H-pyrrolo[2,3-c]pyridin-5-yl)acetate (28 mg, 0.050 mmol) in Methanol (500 μl) and Tetrahydrofuran (THF) (500 μl) was treated with LiOH (150 μl, 0.301 mmol) and stirred at 65° C. After 90 min, additional LiOH (100 uL) was added, and the reaction was stirred for 50 min at 65° C. The mixture was concentrated and purified with reverse phase chromatography (20-100% MeCN/H$_2$O-0.1% TFA, 12 min) to give title compound (20.5 mg, 0.037 mmol, 73.0% yield) as white solid: $^1$H NMR (400 MHz, CHLOROFORM-d) ppm 1.15 (s, 9H), 2.00 (s, 3H), 2.03-2.16 (m, 2H), 2.67 (q, J=6.0 Hz, 2H), 3.70 (s, 3H), 3.78 (s, 3H), 4.19 (t, J=5.0 Hz, 2H), 5.17 (s, 1H), 5.63-5.85 (m, 3H), 6.70 (d, J=8.4 Hz, 1H), 6.85 (d, J=8.5 Hz, 2H), 6.91-7.03 (m, 2H), 7.19-7.33 (m, 2H). LCMS (m/z) ES$^+$=545 (M+1).

Example 54

2-(tert-butoxy)-2-(6-methyl-4-(5-methylchroman-6-yl)-7-oxo-1-((tetrahydro-2H-pyran-4-yl)methyl)-6,7-dihydro-1H-pyrrolo[2,3-c]pyridin-5-yl)acetic acid

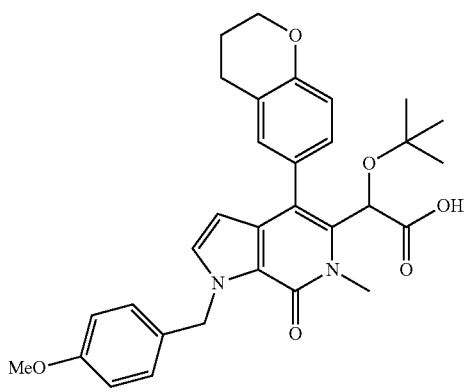 [SMILES: COc1ccc(Cn2ccc3c(-c4ccc5c(c4)CCCO5)c(C(OC(C)(C)C)C(=O)O)n(C)c(=O)c32)cc1]

The title compound was prepared in a manner similar to that described in Example 1 except in Step B, (4-methoxyphenyl)methanamine was used and in Step H, 2-(chroman-6-yl)-4,4,5,5-tetramethyl-1,3,2-dioxaborolane was used. $^1$H NMR (400 MHz, METHANOL-d$_4$)=7.30-7.18 (m, 4H), 7.15-7.08 (m, 1H), 6.89-6.81 (m, 3H), 6.00 (dd, J=2.7, 8.4 Hz, 1H), 5.73 (s, 2H), 5.41 (d, J=6.6 Hz, 1H), 4.26-4.18 (m, 2H), 3.75 (s, 3H), 3.67 (d, J=2.1 Hz, 3H), 2.90-2.73 (m, 2H), 2.10-1.99 (m, 2H), 0.96 (s, 9H)

Scheme 15

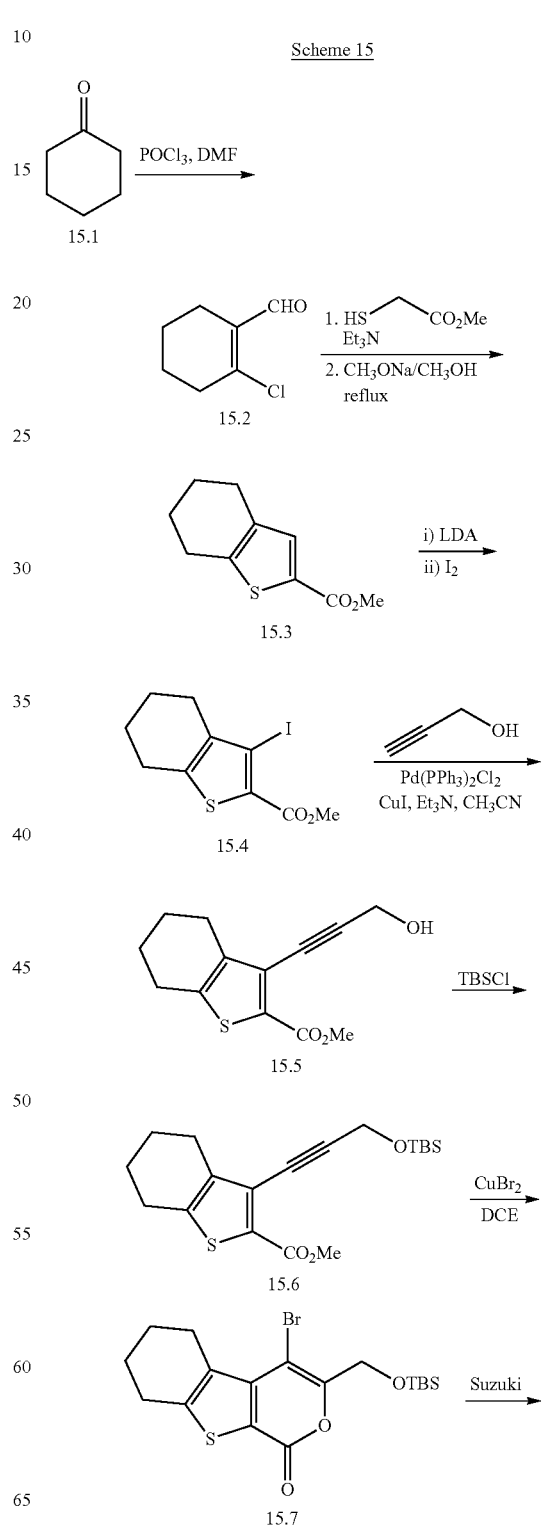

135
-continued
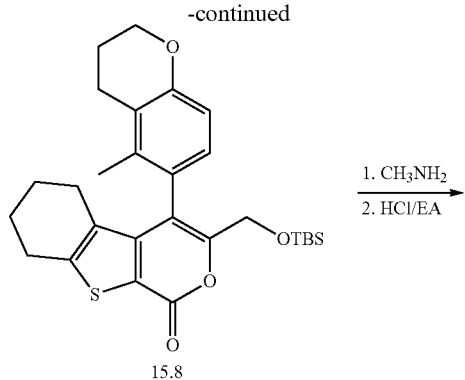
15.8
1. CH₃NH₂
2. HCl/EA
→
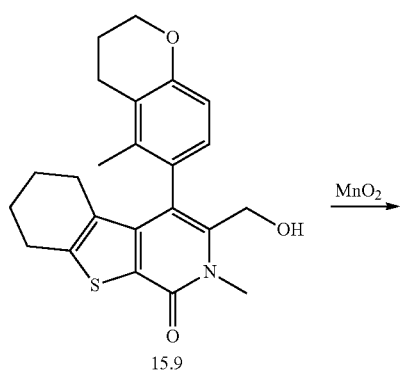
15.9
MnO₂
→
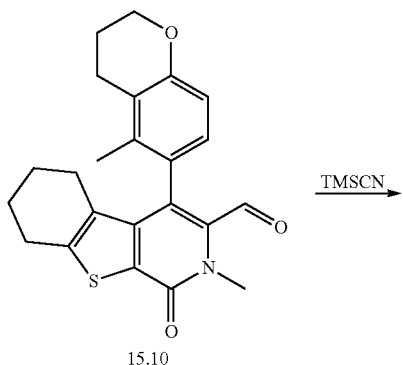
15.10
TMSCN
→
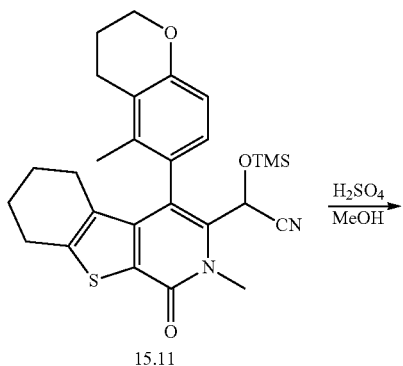
15.11
H₂SO₄
MeOH
→
136
-continued
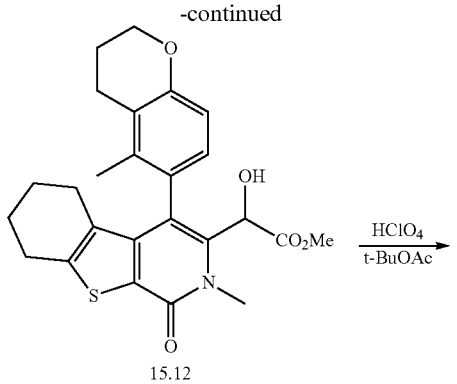
15.12
HClO₄
t-BuOAc
→
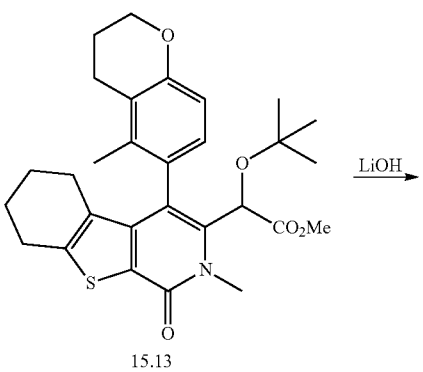
15.13
LiOH
→
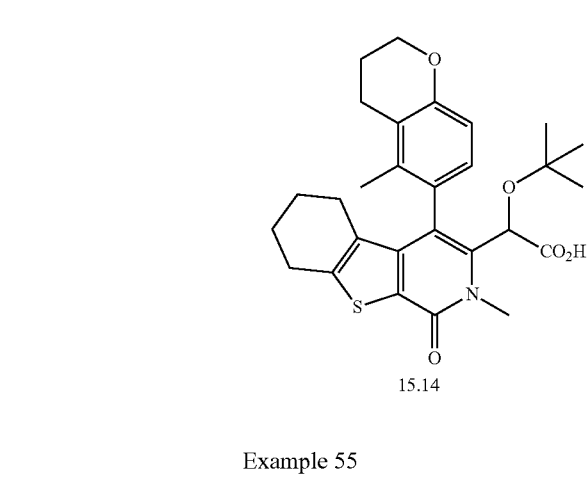
15.14
Example 55
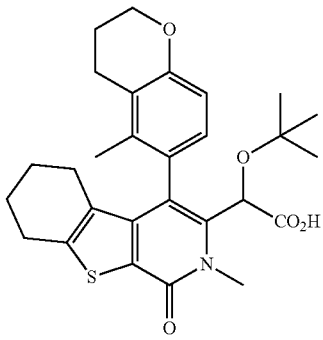 [SMILES: Cc1c(-c2c(C(OC(C)(C)C)C(=O)O)n(C)c(=O)c3sc4c(c23)CCCC4)ccc2c1CCCO2]

tert-Butoxy-[2-methyl-4-(5-methyl-chroman-6-yl)-1-oxo-1,2,5,6,7,8-hexahydro-benzo[4,5]thieno[2,3-c]pyridin-3-yl]-acetic acid Step A 2-chlorocyclohex-1-enecarbaldehyde

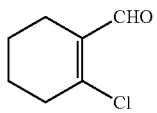

Phosphoryl trichloride (125 g, 815 mmol) was added dropwise into a flame-dried bottom flask containing N,N-dimethylformamide (74.5 g, 1019 mmol) at 0° C. with stirring. After addition, the mixture was warmed to ambient temperature for 30 min, and re-cooled to 0° C. before the dropwise addition of cyclohexanone (50 g, 509 mmol). The mixture was warmed to room temperature for 12 h. The reaction was poured over ice and quenched with NaHCO₃. Once neutralized, the mixture was extracted with ethyl acetate (100 mL×3) and washed with water and brine. The organic phase was dried, filtered, and concentrated to afford the product (160 g, 87% yield). $^1$H NMR: (CDCl3, 400 MHz) δ 1.74~1.75 (m, 2H), 1.76~1.78 (m, 2H), 2.24~2.27 (m, 2H), 2.53~2.59 (m, 2H), 7.25 (s, 1H).

Step B 4,5,6,7-Tetrahydro-benzo[b]thiophene-2-carboxylic acid methyl ester

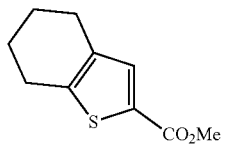 [SMILES: COC(=O)c1cc2c(s1)CCCC2]

To a solution of 2-chlorocyclohex-1-enecarbaldehyde (50 g, 346 mmol) and methyl-2-mercaptoacetate (40 g, 380 mmol) in Pyridine (100 mL) was added triethylamine (105 g, 1037 mmol) at room temperature. The mixture was stirred for 2 h, and partitioned between ethyl acetate (200 mL) and 1N aqueous HCl (50 mL). The separated organic layer was washed with brine, dried over Na₂SO₄ and evaporated to dryness, which was dissolved in Methanol (100 mL). To the above solution was added sodium methoxide (1.9 g, 34.6 mmol), then, the mixture was heated at reflux for 3 hrs, which was poured into ice water and partitioned between ethyl acetate (200 mL) and 1N aqueous NaHCO₃ (50 mL). The separated organic layer was washed with brine, dried over Na₂SO₄ and evaporated to dryness, which was purified by silica gel chromatography eluted with PE:ethyl acetate 10:1 to give title product (25 g, 36% yield) as yellow solid. LCMS (m/z) ES+=197 (M+1)

Step C

3-Iodo-4,5,6,7-tetrahydro-benzo[b]thiophene-2-carboxylic acid methyl ester

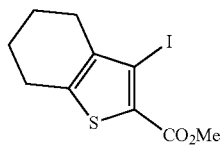

A −78° C. solution of diisopropylamine (23.2 g, 230 mmol) in Tetrahydrofuran (THF) (100 mL) was treated with added n-BuLi (92 mL, 230 mmol) dropwise. The pale yellow solution was stirred at 0° C. for 30 min and recooled to −78° C. To above solution was added the solution of 4,5,6,7-Tetrahydro-benzo[b]thiophene-2-carboxylic acid methyl ester (25 g, 127 mmol) in 20 mL THF dropwise over a period of 5 min. The deep-red solution was stirred at −78° C. for 45 min, the solution of Iodine (48.5 g, 191 mmol) in 20 mL THF was added. The mixture was stirred at −78° C. for 30 min and then warm to room temperature, quenched with saturated aqueous NH₄Cl (100 mL) and saturated aqueous Na₂S₂O₃ (100 mL). The aqueous layer was extracted with ethyl acetate (150 mL×2). The combined ethyl acetate solution was dried over Na₂SO₄ and concentrated, which was purified by silica gel chromatography eluted with PE:EtOAc=10:1 to afford title product (15 g, 36% yield). LCMS (m/z) ES+=323 (M+1)

Step D 3-(3-Hydroxy-prop-1-ynyl)-4,5,6,7-tetrahydro-benzo[b]thiophene-2-carboxylic acid methyl ester

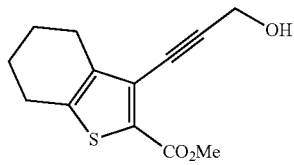 [SMILES: COC(=O)c1sc2c(c1C#CCO)CCCC2]

To a solution of 3-Iodo-4,5,6,7-tetrahydro-benzo[b]thiophene-2-carboxylic acid methyl ester (15 g, 46.6 mmol) and prop-2-yn-1-ol (5.22 g, 93 mmol) in Acetonitrile (100 mL) was added Pd(PPh3)2Cl (3.27 g, 4.66 mmol), copper(I) iodide (0.89 g, 4.66 mmol) and triethylamine (14 g, 140 mmol). The mixture was heated at 85° C. reflux under N₂ for 3 hrs. The reaction was cooled to room temperature, and concentrated to dryness, which was diluted with H₂O (50 mL), extracted with ethyl acetate (200 mL×3), The organic phase was washed with saturated aqueous NaHCO₃ 150 mL, dried over Na₂SO₄, After concentration, the crude product was purified by silica gel chromatography eluted with PE:EtOAc=10:1-4:1 to give afford title product (8.5 g, 73% yield) as yellow oil. LCMS (m/z) ES+=233 (M+1).

Step E

3-[(3-(tert-Butyl-dimethyl-silanyloxy)-prop-1-ynyl]-4,5,6,7-tetrahydro-benzo[b]thiophene-2-carboxylic acid methyl ester

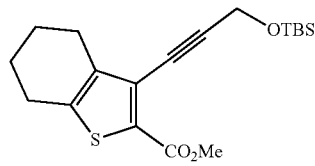 [SMILES: COC(=O)c1sc2c(c1C#CCO[Si](C)(C)C(C)(C)C)CCCC2]

To a solution of methyl 3-(3-hydroxyprop-1-yn-1-yl)-4,5,6,7-tetrahydrobenzo[b]thiophene-2-carboxylate (8.5 g, 34 mmol) in Dichloromethane (DCM) (50 mL) was added 1H-imidazole (5.8 g, 85 mmol) and TBSCl (7.7 g, 50.9 mmol). The mixture was stirred at room temperature for 2 h. The reaction mixture was washed with water, brine, dried over $Na_2SO_4$ and concentrated to dryness. The residue was purified by chromatography column on silica gel chromatography eluted with PE:EtOAc=50:1~20:1 to afford title product (11.9 g, 96% yield). $^1$HNMR: (400 MHz, CDCl3) δ 0.161 (s, 6H), 0.929 (s, 9H), 1.79-1.85 (m, 4H), 2.60-2.63 (m, 2H), 2.72-2.75 (m, 2H), 3.85 (s, 3H), 4.62 (s, 2H).

Step F

4-Bromo-3-(tert-butyl-dimethyl-silanyloxymethyl)-5,6,7,8-tetrahydro-2-oxa-9-thia-fluoren-1-one

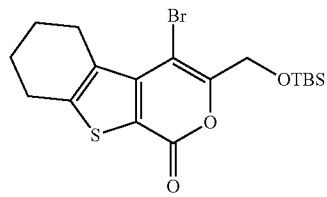 [SMILES: CC(C)(C)[Si](C)(C)OCc1oc(=O)c2sc3c(c2c1Br)CCCC3]

To a suspension of compound methyl 3-(3-((tert-butyldimethylsilyl)oxy)prop-1-yn-1-yl)-4,5,6,7-tetrahydrobenzo[b]thiophene-2-carboxylate (11.9 g, 32.6 mmol) and copper(II) bromide (14.6 g, 65.3 mmol) in 1,2-Dichloroethane (DCE) (100 mL) was added dicyclohexylamine, Hydrobromide (0.86 g, 3.26 mmol). The resultant mixture was stirred at reflux under $N_2$ for 3 h. The reaction mixture was cooled to room temperature and filtered, the cake was washed with 1,2-Dichloroethane (10 mL). The combined organic phases were concentrated to dryness, which was purified by chromatography column on silica gel chromatography eluted with PE:EtOAc=50:1~10:1 to afford title product (5 g, 35% yield). 1HNMR: (400 MHz, CDCl3) δ 0.148 (s, 6H), 0.924 (s, 9H), 1.85~1.87 (m, 4H), 2.88~-2.89 (m, 2H), 3.11~3.13 (m, 2H), 4.73 (s, 2H).

Step G 3-(tert-Butyl-dimethyl-silanyloxymethyl)-4-(5-methyl-chroman-6-yl)-5,6,7,8-tetrahydro-2-oxa-9-thia-fluoren-1-one

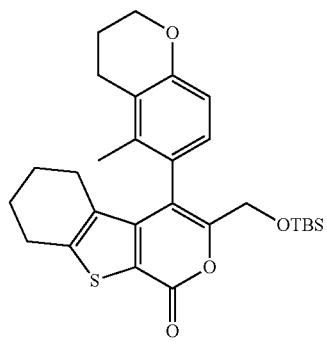 [SMILES: Cc1c(-c2c(CO[Si](C)(C)C(C)(C)C)oc(=O)c3sc4c(c23)CCCC4)ccc2c1CCCO2]

A solution of 4-bromo-3-(((tert-butyldimethylsilyl)oxy)methyl)-5,6,7,8-tetrahydro-1H-benzo[4,5]thieno[2,3-c]pyran-1-one (3 g, 7 mmol) and 4,4,5,5-tetramethyl-2-(5-methylchroman-6-yl)-1,3,2-dioxaborolane (2.87 g, 10.7 mmol), potassium carbonate (2.9 g, 21 mmol) at room temperature was degassed under vacuum and purged with $N_2$ several times. The reaction mixture was treated with $Pd(PPh_3)_4$ (0.8 g, 0.7 mmol), sealed and heated in CEM Discover using initial 150 W to 120° C. for 2.5 hrs. After cooling the reaction mixture was concentrated to dryness. The reaction mixture was partitioned between ethyl acetate (50 mL×3) and 1N aq. $NaHCO_3$ (50 mL). The separated organic layer was washed with brine, dried over $Na_2SO_4$ and evaporated to dryness, which was purified by chromatography column on silica gel chromatography eluted with PE:EtOAc=70:1~20:1 to afford the title product title product (100 mg, 2% yield). LCMS (m/z) ES+=497 (M+1).

Step H

3-Hydroxymethyl-2-methyl-4-(5-methyl-chroman-6-yl)-5,6,7,8-tetrahydro-2H-benzo[4,5]thieno[2,3-c]pyridin-1-one

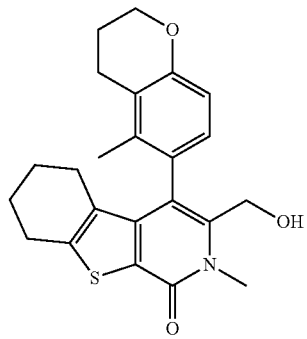 [SMILES: Cc1c(-c2c(CO)n(C)c(=O)c3sc4c(c23)CCCC4)ccc2c1CCCO2]

3-(((tert-butyldimethylsilyl)oxy)methyl)-4-(5-methylchroman-6-yl)-5,6,7,8-tetrahydro-1H-benzo[4,5]thieno[2,3-c]pyran-1-one (100 mg, 0.2 mmol) was dissolved in 4N $MeNH_2$ (g)/EtOH (20 mL) and stirred at 65° C. for 3 hrs. After cooling to room temperature, the mixture was concentrated, and 4N HCl/ethyl acetate (20 ml) was added. The mixture was stirred at room temperature for 15 min and concentrated in vacuo. The residue was partitioned between ethyl acetate and sat. aq. NaHCO$_3$ and the organic layer washed with water, dried over Na$_2$SO$_4$ and evaporated to afford the crude title product (60 mg, 75% yield) which was used for the next step directly. LCMS (m/z) ES$^+$=396 (M+1).

Step I

2-Methyl-4-(5-methyl-chroman-6-yl)-1-oxo-1,2,5,6,7,8-hexahydro-benzo[4,5]thieno[2,3-c]pyridine-3-carbaldehyde

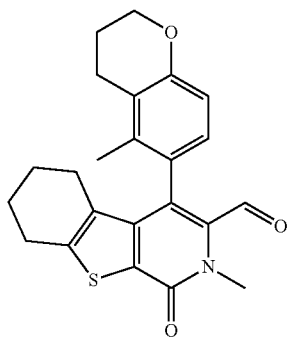 [SMILES: Cc1c(-c2c(C=O)n(C)c(=O)c3sc4c(c23)CCCC4)ccc2c1CCCO2]

To a solution of 3-(hydroxymethyl)-2-methyl-4-(5-methylchroman-6-yl)-5,6,7,8-tetrahydrobenzo[4,5]thieno[2,3-c]pyridin-1(2H)-one (60 mg, 0.15 mmol) in chloroform (15 mL) was added manganese(IV) oxide (132 mg, 1.5 mmol). The mixture was stirred at reflux for 18 h. After the reaction mixture was cooled to room temperature, the suspension was filtered through a pad of silica gel and the pad was washed with ethyl acetate (20 mL×3). The combined filtrates were concentrated to dryness to give crude title product (50 mg, 84% yield), which was used in the next step directly. LCMS (m/z) ES+=396 (M+1).

Step J

[2-Methyl-4-(5-methyl-chroman-6-yl)-1-oxo-1,2,5,6,7,8-hexahydro-benzo[4,5]thieno[2,3-c]pyridin-3-yl]-trimethylsilanyloxy-acetonitrile

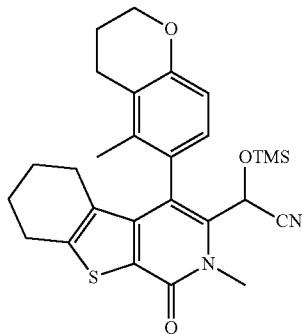

To a solution of 2-methyl-4-(5-methylchroman-6-yl)-1-oxo-1,2,5,6,7,8-hexahydrobenzo[4,5]thieno[2,3-c]pyridine-3-carbaldehyde (50 mg, 0.123 mmol) in Dichloromethane (DCM) (10 mL) was added trimethylsilanecarbonitrile (126 mg, 1.3 mmol) and zinc(II) iodide (122 mg, 0.38 mmol). The mixture was stirred at room temperature for 3 h. The reaction mixture was quenched with 10 mL of saturated aqueous NH$_4$Cl and extract with ethyl acetate (20 mL×3). The combined ethyl acetate were dried over Na$_2$SO$_4$ and concentrated to dryness to give crude title product (55 mg, 88% yield), which was used for the next step directly. LCMS (m/z) ES+=493 (M+1).

Step K

Hydroxy-[2-methyl-4-(5-methyl-chroman-6-yl)-1-oxo-1,2,5,6,7,8-hexahydro-benzo[4,5]thieno[2,3-c]pyridin-3-yl]-acetic acid methyl ester

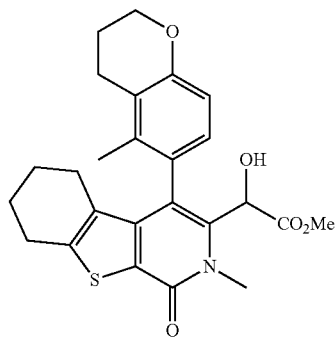 [SMILES: COC(=O)C(O)c1c(-c2ccc3c(c2C)CCCO3)c2c3c(sc2c(=O)n1C)CCCC3]

To a solution of 2-(2-methyl-4-(5-methylchroman-6-yl)-1-oxo-1,2,5,6,7,8-hexahydrobenzo[4,5]thieno[2,3-c]pyridin-3-yl)-2-((trimethylsilyl)oxy)acetonitrile (55 mg, 0.11 mmol) in Methanol (15 mL) was added H$_2$SO$_4$ (5 mL). The mixture was stirred at reflux overnight. After the reaction mixture was cooled to room temperature, it was poured into 20 mL of ice-water carefully, neutralized with 1N aqueous NaOH (3 mL). The resulting solution was extracted with ethyl acetate (15 mL×3). The combined ethyl acetate were dried over Na$_2$SO$_4$ and concentrated to dryness to give title product (30 mg, 59% yield), which was used for the next step directly. LCMS (m/z) ES$^+$=454 (M+1)

Step L tert-Butoxy-[2-methyl-4-(5-methyl-chroman-6-yl)-1-oxo-1,2,5,6,7,8-hexahydro-benzo[4,5]thieno[2,3-c]pyridin-3-yl]-acetic acid methyl ester

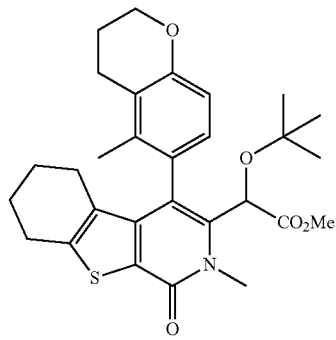 [SMILES: COC(=O)C(OC(C)(C)C)c1c(-c2ccc3c(c2C)CCCO3)c2c3c(sc2c(=O)n1C)CCCC3]

To a solution of compound methyl 2-hydroxy-2-(2-methyl-4-(5-methylchroman-6-yl)-1-oxo-1,2,5,6,7,8-hexahydrobenzo[4,5]thieno[2,3-c]pyridin-3-yl)acetate (30 mg, 0.066 mmol) in t-Butyl acetate (3 mL) was added HClO$_4$ (6.64 mg, 0.066 mmol). The mixture was stirred at room temperature for 30 min. The reaction mixture neutralized with saturated aqueous NaHCO$_3$ (10 mL). The resulting solution was extracted with ethyl acetate (15 mL×3). The combined ethyl acetate were dried over Na$_2$SO$_4$ and concentrated to dryness to give crude product, which was purification with prep-TLC afford title product (20 mg, 59% yield) as a solid. LCMS (m/z) ES$^+$=510 (M+1)

Step M tert-Butoxy-[2-methyl-4-(5-methyl-chroman-6-yl)-1-oxo-1,2,5,6,7,8-hexahydro-benzo[4,5]thieno[2,3-c]pyridin-3-yl]-acetic acid

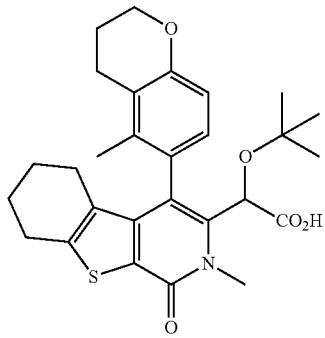 [SMILES: Cc1c(-c2c(C(OC(C)(C)C)C(=O)O)n(C)c(=O)c3sc4c(c23)CCCC4)ccc2c1CCCO2]

To a solution of compound methyl 2-(tert-butoxy)-2-(2-methyl-4-(5-methylchroman-6-yl)-1-oxo-1,2,5,6,7,8-hexahydrobenzo[4,5]thieno[2,3-c]pyridin-3-yl)acetate (20 mg, 0.04 mmol) in Tetrahydrofuran (THF) (3 mL) and Water (3 mL) was added lithium hydroxide hydrate (20 mg, 0.48 mmol). The mixture was stirred at 65° C. for overnight. The reaction was cooled to room temperature, and solvent was removed by concentrated under reduced pressure to afford an oil, which was acidified with 1N aqueous HCl to pH=3, the resulting precipitate was collected by filtration to afford title product (11.5 mg, 59% yield) as white solid. $^1$H NMR: (Methanol-d4, 400 MHz) δ 0.99, 1.15 (s, total, 9H), 1.35~1.52 (m, 2H), 1.69~1.72 (m, 4H), 1.86 (s, 3H), 2.08~2.11 (m, 2H), 2.65~2.75 (m, 2H), 2.85~2.89 (m, 2H), 3.77, 3.80 (s, total, 3H), 6.72~6.78 (m, 1H), 6.98~7.27 (m, 1H). LCMS (m/z) ES$^+$=496 (M+1).

Scheme 16

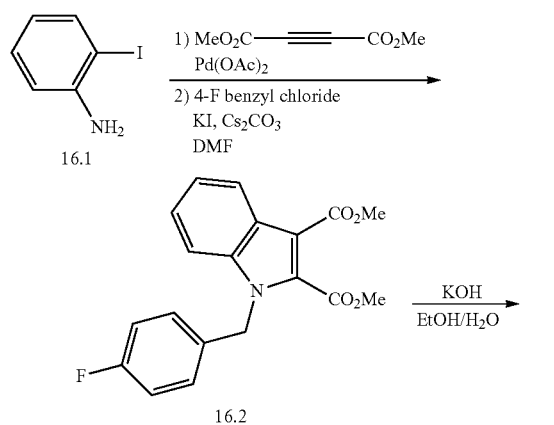

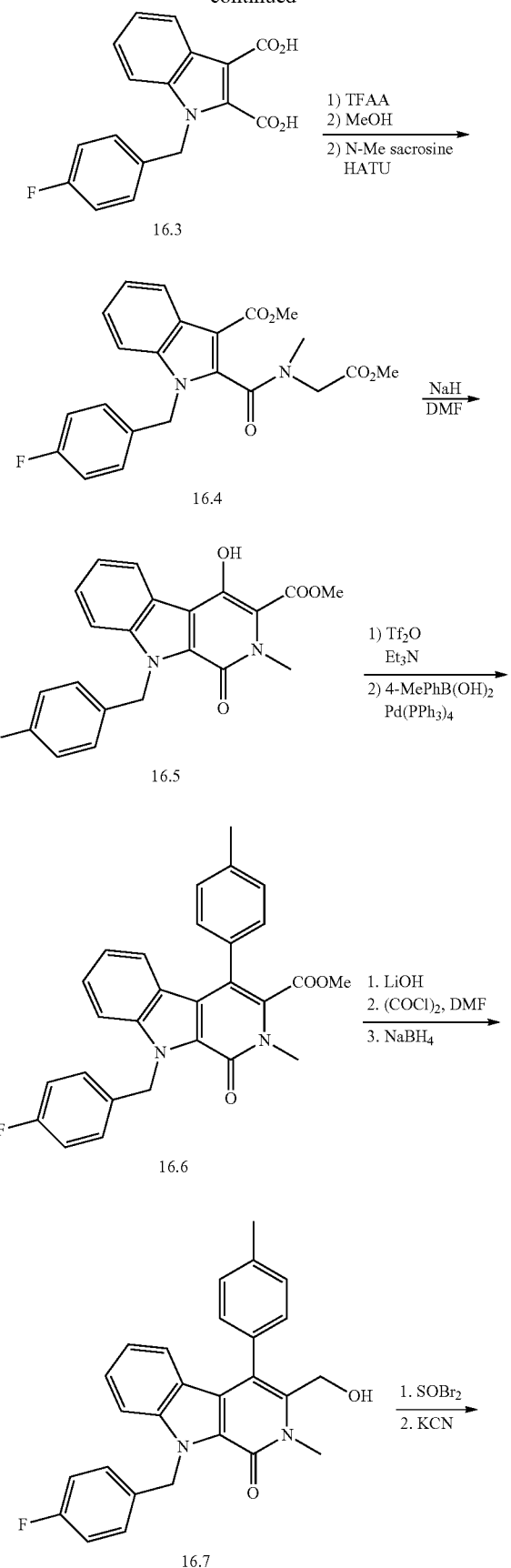

-continued

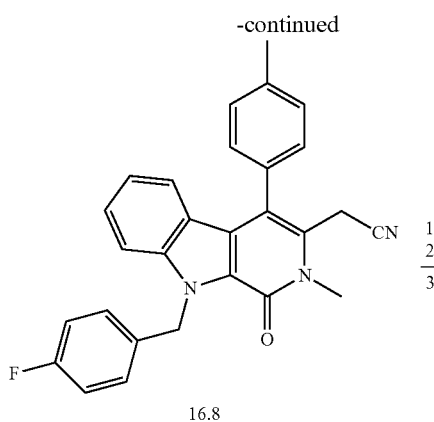

16.8

1. NaOH
2. HCl/AcOH
3. TMS-diazomethane

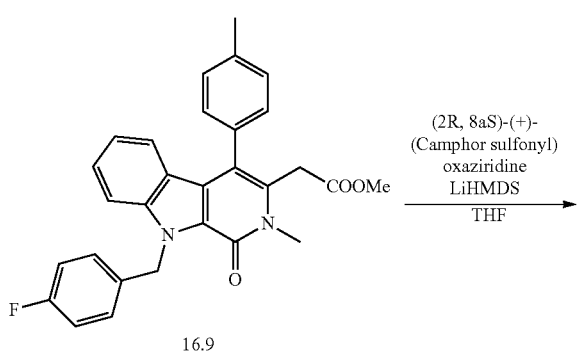

16.9

(2R, 8aS)-(+)-
(Camphor sulfonyl)
oxaziridine
LiHMDS
THF

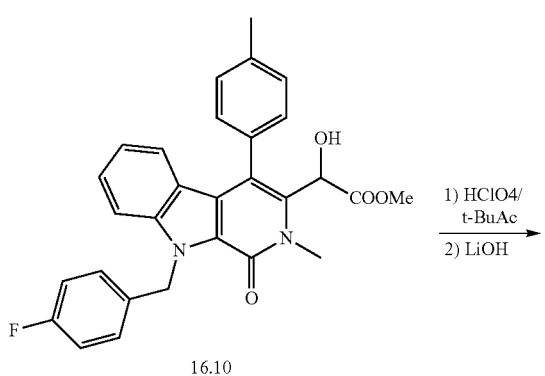

16.10

1) HClO4/
t-BuAc
2) LiOH

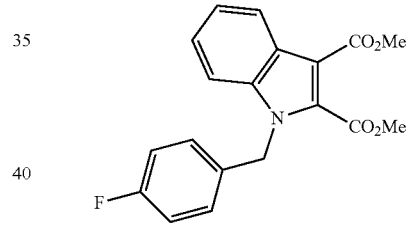

16.11

Example 56

2-(tert-butoxy)-2-(9-(4-fluorobenzyl)-2-methyl-1-oxo-4-(p-tolyl)-2,9-dihydro-1H-pyrido[3,4-b]indol-3-yl)acetic acid

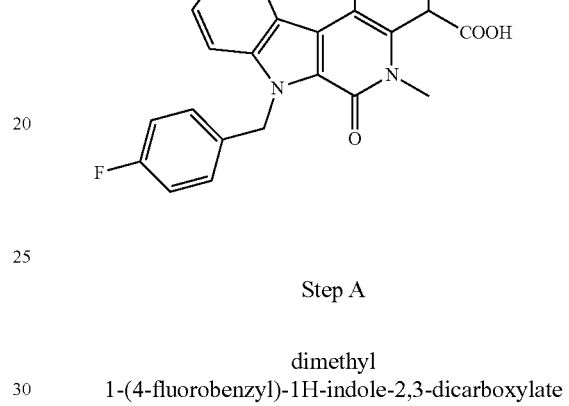

Step A dimethyl 1-(4-fluorobenzyl)-1H-indole-2,3-dicarboxylate

A 300 mL RBF was charged with N,N-Dimethylacetamide (DMA) (144 ml) and Acetic Acid (48.1 ml) was degassed with $O_2$ for 5 min. To this was added aniline (2.94 ml, 32.2 mmol), dimethyl but-2-ynedioate (3.96 ml, 32.2 mmol), and Pd(OAc)$_2$ (0.723 g, 3.22 mmol) and the reaction was heated to 115° C. under an atmosphere of $O_2$. After 18 h, the reaction was cooled to ambient temperature, filtered through a pad of celite, diluted with EtOAc and washed with $H_2O$. The organic was washed with brine, dried (MgSO$_4$), filtered and concentrated. The residue was purified by ISCO (0-50% EtOAc-hexanes: 120 g SiO$_2$) to afford dimethyl 1H-indole-2,3-dicarboxylate (3 g, 12.86 mmol, 39.9% yield) as a yellow solid. The indole was dissolved in DMF (50 mL), treated with Cs$_2$CO$_3$ (6.30 g, 19.33 mmol), 4-Fluorobenzyl chloride (1.929 ml, 16.11 mmol) and KI (5.35 g, 32.2 mmol) and heated to 90° C. After 2 h, the reaction mixture was cooled to ambient temperature and partitioned between EtOAc and sat. aq. NH$_4$Cl. The organic layer was washed with water (5×), brine, dried (MgSO$_4$), filtered and concentrated in vacuo. The residue was purified on ISCO (0-100% EtOAc-hexanes) to afford dimethyl 1-(4-fluorobenzyl)-1H-indole-2,3-dicarboxylate (3.79 g, 11.10 mmol, 34.5% yield) as a yellow solid. LCMS (m/z) ES$^+$=342 (M+1).

Step B

1-(4-fluorobenzyl)-1H-indole-2,3-dicarboxylic acid

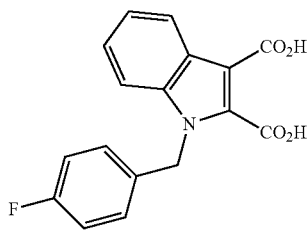 [SMILES: O=C(O)c1c(C(=O)O)n(Cc2ccc(F)cc2)c2ccccc12]

A rbf charged with dimethyl 1-(4-fluorobenzyl)-1H-indole-2,3-dicarboxylate (3.79 g, 11.10 mmol) was treated with a solution of KOH (7.48 g, 133 mmol) in Ethanol (13.88 ml) (0.5 M solution) and heated to reflux (95° C. bath temp). After 18 h, the reaction mixture was cooled to ambient temperature, and acidified to pH 1 with 4M HCl and extracted with EtOAc. The organic layer was washed with brine, dried (MgSO$_4$), filtered and concentrated to afford 1-(4-fluorobenzyl)-1H-indole-2,3-dicarboxylic acid (3.0 g, 9.58 mmol, 86% yield) as a yellowish solid. LCMS (m/z) ES$^+$=314 (M+1).

Step C methyl 1-(4-fluorobenzyl)-2-(2-methoxy-2-oxoethyl)(methyl)carbamoyl)-1H-indole-3-carboxylate

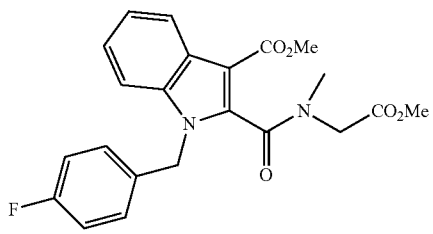 [SMILES: COC(=O)CN(C)C(=O)c1c(C(=O)OC)c2ccccc2n1Cc1ccc(F)cc1]

An ice cold suspension of 1-(4-fluorobenzyl)-1H-indole-2,3-dicarboxylic acid (3.0 g, 9.58 mmol) in Dichloromethane (DCM) (38.5 ml) was treated with TFAA (2.66 ml, 19.15 mmol) and warmed to ambient temperature. After 1 h, the reaction mixture (now homogenous) was concentrated in vacuo to afford the anhydride. The crude material was dissolved in MeOH (50 mL) and heated to reflux (90° C. bath). After 18 h, the reaction mixture was concentrated in vacuo to afford a ~4:1 ratio 1-(4-fluorobenzyl)-3-(methoxycarbonyl)-1H-indole-2-carboxylic acid regioisomers. The residue was dissolved in DMF (50 mL) and treated with N-methyl sarcosine (1.604 g, 11.49 mmol), DIPEA (3.34 ml, 19.15 mmol) and HATU (5.09 g, 13.41 mmol). After 1 h, the reaction mixture was poured into sat. aq. NH$_4$Cl and extracted with EtOAc. the organics were washed with brine, dried (Na$_2$SO$_4$), filtered and concentrated in vacuo. the residue was purified by ISCO (0-50% EtOAc-hexanes) to afford methyl 1-(4-fluorobenzyl)-2-((2-methoxy-2-oxoethyl)(methyl)carbamoyl)-1H-indole-3-carboxylate (3.0 g, 7.27 mmol, 76% yield) as a white solid. LCMS (m/z) ES$^+$=413 (M+1).

Step D methyl 9-(4-fluorobenzyl)-4-hydroxy-2-methyl-1-oxo-2,9-dihydro-1H-pyrido[3,4-b]indole-3-carboxylate

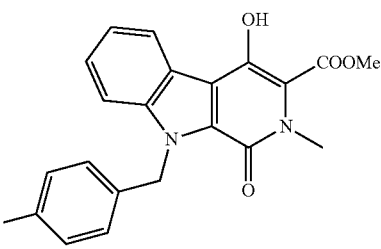

An ice cold solution of methyl 1-(4-fluorobenzyl)-2-((2-methoxy-2-oxoethyl)(methyl)carbamoyl)-1H-indole-3-carboxylate (3 g, 7.27 mmol) in N,N-Dimethylformamide (DMF) (36.4 ml) was treated with NaH (0.378 g, 9.46 mmol). After 1 h, the reaction mixture was cooled to 0° C. and slowly quenched with H$_2$O. The mixture was extracted with EtOAc and the organic layer washed with brine, dried (MgSO$_4$), filtered and concentrated in vacuo. The residue was purified by ISCO (0-3% DCM/MeOH) to afford methyl 9-(4-fluorobenzyl)-4-hydroxy-2-methyl-1-oxo-2,9-dihydro-1H-pyrido[3,4-b]indole-3-carboxylate (1.1 g, 2.89 mmol, 39.8% yield) as an orange solid. LCMS (m/z) ES$^+$=381 (M+1).

Step E methyl 9-(4-fluorobenzyl)-2-methyl-1-oxo-4-(p-tolyl)-2,9-dihydro-1H-pyrido[3,4-b]indole-3-carboxylate

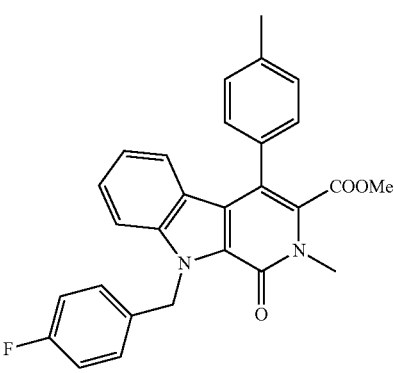 [SMILES: COC(=O)c1c(-c2ccc(C)cc2)c2c3ccccc3n(Cc3ccc(F)cc3)c2c(=O)n1C]

An ice cold solution of methyl 9-(4-fluorobenzyl)-4-hydroxy-2-methyl-1-oxo-2,9-dihydro-1H-pyrido[3,4-b]indole-3-carboxylate (1.1 g, 2.89 mmol) and Et$_3$N (2.004 ml, 14.46 mmol) in DCM (30 mL) was treated with Tf$_2$O (0.977 ml, 5.78 mmol). After 15 min, the reaction mixture was poured into sat. aq. NaHCO$_3$ and extracted with EtOAc. The organic phase was washed with brine, dried (MgSO$_4$), filtered and concentrated in vacuo. The crude residue was dissolved in 1,4-Dioxane (9.57 ml)/Water (1.913 ml), treated with 4-methylphenyl boronic acid (0.550 g, 4.05 mmol) and Na$_2$CO$_3$ (0.920 g, 8.68 mmol) and then degassed with N$_2$ for 5 min. Pd(PPh$_3$)$_4$ (0.334 g, 0.289 mmol) was added and the reaction mixture was warmed to 80° C. After 2 h, the reaction mixture was poured into sat. aq. NH₄Cl and extracted with EtOAc. The organic layer was dried (MgSO₄), filtered and concentrated in vacuo. the residue was purified by ISCO (0-50% EtOAc-hexanes) to afford methyl 9-(4-fluorobenzyl)-2-methyl-1-oxo-4-(p-tolyl)-2,9-dihydro-1H-pyrido[3,4-b]indole-3-carboxylate (625 mg, 1.375 mmol, 47.6% yield) as a yellow solid. ¹H NMR (400 MHz, CHLOROFORM-d)=7.31 (d, J=3.9 Hz, 6H), 7.22 (none, 2H), 6.96 (s, 4H), 6.15 (s, 2H), 3.70 (s, 3H), 3.59 (s, 3H), 2.48 (s, 3H).

Step F 9-(4-fluorobenzyl)-3-(hydroxymethyl)-2-methyl-4-(p-tolyl)-2,9-dihydro-1H-pyrido[3,4-b]indol-1-one

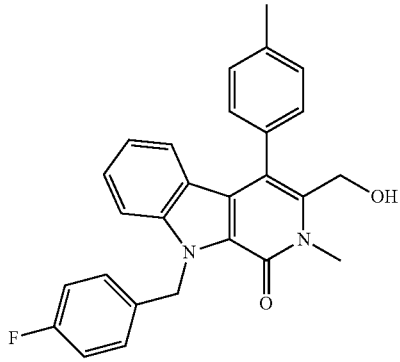 [SMILES: Cc1ccc(-c2c(CC#N)n(C)c(=O)c3c2c2ccccc2n3Cc2ccc(F)cc2)cc1]

A mixture of methyl 9-(4-fluorobenzyl)-2-methyl-1-oxo-4-(p-tolyl)-2,9-dihydro-1H-pyrido[3,4-b]indole-3-carboxylate (625 mg, 1.375 mmol) in Methanol (10 mL) and Tetrahydrofuran (THF) (10.00 mL) was treated with 2M LiOH (20 mL, 40.0 mmol) and then refluxed overnight. The mixture was cooled to 0° C., treated with HCl (1M) until pH<2 and then filtered to afford 9-(4-fluorobenzyl)-2-methyl-1-oxo-4-(p-tolyl)-2,9-dihydro-1H-pyrido[3,4-b]indole-3-carboxylic acid as a white solid (595 mg, 1.35 mmol, 98% yield). A suspension of 9-(4-fluorobenzyl)-2-methyl-1-oxo-4-(p-tolyl)-2,9-dihydro-1H-pyrido[3,4-b]indole-3-carboxylic acid (595 mg, 1.35 mmol) in thionyl chloride (10 mL, 137 mmol) was heated at 70° C. for 2 hours and then concentrated. The residue was dissolved in Tetrahydrofuran (THF) (10.00 mL), treated with sodium borohydride (520 mg, 13.75 mmol) and then heated at 70° C. for 2 hours. Additional NaBH₄ (15 eq.) was added and then mixture was heated at 70° C. overnight. The mixture was concentrated, treated with NH₄Cl (sat. aq) slowly at 0° C. and then extracted with ethyl acetate. The combined extracts were dried over Na₂SO₄, filtered and concentrated to afford 9-(4-fluorobenzyl)-3-(hydroxymethyl)-2-methyl-4-(p-tolyl)-2,9-dihydro-1H-pyrido[3,4-b]indol-1-one (520 mg, 1.22 mmol, 90% yield) as a white solid which was used in the next step without any further purification. ¹H NMR (400 MHz, CHLOROFORM-d) ppm 7.30-7.44 (m, 7H) 7.19-7.27 (m, 3H) 6.95 (s, 4H) 6.62-6.70 (m, 1H) 6.14 (s, 3H) 4.57 (s, 2H) 3.92 (s, 3H) 2.52 (s, 3H); LCMS (m/z) ES⁺=427 (M+1).

Step G 2-(9-(4-fluorobenzyl)-2-methyl-1-oxo-4-(p-tolyl)-2,9-dihydro-1H-pyrido[3,4-b]indol-3-yl)acetonitrile

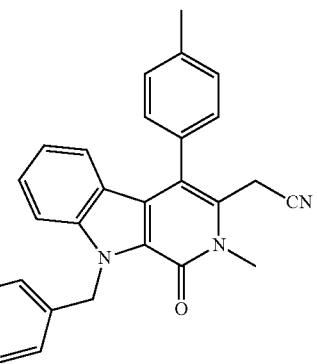

A solution of 9-(4-fluorobenzyl)-3-(hydroxymethyl)-2-methyl-4-(p-tolyl)-2,9-dihydro-1H-pyrido[3,4-b]indol-1-one (125 mg, 0.293 mmol) 1,2-Dichloroethane (DCE) (3 mL) was treated with Thionyl bromide (0.022 mL, 0.293 mmol), heated at 70° C. for 2 hours and then concentrated to dryness. The resultant was dissolved in DMF (2 mL), treated with KCN (76 mg, 1.17 mmol) and then stirred at room temperature overnight. Brine was added and the mixture was extracted with ethyl acetate. The combined extracts were dried over Na₂SO₄, filtered and concentrated. The residue was purified on silica gel (0-70% ethyl acetate/hexanes) to afford 2-(9-(4-fluorobenzyl)-2-methyl-1-oxo-4-(p-tolyl)-2,9-dihydro-1H-pyrido[3,4-b]indol-3-yl)acetonitrile (110 mg, 0.253 mmol, 86% yield) as a white solid. ¹H NMR (400 MHz, CHLOROFORM-d) ppm 7.29-7.44 (m, 4H) 7.17-7.24 (m, 1H) 6.91-6.99 (m, 4H) 6.62-6.70 (m, 1H) 6.10-6.16 (m, 2H) 3.90 (s, 3H) 3.67 (s, 2H) 2.51 (s, 3H); LCMS (m/z) ES⁺=436 (M+1).

Step H methyl 2-(9-(4-fluorobenzyl)-2-methyl-1-oxo-4-(p-tolyl)-2,9-dihydro-1H-pyrido[3,4-b]indol-3-yl)acetate

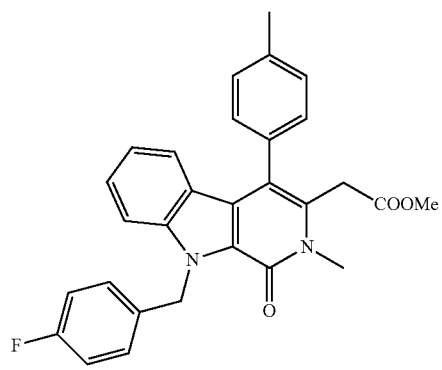 [SMILES: COC(=O)Cc1c(-c2ccc(C)cc2)c2c3ccccc3n(Cc3ccc(F)cc3)c2c(=O)n1C]

A suspension of 2-(9-(4-fluorobenzyl)-2-methyl-1-oxo-4-(p-tolyl)-2,9-dihydro-1H-pyrido[3,4-b]indol-3-yl)acetonitrile (45 mg, 0.103 mmol) in Ethanol (3 mL) and Water (1 mL)

was treated with KOH (5.80 mg, 0.103 mmol) and heated in a sealed tube at 140° C. for 3 days. The mixture was cooled to 0° C. and then treated with 4N HCl until pH<2. The mixture was partly concentrated and then extracted with ethyl acetate. The combined extracts were washed with brine and then concentrated. The residue was dissolved AcOH and concentrated HCl (37%) and irradiated in microwave at 120° C. for 1 hour. The mixture was concentrated to dryness. The residue was diluted with Ethyl acetate, washed with brine, dried over $Na_2SO_4$, filtered and concentrated. The resultant was dissolved in Methanol (3.00 mL), cooled to 0° C., treated with TMS-diazomethane (59.0 mg, 0.517 mmol) and then stirred at 0° C. for 20 minutes. The mixture was concentrated and the residue purified on silica gel (0-100% ethyl acetate/hexanes) to afford methyl 2-(9-(4-fluorobenzyl)-2-methyl-1-oxo-4-(p-tolyl)-2,9-dihydro-1H-pyrido[3,4-b]indol-3-yl)acetate (45 mg, 0.096 mmol, 93% yield) as a white solid. $^1$H NMR (400 MHz, CHLOROFORM-d) ppm 7.31-7.42 (m, 4H) 7.22-7.27 (m, 3H) 6.92-7.00 (m, 3H) 6.87-6.92 (m, 1H) 6.61-6.66 (m, 1H) 6.16 (s, 2H) 3.73 (s, 3H) 3.70 (s, 3H) 2.48 (s, 3H); LCMS (m/z) ES$^+$=469 (M+1).

Step I methyl 2-(9-(4-fluorobenzyl)-2-methyl-1-oxo-4-(p-tolyl)-2,9-dihydro-1H-pyrido[3,4-b]indol-3-yl)-2-hydroxyacetate

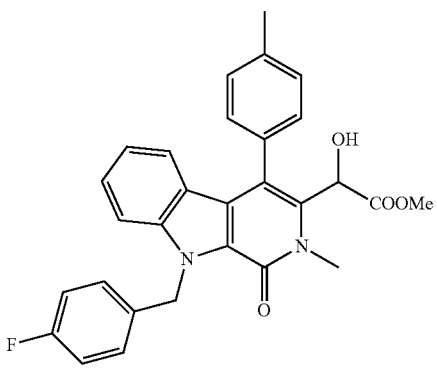 [SMILES: COC(=O)C(O)c1c(-c2ccc(C)cc2)c2c3ccccc3n(Cc3ccc(F)cc3)c2c(=O)n1C]

A −78° C. solution of methyl 2-(9-(4-fluorobenzyl)-2-methyl-1-oxo-4-(p-tolyl)-2,9-dihydro-1H-pyrido[3,4-b]indol-3-yl)acetate (45 mg, 0.096 mmol) in Tetrahydrofuran (THF) (1 mL) was treated with LiHMDS (0.207 mL, 0.207 mmol) and then stirred at −78° C. for 20 minutes. A solution of (1R)-(−)-(10-Camphorsulfonyl)oxaziridine (71.1 mg, 0.310 mmol) in Tetrahydrofuran (THF) (1 mL) was added and the mixture was then warmed to 0° C. for 20 minutes. The mixture was treated with HCl (1M) until pH<2 and then extracted with ethyl acetate. The combined extracts were washed with brine, dried over $Na_2SO_4$, filtered and concentrated. The residue was purified on silica gel (0-100% ethyl acetate/hexanes) to afford methyl 2-(9-(4-fluorobenzyl)-2-methyl-1-oxo-4-(p-tolyl)-2,9-dihydro-1H-pyrido[3,4-b]indol-3-yl)-2-hydroxyacetate (42 mg, 0.087 mmol, 90% yield) as a white solid. $^1$H NMR (400 MHz, CHLOROFORM-d) ppm 7.30-7.45 (m, 5H) 7.16-7.26 (m, 2H) 6.89-7.02 (m, 3H) 6.54-6.63 (m, 1H) 6.29-6.37 (m, 1H) 6.13-6.24 (m, 1H) 6.01-6.11 (m, 1H) 5.34-5.42 (m, 1H) 3.81 (s, 3H) 3.70 (s, 3H) 2.51 (s, 3H); LCMS (m/z) ES$^+$=485 (M+1).

Step J methyl 2-(tert-butoxy)-2-(9-(4-fluorobenzyl)-2-methyl-1-oxo-4-(p-tolyl)-2,9-dihydro-1H-pyrido[3,4-b]indol-3-yl)acetate

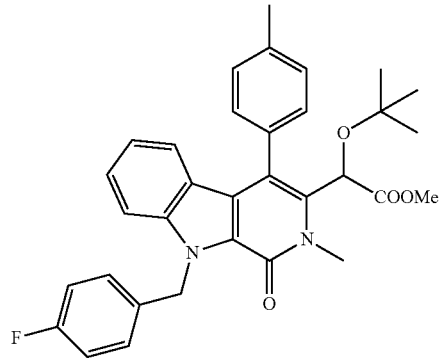 [SMILES: COC(=O)C(OC(C)(C)C)c1c(-c2ccc(C)cc2)c2c3ccccc3n(Cc3ccc(F)cc3)c2c(=O)n1C]

A solution of methyl 2-(9-(4-fluorobenzyl)-2-methyl-1-oxo-4-(p-tolyl)-2,9-dihydro-1H-pyrido[3,4-b]indol-3-yl)-2-hydroxyacetate (42 mg, 0.087 mmol) in t-Butyl acetate (1 mL) was treated with perchloric acid (6.22 µL, 0.103 mmol) and then stirred at room temperature for 1 hour. The mixture was diluted with Ethyl acetate, washed with NaHCO$_3$ and brine, dried over $Na_2SO_4$, filtered and concentrated. The residue was purified on silica gel (0-70% ethyl acetate/hexanes) to afford methyl 2-(tert-butoxy)-2-(9-(4-fluorobenzyl)-2-methyl-1-oxo-4-(p-tolyl)-2,9-dihydro-1H-pyrido[3,4-b]indol-3-yl)acetate as a white solid (30 mg, 0.055 mmol, 64% yield). $^1$H NMR (400 MHz, CHLOROFORM-d) ppm 7.25-7.47 (m, 8H) 6.88-7.00 (m, 3H) 6.57-6.63 (m, 1H) 6.19-6.22 (m, 1H) 6.11-6.17 (m, 1H) 5.29 (s, 1H) 3.79 (s, 3H) 3.78 (s, 3H) 2.54 (s, 3H) 1.04 (s, 9H); LCMS (m/z) ES$^+$=541 (M+1).

Step K 2-(tert-butoxy)-2-(9-(4-fluorobenzyl)-2-methyl-1-oxo-4-(p-tolyl)-2,9-dihydro-1H-pyrido[3,4-b]indol-3-yl)acetic acid

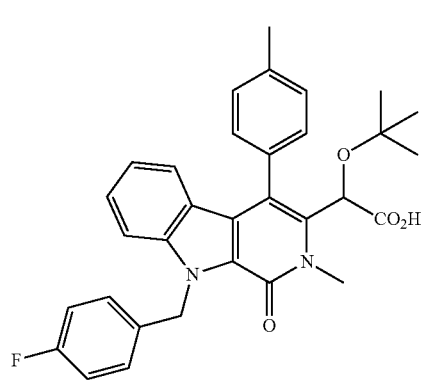 [SMILES: Cc1ccc(-c2c(C(OC(C)(C)C)C(=O)O)n(C)c(=O)c3c2c2ccccc2n3Cc2ccc(F)cc2)cc1]

A solution of methyl 2-(tert-butoxy)-2-(9-(4-fluorobenzyl)-2-methyl-1-oxo-4-(p-tolyl)-2,9-dihydro-1H-pyrido[3,4-b]indol-3-yl)acetate (30 mg, 0.055 mmol) in Tetrahydrofuran (THF) (1 mL) and Methanol (1 mL) was treated with 2M LiOH (1 mL, 2.000 mmol) and then heated at 70° C. for 1 hour. The mixture was cooled to 0° C., treated with HCl (1M) until pH <2 and then extracted with ethyl acetate. The combined extracts were washed with brine, dried over Na$_2$SO$_4$, filtered and concentrated. The residue was purified by reverse phase chromatography (10-90% MeCN/H$_2$O-0.1% TFA, 12 min) to afford 2-(tert-butoxy)-2-(9-(4-fluorobenzyl)-2-methyl-1-oxo-4-(p-tolyl)-2,9-dihydro-1H-pyrido[3,4-b]indol-3-yl)acetic acid (9.2 mg, 0.017 mmol, 32% yield) as a white solid. $^1$H NMR (400 MHz, DMSO-d$_6$) ppm 13.35 (s, 1H), 7.73-7.66 (m, 1H), 7.50-7.32 (m, 7H), 7.19-7.09 (m, 2H), 6.98-6.89 (m, 1H), 6.49-6.51 (m, 1H), 6.14 (s, 2H), 5.17 (s, 1H), 3.66 (m, 3H), 2.49 (s, 3H), 0.97 (s, 9H); LCMS (m/z) ES+=527 (M+1).

Example 57

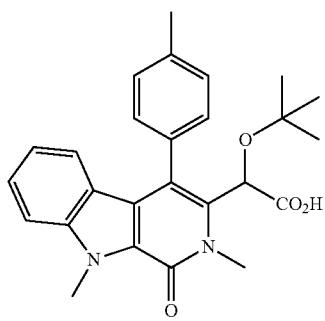 [SMILES: Cc1ccc(-c2c(C(OC(C)(C)C)C(=O)O)n(C)c(=O)c3c2c2ccccc2n3C)cc1]

2-(tert-butoxy)-2-(2,9-dimethyl-1-oxo-4-(p-tolyl)-2,9-dihydro-1H-pyrido[3,4-b]indol-3-yl)acetic acid The title compound was made in a similar manner as Example 55 except using methyl iodide in Step A. $^1$H NMR (400 MHz, DMSO-d6)=7.62 (s, 1H), 7.48-7.30 (m, 5H), 6.97-6.85 (m, 1H), 6.48 (d, J=8.0 Hz, 1H), 5.12 (s, 1H), 4.29 (s, 3H), 3.64 (s, 3H), 2.48 (s, 3H), 0.94 (s, 9H).

Scheme 17

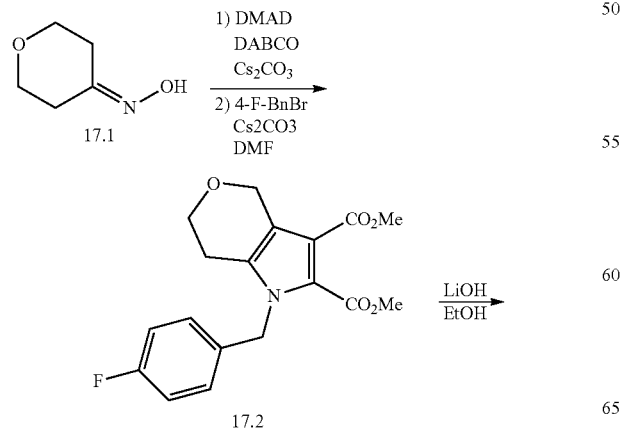

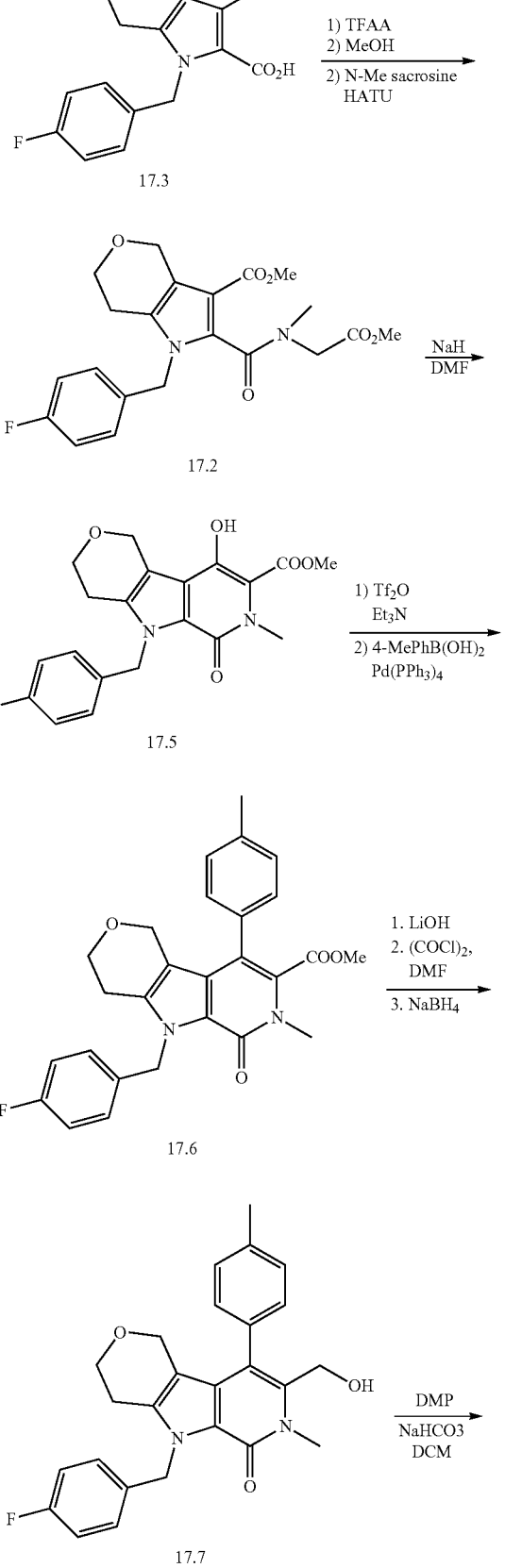

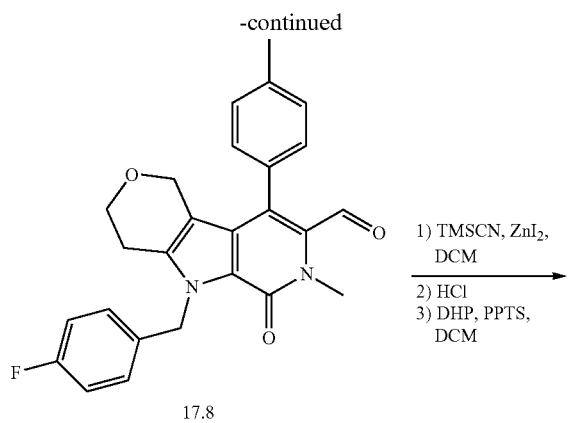

17.8

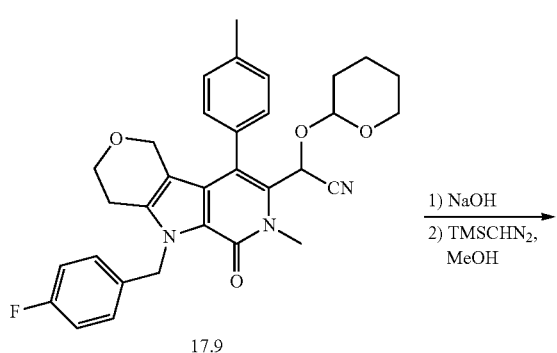

17.9

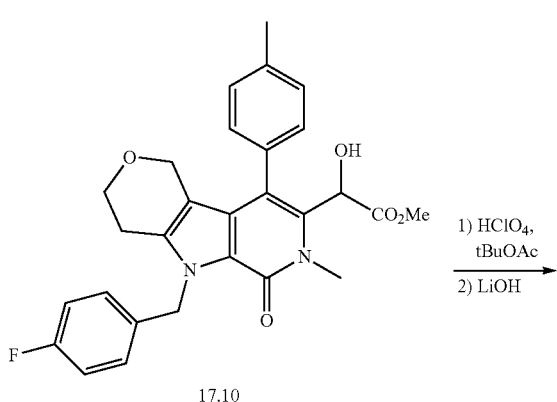

17.10

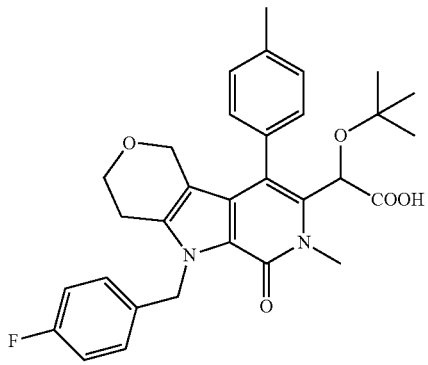 [SMILES: Cc1ccc(-c2c(C(OC(C)(C)C)C(=O)O)n(C)c(=O)c3c2c2c(n3Cc3ccc(F)cc3)CCOC2)cc1]

2-(tert-butoxy)-2-(5-(4-fluorobenzyl)-7-methyl-6-oxo-9-(p-tolyl)-1,3,4,5,6,7-hexahydropyrano[3',4':4,5]pyrrolo[2,3-c]pyridin-8-yl)acetic acid Step A dimethyl 1-(4-fluorobenzyl-1,4,6,7-tetrahydropyrano[4,3-b]pyrrole-2,3-dicarboxylate

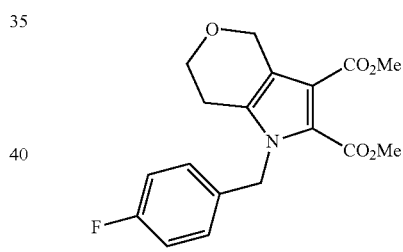

A suspension of dihydro-2H-pyran-4(3H)-one oxime (7 g, 60.8 mmol), dimethylacetylene dicarboxylate (9.72 ml, 79 mmol), and DABCO (2.046 g, 18.24 mmol) in Toluene (27.5 ml) were heated to 165° C. After 2 h, the reaction mixture was cooled to ambient temperature, concentrated in vacuo and purified by ISCO (0-100% EtOAc-hexanes) to afford dimethyl 1,4,6,7-tetrahydropyrano[4,3-b]pyrrole-2,3-dicarboxylate (3.2 g, 13.38 mmol, 22.00% yield) as a yellow solid. The residue was dissolved in DMF (30 mL), and treated with $Cs_2CO_3$ (5.29 g, 16.23 mmol) and 4-fluorobenzyl bromide (2.023 ml, 16.23 mmol). After 2 h, the reaction mixture was partitioned between EtOAc and sat. aq. $NH_4Cl$. The organic layer was washed with water, brine, dried ($MgSO_4$), filtered and concentrated in vacuo. The residue was purified by ISCO (0-50% EtOAc-hexanes; 120 g column) to afford dimethyl 1-(4-fluorobenzyl)-1,4,6,7-tetrahydropyrano[4,3-b]pyrrole-2,3-dicarboxylate (3.92 g, 11.29 mmol, 18.56% yield) as a yellow oil. LCMS (m/z) $ES^+$=348 (M+1).

17.11

Step B 1-(4-fluorobenzyl)-1,4,6,7-tetrahydropyrano[4,3-b]pyrrole-2,3-dicarboxylic acid

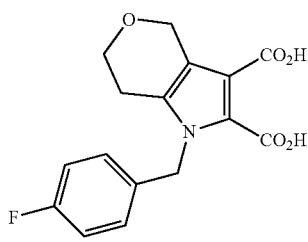 [SMILES: O=C(O)c1c2c(n(Cc3ccc(F)cc3)c1C(=O)O)CCOC2]

A suspension of dimethyl 1-(4-fluorobenzyl)-1,4,6,7-tetrahydropyrano[4,3-b]pyrrole-2,3-dicarboxylate (3.92 g, 11.29 mmol) and KOH (3.17 g, 56.4 mmol) in Ethanol (113 ml) was heated to 90° C. After 18 h, the reaction mixture was poured into 1M HCl and extracted with EtOAc. The organic layer was washed with brine, dried (MgSO$_4$), filtered and concentrated in vacuo to afford 1-(4-fluorobenzyl)-1,4,6,7-tetrahydropyrano[4,3-b]pyrrole-2,3-dicarboxylic acid (3.1 g, 9.71 mmol, 86% yield). LCMS (m/z) ES$^+$=320 (M+1).

Step C methyl 1-(4-fluorobenzyl)-2-(2-methoxy-2-oxoethyl)(methyl)carbamoyl)-1,4,6,7-tetrahydropyrano[4,3-b]pyrrole-3-carboxylate

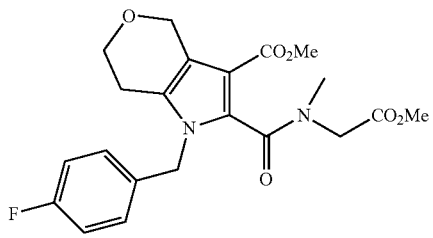 [SMILES: COC(=O)CN(C)C(=O)c1c(C(=O)OC)c2c(n1Cc1ccc(F)cc1)CCOC2]

An ice cooled suspension of 1-(4-fluorobenzyl)-1,4,6,7-tetrahydropyrano[4,3-b]pyrrole-2,3-dicarboxylic acid (3.1 g, 9.71 mmol) in Dichloromethane (DCM) (50 mL) was treated with TFAA (2.70 mL, 19.42 mmol) and warmed to ambient temperature. After 2 h, the reaction mixture was concentrated in vacuo, dissolved in MeOH (5 mL) and heated to reflux (90° C. bath). After 2 h, the reaction mixture was concentrated in vacuo to afford 1-(4-fluorobenzyl)-3-(methoxycarbonyl)-1,4,6,7-tetrahydropyrano[4,3-b]pyrrole-2-carboxylic acid. The crude acid was dissolved in DMF (25 mL) and treated with N-methyl sarcosine methyl ester HCl (2.033 g, 14.56 mmol), DIPEA (2.54 mL, 14.56 mmol) and HATU (4.43 g, 11.65 mmol). After 20 min, the reaction mixture was partitioned between water and EtOAc. The layers were separated and the organic phase was washed with brine, dried (MgSO$_4$), filtered and concentrated in vacuo. The residue was purified by ISCO (0-50% EtOAc-hexanes) to afford methyl 1-(4-fluorobenzyl)-2-((2-methoxy-2-oxoethyl)(methyl)carbamoyl)-1,4,6,7-tetrahydropyrano[4,3-b]pyrrole-3-carboxylate (3.2 g, 7.65 mmol, 79% yield) as a white solid. LCMS (m/z) ES$^+$=419 (M+1).

Step D methyl 5-(4-fluorobenzyl)-9-hydroxy-7-methyl-6-oxo-1,3,4,5,6,7-hexahydropyrano[3',4':4,5]pyrrolo[2,3-c]pyridine-8-carboxylate

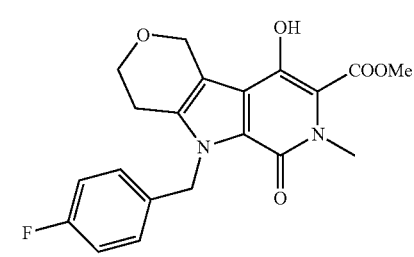 [SMILES: COC(=O)c1c(O)c2c3c(n(Cc4ccc(F)cc4)c2c(=O)n1C)CCOC3]

An ice cold solution of methyl 1-(4-fluorobenzyl)-2-((2-methoxy-2-oxoethyl)(methyl)carbamoyl)-1,4,6,7-tetrahydropyrano[4,3-b]pyrrole-3-carboxylate (3.2 g, 7.65 mmol) in N,N-Dimethylformamide (DMF) (38.2 ml) was treated with NaH (0.398 g, 9.94 mmol). After 5 min, the reaction mixture was warmed to ambient temperature. After 45 min, the reaction mixture was poured into sat. aq. NH$_4$Cl and extracted with EtOAc. The organics were washed with brine, dried (MgSO$_4$), filtered and concentrated in vacuo to afford methyl 5-(4-fluorobenzyl)-9-hydroxy-7-methyl-6-oxo-1,3,4,5,6,7-hexahydropyrano[3',4':4,5]pyrrolo[2,3-c]pyridine-8-carboxylate (2.54 g, 6.57 mmol, 86% yield) as a yellow solid. LCMS (m/z) ES$^+$=387 (M+1).

Step E methyl 5-(4-fluorobenzyl)-7-methyl-6-oxo-9-(p-tolyl)-1,3,4,5,6,7-hexahydropyrano[3',4':4,5]pyrrolo[2,3-c]pyridine-8-carboxylate

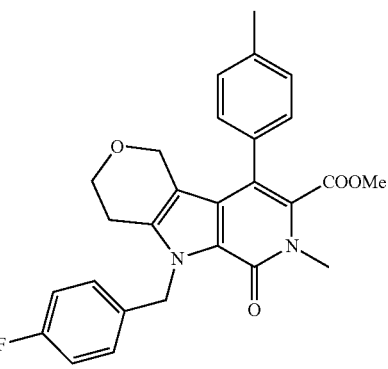

An ice cold solution of methyl 5-(4-fluorobenzyl)-9-hydroxy-7-methyl-6-oxo-1,3,4,5,6,7-hexahydropyrano[3',4':4,5]pyrrolo[2,3-c]pyridine-8-carboxylate (2.54 g, 6.57 mmol) and Et3N (4.56 ml, 32.9 mmol) in DCM (40 mL) was treated with Tf2O (2.221 ml, 13.15 mmol). After 15 min, the reaction mixture was poured into sat. aq. NaHCO$_3$ and extracted with EtOAc. The organic phase was washed with brine, dried (MgSO$_4$), filtered and concentrated in vacuo. The crude residue was dissolved in 1,4-Dioxane (21.74 ml)/Water (4.35 ml), treated with 4-methylphenyl boronic acid (1.251 g, 9.20 mmol) and Na$_2$CO$_3$ (2.091 g, 19.72 mmol) and then degassed with N2 for 5 min. Pd(PPh3)$_4$ (0.759 g, 0.657 mmol) was added and the reaction mixture was warmed to 80° C. After 2 h, the reaction mixture was poured into sat. aq. NH$_4$Cl and extracted with EtOAc. The organic layer was dried (MgSO$_4$), filtered and concentrated in vacuo. the residue was loaded onto celite and purified by ISCO (0-50% EtOAc-hexanes) to afford methyl 5-(4-fluorobenzyl)-7-methyl-6-oxo-9-(p-tolyl)-1,3,4,5,6,7-hexahydropyrano[3',4':4,5]pyrrolo[2,3-c]pyridine-8-carboxylate (400 mg, 0.869 mmol, 13.21% yield) as a yellow foam. $^1$H NMR (400 MHz, CHLOROFORM-d)=7.17 (d, 6H), 7.03-6.96 (m, 2H), 5.83 (s, 2H), 3.96 (s, 2H), 3.86 (t, J=5.6 Hz, 2H), 3.60 (s, 3H), 3.56 (s, 3H), 2.64 (t, J=5.5 Hz, 2H), 2.40 (s, 3H).

Step F 5-(4-fluorobenzyl)-8-(hydroxymethyl)-7-methyl-9-(p-tolyl)-3,4,5,7-tetrahydropyrano[3',4':4,5]pyrrolo[2,3-c]pyridin-6(1H)-one

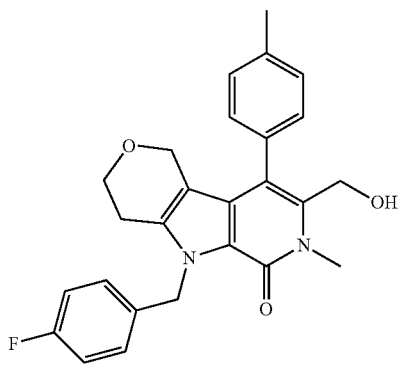 [SMILES: Cc1ccc(-c2c(CO)n(C)c(=O)c3c2c2c(n3Cc3ccc(F)cc3)CCOC2)cc1]

A solution of methyl 5-(4-fluorobenzyl)-7-methyl-6-oxo-9-(p-tolyl)-1,3,4,5,6,7-hexahydropyrano[3',4':4,5]pyrrolo[2,3-c]pyridine-8-carboxylate (0.4 g, 0.869 mmol) in Tetrahydrofuran (THF) (2.77 ml)/Methanol (2.77 ml) was treated with 2M LiOH (3.04 ml, 6.08 mmol) and heated to reflux (80° C. bath). After 18 h, the reaction mixture was cooled to ambient temperature and poured into 1M HCl. The layers were partitioned and the organic phase was washed with brine, dried (MgSO$_4$), filtered and concentrated in vacuo to afford 5-(4-fluorobenzyl)-7-methyl-6-oxo-9-(p-tolyl)-1,3,4,5,6,7-hexahydropyrano[3',4':4,5]pyrrolo[2,3-c]pyridine-8-carboxylic acid as a beige solid. A solution of 5-(4-fluorobenzyl)-7-methyl-6-oxo-9-(p-tolyl)-1,3,4,5,6,7-hexahydropyrano[3',4':4,5]pyrrolo[2,3-c]pyridine-8-carboxylic acid in THF (10 mL) was treated with oxalyl chloride (0.110 ml, 1.303 mmol) and 1 drop of DMF. After 15 min, the reaction mixture was concentrated in vacuo to afford 5-(4-fluorobenzyl)-7-methyl-6-oxo-9-(p-tolyl)-1,3,4,5,6,7-hexahydropyrano[3',4':4,5]pyrrolo[2,3-c]pyridine-8-carbonyl chloride (375 mg, 0.807 mmol, 93% yield). An ice cold solution of 5-(4-fluorobenzyl)-7-methyl-6-oxo-9-(p-tolyl)-1,3,4,5,6,7-hexahydropyrano[3',4':4,5]pyrrolo[2,3-c]pyridine-8-carbonyl chloride (375 mg, 0.807 mmol, 93% yield) in 1,2-DME (10 mL) was treated with NaBH4 (0.161 g, 4.34 mmol) and then warmed to ambient temperature. After 1 h, the reaction mixture was cooled to 0° C. and quenched with MeOH (1 mL) and 1M HCl (~20 mL). EtOAc was added and the layers were partitioned and the organic layer was washed with brine, dried (MgSO$_4$), filtered and concentrated to afford 5-(4-fluorobenzyl)-8-(hydroxymethyl)-7-methyl-9-(p-tolyl)-3,4,5,7-tetrahydropyrano[3',4':4,5]pyrrolo[2,3-c]pyridin-6(1H)-one (333 mg, 0.770 mmol, 89% yield) as a white solid. The residue was used without further purification. LCMS (m/z) ES$^+$=433 (M+1).

Step G 5-(4-fluorobenzyl)-7-methyl-6-oxo-9-(p-tolyl)-1,3,4,5,6,7-hexahydropyrano[3',4':4,5]pyrrolo[2,3-c]pyridine-8-carbaldehyde

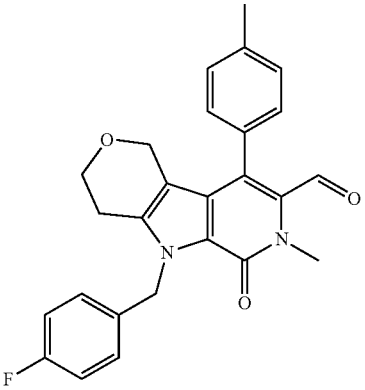 [SMILES: Cc1ccc(-c2c(C=O)n(C)c(=O)c3c2c2c(n3Cc3ccc(F)cc3)CCOC2)cc1]

An ice cold suspension of 5-(4-fluorobenzyl)-8-(hydroxymethyl)-7-methyl-9-(p-tolyl)-3,4,5,7-tetrahydropyrano[3',4':4,5]pyrrolo[2,3-c]pyridin-6(1H)-one (333 mg, 0.770 mmol) and NaHCO$_3$ (323 mg, 3.85 mmol) in Dichloromethane (DCM) (7700 µl) was treated with DMP (653 mg, 1.540 mmol). Upon complete addition of the DMP the cooling bath was removed. After 2 h, the reaction mixture was quenched by the addition of sat. aq. Na$_2$S$_2$O$_3$ and the mixture was stirred for 10 min. EtOAc was added and the layers partitioned. The organic layer was washed with brine, dried (Na2SO$_4$), filtered and concentrated. The residue was purified by ISCO (0-50% EtOAc-hexanes) to afford 5-(4-fluorobenzyl)-7-methyl-6-oxo-9-(p-tolyl)-1,3,4,5,6,7-hexahydropyrano[3',4':4,5]pyrrolo[2,3-c]pyridine-8-carbaldehyde (150 mg, 0.348 mmol, 45.3% yield). LCMS (m/z) ES$^+$=431 (M+1).

Step H 2-(5-(4-fluorobenzyl)-7-methyl-6-oxo-9-(p-tolyl)-1,3,4,5,6,7-hexahydropyrano[3',4':4,5]pyrrolo[2,3-c]pyridin-8-yl)-2-((tetrahydro-2H-pyran-2-yl)oxy)acetonitrile

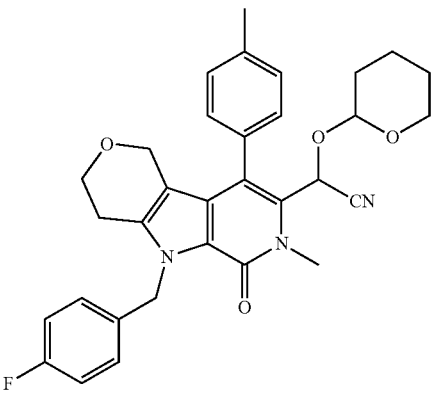 [SMILES: Cc1ccc(-c2c(C(C#N)OC3CCCCO3)n(C)c(=O)c3c2c2c(n3Cc3ccc(F)cc3)CCOC2)cc1]

An ice cold solution of 5-(4-fluorobenzyl)-7-methyl-6-oxo-9-(p-tolyl)-1,3,4,5,6,7-hexahydropyrano[3',4':4,5]pyrrolo[2,3-c]pyridine-8-carbaldehyde (150 mg, 0.348 mmol) and Zinc iodide (86 mg, 0.697 mmol) in Dichloromethane (DCM) (1783 µl) was treated with TMS-CN (909 µl, 3.48 mmol) dropwise. After 30 min, the reaction mixture was quenched with a 10% solution of $Na_2S_2O_3$. DCM was added and the layers were partitioned. The organic layer was washed with brine, dried ($Na_2SO_4$), filtered and concentrated. The residue was dissolved in MeOH (3 mL), cooled to 0° C. and treated dropwise with 1M HCl in 1,4-dioxane (697 µl, 0.697 mmol). After 1 h, the reaction mixture was concentrated in vacuo. The residue was then dissolved in DCM (3 mL) and treated with DHP (96 µl, 1.045 mmol) and PPTS (4.38 mg, 0.017 mmol). After 45 min, Et3N (0.5 mL) was added and the reaction mixture was poured into sat. aq. $NaHCO_3$. EtOAc was added and the layers partitioned. The organic phase was washed with brine, dried ($Na_2SO_4$), filtered and concentrated in vacuo. The residue was purified by ISCO (0-50% EtOAc-hexanes) to afford 2-(5-(4-fluorobenzyl)-7-methyl-6-oxo-9-(p-tolyl)-1,3,4,5,6,7-hexahydropyrano[3',4':4,5]pyrrolo[2,3-c]pyridin-8-yl)-2-((tetrahydro-2H-pyran-2-yl)oxy)acetonitrile (170 mg, 0.314 mmol, 90% yield) as a white foam. LCMS (m/z) $ES^+$=542 (M+1).

Step I methyl 2-(5-(4-fluorobenzyl)-7-methyl-6-oxo-9-(p-tolyl)-1,3,4,5,6,7-hexahydropyrano[3',4':4,5]pyrrolo[2,3-c]pyridin-8-yl)-2-hydroxyacetate

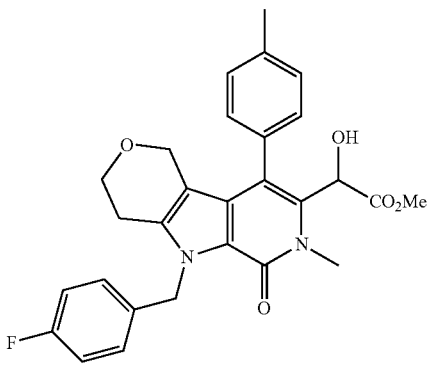 [SMILES: COC(=O)C(O)c1c(-c2ccc(C)cc2)c2c3c(n(Cc4ccc(F)cc4)c2c(=O)n1C)CCOC3]

A 6 mL microwave vial was charged with 2-(5-(4-fluorobenzyl)-7-methyl-6-oxo-9-(p-tolyl)-1,3,4,5,6,7-hexahydropyrano[3',4':4,5]pyrrolo[2,3-c]pyridin-8-yl)-2-((tetrahydro-2H-pyran-2-yl)oxy)acetonitrile (170 mg, 0.314 mmol), Ethanol (5 ml) and 20% NaOH (2.54 ml, 14.60 mmol). The reaction vessel was sealed and heated in a 140° C. oil bath. After 18 h, the reaction mixture was cooled in an ice bath and conc HCl was added until pH <2. The residue was suspended in a mixture of MeOH (2 mL) and Et2O (2 mL), cooled to 0° C. and treated dropwise with TMS diazomethane (0.628 ml, 1.256 mmol). The reaction mixture was concentrated in vacuo and purified by ISCO (0-50% EtOAc-hexanes) to afford methyl 2-(5-(4-fluorobenzyl)-7-methyl-6-oxo-9-(p-tolyl)-1,3,4,5,6,7-hexahydropyrano[3',4':4,5]pyrrolo[2,3-c]pyridin-8-yl)-2-hydroxyacetate (26 mg, 0.053 mmol, 16.89% yield) as a white solid. LCMS (m/z) $ES^+$=491 (M+1).

Step J 2-(tert-butoxy)-2-(5-(4-fluorobenzyl)-7-methyl-6-oxo-9-(p-tolyl)-1,3,4,5,6,7-hexahydropyrano[3',4':4,5]pyrrolo[2,3-c]pyridin-8-yl)acetic acid

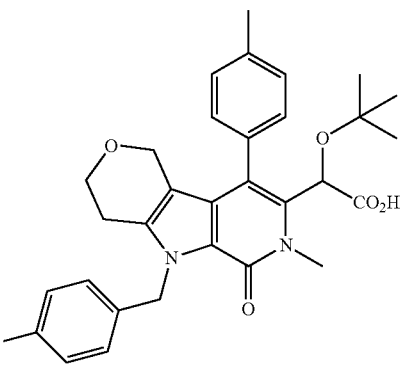

A solution of methyl 2-(5-(4-fluorobenzyl)-7-methyl-6-oxo-9-(p-tolyl)-1,3,4,5,6,7-hexahydropyrano[3',4':4,5]pyrrolo[2,3-c]pyridin-8-yl)-2-hydroxyacetate (26 mg, 0.053 mmol) was dissolved in tert butyl acetate (618 µl, 5.30 mmol), cooled to 0° C. and treated with perchloric acid (7.21 µl, 0.053 mmol) and the reaction vessel was transferred to the fridge. After 72 h (weekend), the reaction mixture was partitioned between EtOAc and sat. aq. $NaHCO_3$ and the organic layer was washed with brine, dried ($MgSO_4$), filtered and concentrated in vacuo. The residue was dissolved in THF (0.2 mL) and MeOH (0.2 mL), treated with 2M LiOH (133 µl, 0.265 mmol) and heated to 50° C. After 2 h, The reaction mixture was poured into 1M HCl and extracted with EtOAc. The organic layer was washed with brine, dried ($MgSO_4$), filtered and concentrated. The residue was purified by reverse phase HPLC to afford 2-(tert-butoxy)-2-(5-(4-fluorobenzyl)-7-methyl-6-oxo-9-(p-tolyl)-1,3,4,5,6,7-hexahydropyrano[3',4':4,5]pyrrolo[2,3-c]pyridin-8-yl)acetic acid (15 mg, 0.028 mmol, 53.1% yield) as a white solid. $^1$H NMR (400 MHz, CHLOROFORM-d)=7.50-7.43 (m, 1H), 7.17 (none, 5H), 7.03-6.95 (m, 2H), 5.95-5.86 (m, 1H), 5.77-5.69 (m, 1H), 5.29 (s, 1H), 4.08 (s, 1H), 3.94-3.86 (m, 1H), 3.79-3.70 (m, 1H), 3.66 (s, 3H), 3.60 (d, J=14.1 Hz, 1H), 2.70-2.53 (m, 2H), 2.42 (s, 3H), 1.05 (s, 9H). LCMS (m/z) $ES^+$=533 (M+1).

Example 59

2-(tert-butoxy)-2-(9-(4-fluorobenzyl)-2-methyl-1-oxo-4-(p-tolyl)-2,5,6,7,8,9-hexahydro-1H-pyrido[3,4-b]indol-3-yl)acetic acid

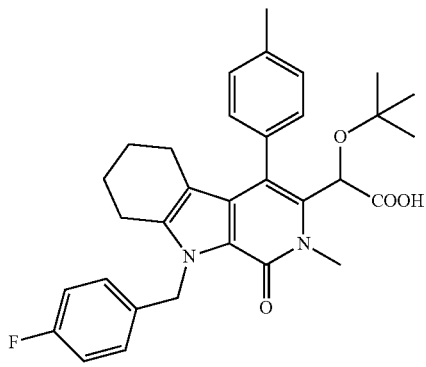

The title compound was prepared in a manner similar to that described in Example 58 except starting with cyclohexanone oxime in Step A and using Steps G-K of Example 56. ¹H NMR (400 MHz, CHLOROFORM-d) ppm 7.53-7.48 (m, 1H), 7.27-7.21 (m, 3H), 7.15-7.09 (m, 2H), 7.02-6.95 (m, 2H), 5.99-5.91 (m, 1H), 5.75-5.67 (m, 1H), 5.34-5.31 (s, 1H), 3.66 (s, 3H), 2.62-2.52 (m, 2H), 2.46 (s, 3H), 2.00-1.89 (m, 1H), 1.84-1.75 (m, 1H), 1.67-1.57 (m, 1H), 1.56-1.48 (m, 1H), 1.38-1.25 (m, 2H), 1.05 (s, 9H); LCMS (m/z) ES⁺=531 (M+1).

Example 60

2-(tert-butoxy)-2-(2,9-dimethyl-1-oxo-4-(p-tolyl)-2,5,6,7,8,9-hexahydro-1H-pyrido[3,4-b]indol-3-yl)acetic acid

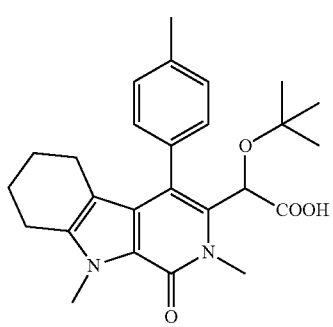 [SMILES: Cc1ccc(-c2c(C(OC(C)(C)C)C(=O)O)n(C)c(=O)c3c2c2c(n3C)CCCC2)cc1]

The title compound was prepared in a similar manner to that described in Example 58 except starting with cyclohexanone oxime and using methyl idode in Step A. LCMS (m/z) ES⁺=438 (M+1).

Example 61

2-(tert-butoxy)-2-(9-(4-methoxybenzyl)-2-methyl-1-oxo-4-(p-tolyl)-2,5,6,7,8,9-hexahydro-1H-pyrido[3,4-b]indol-3-yl)acetic acid

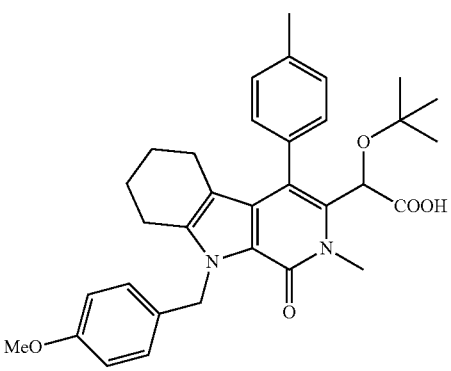 [SMILES: COc1ccc(Cn2c3c(c4c(-c5ccc(C)cc5)c(C(OC(C)(C)C)C(=O)O)n(C)c(=O)c42)CCCC3)cc1]

The title compound was prepared in a similar manner to that described in Example 58 except starting with cyclohexanone oxime and using p-methoxy benzyl chloride in Step A. LCMS (m/z) ES⁺=544 (M+1).

Example 62

2-(tert-butoxy)-2-(9-(4-methoxybenzyl)-2-methyl-4-(5-methylchroman-6-yl)-1-oxo-2,5,6,7,8,9-hexahydro-1H-pyrido[3,4-b]indol-3-yl)acetic acid

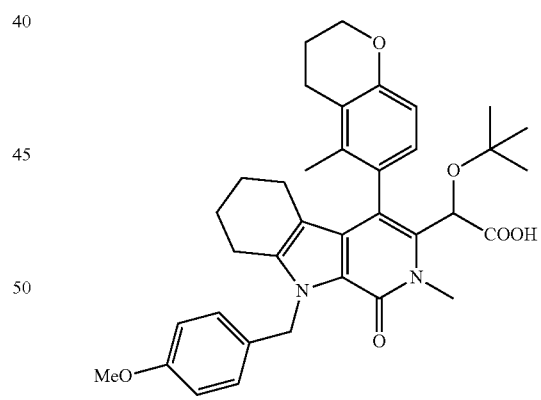

The title compound was prepared in a manner similar to that described in Example 58 except starting with cyclohexanone oxime and p-methoxybenzyl chloride in Step A and using 4,4,5,5-tetramethyl-2-(5-methylchroman-6-yl)-1,3,2-dioxaborolane in Step E. Homologation of the ester was done in a manner similar to steps G-K of Example 56. ¹H NMR (400 MHz, CHLOROFORM-d)=7.11 (d, J=8.4 Hz, 2H), 7.06-6.99 (m, 1H), 6.83 (d, J=8.4 Hz, 2H), 6.77-6.66 (m, 1H), 5.83 (br. s., 1H), 5.77-5.64 (m, 1H), 5.21 (s, 1H), 4.20 (t, J=5.0 Hz, 2H), 3.77 (s, 3H), 3.67 (s, 3H), 2.74-2.65 (m, 2H), 2.57-2.42 (m, 3H), 2.04 (s, 3H), 1.74-1.42 (m, 8H), 1.19 (s, 9H);

Scheme 18
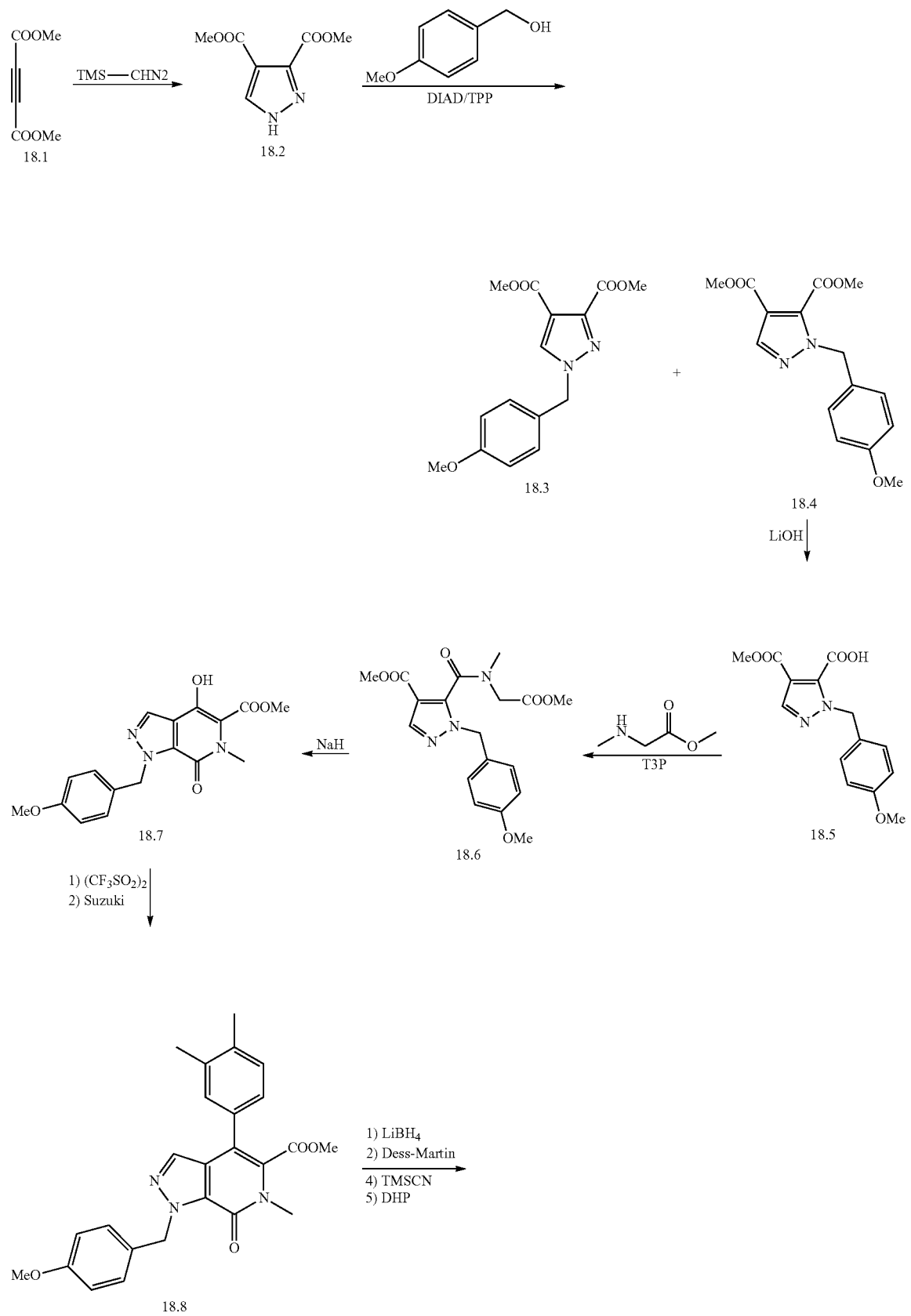

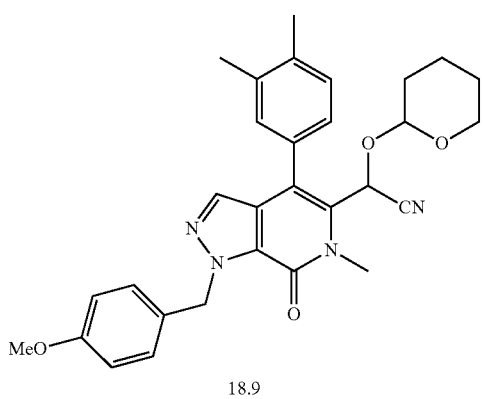

1) NaOH
2) TMS—CHN₂
3) t-BuOAc
4) LiOH

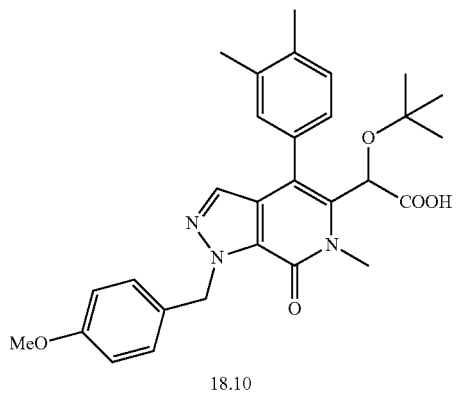

18.9 → 18.10

Example 63

2-(tert-Butoxy)-2-(4-(3,4-dimethylphenyl)-1-(4-methoxybenzyl)-6-methyl-7-oxo-6,7-dihydro-1H-pyrazolo[3,4-c]pyridin-5-yl)acetic

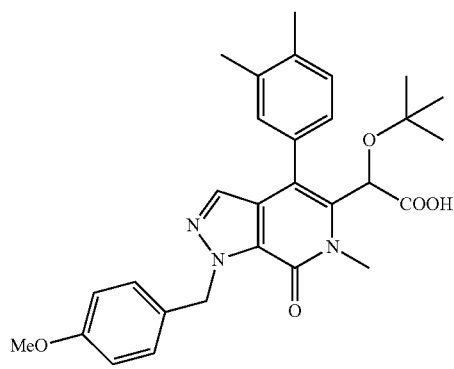 [SMILES: COc1ccc(Cn2ncc3c(-c4ccc(C)c(C)c4)c(C(OC(C)(C)C)C(=O)O)n(C)c(=O)c32)cc1]

Step A

Dimethyl 1H-pyrazole-3,4-dicarboxylate

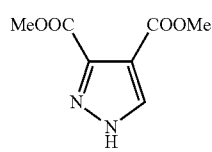

To a solution of dimethyl acetylenedicarboxylate (1.73 mL, 14.07 mmol) in THF (65 mL) at 0° C. was added dropwise TMS-diazomethane (7.74 mL, 15.48 mmol, 2M/hexanes) and the mixture was allowed to warm to ambient temperature in 2 h. After 18 h, 1M hydrochloric acid (10 mL) was added until bubbling stopped and stirring at ambient temperature continued for 30 min. The mixture was diluted with EtOAc and washed with saturated sodium bicarbonate/water. The organic layer was dried over sodium sulfate and concentrated to provide the title compound as a yellowish solid (2.9 g, 99%). ¹H NMR (400 MHz, DMSO-$d_6$) δ ppm 13.95 (s, 1H), 8.2 (s, 1H), 3.8 (s, 3H), 3.7 (s, 3H); ES-LCMS: 184.9 (M+1).

Step B

Dimethyl 1-(4-methoxybenzyl)-1H-pyrazole-4,5-dicarboxylate

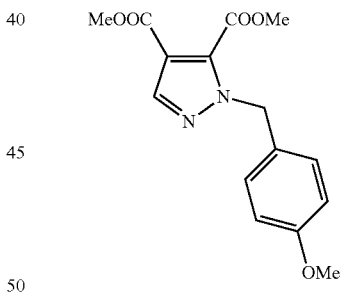

To a solution of dimethyl 1H-pyrazole-3,4-dicarboxylate (2.5 g, 13.6 mmol) in THF (100 mL) was added 4-methoxybenzyl alcohol (1.78 mL, 14.2 mmol) and triphenylphosphine 3.74 g, 14.2 mmol) followed by dropwise addition of DIAD (2.8 mL, 14.2 mmol) and the mixture was stirred at ambient temperature under nitrogen atmosphere for 3 h. The mixture was diluted with EtOAc and washed with saturated sodium bicarbonate/water. The organic phase was dried over sodium sulfate, concentrated and purified on silica using EtOAc/hexanes 0-50% to provide the title compound (1.4 g, 32%) and isomer dimethyl 1{{4-(methyloxy)phenyl]methyl}-1H-pyrazole-3,4-dicarboxylate (1.3 g, 29%). ¹H NMR (400 MHz, DMSO-$d_6$) δ ppm 7.98 (s, 1H), 7.18 (d, 2H), 6.9 (d, 2H), 5.4 (s, 2H), 3.92 (s, 3H), 3.89 (s, 3H), 3.87 (s, 3H); ES-LCMS: 305.28 (M+1).

Step C

1-(4-Methoxybenzyl)-4-(methoxycarbonyl)-1H-pyrazole-5-carboxylic

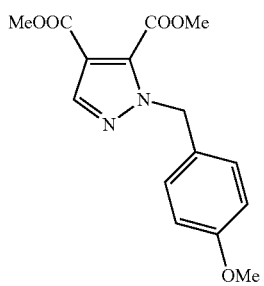 [SMILES: COC(=O)c1cnn(Cc2ccc(OC)cc2)c1C(=O)OC]

To a stirred solution of dimethyl 1-(4-methoxybenzyl)-1H-pyrazole-4,5-dicarboxylate (1.45 g, 4.8 mmol) in THF (30 mL)/MeOH (10 mL) at 0° C. was added a solution of LiOH (0.27 g, 6.34 mmol) in water (2 mL) in four equal portions over 2 h. After 30 min at 0° C. acetic acid was added to pH 3 and the mixture was concentrated to provide the title compound (1.3 g) used as crude in the next step.

Step D

Methyl 5-((2-methoxy-2-oxoethyl)(methyl)carbamoyl)-1-(4-methoxybenzyl)-1H-pyrazole-4-carboxylate

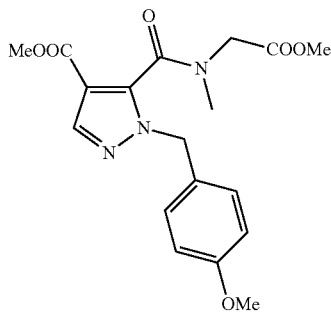 [SMILES: COC(=O)CN(C)C(=O)c1c(C(=O)OC)cnn1Cc1ccc(OC)cc1]

To a solution of the crude 1-(4-methoxybenzyl)-4-(methoxycarbonyl)-1H-pyrazole-5-carboxylic obtained in the previous experiment (1.3 g) in DMF (20 mL) was added sarcosine methyl ester hydrochloride (1.26 g, 9.0 mmol) and DIPEA (3.8 mL, 21.8 mmol) followed by dropwise addition of T3P (5.73 g, 9 mmol, 50% wt/EtOAc) and the mixture was stirred at ambient temperature for 4 h. The mixture was concentrated and partitioned between EtOAc and saturated sodium bicarbonate/water. The organic phase was dried over sodium sulfate, concentrated and purified on silica using EtOAc/hexanes 0-80% to provide the title compound (1.1 g, 60%). $^1$H NMR (400 MHz, DMSO-$d_6$) δ ppm 7.98 (s, 1H), 7.3 (d, 2H), 6.9 (d, 3H), 5.05-5.15 (m, 2H), 4.5 (d, 1H), 4.2 (d, 2H), 3.7 (s, 6H), 3.4 (s, 3H), 2.8 (s, 3H); ES-LCMS: 376.13 (M+1).

Step E

Methyl 4-hydroxy-1-(4-methoxybenzyl)-6-methyl-7-oxo-6,7-dihydro-1H-pyrazolo[3,4-c]pyridine-5-carboxylate

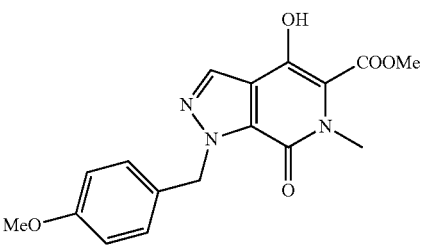 [SMILES: COC(=O)c1c(O)c2cnn(Cc3ccc(OC)cc3)c2c(=O)n1C]

To a solution of methyl 5-((2-methoxy-2-oxoethyl)(methyl)carbamoyl)-1-(4-methoxybenzyl)-1H-pyrazole-4-carboxylate (1.1 g, 2.93 mmol) in DMF (20 mL) was added NaH (0.12 g, 2.85 mmol, 60% in mineral oil) and the mixture was stirred a ambient temperature under nitrogen atmosphere for 50 min. Saturated NH$_4$Cl/water was slowly added and stirring at ambient temperature continued for 50 min. The solid was filtered, dissolved in dichloromethane and the filtrate dried over sodium sulfate and concentrated to provide the title compound (0.60 g, 60%). $^1$H NMR (400 MHz, DMSO-$d_6$) δ ppm 10.2 (s, 1H), 8.1 (s 1H), 7.22 (d, 2H), 6.9 (d, 2H), 5.8 (s, 2H), 3.9 (s, 3H), 3.7 (s, 3H), 3.42 (s, 3H); ES-LCMS: 344 (M+1).

Step F

Methyl 4-(3,4-dimethylphenyl)-1-(4-methoxybenzyl)-6-methyl-7-oxo-6,7-dihydro-1H-pyrazolo[3,4-c]pyridine-5-carboxylate

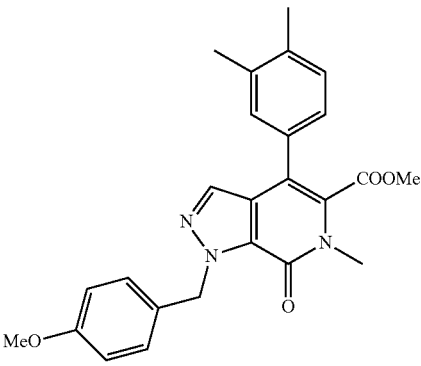 [SMILES: COC(=O)c1c(-c2ccc(C)c(C)c2)c2cnn(Cc3ccc(OC)cc3)c2c(=O)n1C]

To a solution of methyl 4-hydroxy-1-(4-methoxybenzyl)-6-methyl-7-oxo-6,7-dihydro-1H-pyrazolo[3,4-c]pyridine-5-carboxylate (585 mg, 1.7 mmol) in dichloromethane (15 mL) was added TEA (0.48 mL, 3.4 mmol) and the mixture was cooled to 0° C. and triflic anhydride (0.32 mL, 1.87 mmol) was added dropwise. After 1 h the mixture was washed with saturated sodium bicarbonate/water and brine. The organic phase was dried over sodium sulfate and concentrated. To a solution of crude triflate in 1,4-dioxane (14 mL) was added (3,4-dimethylphenyl)boronic acid (0.33 g, 2.2 mmol), Palladium tetrakis (0.19 g, 0.17 mmol) and a solution of sodium carbonate (0.54 g, 5.05 mmol) in water (3.5 mL) and the mixture was heated to 70° C. under nitrogen atmosphere for 1 h. EtOAc and water was added and the mixture was washed with saturated sodium bicarbonate/water. The organic phase was dried over sodium sulfate, concentrated and purified on silica using EtOAc/hexanes 0-30% to provide the title compound (645 mg, 84%). $^1$H NMR (400 MHz, DMSO-$d_6$) δ ppm 7.65 (s, 1H), 7.4 (d, 2H), 7.2 (d, 1H), 7.14 (s, 1H), 7.08 (d, 1H), 6.85 (d, 2H), 5.92 (s, 2H), 3.8 (s, 3H), 3.64 (s, 3H), 3.6 (s, 3H), 2.28 (s, 3H), 2.26 (s, 3H); ES-LCMS: 432.24 (M+1).

Step G 2-(4-(3,4-Dimethylphenyl)-1-(4-methoxybenzyl)-6-methyl-7-oxo-6,7-dihydro-1H-pyrazolo[3,4-c]pyridin-5-yl)-2-((tetrahydro-2H-pyran-2-yl)oxy)acetonitrile

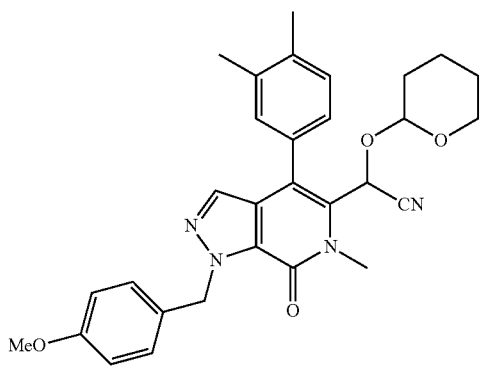 [SMILES: COc1ccc(Cn2ncc3c(-c4ccc(C)c(C)c4)c(C(C#N)OC4CCCCO4)n(C)c(=O)c32)cc1]

To a solution of methyl 4-(3,4-dimethylphenyl)-1-(4-methoxybenzyl)-6-methyl-7-oxo-6,7-dihydro-1H-pyrazolo[3,4-c]pyridine-5-carboxylate (640 mg, 1.49 mmol) in toluene (10 mL) was added 2M lithium borohydride/THF (3.7 mL, 7.4 mmol) and the mixture was stirred under nitrogen at 65° C. for 24 h. The mixture was quenched with 1M hydrochloric acid and partitioned between saturated sodium bicarbonate and EtOAc. The organic phase was dried over sodium sulfate and purified on silica using EtOAc/hexanes 0-100% to provide the corresponding alcohol intermediate (430 mg, 70%); ES-LCMS: 404.24 (M+1). This intermediate was dissolved in dichloromethane (10 mL) and Dess-Martin periodinane (491 mg, 1.16 mmol) was added in two portions. After stirring for 30 min at ambient temperature, the mixture was washed with saturated sodium thiosulfate/water and saturated sodium bicarbonate/water. The organic phase was dried over sodium sulfate and concentrated to provide the corresponding aldehyde intermediate (341 mg, 79%); ES-LCMS: 402.15 (M+1). A portion of this intermediate (236 mg, 0.6 mmol) was dissolved in dichloromethane (6 mL) and zinc iodide was added followed by dropwise addition of TMSCN (0.24 mL, 1.76 mmol) and the mixture was stirred at ambient temperature for 3 h. Dichloromethane was added and the mixture was washed with water and brine. The organic phase was dried over sodium sulfate and concentrated to provide the corresponding silyl-protected cyanohydrine intermediate (300 mg, 99%). This intermediate was dissolved in MeOH (3 mL) and cooled to 0° C. To this mixture was added 1 M hydrochloric acid (0.3 mL, 0.3 mmol) and after stirring for 5 min the mixture was concentrated and dried in vacuo. The residue was dissolved in dichloromethane (4 mL) and DHP (0.15 mL, 1.65 mmol) and PPTS (14 mg, 0.055 mmol) were added. After stirring for 2 h at ambient temperature dichloromethane was added and the mixture was washed with saturated sodium bicarbonate/water. The organic phase was dried over sodium sulfate, concentrated and purified on silica using EtOAc/hexanes 0-30% to provide the title compound (270 mg, 94%). $^1$H NMR (400 MHz, CDCl$_3$) δ ppm 7.4-7.5 (m, 3H), 7.20-7.25 (m, 1H), 6.95-7.05 (m, 2H), 5.95 (s, 2H), 5.6 (d, 1H), 4.6 (s, 1H), 3.95 (s, 3H), 3.8 (s, 3H), 3.2-3.5 (m, 2H), 2.4 (s, 3H), 2.3 (s, 3H), 1.4-1.8 (m, 6H); ES-LCMS: 513.27 (M+1).

Step H

Methyl 2-(4-(3,4-dimethylphenyl)-1-(4-methoxybenzyl)-6-methyl-7-oxo-6,7-dihydro-1H-pyrazolo[3,4-c]pyridin-5-yl)-2-hydroxyacetate

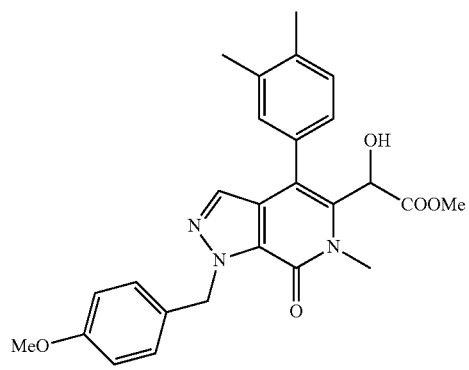 [SMILES: COC(=O)C(O)c1c(-c2ccc(C)c(C)c2)c2cnn(Cc3ccc(OC)cc3)c2c(=O)n1C]

A mixture of 2-(4-(3,4-dimethyl phenyl)-1-(4-methoxybenzyl)-6-methyl-7-oxo-6,7-dihydro-1H-pyrazolo[3,4-c]pyridin-5-yl)-2-((tetrahydro-2H-pyran-2-yl)oxy)acetonitrile 267 mg, 0.52 mmol), 20% sodium hydroxide/water (5.0 g, 25 mmol) and EtOH (5 mL) was heated in a sealed tube at 140° C. for 18 h. The mixture was acidified to pH 3 with 1 M hydrochloric acid, diluted with water and extracted with EtOAc. The organic phase was dried over sodium sulfate and concentrated. The residue was dissolved in MeOH (10 mL) and PTS (80 mg, 0.421 mmol) was added. After 1 h at ambient temperature the mixture was treated with TMS-diazomethane (3 mL, 6 mmol, 2M/hexanes) and stirring continued for 1.5 h. Acetic acid was added until bubbling stopped and the mixture was concentrated and purified on silica using EtOAc/hexanes 0-50% to provide the title compound (175 mg, 72%). $^1$H NMR (400 MHz, CDCl$_3$) δ ppm 7.4-7.5 (m, 3H), 7.1-7.3 (m, 3H), 6.85 (d, 2H), 5.95 (s, 2H), 5.35 (d, 1H), 3.79 (s, 3H), 3.78 (s, 3H), 3.6 (s, 3H), 2.33 (s, 3H), 2.32 (s, 3H); ES-LCMS: 462.22 (M+1).

Step I 2-(tert-Butoxy)-2-(4-(3,4-dimethylphenyl)-1-(4-methoxybenzyl)-6-methyl-7-oxo-6,7-dihydro-1H-pyrazolo[3,4-c]pyridin-5-yl)acetic acid

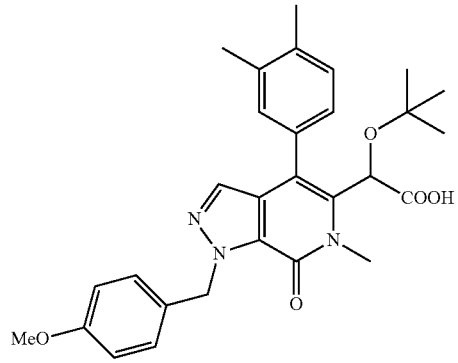 [SMILES: COc1ccc(Cn2ncc3c(-c4ccc(C)c(C)c4)c(C(OC(C)(C)C)C(=O)O)n(C)c(=O)c32)cc1]

To a solution of methyl 2-(4-(3,4-dimethylphenyl)-1-(4-methoxybenzyl)-6-methyl-7-oxo-6,7-dihydro-1H-pyrazolo[3,4-c]pyridin-5-yl)-2-hydroxyacetate (170 mg, 0.37 mmol) in dichloromethane (2.5 mL) and t-butyl acetate (2.5 mL) was added perchloric acid (0.23 mL, 2.68 mmol) and the mixture was stirred at ambient temperature for 3 h. The mixture was diluted with dichloromethane and washed with saturated sodium bicarbonate/water. The org. phase was dried over sodium sulfate, concentrate and purified on silica using EtOAc/hexanes 0-50% to provide the t-butyl ester intermediate (49 mg, 35%); ES-LCMS: 518.24 (M+1). This intermediate was dissolved in THF (1 mL)/MeOH (0.5 mL) and LiOH monohydrate (8 mg, 0.19 mmol) and water (0.2 mL) was added. After stirring at ambient temperature for 4 h, acetic acid was added (0.1 mL) and the mixture was purified by reverse phase HPLC on a $C_{18}$ column using MeCN/water 10-90% containing 0.05% TFA to provide the title compound (35 mg, 72%). $^1$H NMR (400 MHz, CD$_3$OD) δ ppm 7.43 (d, 1H), 7.18-7.40 (m, 4H), 6.85 (d, 2H), 5.95 (dd, 2H), 5.4 (d, 1H), 3.75 (s, 3H), 3.69 (s, 3H), 2.35 (s, 3H), 2.33 (s, 3H), 0.93 (s, 9H); ES-LCMS: 504.29 (M+1).

The following compounds were prepared according to Scheme 18 following the procedures described in example 63.

Example 64

2-(tert-Butoxy)-2-(1-(4-fluorobenzyl)-6-methyl-7-oxo-4-(p-tolyl)-6,7-dihydro-1H-pyrazolo[3,4-c]pyridin-5-yl)acetic acid

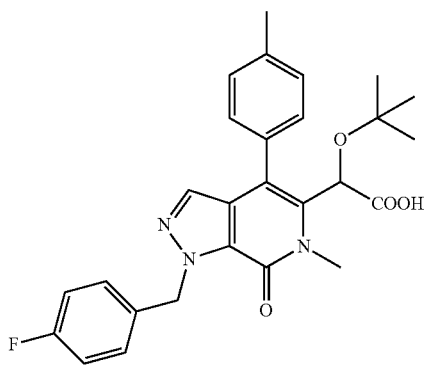

$^1$H NMR (400 MHz, CD$_3$OD) δ ppm 7.45-7.50 (m, 2H), 7.30-7.40 (m, 5H), 7.0 (t, 2H), 5.8 (s, 2H), 5.3 (s, 1H), 3.7 (s, 3H), 2.4 (s, 3H), 0.84 (s, 9H); ES-LCMS: 478.30 (M+1).

Example 65

2-(tert-Butoxy)-2-(1-(4-methoxybenzyl)-6-methyl-4-(5-methylchroman-6-yl)-7-oxo-6,7-dihydro-1H-pyrazolo[3,4-c]pyridin-5-yl)acetic acid yl)acetic

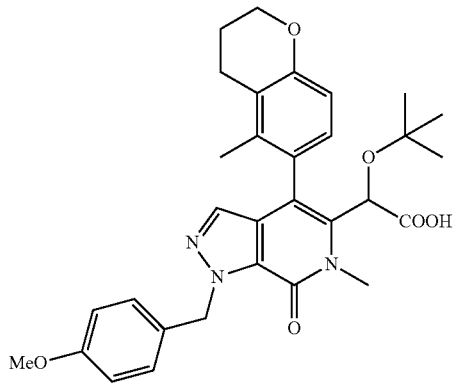 [SMILES: COc1ccc(Cn2ncc3c(-c4ccc5c(c4C)CCCO5)c(C(OC(C)(C)C)C(=O)O)n(C)c(=O)c32)cc1]

The proton NMR of this compound showed the presence of four possible isomers and signals for the most prominent isomer are given. $^1$H NMR (400 MHz, CD$_3$OD) δ ppm 7.25-7.30 (m, 3H), 7.18-7.20 (m, 1H), 6.8 (d, 2H), 6.70-6.76 (m, 1H), 5.85 (dd, 2H), 5.35 (s, 1H), 4.1-4.2 (m, 2H), 3.7 (s, 3H), 2.75-2.80 (m, 2H), 2.05-2.12 (m, 2H), 1.95 (s, 3H), 1.1 (s, 3H), 0.98 (s, 9H); ES-LCMS: 546.27 (M+1).

Scheme 19

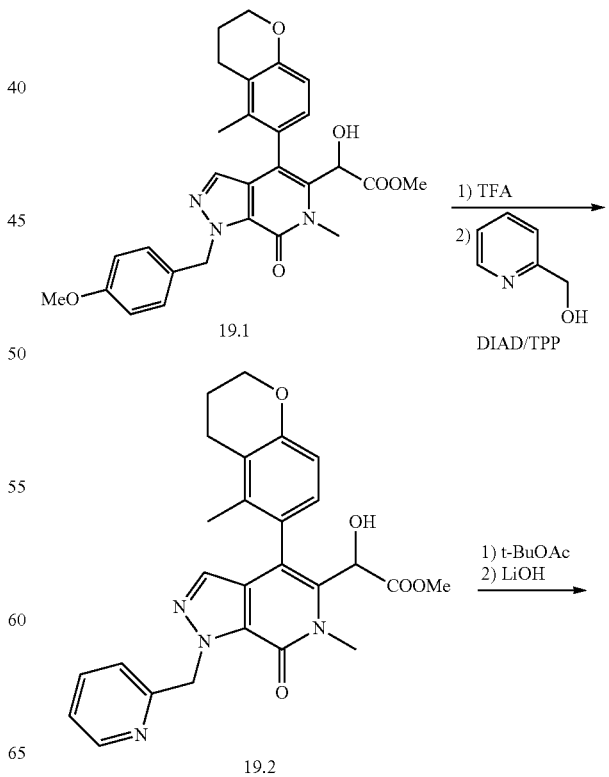

-continued

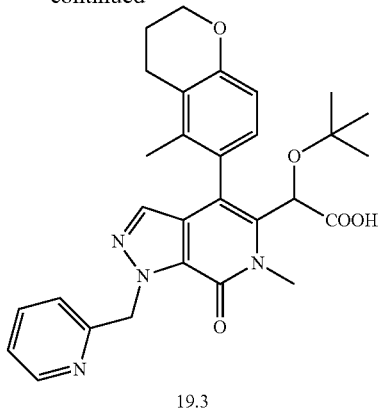

19.3

Intermediate 19.1 was prepared according to Scheme 18 following the procedures described in steps A-H for example 63. The following compounds were prepared from intermediate 19.1 according to Scheme 19.

Example 66

2-(tert-Butoxy)-2-(6-methyl-4-(5-methylchroman-6-yl)-7-oxo-1-(pyridin-2-ylmethyl)-6,7-dihydro-1H-pyrazolo[3,4-c]pyridin-5-yl)acetic acid

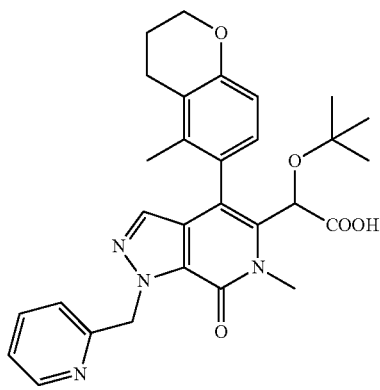 [SMILES: Cc1c(-c2c(C(OC(C)(C)C)C(=O)O)n(C)c(=O)c3c2cnn3Cc2ccccn2)ccc2c1CCCO2]

Step A

Methyl 2-hydroxy-2-(6-methyl-4-(5-methylchroman-6-yl)-7-oxo-1-(pyridin-2-ylmethyl)-6,7-dihydro-1H-pyrazolo[3,4-c]pyridin-5-yl)acetate

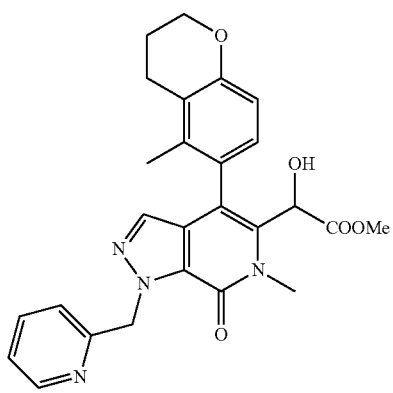 [SMILES: COC(=O)C(O)c1c(-c2ccc3c(c2C)CCCO3)c2cnn(Cc3ccccn3)c2c(=O)n1C]

A solution of methyl 2-hydroxy-2-(1-(4-methoxybenzyl)-6-methyl-4-(5-methylchroman-6-yl)-7-oxo-6,7-dihydro-1H-pyrazolo[3,4-c]pyridin-5-yl)acetate (100 mg, 0.2 mmol) in TFA (1 mL)/dichloromethane (1 mL) was stirred at 55° C. for 6 h and then concentrated. The residue was partitioned between EtOAc and saturated sodium bicarbonate/water. The organic phase was dried over sodium sulfate and concentrated. The residue was dissolved in THF (2.5 mL) and to this solution triphenylphosphine (103 mg, 0.4 mmol) and pyridine-2-ylmethanol (43 mg, 0.4 mmol) was added followed by DIAD (0.076 mL, 0.4 mmol) and the mixture was stirred at ambient temperature for 2.5 h. The mixture was concentrated and purified on silica using EtOAc/hexanes 0-50% to provide the title compound (47 mg, 68%). $^1$H NMR (400 MHz, CDCl$_3$) δ ppm 8.6 s (1H), 6.8-7.8 (m, 5H), 6.7 (d, 1H), 6.2-6.4 (m, 2H), 5.3 (s, 1H), 4.3 (broad s, 2H), 3.9 (s, 3H), 3.7 (s, 3H), 2.7 (broad s, 2H), 2.0 (s, 3H), 1.7 (broad s, 2H); ES-LCMS: 475.2 (M+1).

Step B 2-(tert-Butoxy)-2-(6-methyl-4-(5-methylchroman-6-yl)-7-oxo-1-(pyridin-2-ylmethyl)-6,7-dihydro-1H-pyrazolo[3,4-c]pyridin-5-yl)acetic

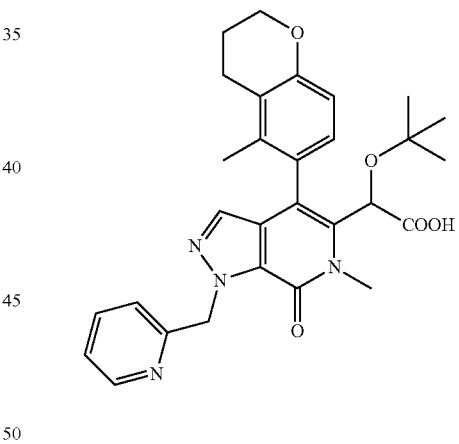

This compound was prepared from methyl 2-hydroxy-2-(6-methyl-4-(5-methylchroman-6-yl)-7-oxo-1-(pyridin-2-ylmethyl)-6,7-dihydro-1H-pyrazolo[3,4-c]pyridin-5-yl)acetate following the procedures described for example 63. The proton NMR of this compound showed the presence of four possible isomers and signals for the most prominent isomer are given. $^1$H NMR (400 MHz, CD$_3$OD) δ ppm 8.6 (d, 1H), 8.02 (t, 1H), 7.6 (t, 1H), 7.4 (s, 1H), 7.37 (broad s, 1H), 7.22 (d, 1H), 6.8 (d, 1H), 6.1-6.2 (m, 2H), 5.4 (s, 1H), 4.15-4.25 (m, 2H), 3.7 (s, 3H), 2.65-2.75 (m, 2H), 2.05-2.15 (m, 2H), 1.0 (s, 9H); ES-LCMS: 517.26 (M+1).

Example 67

2-(tert-butoxy)-2-(1-(4-fluorobenzyl)-6-methyl-4-(5-methylchroman-6-yl)-7-oxo-6,7-dihydro-1H-pyrazolo[3,4-c]pyridin-5-yl)acetic acid

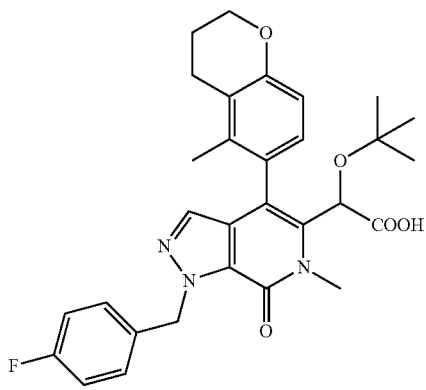 [SMILES: Cc1c(-c2c(C(OC(C)(C)C)C(=O)O)n(C)c(=O)c3c2cnn3Cc2ccc(F)cc2)ccc2c1CCCO2]

This compound was prepared according to Scheme 19 following the procedures described in steps A-B for example 65. The proton NMR of this compound showed the presence of four possible isomers and signals for the most prominent isomer are given. $^1$H NMR (400 MHz, CD$_3$OD) δ ppm 7.3-7.4 (m, 2H), 7.25 (s, 1H), 7.2 (d, 1H), 6.9-7.0 (m, 2H), 6.7-6.8 (m, 1H), 5.9 (dd, 2H), 5.3 (s, 1H), 4.15-4.25 (m, 2H), 3.7 (s, 3H), 2.7-2.8 (m, 2H), 2.10-2.20 (m, 2H), 1.9 (s, 3H), 0.98 (s, 9H). ES-LCMS: 534.25 (M+1).

Administration and Formulation

In another embodiment, there is provided a pharmaceutical composition comprising a pharmaceutically acceptable diluent and a therapeutically effective amount of a compound of Formula (I) or a pharmaceutically acceptable salt thereof.

The compounds of the present invention can be supplied in the form of a pharmaceutically acceptable salt. The terms "pharmaceutically acceptable salt" refer to salts prepared from pharmaceutically acceptable inorganic and organic acids and bases. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication. The skilled artisan will appreciate that pharmaceutically acceptable salts of compounds according to Formulas I or II may be prepared. These pharmaceutically acceptable salts may be prepared in situ during the final isolation and purification of the compound, or by separately reacting the purified compound in its free acid or free base form with a suitable base or acid, respectively.

Illustrative pharmaceutically acceptable acid salts of the compounds of the present invention can be prepared from the following acids, including, without limitation formic, acetic, propionic, benzoic, succinic, glycolic, gluconic, lactic, maleic, malic, tartaric, citric, nitic, ascorbic, glucuronic, maleic, fumaric, pyruvic, aspartic, glutamic, benzoic, hydrochloric, hydrobromic, hydroiodic, isocitric, trifluoroacetic, pamoic, propionic, anthranilic, mesylic, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, β-hydroxybutyric, galactaric and galacturonic acids. Preferred pharmaceutically acceptable salts include the salts of hydrochloric acid and trifluoroacetic acid.

Illustrative pharmaceutically acceptable inorganic base salts of the compounds of the present invention include metallic ions. More preferred metallic ions include, but are not limited to, appropriate alkali metal salts, alkaline earth metal salts and other physiological acceptable metal ions. Salts derived from inorganic bases include aluminum, ammonium, calcium, copper, ferric, ferrous, lithium, magnesium, manganic salts, manganous, potassium, sodium, zinc, and the like and in their usual valences. Exemplary base salts include aluminum, calcium, lithium, magnesium, potassium, sodium and zinc. Other exemplary base salts include the ammonium, calcium, magnesium, potassium, and sodium salts. Still other exemplary base salts include, for example, hydroxides, carbonates, hydrides, and alkoxides including NaOH, KOH, Na$_2$CO$_3$, K$_2$CO$_3$, NaH, and potassium-t-butoxide.

Salts derived from pharmaceutically acceptable organic non-toxic bases include salts of primary, secondary, and tertiary amines, including in part, trimethylamine, diethylamine, N,N'-dibenzylethylenediamine, chloroprocaine, choline, diethanolamine, ethylenediamine, meglumine (N-methylglucamine) and procaine; substituted amines including naturally occurring substituted amines; cyclic amines; quaternary ammonium cations; and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

All of the above salts can be prepared by those skilled in the art by conventional means from the corresponding compound of the present invention. For example, the pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salt may precipitate from solution and be collected by filtration or may be recovered by evaporation of the solvent. The degree of ionisation in the salt may vary from completely ionised to almost non-ionised. Lists of suitable salts are found in *Remington's Pharmaceutical Sciences*, 17th ed. (Mack Publishing Company, Easton, Pa., 1985, p. 1418) the disclosure of which is hereby incorporated by reference only with regards to the lists of suitable salts.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. $D_2O$, $d_6$-acetone, $d_6$-DMSO.

Compounds of Formula (I) containing one or more asymmetric carbon atoms can exist as two or more stereoisomers. Where a compound of Formula (I) contains an alkenyl or alkenylene group or a cycloalkyl group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the claimed compounds present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Isotopically-labelled compounds of formula (I) can generally be prepared by conventional techniques known to those skilled in the art or by processes analogous to those described in the accompanying Examples and Preparations using an appropriate isotopically-labelled reagent in place of the non-labelled reagent previously employed.

The compounds of the present invention may be administered as prodrugs. Thus, certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'.

Administration of the chemical entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarily, vaginally, rectally, or intraocularly. In some embodiments, oral or parenteral administration is used.

Pharmaceutical compositions or formulations include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see *Remington's Pharmaceutical Sciences*, Mack Publishing Company, Easton, Pa.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent in solution.

Pharmaceutical compositions of the chemical entities described herein may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

In general, the chemical entities provided will be administered in a therapeutically effective amount by any of the accepted modes of administration for agents that serve similar utilities. The actual amount of the chemical entity, i.e., the active ingredient, will depend upon numerous factors such as the severity of the disease to be treated, the age and relative health of the subject, the potency of the chemical entity used, the route and form of administration, and other factors. The drug can be administered more than once a day, such as once or twice a day.

Therapeutically effective amounts of the chemical entities described herein may range from approximately 0.01 to 200 mg per kilogram body weight of the recipient per day; such as about 0.01-100 mg/kg/day, for example, from about 0.1 to 50 mg/kg/day. Thus, for administration to a 70 kg person, the dosage range may be about 7-3500 mg per day.

In general, the chemical entities will be administered as pharmaceutical compositions by any one of the following routes: oral, systemic (e.g., transdermal, intranasal or by suppository), or parenteral (e.g., intramuscular, intravenous or subcutaneous) administration. In certain embodiments, oral administration with a convenient daily dosage regimen that can be adjusted according to the degree of affliction may be used. Compositions can take the form of tablets, pills, capsules, semisolids, powders, sustained release formulations, solutions, suspensions, elixirs, aerosols, or any other appropriate compositions. Another manner for administering the provided chemical entities is inhalation.

The choice of formulation depends on various factors such as the mode of drug administration and bioavailability of the drug substance. For delivery via inhalation the chemical entity can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDIs typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical compositions have been developed for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, at least one chemical entity described herein in combination with at least one pharmaceutically acceptable excipient. Acceptable excipients are non-toxic, aid administration, and do not adversely affect the therapeutic benefit of the at least one chemical entity described herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, for injectable solutions, include water, saline, aqueous dextrose, and glycols.

Compressed gases may be used to disperse a chemical entity described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the chemical entity in a composition can vary within the full range employed by those skilled in the art. Typically, the composition will contain, on a weight percent (wt %) basis, from about 0.01-99.99 wt % of at least one chemical entity described herein based on the total composition, with the balance being one or more suitable pharmaceutical excipients. In certain embodiments, the at least one chemical entity described herein is present at a level of about 1-80 wt %. Representative pharmaceutical compositions containing at least one chemical entity described herein are described below.

The following examples serve to more fully describe the manner of making and using the above-described invention. It is understood that these examples in no way serve to limit the true scope of the invention, but rather are presented for illustrative purposes.

BIOLOGICAL EXAMPLES

Example 68

Anti-HIV Activity

MT4 Assay
Antiviral HIV activity and cytotoxicity values for compounds of the invention from Table 1 were measured in parallel in the HTLV-1 transformed cell line MT-4 based on the method previously described (Hazen et al., 2007, In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV (Hazen et al., "In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV", *Antimicrob. Agents Chemother.* 2007, 51: 3147-3154; and Pauwels et al., "Sensitive and rapid assay on MT-4 cells for the detection of antiviral compounds against the AIDS virus", (*J. of Virological Methods* 1987, 16: 171-185).

Luciferase activity was measured 96 hours later by adding a cell titer glo (Promega, Madison, Wis.). Percent inhibition of cell protection data was plotted relative to no compound control. Under the same condition, cytotoxicity of the compounds was determined using cell titer Glo™ (Promega, Madison, Wis.). $IC_{50}$s were determined from a 10 point dose response curve using 3-4-fold serial dilution for each compound, which spans a concentration range >1000 fold.

These values are plotted against the molar compound concentrations using the standard four parameter logistic equation:

$$y=((V\max*x\hat{}n)/(K\hat{}n+x\hat{}n))+Y^2$$

where:
$Y^2$=minimum y n=slope factor
Vmax=maximum y x=compound concentration [M]
K=$EC_{50}$ When tested in the MT4 assay, certain compounds of Table 1 were found to have $IC_{50}$ values listed in Table 3.

When tested in biological in vitro models, certain compounds of Table 1 were found to have $IC_{50}$ values listed in Table 3.

TABLE 3

| Compound Number (From Table 1) | HIV MT4 Assay $IC_{50}$ (uM) |
|---|---|
| 1 | 0.22 |
| 2 | 0.16 |
| 3 | 0.46 |
| 4 | 1.55 |
| 5 | 5.00 |
| 6 | 0.14 |
| 7 | 1.00 |
| 8 | 0.13 |
| 9 | 1.25 |
| 10 | 3.00 |
| 11 | 0.31 |
| 12 | 3.25 |
| 13 | 0.40 |
| 14 | 0.75 |
| 15 | 1.62 |
| 16 | 1.80 |
| 17 | 1.20 |
| 18 | 50.00 |
| 19 | 0.08 |
| 20 | 0.16 |
| 21 | 2.70 |
| 22 | 8.70 |
| 23 | 1.50 |
| 24 | 0.04 |
| 25 | 0.22 |
| 26 | 2.25 |
| 27 | 3.85 |
| 28 | 0.08 |
| 29 | 0.17 |
| 30 | 1.10 |

TABLE 3-continued

| Compound Number (From Table 1) | HIV MT4 Assay $IC_{50}$ (uM) |
|---|---|
| 31 | 0.11 |
| 32 | 0.08 |
| 33 | 0.21 |
| 34 | 0.77 |
| 35 | 1.00 |
| 36 | 0.06 |
| 37 | 0.67 |
| 38 | 0.07 |
| 39 | 1.36 |
| 40 | 0.50 |
| 41 | 0.01 |
| 42 | 0.54 |
| 43 | 1.10 |
| 44 | 0.05 |
| 45 | 0.08 |
| 46 | 0.09 |
| 47 | 0.04 |
| 48 | 0.03 |
| 49 | 0.04 |
| 50 | 0.23 |
| 51 | 0.10 |
| 52 | 0.35 |
| 53 | 0.01 |
| 54 | 0.10 |
| 55 | 0.13 |
| 56 | 0.74 |
| 57 | 0.08 |
| 58 | 0.75 |
| 59 | 0.28 |
| 60 | 0.05 |
| 61 | 0.10 |
| 62 | 0.05 |
| 63 | 1.20 |
| 64 | 0.18 |
| 65 | 0.41 |
| 66 | 1.36 |
| 67 | 0.08 |

FORMULATION EXAMPLES

The following are representative pharmaceutical formulations containing a compound of Formula (I) or a pharmaceutically acceptable salt thereof.

Example 69

Tablet Formulation

The following ingredients are mixed intimately and pressed into single scored tablets.

| Ingredient | Quantity per tablet (mg) |
|---|---|
| compound | 400 |
| cornstarch | 50 |
| croscarmellose sodium | 25 |
| lactose | 120 |
| magnesium stearate | 5 |

Example 70

Capsule Formulation

The following ingredients are mixed intimately and loaded into a hard-shell gelatin capsule.

| Ingredient | Quantity per capsule (mg) |
|---|---|
| compound | 200 |
| Lactose, spray-dried | 148 |
| magnesium stearate | 2 |

Example 71

Suspension Formulation

The following ingredients are mixed to form a suspension for oral administration.

| Ingredient | Amount |
|---|---|
| compound | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| Distilled water | q.s. (quantity sufficient) to 100 mL |

Example 72

Injectable Formulation

The following ingredients are mixed to form an injectable formulation.

| Ingredient | Amount |
|---|---|
| compound | 0.2 mg-20 mg |
| sodium acetate buffer solution, | 0.4 M 2.0 mL |
| HCl (1 N) or NaOH (1 N) | q.s. to suitable pH |
| water (distilled, sterile) | q.s. to 20 mL |

Example 73

Suppository Formulation

A suppository of total weight 2.5 g is prepared by mixing the compound with Witepsol® H-15 (triglycerides of saturated vegetable fatty acid; Riches-Nelson, Inc., New York), and has the following composition:

| Ingredient | Amount |
|---|---|
| compound | 500 mg |
| Witepsol ® H-15 | balance |

Although the invention has been shown and described above with reference to some embodiments, those skilled in the art will readily appreciate that the specific experiments detailed are only illustrative of the invention. It should be understood that various modifications can be made without departing from the spirit of the invention.

For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims. Accordingly, the invention is limited only by the following claims. All publications, issued patents, patent applications, books and journal articles, cited in this application are each herein incorporated by reference in their entirety.

What is claimed is:

1. A compound selected from the group consisting of:
2-(1-benzyl-4-(4-chlorophenyl)-6-methyl-7-oxo-6,7-dihydro-1H-pyrrolo[2,3-c]pyridin-5-yl)-2-(tert-butoxy) acetic acid,
2-(tert-butoxy)-2-(4-(4-chlorophenyl)-1-(4-fluorobenzyl)-6-methyl-7-oxo-6,7-dihydro-1H-pyrrolo[2,3-c] pyridin-5-yl)acetic acid,
2-(tert-butoxy)-2-(4-(4-chlorophenyl)-1-(4-methoxybenzyl)-6-methyl-7-oxo-6,7-dihydro-1H-pyrrolo[2,3-c] pyridin-5-yl)acetic acid,
2-(tert-butoxy)-2-(4-(4-chlorophenyl)-1-(2-methoxyethyl)-6-methyl-7-oxo-6,7-dihydro-1H-pyrrolo[2,3-c] pyridin-5-yl)acetic acid,
2-(tert-butoxy)-2-(4-(4-chlorophenyl)-1-isobutyl-6-methyl-7-oxo-6,7-dihydro-1H-pyrrolo[2,3-c]pyridin-5-yl) acetic acid,
(S)-2-(tert-butoxy)-2-(4-(4-chlorophenyl)-1-(3,4-difluorobenzyl)-6-methyl-7-oxo-6,7-dihydro-1H-pyrrolo[2,3-c]pyridin-5-yl)acetic acid,
2-(tert-butoxy)-2-(4-(4-chlorophenyl)-6-methyl-7-oxo-1-(2-(piperidin-1-yl)ethyl)-6,7-dihydro-1H-pyrrolo[2,3-c]pyridin-5-yl)acetic acid,
2-(tert-butoxy)-2-(4-(4-chlorophenyl)-6-methyl-7-oxo-1-(2-(piperidin-1-yl)ethyl)-6,7-dihydro-1H-pyrrolo[2,3-c]pyridin-5-yl)acetic acid,
2-(tert-butoxy)-2-(4-(4-chlorophenyl)-6-methyl-7-oxo-1-((5-(trifluoromethyl)furan-2-yl)methyl)-6,7-dihydro-1H-pyrrolo[2,3-c]pyridin-5-yl)acetic acid,
2-(tert-butoxy)-2-(4-(4-chlorophenyl)-1-(imidazo[1,2-a] pyridin-2-ylmethyl)-6-methyl-7-oxo-6,7-dihydro-1H-pyrrolo[2,3-c]pyridin-5-yl)acetic acid,
2-(tert-butoxy)-2-(4-(4-chlorophenyl)-6-methyl-1-((2-methylthiazol-4-yl)methyl)-7-oxo-6,7-dihydro-1H-pyrrolo[2,3-c]pyridin-5-yl)acetic acid,
2-(tert-butoxy)-2-(4-(4-chlorophenyl)-1-(2((2-hydroxy-4-methylphenyl)amino)-2-oxoethyl)-6-methyl-7-oxo-6,7-dihydro-1H-pyrrolo[2,3-c]pyridin-5-yl)acetic acid,
2-(tert-butoxy)-2-(4-(4-chlorophenyl)-6-methyl-7-oxo-1-(1-phenylethyl)-6,7-dihydro-1H-pyrrolo[2,3-c]pyridin-5-yl)acetic acid,
2-(1-benzyl-3-bromo-4-(4-chlorophenyl)-6-methyl-7-oxo-6,7-dihydro-1H-pyrrolo[2,3-c]pyridin-5-yl)-2-(tert-butoxy)acetic acid,
2-(1-benzyl-4-(4-chlorophenyl)-3,6-dimethyl-7-oxo-6,7-dihydro-1H-pyrrolo[2,3-c]pyridin-5-yl)-2-(tert-butoxy)acetic acid,
2-(tert-butoxy)-2-(4-(4-chlorophenyl)-1-((4-fluorophenyl)sulfonyl)-6-methyl-7-oxo-6,7-dihydro-1H-pyrrolo [2,3-c]pyridin-5-yl)acetic acid,
2-(tert-butoxy)-2-(4-(4-chlorophenyl)-6-methyl-7-oxo-1-tosyl-6,7-dihydro-1H-pyrrolo[2,3-c]pyridin-5-yl)acetic acid,
2-(tert-butoxy)-2-(4-(4-chlorophenyl)-1-((1-(2-hydroxyethyl)-1H-1,2,3-triazol-4-yl)methyl)-6-methyl-7-oxo-6,7-dihydro-1H-pyrrolo[2,3-c]pyridin-5-yl)acetic acid,
2-(1-benzyl-6-methyl-7-oxo-4-(p-tolyl)-6,7-dihydro-1H-pyrrolo[2,3-c]pyridin-5-yl)-2-(tert-butoxy)acetic acid, 2-(1-(benzo[c][1,2,5]oxadiazol-5-ylmethyl)-6-methyl-7-oxo-4-(p-tolyl)-6,7-dihydro-1H-pyrrolo[2,3-c]pyridin-5-yl)-2-(tert-butoxy)acetic acid,
2-(1-(4-boronobenzyl)-6-methyl-7-oxo-4-(p-tolyl)-6,7-dihydro-1H-pyrrolo[2,3-c]pyridin-5-yl)-2-(tert-butoxy)acetic acid,
2-(tert-butoxy)-2-(1-(4-carbamoylbenzyl)-6-methyl-7-oxo-4-(p-tolyl)-6,7-dihydro-1H-pyrrolo[2,3-c]pyridin-5-yl)acetic acid,
2-(tert-butoxy)-2-(6-methyl-7-oxo-4-(p-tolyl)-1-(4-((trifluoromethyl)thio)benzyl)-6,7-dihydro-1H-pyrrolo[2,3-c]pyridin-5-yl)acetic acid,
(S)-2-(tert-butoxy)-2-(1-(4-fluorobenzyl)-6-methyl-7-oxo-4-(p-tolyl)-6,7-dihydro-1H-pyrrolo[2,3-c]pyridin-5-yl)acetic acid,
2-(tert-butoxy)-2-(6-methyl-7-oxo-1-(thiophen-2-ylmethyl)-4-(p-tolyl)-6,7-dihydro-1H-pyrrolo[2,3-c]pyridin-5-yl)acetic acid,
2-(tert-butoxy)-2-(1-(4-fluorophenethyl)-6-methyl-7-oxo-4-(p-tolyl)-6,7-dihydro-1H-pyrrolo[2,3-c]pyridin-5-yl)acetic acid,
2-(tert-butoxy)-2-(6-methyl-1-(4-(methylsulfonyl)benzyl)-7-oxo-4-(p-tolyl)-6,7-dihydro-1H-pyrrolo[2,3-c]pyridin-5-yl)acetic acid,
2-(tert-butoxy)-2-(1-(3,4-difluorobenzyl)-6-methyl-7-oxo-4-(p-tolyl)-6,7-dihydro-1H-pyrrolo[2,3-c]pyridin-5-yl)acetic acid,
2-(tert-butoxy)-2-(1-(4-methoxybenzyl)-6-methyl-7-oxo-4-(p-tolyl)-6,7-dihydro-1H-pyrrolo[2,3-c]pyridin-5-yl)acetic acid,
2-(tert-butoxy)-2-(1,6-dimethyl-7-oxo-4-(p-tolyl)-6,7-dihydro-1H-pyrrolo[2,3-c]pyridin-5-yl)acetic acid,
2-(tert-butoxy)-2-(1-(4-chloro-3-fluorobenzyl)-6-methyl-7-oxo-4-(p-tolyl)-6,7-dihydro-1H-pyrrolo[2,3-c]pyridin-5-yl)acetic acid,
2-(tert-butoxy)-2-(6-methyl-7-oxo-4-(p-tolyl)-1-(3,4,5-trifluorobenzyl)-6,7-dihydro-1H-pyrrolo[2,3-c]pyridin-5-yl)acetic acid,
2-(1-(benzo[d][1,3]dioxol-5-ylmethyl)-6-methyl-7-oxo-4-(p-tolyl)-6,7-dihydro-1H-pyrrolo[2,3-c]pyridin-5-yl)-2-(tert-butoxy)acetic acid,
2-(tert-butoxy)-2-(1-(4-fluorophenyl)-6-methyl-7-oxo-4-(p-tolyl)-6,7-dihydro-1H-pyrrolo[2,3-c]pyridin-5-yl)acetic acid,
2-(tert-butoxy)-2-(1-(2-((4-fluorophenyl)amino)-2-oxoethyl)-6-methyl-7-oxo-4-(p-tolyl)-6,7-dihydro-1H-pyrrolo[2,3-c]pyridin-5-yl)acetic acid,
2-(tert-butoxy)-2-(1-(4-fluorobenzyl)-4-(4-methoxyphenyl)-6-methyl-7-oxo-6,7-dihydro-1H-pyrrolo[2,3-c]pyridin-5-yl)acetic acid,
2-(tert-butoxy)-2-(1-(4-fluorobenzyl)-4-(4-fluorophenyl)-6-methyl-7-oxo-6,7-dihydro-1H-pyrrolo[2,3-c]pyridin-5-yl)acetic acid,
2-(1-benzyl-6-methyl-4-(5-methylchroman-6-yl)-7-oxo-6,7-dihydro-1H-pyrrolo[2,3-c]pyridin-5-yl)-2-(tert-butoxy)acetic acid,
2-(1-benzyl-6-methyl-4-(5-methylchroman-6-yl)-7-oxo-6,7-dihydro-1H-pyrrolo[2,3-c]pyridin-5-yl)-2-(tert-butoxy)acetic acid,
2-(tert-butoxy)-2-(1,6-dimethyl-4-(5-methylchroman-6-yl)-7-oxo-6,7-dihydro-1H-pyrrolo[2,3-c]pyridin-5-yl)acetic acid,
(S)(M)-2-(tert-butoxy)-2-(1-(4-fluorobenzyl)-6-methyl-4-(5-methylchroman-6-yl)-7-oxo-6,7-dihydro-1H-pyrrolo[2,3-c]pyridin-5-yl)acetic acid,
2-(tert-butoxy)-2-(6-methyl-4-(5-methylchroman-6-yl)-7-oxo-1-(pyridin-2-ylmethyl)-6,7-dihydro-1H-pyrrolo[2,3-c]pyridin-5-yl)acetic acid,
2-(tert-butoxy)-2-(1-(2-methoxyethyl)-6-methyl-4-(5-methylchroman-6-yl)-7-oxo-6,7-dihydro-1H-pyrrolo[2,3-c]pyridin-5-yl)acetic acid,
2-(tert-butoxy)-2-(1-(4-chlorobenzyl)-6-methyl-4-(5-methylchroman-6-yl)-7-oxo-6,7-dihydro-1H-pyrrolo[2,3-c]pyridin-5-yl)acetic acid,
2-(tert-butoxy)-2-(1-(3-fluorobenzyl)-6-methyl-4-(5-methylchroman-6-yl)-7-oxo-6,7-dihydro-1H-pyrrolo[2,3-c]pyridin-5-yl)acetic acid,
2-(tert-butoxy)-2-(6-methyl-4-(5-methylchroman-6-yl)-7-oxo-1-(4-(trifluoromethyl)benzyl)-6,7-dihydro-1H-pyrrolo[2,3-c]pyridin-5-yl)acetic acid,
2-(tert-butoxy)-2-(6-methyl-4-(5-methylchroman-6-yl)-1-(4-nitrobenzyl)-7-oxo-6,7-dihydro-1H-pyrrolo[2,3-c]pyridin-5-yl)acetic acid,
2-(tert-butoxy)-2-(1-(2,5-difluorobenzyl)-6-methyl-4-(5-methylchroman-6-yl)-7-oxo-6,7-dihydro-1H-pyrrolo[2,3-c]pyridin-5-yl)acetic acid,
2-(tert-butoxy)-2-(1-(3-fluoro-4-methylbenzyl)-6-methyl-4-(5-methylchroman-6-yl)-7-oxo-6,7-dihydro-1H-pyrrolo[2,3-c]pyridin-5-yl)acetic acid,
2-(tert-butoxy)-2-(6-methyl-4-(5-methylchroman-6-yl)-7-oxo-1-(thiazol-4-ylmethyl)-6,7-dihydro-1H-pyrrolo[2,3-c]pyridin-5-yl)acetic acid,
2-(tert-butoxy)-2-(1-(cyclohexylmethyl)-6-methyl-4-(5-methylchroman-6-yl)-7-oxo-6,7-dihydro-1H-pyrrolo[2,3-c]pyridin-5-yl)acetic acid,
2-(tert-butoxy)-2-(6-methyl-4-(5-methylchroman-6-yl)-7-oxo-1-((tetrahydro-2H-pyran-4-yl)methyl)-6,7-dihydro-1H-pyrrolo[2,3-c]pyridin-5-yl)acetic acid,
2-(tert-butoxy)-2-(6-methyl-4-(5-methylchroman-6-yl)-7-oxo-1-((tetrahydro-2H-pyran-4-yl)methyl)-6,7-dihydro-1H-pyrrolo[2,3-c]pyridin-5-yl)acetic acid,
2-(tert-butoxy)-2-(6-methyl-4-(5-methylchroman-6-yl)-7-oxo-1-((tetrahydro-2H-pyran-4-yl)methyl)-6,7-dihydro-1H-pyrrolo[2,3-c]pyridin-5-yl)acetic acid,
tert-Butoxy-[2-methyl-4-(5-methyl-chroman-6-yl)-1-oxo-1,2,5,6,7,8-hexahydro-benzo[4,5]thieno[2,3-c]pyridin-3-yl]-acetic acid,
2-(tert-butoxy)-2-(9-(4-fluorobenzyl)-2-methyl-1-oxo-4-(p-tolyl)-2,9-dihydro-1H-pyrido[3,4-b]indol-3-yl)acetic acid,
2-(tert-butoxy)-2-(2,9-dimethyl-1-oxo-4-(p-tolyl)-2,9-dihydro-1H-pyrido[3,4-b]indol-3-yl)acetic acid,
2-(tert-butoxy)-2-(5-(4-fluorobenzyl)-7-methyl-6-oxo-9-(p-tolyl)-1,3,4,5,6,7-hexahydropyrano[3',4':4,5]pyrrolo[2,3-c]pyridin-8-yl)acetic acid,
2-(tert-butoxy)-2-(9-(4-fluorobenzyl)-2-methyl-1-oxo-4-(p-tolyl)-2,5,6,7,8,9-hexahydro-1H-pyrido[3,4-b]indol-3-yl)acetic acid,
2-(tert-butoxy)-2-(2,9-dimethyl-1-oxo-4-(p-tolyl)-2,5,6,7,8,9-hexahydro-1H-pyrido[3,4-b]indol-3-yl)acetic acid,
2-(tert-butoxy)-2-(9-(4-methoxybenzyl)-2-methyl-1-oxo-4-(p-tolyl)-2,5,6,7,8,9-hexahydro-1H-pyrido[3,4-b]indol-3-yl)acetic acid,
2-(tert-butoxy)-2-(9-(4-methoxybenzyl)-2-methyl-4-(5-methylchroman-6-yl)-1-oxo-2,5,6,7,8,9-hexahydro-1H-pyrido[3,4-b]indol-3-yl)acetic acid,
2-(tert-Butoxy)-2-(4-(3,4-dimethylphenyl)-1-(4-methoxybenzyl)-6-methyl-7-oxo-6,7-dihydro-1H-pyrazolo[3,4-c]pyridin-5-yl)acetic, 2-(tert-Butoxy)-2-(1-(4-fluorobenzyl)-6-methyl-7-oxo-4-(p-tolyl)-6,7-dihydro-1H-pyrazolo[3,4-c]pyridin-5-yl)acetic acid, 2-(tert-Butoxy)-2-(1-(4-methoxybenzyl)-6-methyl-4-(5-methylchroman-6-yl)-7-oxo-6,7-dihydro-1H-pyrazolo[3,4-c]pyridin-5-yl)acetic acid yl)acetic, 2-(tert-Butoxy)-2-(6-methyl-4-(5-methylchroman-6-yl)-7-oxo-1-(pyridin-2-ylmethyl)-6,7-dihydro-1H-pyrazolo[3,4-c]pyridin-5-yl)acetic acid, 2-(tert-butoxy)-2-(1-(4-fluorobenzyl)-6-methyl-4-(5-methylchroman-6-yl)-7-oxo-6,7-dihydro-1H-pyrazolo[3,4-c]pyridin-5-yl)acetic acid, and pharmaceutically acceptable salts thereof.

2. A pharmaceutical composition comprising a pharmaceutically acceptable diluent and a therapeutically effective amount of a compound as defined in claim 1.

3. A method for treating a viral infection in a mammal mediated at least in part by a virus in the retrovirus family of viruses which method comprises administering to a mammal, that has been diagnosed with said viral infection or is at risk of developing said viral infection, a compound of claim 1.

4. The method of claim 3, wherein said virus is an HIV virus.

5. The method according to claim 4, further comprising administration of a therapeutically effective amount of one or more agents active against an HIV virus.

6. The method according to claim 5, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

* * * * *